(12) United States Patent
Abate et al.

(10) Patent No.: US 11,732,287 B2
(45) Date of Patent: Aug. 22, 2023

(54) SEQUENCING OF NUCLEIC ACIDS VIA BARCODING IN DISCRETE ENTITIES

(71) Applicant: The Regents of the University of California, Oakland, CA (US)

(72) Inventors: Adam R. Abate, San Francisco, CA (US); John R. Haliburton, San Francisco, CA (US); Freeman Lan, San Francisco, CA (US); Adam R. Sciambi, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/940,850

(22) Filed: Mar. 29, 2018

(65) Prior Publication Data
US 2018/0216160 A1 Aug. 2, 2018

Related U.S. Application Data

(62) Division of application No. 15/015,015, filed on Feb. 3, 2016, now Pat. No. 11,111,519.

(60) Provisional application No. 62/112,075, filed on Feb. 4, 2015.

(51) Int. Cl.
| | | |
|---|---|---|
| C12Q 1/6804 | (2018.01) | |
| C12Q 1/6806 | (2018.01) | |
| C12N 15/10 | (2006.01) | |
| C12Q 1/68 | (2018.01) | |
| B01L 3/00 | (2006.01) | |
| B01F 25/433 | (2022.01) | |
| B01F 33/302 | (2022.01) | |
| C12Q 1/6874 | (2018.01) | |
| B01L 7/00 | (2006.01) | |
| B01F 21/00 | (2022.01) | |

(52) U.S. Cl.
CPC ........ *C12Q 1/6804* (2013.01); *B01F 25/4338* (2022.01); *B01F 33/3021* (2022.01); *B01L 3/502784* (2013.01); *C12N 15/1096* (2013.01); *C12Q 1/68* (2013.01); *C12Q 1/6806* (2013.01); *C12Q 1/6874* (2013.01); *B01F 21/00* (2022.01); *B01L 3/502707* (2013.01); *B01L 3/502715* (2013.01); *B01L 3/502761* (2013.01); *B01L 7/52* (2013.01); *B01L 2200/0647* (2013.01); *B01L 2200/0652* (2013.01); *B01L 2300/021* (2013.01); *B01L 2300/0645* (2013.01); *B01L 2300/0864* (2013.01); *B01L 2300/0867* (2013.01); *B01L 2300/123* (2013.01); *B01L 2400/043* (2013.01); *B01L 2400/0409* (2013.01); *B01L 2400/0415* (2013.01); *B01L 2400/0424* (2013.01)

(58) Field of Classification Search
CPC .............. B01F 13/0071; C12Q 1/6806; C12N 15/1096; B01L 2200/0647; B01L 2300/021
See application file for complete search history.

(56) References Cited

U.S. PATENT DOCUMENTS

| | | | |
|---|---|---|---|
| 7,638,276 | B2 | 12/2009 | Griffiths et al. |
| RE41,780 | E | 9/2010 | Anderson et al. |
| 8,067,159 | B2 | 11/2011 | Brown et al. |
| 8,257,925 | B2 | 9/2012 | Brown et al. |
| 8,765,485 | B2 | 7/2014 | Link et al. |
| 9,150,852 | B2 | 10/2015 | Samuels et al. |
| 10,161,007 | B2 | 12/2018 | Abate et al. |
| 10,745,762 | B2 | 8/2020 | Mate et al. |
| 2002/0086042 | A1 | 7/2002 | Delrieu et al. |
| 2003/0156993 | A1 | 8/2003 | Staats |
| 2003/0180737 | A1 | 9/2003 | Gu et al. |
| 2005/0019902 | A1 | 1/2005 | Mathies et al. |
| 2005/0112639 | A1* | 5/2005 | Wang ................ C12N 15/1096 435/6.12 |
| 2005/0172476 | A1 | 8/2005 | Stone et al. |
| 2007/0039866 | A1 | 2/2007 | Schroeder et al. |
| 2007/0077572 | A1 | 4/2007 | Tawfik et al. |
| 2007/0141593 | A1 | 6/2007 | Lee et al. |
| 2007/0231880 | A1 | 10/2007 | Chang-Yen et al. |
| 2008/0014589 | A1 | 1/2008 | Link et al. |
| 2009/0045064 | A1 | 2/2009 | Simmons et al. |
| 2009/0098555 | A1 | 4/2009 | Roth et al. |
| 2009/0111188 | A1 | 4/2009 | Cai et al. |

(Continued)

FOREIGN PATENT DOCUMENTS

| | | |
|---|---|---|
| AU | 2013203624 | 5/2013 |
| AU | 2013302867 A1 | 2/2015 |

(Continued)

OTHER PUBLICATIONS

Eastburn et al.(Analytical chemistry 85.16 (2013): 8016-8021). (Year: 2013).*
Abate Adam. R, et al; (2010) "Microfluidic sorting with high-speed single-layer membrane valves"; *Applied Physics Letters 96*; pp. 203509-1-203509-3.
Abate Adam. R., et al; "High-throughput injection with microfluidics using picoinjectors"; *PNAS* vol. 1071 No. 45; Nov. 9, 2010; pp. 19163-19166.

(Continued)

*Primary Examiner* — Sahana S Kaup
(74) *Attorney, Agent, or Firm* — Edward J. Baba; Bozicevic, Field & Francis LLP

(57) ABSTRACT

Microfluidic methods for barcoding nucleic acid target molecules to be analyzed, e.g., via nucleic acid sequencing techniques, are provided. Also provided are microfluidic, droplet-based methods of preparing nucleic acid barcodes for use in various barcoding applications. The methods described herein facilitate high-throughput sequencing of nucleic acid target molecules as well as single cell and single virus genomic, transcriptomic, and/or proteomic analysis/profiling. Systems and devices for practicing the subject methods are also provided.

20 Claims, 29 Drawing Sheets

(56) References Cited

U.S. PATENT DOCUMENTS

| | | |
|---|---|---|
| 2010/0015614 A1 | 1/2010 | Beer et al. |
| 2010/0028915 A1 | 2/2010 | Gualberto et al. |
| 2010/0055677 A1 | 3/2010 | Colston, Jr. et al. |
| 2010/0137163 A1 | 6/2010 | Link et al. |
| 2010/0173394 A1 | 7/2010 | Colston, Jr. et al. |
| 2010/0248237 A1 | 9/2010 | Froehlich et al. |
| 2010/0285975 A1 | 11/2010 | Mathies et al. |
| 2010/0318528 A1 | 12/2010 | Kupershmidt et al. |
| 2011/0053798 A1 | 3/2011 | Hindson et al. |
| 2011/0056575 A1 | 3/2011 | Hong et al. |
| 2011/0059556 A1 | 3/2011 | Stray et al. |
| 2011/0086352 A1 | 4/2011 | Bashir et al. |
| 2011/0103176 A1 | 5/2011 | Van Dam et al. |
| 2011/0104816 A1 | 5/2011 | Pollack et al. |
| 2011/0118151 A1 | 5/2011 | Eshoo et al. |
| 2011/0160078 A1 | 6/2011 | Fodor et al. |
| 2011/0217736 A1 | 9/2011 | Hindson |
| 2011/0311978 A1 | 12/2011 | Makarewicz et al. |
| 2012/0010086 A1 | 1/2012 | Froehlich et al. |
| 2012/0045765 A1 | 2/2012 | Curran et al. |
| 2012/0122714 A1* | 5/2012 | Samuels ............. G01N 33/532 506/18 |
| 2012/0132288 A1 | 5/2012 | Weitz et al. |
| 2012/0309002 A1 | 6/2012 | Link |
| 2012/0190032 A1 | 7/2012 | Ness et al. |
| 2012/0190033 A1 | 7/2012 | Ness et al. |
| 2012/0196288 A1 | 8/2012 | Beer |
| 2012/0219947 A1 | 8/2012 | Yurkovetsky et al. |
| 2012/0220494 A1* | 8/2012 | Samuels ................ C40B 50/08 506/26 |
| 2012/0258870 A1* | 10/2012 | Schwartz .............. C12Q 1/6834 506/4 |
| 2012/0264646 A1 | 10/2012 | Link et al. |
| 2012/0270739 A1 | 10/2012 | Rava et al. |
| 2012/0316074 A1 | 12/2012 | Saxonov et al. |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0213488 A1 | 8/2013 | Weitz et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Miller et al. |
| 2014/0155295 A1* | 6/2014 | Hindson ........... B01L 3/502715 506/16 |
| 2014/0179544 A1 | 6/2014 | Steenblock et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0357500 A1 | 12/2014 | Vigneault et al. |
| 2014/0378345 A1 | 12/2014 | Hindson et al. |
| 2014/0378349 A1 | 12/2014 | Hindson et al. |
| 2015/0232942 A1 | 5/2015 | Abate et al. |
| 2015/0298091 A1 | 10/2015 | Weitz et al. |
| 2016/0177375 A1 | 6/2016 | Abate et al. |
| 2016/0265043 A1 | 9/2016 | Geng et al. |
| 2017/0009274 A1 | 1/2017 | Abate et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |
| 2019/0127789 A1 | 5/2019 | Weitz et al. |
| 2019/0169700 A1 | 6/2019 | Abate et al. |
| 2019/0218594 A1 | 7/2019 | Abate et al. |
| 2019/0241965 A1 | 8/2019 | Abate et al. |
| 2019/0330701 A1 | 10/2019 | Abate et al. |

FOREIGN PATENT DOCUMENTS

| | | | |
|---|---|---|---|
| AU | 2016215298 A1 | 8/2017 | |
| AU | 2016215304 A1 | 8/2017 | |
| AU | 2017382905 A1 | 7/2019 | |
| AU | 2019226236 A1 | 9/2019 | |
| CA | 2881783 A1 | 2/2014 | |
| CA | 3001986 A1 | 4/2016 | |
| CA | 2974299 A1 | 8/2016 | |
| CA | 2974306 A1 | 8/2016 | |
| CA | 3047328 A1 | 6/2018 | |
| CN | 1693478 A | 11/2005 | |
| CN | 104736725 A | 6/2015 | |
| CN | 107107058 A | 8/2017 | |
| CN | 107429426 A | 12/2017 | |
| CN | 107530654 A | 1/2018 | |
| CN | 108350488 A | 7/2018 | |
| CN | 110088290 A | 8/2019 | |
| CN | 110462053 A | 11/2019 | |
| DE | 10339452 | 3/2005 | |
| EP | 1547677 | 6/2005 | |
| EP | 2145955 | 2/2012 | |
| EP | 2565650 | 3/2013 | |
| EP | 2882872 A2 | 6/2015 | |
| EP | 3160654 A2 | 5/2017 | |
| EP | 3209419 A1 | 8/2017 | |
| EP | 3253479 A2 | 12/2017 | |
| EP | 3253910 A1 | 12/2017 | |
| EP | 3337907 A1 | 6/2018 | |
| EP | 3497228 A1 | 6/2019 | |
| EP | 3571308 A1 | 11/2019 | |
| GB | 2519906 A | 5/2015 | |
| GB | 2539836 A | 12/2016 | |
| JP | 2013503630 A | 2/2013 | |
| JP | 2014521334 A | 8/2014 | |
| JP | 2015533079 A | 11/2015 | |
| JP | 2018505671 A | 3/2018 | |
| JP | 2018508198 A | 3/2018 | |
| JP | 2018525004 A | 9/2018 | |
| WO | WO 1994012216 | 6/1994 | |
| WO | WO 2007140015 | 12/2007 | |
| WO | WO-2007140015 A2 * | 12/2007 | ........ B01L 3/502784 |
| WO | WO 2009050512 | 4/2009 | |
| WO | WO 2009054870 | 4/2009 | |
| WO | WO 2009111014 | 9/2009 | |
| WO | WO 2010148039 | 12/2010 | |
| WO | WO 2011047307 | 4/2011 | |
| WO | WO 2012011091 | 1/2012 | |
| WO | WO 2012048341 | 4/2012 | |
| WO | WO 2012162267 | 5/2012 | |
| WO | WO 2012083225 | 6/2012 | |
| WO | 2012109600 | 8/2012 | |
| WO | WO-2012106385 A2 * | 8/2012 | ........... C12Q 1/6816 |
| WO | WO 2012142213 | 10/2012 | |
| WO | 2013015793 A1 | 1/2013 | |
| WO | 2013095469 A1 | 6/2013 | |
| WO | WO 2013119753 | 8/2013 | |
| WO | WO 2013126741 | 8/2013 | |
| WO | WO 2013130512 | 9/2013 | |
| WO | WO 2013134261 | 9/2013 | |
| WO | WO 2013173394 | 11/2013 | |
| WO | WO 2014028378 | 2/2014 | |
| WO | WO 2014028537 | 2/2014 | |
| WO | WO 2014047556 | 3/2014 | |
| WO | WO 2014083435 | 6/2014 | |
| WO | WO 2014093676 | 6/2014 | |
| WO | 2014108323 | 7/2014 | |
| WO | 2014108323 A1 | 7/2014 | |
| WO | WO 2014138132 | 9/2014 | |
| WO | WO 2014151658 | 9/2014 | |
| WO | WO 2014153071 | 9/2014 | |
| WO | WO 2015120398 | 2/2015 | |
| WO | 2015031691 | 3/2015 | |
| WO | WO-2015031691 A1 * | 3/2015 | .......... B01L 3/50857 |
| WO | 2015069798 A1 | 5/2015 | |
| WO | WO 2015200717 | 6/2015 | |
| WO | 2015157369 | 10/2015 | |
| WO | WO2015179848 A1 | 11/2015 | |
| WO | 2015189336 A1 | 12/2015 | |

(56) References Cited

FOREIGN PATENT DOCUMENTS

| WO | 2015200893 A2 | 12/2015 |
| --- | --- | --- |
| WO | WO 2016064755 | 4/2016 |
| WO | WO 2016065056 | 4/2016 |
| WO | WO 2016126865 | 8/2016 |
| WO | WO 2016126871 | 8/2016 |
| WO | 2017031125 A1 | 2/2017 |
| WO | WO2018031691 A1 | 2/2018 |
| WO | 20180119301 A1 | 6/2018 |
| WO | WO2019099908 A1 | 5/2019 |

OTHER PUBLICATIONS

Abate AR, et al; (2011) "Efficient encapsulation with plug-triggered drop formation"; *Physical Review E.*;84(3):031502.

Abate AR and Weitz DA; (2011) "Faster multiple emulsification with drop splitting". *Lab on a Chip*; 11(11); pp. 1911-1915.

Abate AR, et al; (2011) "One-step formation of multiple emulsions in micro fluidics"; *Lab on a Chip11*(2); pp. 253-258.

Abate AR, et al; (2008) "Photoreactive coating for high-contrast spatial patterning of microfluidic device wettability"; *Lab on a Chip* 8(12); pp. 2157-2160.

Ali et al. "Rolling circle amplification: a versatile tool for chemical biology, materials science and medicine"; *Chem Soc Rev.* vol. 43; Mar. 18, 2014; pp. 3324-3341.

Agresti JJ, et al; "Ultrahigh-throughput screening in drop-based microfluidics for directed evolution"; *PNAS* vol. 107, No. 9; Mar. 2, 2010; pp. 4004-4009.

Agresti J., et al; (2010) "Correction for Ultrahigh-throughput screening in drop-based microfluidics for directed evolution"; *Proc. Nat.l Acad. Sci. USA*, 107; pp. 6550-6551.

Ahn K, et al; (2006) "Electrocoalescence of drops synchronized by size-dependent flow in microfluidic channels"; *Appl Phys Lett 88*; pp. 264105-1-264105-3.

Allen LZ, et al; (2011) "Single virus genomics: a new tool for virus discovery"; *PLoS One* 6(3):e17722.

Arriaga LR, et al. (2014) "Ultrathin Shell Double Emulsion Templated Giant Unilamellar Lipid Vesicles with Controlled Microdomain Formation"; *Small* 10(5); pp. 950-956.; Epub Oct. 2, 20132.

Atten P; (1993) "Electrocoalescence of Water Droplets in an Insulating Liquid"; *J Electrostat 30*; pp. 259-269.

Barenholz Y. et al; (1977) "A simple method for the preparation of homogeneous phospholipid vesicles" *Biochemistry* 16(12); pp. 2806-2810.

Baret J-C, et al. (2009) "Fluorescence-activated droplet sorting (FADS): efficient microfluidic cell sorting based on enzymatic activity"; *Lab on a Chip*;9(13); pp. 1850-1858.

Battaglia G, et al; (2006) "Polymeric vesicle peimeability: a facile chemical assay"; *Langmuir* 22(11); pp. 4910-4913.

Beer NR, et al; (2008) "On-chip single-copy real-time reverse-transcription PCR in isolated picoliter droplets"; *Anal Chem 80*; pp. 1854-1858.

Bernath, et al; (2004) "In vitro compartmentalization by double emulsions: sorting and gene enrichment by fluorescence activated cell sorting"; *Analytical Biochemistry 325*; pp. 151-157.

Bird et al., (1988) "Single-chain antigen-binding proteins"; *Science 242*; pp. 423-426.

Blainey PC. (2013) "The future is now: single-cell genomics of bacteria and archaea"; *FEMS microbiology reviews* 37(3); pp. 407-427.

Brouzes E, et al; "Droplet microfluidic technology for single-cell high-throughput screening"; *PNAS* vol. 106, No. 34; Aug. 25, 2009; pp. 14195-14200.

Brown, R. B. et al: (2008) "Current techniques for single-cell lysis"; *J. R. Soc. Interface 5*; pp. S131-S138.

Caron G.; (1998) "Assessment of bacterial viability status by flow cytometry and single cell sorting"; *Journal of applied microbiology* 84(6): pp. 988-998.

Chaffer C. L. and Weinberg R. A.; "A Perspective on Cancer Cell Metastasis"; *Science*, vol. 331; Mar. 25, 2011; pp. 1559-1564.

Chabert M, et al; (2005) "Droplet fusion by alternating current (AC) field electrocoalescence in microchannels"; *Electrophoresis 26*; pp. 3706-3715.

Chen C-M, et al; (2000) "Influence of pH on the stability of oil-in-water emulsions stabilized by a splittable surfactant"; *Colloids and Surfaces A: Physicochemical and Engineering Aspects* 170(2); pp. 173-179.

Chung, C. et al; (2010) "Droplet dynamics passing through obstructions in confined microchannel flow"; *Microfluidics Nanofluidics*, 9(6), pp. 1151-1163.

Clausell-Tormos, Jennifer, et al; "Droplet-based microfluidic platforms for the encapsulation and screening of Mammalian cells and multicellular organisms"; *Chemistry and Biology 15*; (May 2008); pp. 427-437.

Dejournette CJ, et al; (2013) "Creating Biocompatible Oil-Water Interfaces without Synthesis: Direct Interactions between Primary Amines and Carboxylated Perfluorocarbon Surfactants"; *Analytical chemistry.*;85(21); pp. 10556-10564.

Dietrich et al; "Effects of UV irradiation and hydrogen peroxide on DNA fragmentation, motility and fertilizing ability of rainbow trout (*Oncorhynchus mykiss*) spermatozoa"; *Theriogenology.* vol. 64; (Nov. 2005) pp. 1809-1822.

Duffy DC, et al; (1998) "Rapid Prototyping of Microfluidic Systems in Poly (dimethylsiloxane)"; *Anal. Chem. 70*; pp. 4974-4984.

Eastburn Dennis J., et al.; (2013) "Ultrahigh-Throughput Mammalian Single-Cell Reverse-Transcriptase Polymerase Chain Reaction in Microfluidic Drops"; *Anal. Chem. 85*; pp. 8016-8021.

Eastburn DJ,et al; (2013) "Picoinjection Enables Digital Detection of RNA with Droplet RT-PCR"; *PloS one.*;8(4):e62961.

Edd et al., (2008) Controlled encapsulation of single cells into monodisperse picoliter drop *Lab on a Chip*, 8(8); pp. 1262-1264.

European search report and opinion dated Feb. 8, 2016 for EP Application No. 13829925.

Frenz L, et al; (2009) "Reliable microfluidic on-chip incubation of droplets in delay-lines"; *Lab on a Chip* 9(10); pp. 1344-1348.

Garstecki P. et al.; "Formation of droplets and bubbles in a microfluidic T-junction-scaling and mechanism of break-up"; *Lab Chip 6*; (2006); pp. 437-446.

Gevensleben H, et al; (2013) "Noninvasive Detection of HER2 Amplification with Plasma DNA Digital PCR"; *Clinical Cancer Research.*; 19(12); pp. 3276-3284.

Gribskov, et al; (1986) "Sigma factors from *E. coli, B. subtilis*, phage SP01, and phage T4 are homologous proteins"; *Nucl. Acids Res.* 14(6):6745-6763.

Hayward RC, et al; (2006) "Dewetting instability during the foimation of polymersomes from block-copolymer-stabilized double emulsions"; *Langmuir* 22(10); pp. 4457-4461.

Herminghaus S, "Dynamical Instability of Thin Liquid Films Between Conducting Media"; *Physical Review Letter*, vol. 83, No. 12; Sep. 20, 1999; pp. 2359-2361.

Holland, et al; (1991) "Detection of specific polymerase chain reaction product by utilizing the 5'-----3' exonuclease activity of Thermus aquaticus DNA polymerase"; PNAS, 88 (16); 7276-7280.

Holtze C., et al; (2008) "Biocompatible surfactants for water-in-fluorocarbon emulsions"; *Lab Chip 8*; pp. 1632-1639.

Horton et al; "Gene splicing by overlap extension: tailor-made genes using the polymerase chain reaction"; *Biotechniques*, vol. 54; Mar. 1, 2013; pp. 129-133.

Hu, Hoa et al; (2009) "Mutation screening in 86 known X-linked mental retardation genes by droplet-based multiplex PCR and massive parallel sequencing"; *Hugo J.3*; pp. 41-49.

Huebner et al; (2008) "Microdroplets: A sea of applications?"; *Lab on a Chip*, 8; pp. 1244-1254.

Hunkapiller and Hood, (1986) "Immunology: The growing immunoglobulin gene superfamily"; *Nature*, 323; pp. 15-16.

Hunt JA, et al; (1994) "Effect of pH on the stability and surface composition of emulsions made with whey protein isolate"; *Journal of Agricultural and Food Chemistry.* ;42(10); pp. 2131-2135.

Huston et al; (1988) "Protein engineering of antibody binding sites: recovery of specific activity in an anti-digoxin single-chain Fv analogue produced in *Escherichia coli*"; *Proc. Natl. Acad. Sci. U.S.A.*, 85; pp. 5879-5883.

(56) References Cited

OTHER PUBLICATIONS

International search report and written opinion dated Feb. 21, 2014 for PCT/US2013/054517.
Ki, JS., et al. (2005) "Integrated method for single-cell DNA extraction, PCR amplification, and sequencing of ribosomal DNA from harmful Dinoflagellates Cochlodium polykrikoides and Alexandrium catenella"; Marine Biotechnology, vol. 6; pp. 587-593.
Kiss MM, et al.(2008) "High-Throughput Quantitative Polymerase Chain Reaction in Picoliter Droplets"; Anal Chem 80(23); pp. 8975-8981.
Kritikou Ekat; "It's cheaper in the Picolab"; Nat Rev Genet, 6; (Sep. 2005); pp. 668.
Küster, et al (2013) "Interfacing droplet microfluidics with matrix-assisted laser desorption/ionization mass spectrometry: label-free content analysis of single droplets"; Anal Chem. 5;85(3); pp. 1285-1289.
Lagally ET, et al; (2001) "Single-Molecule DNA Amplification and Analysis in an Integrated Microfluidic Device"; Analytical Chemistry. ;73(3); pp. 565-570.
Lanzavecchia et al; (1987) "The use of hybrid hybridomas to target human cytotoxic T lymphocytes"; Eur. J. Immunol. 17(1); pp. 105-111.
Leary JF. (1994) "Strategies for rare cell detection and isolation"; Methods Cell Biol.;42(Pt B); pp. 331-358.
Lim, Shuan and Abate Adam, (2013) "Ultrahigh-throughput sorting of microfluidic drops with flow cytometry"; Lab Chip13; pp. 4563-4572.
Link, et al; (2004) "Geometrically mediated breakup of drops in microfluidic devices"; Phys Rev Lett. 92(5):054503.
Livak KJ and Schmittgen TD; (2001) "Analysis of Relative Gene Expression Data Using Real-Time Quantitative PCR and the $2^{-\Delta\Delta CT}$ Method"; methods.; 25 (4); pp. 402-408.
Longo MC, et al; (1990) "Use of uracil DNA glycosylase to control carry-over contamination in polymerase chain reactions"; Gene. ;93(1); pp. 125-128.
Malloggi F, et al; "Electrowetting-controlled droplet generation in a microfluidic flow-focusing device"; J. Phys.: Condens. Matter 19; (2007); 462101; 7 pages.
Markou Athina,et al; (2011) "Molecular Characterization of Circulating Tumor Cells in Breast Cancer by a Liquid Bead Array Hybridization Assay"; Clinical Chemistry 57:3; pp. 421-430.
Marcus et al., "Parallel Picoliter RT-PCR Assays Using Microfluidics"; Analytical Chemistry, 78(3); (2006); pp. 956-958.
Mary P. Pascaline, et al; "Controlling droplet incubation using close-packed plug flow"; Biomicrofluidics 5; (2011); pp. 024101-1-024101-6.
Mazutis L, et al; (2013) "Single-cell analysis and sorting using droplet-based microfluidics"; Nature protocols.8(5); pp. 870-891.
McDonald, et al.; (2000) "Fabrication of microfluidic systems in poly (dimethylsiloxane"; Electrophoresis, 21(1); pp. 27-40.
Medkova, Martina et al; "Analyzing Cancer at Single Cell Resolution with Droplet Technology"; American Association of Cancer Research (AACR); Apr. 19, 2010; 1 page.
Metzker, Michael L. "Sequencing technologies—the next generation"; Nature Reviews Genetics, vol. 11 (Jan. 2010); pp. 31-46.
Miyazaki, K; (2002) "Random DNA fragmentation with endonuclease V: application to DNA shuffling"; Nucleic Acids Res. 30(24); e139.
Miyazaki et al. (2013) "A new large-DNA-fragment delivery system based on integrase activity from an integrative and conjugative element"; Appl Environ Microbiol 79(14); pp. 4440-4447.
MOON Sangjun, et al; "Drop-on-Demand Single Cell Isolation and Total RNA Analysis"; PloS ONE, vol. 6, Issue 3; e17455 (Mar. 2011); pp. 1-10.
Morton et al; (2008) "Crossing microfluidic streamlines to lyse, label and wash cells"; Lab on a Chip, 8(9); pp. 1448-1453.
Mui B, et al; (1993) "Osmotic properties of large unilamellar vesicles prepared by extrusion"; Biophysical journal 64(2); pp. 443-453.

Nagrath Sunitha, et al; "Isolation of rare circulating tumour cells in cancer patients by microchip technology"; Nature 450(7173); Dec. 20; 2007; pp. 1235-1239.
Nakano M, et al. (2005) "Single-molecule reverse transcription polymerase chain reaction using water-in-oil emulsion"; J Biosci Bioeng 99; pp. 293-295.
Nikolova An and Jones MN; (1996) "Effect of grafted PEG-2000 on the size and peimeability of vesicles"; Biochimica et Biophysica Acta (BBA)-Lipids and Lipid Metabolism.; 1304(2); pp. 120-128.
Novak, et al; (2011) "Single-cell multiplex gene detection and sequencing with microfluidically generated agarose emulsions"; Angew Chem Int Ed Engl. 50(2):390-395.
Nunes et al. (2013) "Dripping and jetting in microfluidic multiphase flows applied to particle and fiber synthesis"; J Phys D Appl Phys. 46(11); pii: 114002.
Oberholzer,Thomas, et al; (1995) "Polymerase chain reaction in liposomes"; Chemistry & Biology vol. 2 No. 10; pp. 677-682.
O'Donovan B, et al; (2012) "Electrode-free picoinjection of microfluidic drops"; Lab Chip 12; pp. 4029-4032.
Okochi M et al; (2010) "Droplet-based gene expression analysis using a device with magnetic force-based-droplet-handling system"; J Biosci Bioeng. 109(2); pp. 193-197.
Perry DJ; (1999) "Solid-Phase Sequencing of Biotinylated PCR Products with Streptavidin-Coated Magnetic Beads"; Hemostasis and Thrombosis Protocols: Springer;, p. 49-54.
Piatek AS, et al; (1998) "Molecular beacon sequence analysis for detecting drug resistance in Mycobacterium tuberculosis";. Nat Biotechnol. 16(4); pp. 359-363.
Priest Craig, et al; (2006) "Controlled electrocoalescence in microfluidics: Targeting a single lamella"; Appl Phys Lett, 89; pp. 134101-1-134101-3.
Sciambi et al. (2013) "Adding reagent to droplets with controlled rupture of encapsulated double emulsions"; Biomicrofluidics 7(4); pp. 1-6.
Scott S. H, et al; (2011) "Microfluidic immuno magnetic multi-target sorting—a model for controlling deflection of paramagnetic beads"; Lab Chip 11; pp. 2577-2582.
Seemann R, et al; (2012) "Droplet based microfluidics"; Rep Prog Phys 75; pp. 016601.
Shui et al; (2011) "Microfluidic DNA fragmentation for on-chip genomic analysis" Nanotechnology 22(49): 494013. 7 pages.
Siegel Adam C,et al; (2007) "Microsolidics: Fabrication of Three-Dimensional Metallic Micro structures inPoly( dimethylsiloxane )"; Adv Mater 19; pp. 727-733.
Song H, et al; (2006) "Reactions in droplets in microfluidic channels" Angew Chem Int Ed Engl 45; pp. 7336-7356.
Squires Tom M.; "Microfluidics: Fluid physics at the nanoliter scale"; Reviews of modern physics.;77(3); (Jul. 2005) pp. 977-1026.
Stone HA, et al.; (2004) "Engineering flows in small devices: microfluidics toward a lab-on-a-chip"; Annu Rev Fluid Mech.;36; pp. 381-411.
Stott Shannon L.; et al.; "Isolation of circulating tumor cells using a microvortex-generating herringbone-chip"; PNAS vol. 107, No. 43; Oct. 26, 2010; pp. 18392-18397.
Syed et al. (2009) "Next-generation sequencing library preparation: simultaneous fragmentation and tagging using in vitro transposition"; Nature Methods vol. 6; pp. 1-2.
Tadmor AD, et al; (2011) "Probing individual environmental bacteria for viruses by using microfluidic digital PCR"; Science. ;333(6038); pp. 58-62.
Takagi et al. (2005) "Continuous particle separation in a microchannel having asymmetrically arranged multiple branches" Lab Chip, 5(7); pp. 778-784.
Teh SY,et al; (2008) "Droplet microfluidics"; Lab Chip 8; pp. 198-220.
Tewhey Ryan, et al; "Microdroplet-based PCR enrichment for large-scale targeted sequencing"; Nature Biotechnology, vol. 27 No. 11; (Nov. 2009); pp. 1025-1035.
Thomann Y, et al; (2005) "PMMA Gradient Materials and in situ Nanocoating via Self-Assembly of Semifluorinated Hyperbranched Amphiphiles"; Macromolecular Chemistry and Physics.;206(1); pp. 135-141.

(56) References Cited

OTHER PUBLICATIONS

Thorsen T, et al; (2001) "Dynamic pattern formation in a vesicle-generating microfluidic device"; *Phys Rev Lett 86*; pp. 4163-4166.
Tsai Scott S. H., et al; (2011) "Microfluidic immuno magnetic multi-target sorting—a model for controlling deflection of paramagnetic beads"; *Lab Chip 11*; pp. 2577-2582.
Ullal, et al; (2014) "Cancer cell profiling by barcoding allows multiplexed protein analysis in fine needle aspirates"; *Sci Transl Med.* 6(219):219ra9; pp. 1-22.
Utada, et al; (2007) "Dripping to jetting transitions in coflowing liquid streams"; *Phys Rev Lett.* Aug. 31, 2007;99(9; pp. :094502-1-094502-4.
Vanapalli SA,et al; "Hydrodynamic resistance of single confined moving drops in rectangular microchannels"; *Lab Chip 9* (2009); pp. 982-990.
Vickers, et al., (2006) "Generation of Hydrophilic Poly(dimethylsiloxane) for High-Performance Microchip Electrophoresis"; *Anal. Chem,* 78(21); pp. 7446-7452.
Wang C, et al; (2012) "Amphiphilic building blocks for self-assembly: from amphiphiles to supra-amphiphiles"; *Accounts of Chemical Research* 45(4); pp. 608-618.
Whitcombe D, et al; (1999) "Detection of PCR products using self-probing amplicons and fluorescence"; *Nature biotechnology* 17(8); pp. 804-807.
Whitesides GM. (2006) The origins and the future of microfluidics. *Nature* 442(7101); pp. 368-373.
Xia YN, et al; (1998) "Soft lithography"; *Angew Chem Int Edit 37*; pp. 551-575.
Zeng Yong, et al; "High-Performance Single Cell Genetic Analysis Using Microfluidic Emulsion Generator Arrays"; *Anal Chem.* 82(8); Apr. 15; 2010; pp. 3183-3190.
Zheng B, et al; (2004) "Formation of droplets of in microfluidic channels alternating composition and applications to indexing of concentrations in droplet-based assays"; *Anal Chem 76*; pp. 4977-4982.
Zhong Qun, et al; (2011) "Multiplex digital PCR: breaking the one target per color barrier of quantitative PCR"; *Lab Chip 11*; pp. 2167-2174.
Zhu et al., (2001) "Reverse transcriptase template switching: a SMART approach for full-length cDNA library construction"; *BioTechniques 30*: pp. 892-897.
Zhu Z, et al (2012) "Highly sensitive and quantitative detection of rare pathogens through agarose droplet microfluidic emulsion PCR at the single-cell level"; *Lab on a Chip* 12(20); pp. 3907-3913.
Zien TF; (1969) "Hydrodynamics of bolus flow-an analytical approach to blood flow in capillaries"; *Math Biophys,* 31; pp. 681-694.
Grover, et al (2009) "Multiple displacement amplification as a pre-polymerase chain reaction (pre-PCR) to detect ultra low population of Ralstonia solanacearum (Smith 1896) Yabuchi et al. (1996)" Lett Appl Microbiol. 49(5); pp. 539-543.
Kawasaki (1990) "Sample Preparation From Blood, Cells, and Other Fluids"; Chapter 18; pp. 146-152 in PCR protocols: A guide to methods and Applications, edited by Michael A. Innis, David H. Gelfand, John J. Sninsky, Thomas J. White.
Sidore, et al (2016) "Enhanced sequencing coverage with digital droplet multiple displacement amplification"; Nucleic Acids Res. 44(7):e66.; pp. 1-9.
Tamminen, et al (2015) "Single gene-based distinction of individual microbial genomes from a mixed population of microbial cells"; Front Microbiol. 6:195; pp. 1-10.
Yu, et al (2014) "Mung bean nuclease treatment increases capture specificity of microdroplet-PCR based targeted DNA enrichment"; PLoS One 9(7):e103491; pp. 1-7.
U.S. Appl. No. 15/753,132, filed Feb. 15, 2018, Abate, Adam R., et al.
Wheeler et al (2005) "Digital microfluidics with in-line sample purification for proteomics analyses with MALDI-MS" Anal Chem. 77(2); 534-40.
U.S. Appl. No. 16/324,532, filed Feb. 8, 2019, Abate, Adam et al.
U.S. Appl. No. 16/164,707, filed Oct. 18, 2018, Abate, Adam et al.
U.S. Appl. No. 16/382,080, filed Apr. 11, 2019, Abate, Adam et al.
Fu, Yusi et al (2015) "Uniform and accurate single-cell sequencing based on emulsion whole-genome amplification"; Proc Natl Acad Sci U S A. 112(38); pp. 11923-11928.
Nishikawa, Yohei et al (2015) "Monodisperse Picoliter Droplets for Low-Bias and Contamination-Free Reactions in Single-Cell Whole Genome Amplification" PLoS One 10(9); pp. e0138733.
Sciambia Adam and Abate Adam R., (2015) "Accurate microfluidic sorting of droplets at 30 kHz"; Lab Chip 15(1); pp. 47-51.
EmPCR-amplificationmanual for GS-FLX series (May 2011); 454 Life Science Corp; 12 pages.
Extended European Search Report received for European Patent Application Serial No. 15812857.9 dated Oct. 17, 2017, 7 pages.
Extended European Search Report received for European Patent Application Serial No. 15853268.9 dated Sep. 3, 2018, 12 pages.
Extended European Search Report received for European Patent Application Serial No. 16747224.0 dated May 24, 2018, 9 pages.
Extended European Search Report received for European Patent Application Serial No. 16747229.9 dated Sep. 10, 2019, 8 pages.
Extended European Search Report received for European Patent Application Serial No. 16837703.4 dated Nov. 29, 2018, 9 pages.
First search received for Chinese Patent Application Serial No. 2013800532581 dated Feb. 22, 2016, 2 pages.
First search received for Chinese Patent Application Serial No. 2015800704110 dated Dec. 13, 2018, 2 pages.
International Preliminary Report on Patentability received for PCT Application Serial No. PCT/US2013/054517 dated Feb. 26, 2015, 14 pages.
International Preliminary Report on Patentability received for PCT Application Serial No. PCT/US2015/037822 dated Jan. 5, 2017, 7 pages.
International Preliminary Report on Patentability received for PCT Application Serial No. PCT/US2015/056743 dated May 4, 2017, 9 pages.
International Preliminary Report on Patentability received for PCT Application Serial No. PCT/US2016/016438 dated Aug. 17, 2017, 10 pages.
International Preliminary Report on Patentability received for PCT Application Serial No. PCT/US2016/016444 dated Aug. 17, 2017, 40 pages.
International Preliminary Report on Patentability received for PCT Application Serial No. PCT/US2016/047199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2017/068006 dated Jul. 4, 2019, 7 pages.
International Search Report and Written Opinion received for PCT Application Serial No. PCT/US2015/037822 dated Feb. 2, 2016, 9 pages.
International Search Report and Written Opinion received for PCT Application Serial No. PCT/US2015/056743 dated Mar. 3, 2016, 12 pages.
International Search Report and Written Opinion received for PCT Application Serial No. PCT/US2016/016438 dated Jun. 10, 2016, 14 pages.
International Search Report and Written Opinion received for PCT Application Serial No. PCT/US2016/016444 dated Jul. 27, 2016, 43 pages.
International Search Report and Written Opinion received for PCT Application Serial No. PCT/US2016/047199 dated Dec. 12, 2016, 10 pages.
International Search Report and Written Opinion received for PCT Application Serial No. PCT/US2017/046159 dated Nov. 21, 2017, 12 pages.
International Search Report and Written Opinion received for PCT Application Serial No. PCT/US2017/068006 dated Mar. 26, 2018, 9 pages.
Rolando, Monica , et al., "Legionella pneumophila Effector RomA Uniquely Modifies Host Chromatin to Repress Gene Expression and

(56) References Cited

OTHER PUBLICATIONS

Promote Intracellular Bacterial Replication", Cell Host & Microbe, vol. 13(4), Apr. 17, 2013, 395-405.
Gong, Jian, et al.. Characterization and Design of Digitizing Processess for uniform and controllable droplet volume in ewod Digital Microfluidics, Solid-State Sensor, Actuator and Microsystem Workshop, Jun. 5, 2006, (Year: 2006).
Kumaresan P, Yang CJ, Cronier SA, Blazej RG, Mathies RA, High-throughput single copy DNA amplification and cell analysis in engineered nanoliter droplets. Analytical chemistry, May 15, 2008; 80(10):3522-9, (Year:2008).
Pekin D, Skhiri Y, Baretjc, Le Corre D, Mazutis L, Ben Salem C, Millot F, El Harrak A, Hutchison JB, Larson JW, Link DR, Laurent-Pulg P, Griffiths AD, Taly V (2011) Lab Chip 11:2156-2166 (Year: 2011).
Demaree et al, (2018) "An Ultranigh-throughput Microfluidic Platform for Single-cell Genome Sequencing", Journal of Visualized Experiments, No. 135.
Freeman et al, (2017) "Single-cell genome sequencing at ultra-high-throughput with microfluidic droplet barcoding (includes Online Methods)", Nature Biotechnology, vol. 35, No. 7, pp. 640-646.
Rakszewska et al, (2014) "One drop at a time: toward droplet microfluidics as a versatile tool for single-cell analysis", NPG Asia Materials, vol. 6, No. 10, pp. 1-11.
Shembekar et al, (2016) "Droplet-based microfluidics in drug discovery, transcriptomics and high-throughput molecular genetics", Lab on a Chip, vol. 16, No. 8, pp. 1314-1331.
Ichii et al., (2010) Amplification of RNA in Growing and Dividing Micro-Droplets, 2010, 14th International Conference on Miniaturized Systems for Chemistry and Life Sciences, pp. 2089-2091.
Extended European Search Report received for European Patent Application Serial No. 17840230.1 dated Apr. 30, 2020, 12 pages.
Extended European Search Report received for European Patent Application Serial No. 17885180.4 dated Jul. 20, 2020, 11 pages.
International Search Report and Written Opinion received for PCT Application Serial No. PCT/US2013/054517 dated Feb. 21, 2014, 19 pages.
Integrated DNA Technologies "Molecular Facts and Figures", 2011, pp. 1-9.
Abate, Adam R., et al., (2013) "DNA sequence analysis with droplet-based microfluids", Lab Chip, vol. 13(24), pp. 4864-4869.
Abate, Adam R., et al., (2009) "Beating Poisson encapsulation statistics using close-packed ordering", Lab Chip, vol. 9, pp. 2628-2631.
Abbaspourrad, et al., (2015) "Label-free single-cell protein quantification using a dropbased mix-and-read system", Sci. Rep., 5, p. 12756.
Agargel, (2019) "Agar-Agar", retrieved on Jun. 6, 2019 from https://web.archive.org/web/20170527222040/http://www.agargel.com.br/agar-tecen. html, 3 pages.
Autour, et al., (2017) "Ultrahigh-throughput improvement and discovery of enzymes using droplet-based microfluidic screening" Micromachines, vol. 8(128), pp. 1-21.
Baker, (2012) "Digital PCR hits its stride", Nat. Methods, vol. 9(6), pp. 541-544.
Bjork, et al., (2012) "Metabolite profiling of microfluidic cell culture conditions for droplet based screening", Biomicrojluidics, vol. 9, p. 044128.
Blainey, et al., (2014) "Dissecting genomic diversity, one cell at a time" Nat. Methods, vol. 11(1), pp. 19-21.
Chang, et al., (2012) "Single Molecule Enzyme-Linked Immunosorbent Assays: Theoretical Considerations", J Immunol Methods, vol. 378(1-2), pp. 102-115.
Chen et al., (2017) "Centrifugal micro-channel array droplet generation for highly parallel digital PCR", Lab Chip, 17, pp. 235-240.
Chen et al., (2016) "Spinning micropipette liquid emulsion generator for single cell whole genome amplification", Lab Chip, 16, pp. 4512-4516.
Civelek et al., (2014) "Systems genetics approaches to understand complex traits", Nat. Rev. Genet., 15(1), pp. 34-48.
Collins et al., (2015) "The Poisson distribution and beyond: methods for microfluidic droplet production and single cell encapsulation", Lab on a Chip, 15, pp. 3439-3459.
Costa et al., (2008) "Complex networks: The key to systems biology", Genet. Mol. Biol., 31(3), pp. 591-601.
Elnifro, et al., (2000) "Multiplex PCR: Optimization and Application in Diagnostic Virology", Clin. Microbial. Rev., 13, pp. 559-570.
Fritzsch et al., (2012), "Single-Cell Analysis in Biotechnology, Systems Biology, and Biocatalysis", Annu. Rev. Chem. Biomol. Eng. 3, pp. 129-155.
Gielen, et al., (2016) "Ultrahigh-throughput-directed enzyme evolution by absorbance activated droplet sorting (AADS)", PNAS, pp. E7383-E7389.
Griffiths, et al., (2006) "Miniaturising the laboratory in emulsion droplets", Trends Biotechnol., 24, pp. 395-402.
Guo, et al., (2012) "Droplet microfluidics for highthroughput biological assays.", Lab Chip, pp. 2146-2155.
Halldorsson et al., (2015) "Advantages and challenges of microfluidic cell culture in polydimethylsiloxane devices", Biosens. Bioelectron., 63, pp. 218-231.
Huang, et al., (2017) "Collective generation of milliemulsions by step-emulsification", RSC Advances, 7, pp. 14932-14938.
Joanicot, et al., (2005) "Droplet control for microfluidics", Science, 309(5736), pp. 887-888.
Katepalli, et al., (2014) "Bose, A. Response of Surfactant Stabilized Oil-in-Water Emulsions to the Addition of Particles in an Aqueous Suspension", Langmuir, 30(43), pp. 12736-12742.
Kim, et al., (2017) "Measurement of copy number variation in single cancer cells using rapid-emulsification digital droplet MPA", Microsystems & Nanoengineering 3:17018, pp. 1-7.
Kim, et al., (2014) "Droplet Microfluidics for Producing Functional Microparticles", Langmuir, 30, pp. 1473-1488.
Kimmerling et al., (2016) "A microfluidic platform enabling single-cell RNA-seq of multigenerational lineages", Nature Commun., 7, p. 10220.
Kolodziejczyk, et al., (2015) "The Technology and Biology of Single-Cell RNA Sequencing", Mol. Cell, 58(4), pp. 610-620.
Lage, J. M.., et al., (2003) "Whole Genome Analysis of Genetic Alterations in Small DNA Samples Using Hyperbranched Strand Displacement Amplification and Array-CGH", Genome Res., 13, pp. 294-307.
Lance, et al., (2016) "Peering below the diffraction limit: robust and specific sorting of viruses with flow cytometry", Viral J, 13, p. 201.
Macosko, et al., (2015) "Highly parallel genome-wide expression profiling of individual cells using nanoliter droplets" Cell, 161, pp. 1202-1214.
Margulies, et al., (2005) "Genome sequencing in microfabricated high-density picolitre reactors", Nature, 437, pp. 376-380.
Mashaghi, et al., (2016) "Droplet microfluidics: A tool for biology, chemistry and nanotechnology", TrAC—Trends Anal. Chem., 82, pp. 118-125.
Morimoto, et al., (2013) "Three-dimensional cell culture based on microfluidic techniques to mimic living tissues", Biomaterials Science, vol. 1, No. 3, pp. 257-264.
Morimoto, et al., (2009) "Reconstruction of 3D Hierarchic Micro-Tissues using Monodisperse Collagen Microbeads", Micro Electro Mechanical Systems, IEEE 22nd International Conference, pp. 56-59.
Pinheiro, et al., (2012) Evaluation of a droplet digital polymerase chain reaction format for DNA copy number quantification, Anal. Chem., 84, pp. 1003-1011.
Romero, et al., (2015) "Dissecting enzyme function with microfluidic-based deep mutational scanning", PNAS, 112(23), pp. 7159-7164.
Sandberg, et al., (2009) "Flow cytometry for enrichment and titration in massively parallel DNA sequencing", Nucleic Acids Res, 37(8), p. e63.
Song, et al., (2006) "On-Chip Titration of an Anticoagulant Argatroban and Determination of the Clotting Time within Whole Blood or Plasma Using a Plug-Based Microfluidic System", Anal. Chem., 78(14), pp. 4839-4849.
Soon, et al., (2013) "High-throughput sequencing for biology and medicine", Mol. Syst. Biol., 9(64), pp. 1-14.

(56) References Cited

OTHER PUBLICATIONS

Spencer, Sarah J., et al., (2016) "Massively parallel sequencing of single cells by epicPCR links functional genes with phylogenetic markers", The ISME Journal 10, 427-436.
Spies, et al., (2017) "Genome-wide reconstruction of complex structural variants using read clouds", Nat. Methods, 14(9), pp. 915-920.
Sukovich, et al., (2017) "Sequence specific sorting of DNA molecules with FACS using 3dPCR", Sci. Rep., 7, p. 39385.
Taly, et al., (2013) "Multiplex picodroplet digital PCR to detect KRAS mutations in circulating DNA from the plasma of colorectal cancer patients", Clin. Chem., 59, pp. 1722-1731.
Tran, et al., (2013) "From tubes to drops: dropletbased biology microfluidics for ultrahigh-throughput", J Phys. D. Appl. Phys., 46, p. 114004.
Weaver, et al., (2014) "Advances in high-throughput single-cell microtechnologies", Curr. Opin. Biotechnol., 0, pp. 114-123.
Yan, et al., (2017) "Intestinal Enteroendocrine Lineage Cells Possess Homeostatic and Injury-Inducible Stem Cell Activity", Cell Stem Cell, 21, pp. 78-90.
Zhu, et al., (2017) "Hydrogel Droplet Microfluidics for High-Throughput Single Molecule/Cell Analysis", Acc. Chem. Res., 50(1), pp. 22-31.
Zilionis, et al., (2017) "Single-cell barcoding and sequencing using droplet microfluidics", Nat. Protoc., 12(1), pp. 44-73.
Caruccio, et al., "Preparation of next-generation sequencing libraries using Nextera™ technology: simultaneous DNA fragmentation and adaptor tagging by in vitro transposition", Methods in Molecular Biology, 2011, vol. 733, pp. 241-255.
Hindson, et al., "High-throughput droplet digital PCR system for Absolute Quatitation of DNA copy number", Analytical chemistry, 83(22), 2011, 8604-8610.
Lan, Freeman, et al., "Single-cell genome sequencing at ultra-high-throughput with microfluidic droplet barcoding", Mature Biotechnology 35(7), 2017, 640-646.
Le Goff, et al., "Hydrogel microparticles for biosensing", Eur Polym J., 2015, vol. 72,, 49 pages.
Islam, et al., (2017) A Review of Macroscale and Microscale Cell Lysis Methods, Micromachines 8(83)1-27.
Yang, et al., (2010) Agarose Droplet Microfluidics For Highly Parallel and Efficient Emulsion PCR, 14th International Conference on Miniaturized Systems for Chemistry and Life Sciences, The Netherlands, 710-712.
Moral et al., "Heat-labile proteases in molecular biology applications", FEMS Microbiology Letters, 197, pp. 59-63, 2001.
Kemna, E. et al. (2012), High-yield cell ordering and deterministic cell-in-droplet encapsulation using Dean flow in a curved microchannel, Lab Chip, 12, pp. 2881-2887.

\* cited by examiner

Single Cell Barcoding

- Two sets of drops are reinjected into the device.

① Cell Prep: PK treatment

② Barcode Prep: Digital PCR

③ Single Cell Barcoding Device scBarcode Device: Inlets/Outlets

Method for combining droplets with another fluid. In (A), reinjected drops travel down one of the oil side-channels of a symmetric flow-focus drop-maker and electrocoalesce with the aqueous phase before drop generation. In (B), drops similarly join with a jetting drop maker. Bubbling can be used to break stable jets.

Method for processing small volumes of fluid using jet-based microfluidics. Droplets are reinjected and electrocoalesced with a aqueous-in-oil jet. The drop fluid remains as a bolus and can be split, diluted, and created as a drop later.

Fan blade

Step 1 Encapsulation and Amplification

Step 2 Tagmentation

Step 3 Barcoding PCR

Antibodies are comprised of two separate proteins

The sequence of each Ab protein differs on a cell-to-cell basis

SEQUENCING OF NUCLEIC ACIDS VIA BARCODING IN DISCRETE ENTITIES

CROSS-REFERENCE

This application is a Divisional of U.S. application Ser. No. 15/015,015, filed Feb. 3, 2016, which application claims priority benefit of U.S. Provisional Application No. 62/112,075, filed Feb. 4, 2015, which applications are incorporated herein by reference in their entireties and for all purposes.

GOVERNMENT SUPPORT

This invention was made with government support under grant nos. HG007233, R01 EB019453, and AR068129, awarded by the National Institutes of Health; grant nos. HR0011-12-C-0065 and HR0011-12-C-0066, awarded by the Department of Defense; grant no. N66001-12-C-4211, awarded by the Department of the Navy; and grant no. 1253293, awarded by the National Science Foundation. The government has certain rights in the invention.

INTRODUCTION

Nucleic acid barcoding techniques, wherein nucleic acid sequences representing barcodes are linked to molecular targets to be analyzed, are useful in a variety of applications including, e.g., sequencing applications where many individual samples are to be sequenced in parallel. Nucleic acid barcodes find particular use in the high-throughput genomic, transcriptomic, and/or proteomic analysis and/or profiling of cells.

SUMMARY

The present disclosure provides microfluidic methods for barcoding nucleic acid target molecules to be analyzed, e.g., via nucleic acid sequencing techniques. Also provided are microfluidic, droplet-based methods of preparing nucleic acid barcodes for use in various barcoding applications. The methods described herein facilitate high-throughput sequencing of nucleic acid target molecules as well as single cell and single virus genomic, transcriptomic, and/or proteomic analysis/profiling. Systems and devices for practicing the subject methods are also provided.

BRIEF DESCRIPTION OF THE DRAWINGS

The invention may be best understood from the following detailed description when read in conjunction with the accompanying drawings. Included in the drawings are the following figures:

FIG. 3 (right) depicts schematically the incorporation of nucleic acid barcodes into cDNA products.

DETAILED DESCRIPTION

Figure 1:
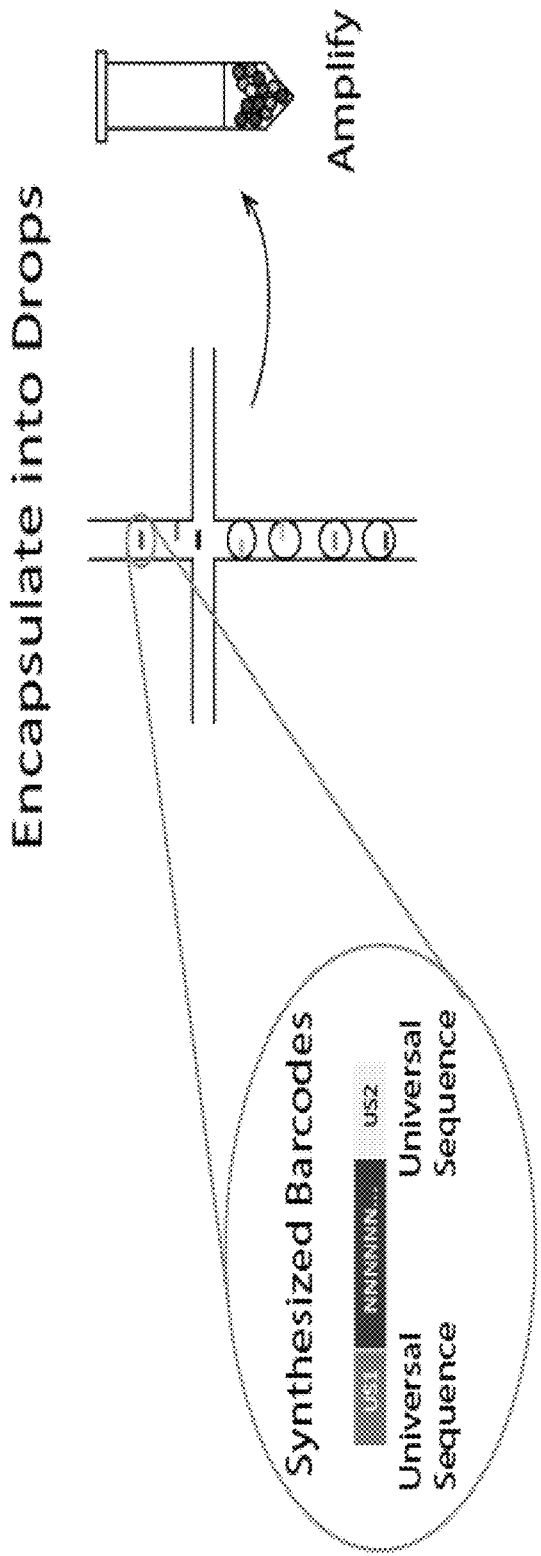
FIG. 1 provides a schematic depicting a method of generating a nucleic acid barcode library.

The present disclosure provides microfluidic methods for barcoding nucleic acid target molecules to be analyzed, e.g., via nucleic acid sequencing techniques. Also provided are microfluidic, droplet-based methods of preparing nucleic acid barcodes for use in various barcoding applications. The methods described herein facilitate high-throughput sequencing of nucleic acid target molecules as well as single cell and single virus genomic, transcriptomic, and/or proteomic analysis/profiling. Systems and devices for practicing the subject methods are also provided.

Before the present invention is described in greater detail, it is to be understood that this invention is not limited to the particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a droplet" includes a plurality of such droplets.

It is further noted that the claims may be drafted to exclude any element, e.g., any optional element. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Further, the dates of publication provided may be different from the actual publication dates which may need to be independently confirmed. To the extent the disclosure or the definition or usage of any term herein conflicts with the disclosure or the definition or usage of any term in an application or publication incorporated by reference herein, the instant application shall control.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The terms "nucleic acid barcode sequence", "nucleic acid barcode", "barcode", and the like as used herein refer to a nucleic acid having a sequence which can be used to identify and/or distinguish one or more first molecules to which the nucleic acid barcode is conjugated from one or more second molecules. Nucleic acid barcode sequences are typically short, e.g., about 5 to 20 bases in length, and may be conjugated to one or more target molecules of interest or amplification products thereof. Nucleic acid barcode sequences may be single or double stranded.

The term "unique molecular identifier (UMI)" or "UMI" as used herein refers to nucleic acid having a sequence which can be used to identify and/or distinguish one or more first molecules to which the UMI is conjugated from one or more second molecules. UMIs are typically short, e.g., about 5 to 20 bases in length, and may be conjugated to one or more target molecules of interest or amplification products thereof. UMIs may be single or double stranded. In some embodiments, both a nucleic acid barcode sequence and a UMI are incorporated into a nucleic acid target molecule or an amplification product thereof. Generally a UMI is used to distinguish between molecules of a similar type within a population or group, whereas a nucleic acid barcode sequence is used to distinguish between populations or groups of molecules. In some embodiments, where both a UMI and a nucleic acid barcode sequence are utilized, the UMI is shorter in sequence length than the nucleic acid barcode sequence. In some embodiments, where both a UMI and a nucleic acid barcode sequence are utilized, the UMI is incorporated into the target nucleic acid or an amplification product thereof prior to the incorporation of the nucleic acid barcode sequence. In some embodiments, where both a UMI and a nucleic acid barcode sequence are utilized, the nucleic acid barcode sequence is incorporated into the UMI or an amplification product thereof subsequent to the incorporation of the UMI into a target nucleic acid or an amplification product thereof.

The term "conjugated" as used herein refers to a covalent or ionic interaction between two entities, e.g., molecules, compounds or combinations thereof.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and native leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, a nucleic acid barcode sequence, and the like. The antibodies may be further conjugated to other moieties, such as members of specific binding pairs, e.g., biotin (member of biotin-avidin specific binding pair), and the like. Also encompassed by the terms are Fab', Fv, F(ab')₂, and other antibody fragments that retain specific binding to antigen.

Antibodies may exist in a variety of other forms including, for example, Fv, Fab, and (Fab)₂, as well as bi-functional (i.e. bi-specific) hybrid antibodies (e.g., Lanzavecchia et al., *Eur. J. Immunol.* 17, 105 (1987)) and in single chains (e.g., Huston et al., *Proc. Natl. Acad. Sci. U.S.A.,* 85, 5879-5883 (1988) and Bird et al., *Science,* 242, 423-426 (1988), which are incorporated herein by reference). (See, generally, Hood et al., *Immunology*, Benjamin, N.Y., 2nd ed. (1984), and Hunkapiller and Hood, *Nature,* 323, 15-16 (1986).

"Binding" as used herein generally refers to a covalent or non-covalent interaction between two molecules (referred to herein as "binding partners", e.g., a substrate and an enzyme or an antibody and an epitope), which binding is usually specific.

As used herein, "specifically binds" or "binds specifically" refers to interaction between binding partners such that the binding partners bind to one another, but do not bind other molecules that may be present in the environment (e.g., in a biological sample, in tissue) at a significant or substantial level under a given set of conditions (e.g., physiological conditions).

The terms "nucleic acid", "nucleic acid molecule", "oligonucleotide" and "polynucleotide" are used interchangeably and refer to a polymeric form of nucleotides of any length, either deoxyribonucleotides or ribonucleotides, or analogs thereof. The terms encompass, e.g., DNA, RNA and modified forms thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "nucleic acid sequence" or "oligonucleotide sequence" refers to a contiguous string of nucleotide bases and in particular contexts also refers to the particular placement of nucleotide bases in relation to each other as they appear in a oligonucleotide. Similarly, the term "polypeptide sequence" or "amino acid sequence" refers to a contiguous string of amino acids and in particular contexts also refers to the particular placement of amino acids in relation to each other as they appear in a polypeptide.

The terms "complementary" or "complementarity" refer to polynucleotides (i.e., a sequence of nucleotides) related by base-pairing rules. For example, the sequence "5'-AGT-3'," is complementary to the sequence "5'-ACT-3'". Complementarity may be "partial," in which only some of the nucleic acids' bases are matched according to the base pairing rules, or there may be "complete" or "total" complementarity between the nucleic acids. The degree of complementarity between nucleic acid strands can have significant effects on the efficiency and strength of hybridization between nucleic acid strands under defined conditions. This is of particular importance for methods that depend upon binding between nucleic acids.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the Tm of the formed hybrid. "Hybridization" methods involve the annealing of one nucleic acid to another, complementary nucleic acid, i.e., a nucleic acid having a complementary nucleotide sequence.

Hybridization is carried out in conditions permitting specific hybridization. The length of the complementary sequences and GC content affects the thermal melting point Tm of the hybridization conditions necessary for obtaining specific hybridization of the target site to the target nucleic acid. Hybridization may be carried out under stringent conditions. The phrase "stringent hybridization conditions" refers to conditions under which a probe will hybridize to its target subsequence, typically in a complex mixture of nucleic acid, but to no other sequences at a detectable or significant level. Stringent conditions are sequence-dependent and will be different in different circumstances. Stringent conditions are those in which the salt concentration is less than about 1.0 M sodium ion, such as less than about 0.01 M, including from about 0.001 M to about 1.0 M sodium ion concentration (or other salts) at a pH between about 6 to about 8 and the temperature is in the range of about 20° C. to about 65° C. Stringent conditions may also be achieved with the addition of destabilizing agents, such as but not limited to formamide.

The terms "thermal melting point", "melting temperature" or "Tm" refer herein to the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). In some cases, the term "Td" is used to define the temperature at which at least half of the probe dissociates from a perfectly matched target nucleic acid.

The formation of a duplex molecule with all perfectly formed hydrogen-bonds between corresponding nucleotides is referred as "matched" or "perfectly matched", and duplexes with single or several pairs of nucleotides that do not correspond are referred to as "mismatched." Any combination of single-stranded RNA or DNA molecules can form duplex molecules (DNA:DNA, DNA:RNA, RNA:DNA, or RNA:RNA) under appropriate experimental conditions.

The phrase "selectively (or specifically) hybridizing" refers to the binding, duplexing, or hybridizing of a molecule only to a particular nucleotide sequence under stringent hybridization conditions when that sequence is present in a complex mixture (e.g. total cellular or library DNA or RNA).

Those of ordinary skill in the art will readily recognize that alternative hybridization and wash conditions can be utilized to provide conditions of similar stringency and will recognize that the combination of parameters is much more important than the measure of any single parameter.

A "substitution" results from the replacement of one or more amino acids or nucleotides by different amino acids or nucleotides, respectively as compared to an amino acid sequence or nucleotide sequence of a polypeptide. If a substitution is conservative, the amino acid that is substituted into a polypeptide has similar structural or chemical properties (e.g., charge, polarity, hydrophobicity, and the like) to the amino acid that it is substituting. Conservative substitutions of naturally occurring amino acids usually result in a substitution of a first amino acid with second amino acid from the same group as the first amino acid, where exemplary amino acid groups are as follows: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral non-polar amino acids such as alanine, leucine, isoleucine, valine, proline, phenylalanine, tryptophan, and methionine. In some embodiments, polypeptide variants may have "non-conservative" changes, where the substituted amino acid differs in structural and/or chemical properties.

A "deletion" is defined as a change in either amino acid or nucleotide sequence in which one or more amino acid or nucleotide residues, respectively, are absent as compared to an amino acid sequence or nucleotide sequence of a naturally occurring polypeptide. In the context of a polypeptide or polynucleotide sequence, a deletion can involve deletion of 2, 5, 10, up to 20, up to 30 or up to 50 or more amino acids, taking into account the length of the polypeptide or polynucleotide sequence being modified.

An "insertion" or "addition" is that change in an amino acid or nucleotide sequence which has resulted in the addition of one or more amino acid or nucleotide residues, respectively, as compared to an amino acid sequence or nucleotide sequence of a naturally occurring polypeptide. "Insertion" generally refers to addition to one or more amino acid residues within an amino acid sequence of a polypeptide, while "addition" can be an insertion or refer to amino acid residues added at the N- or C-termini. In the context of a polypeptide or polynucleotide sequence, an insertion or addition may be of up to 10, up to 20, up to 30 or up to 50 or more amino acids.

"Non-native", "non-endogenous", and "heterologous", in the context of a polypeptide, are used interchangeably herein to refer to a polypeptide having an amino acid sequence or, in the context of an expression system or a viral particle, present in an environment different to that found in nature.

"Exogenous" in the context of a nucleic acid or polypeptide is used to refer to a nucleic acid or polypeptide that has been introduced into a host cell. "Exogenous" nucleic acids and polypeptides can be native or non-native to the host cell, where an exogenous, native nucleic acid or polypeptide provides for elevated levels of the encoded gene product or polypeptide in the recombinant host cell relative to that found in the host cell prior to introduction of the exogenous molecule.

As used herein, the terms "determining," "measuring," "assessing," and "assaying" are used interchangeably and include both quantitative and qualitative determinations.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, 75% free, or 90% free from other components with which it is naturally associated.

A "coding sequence" or a sequence that "encodes" a selected polypeptide, is a nucleic acid molecule which is transcribed (in the case of DNA) and translated (in the case of mRNA) into a polypeptide, for example, in-vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence.

"Encoded by" refers to a nucleic acid sequence which codes for a gene product, such as a polypeptide. Where the gene product is a polypeptide, the polypeptide sequence or a portion thereof contains an amino acid sequence of at least 3 to 5 amino acids, 8 to 10 amino acids, or at least 15 to 20 amino acids from a polypeptide encoded by the nucleic acid sequence.

"Operably linked" refers to an arrangement of elements wherein the components so described are configured so as to perform their usual function. In the case of a promoter, a promoter that is operably linked to a coding sequence will have an effect on the expression of a coding sequence. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

By "nucleic acid construct" it is meant a nucleic acid sequence that has been constructed to include one or more functional units not found together in nature. Examples include circular, linear, double-stranded, extrachromosomal DNA molecules (plasmids), cosmids (plasmids containing COS sequences from lambda phage), viral genomes including non-native nucleic acid sequences, and the like.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells, which can be accomplished by genomic integration of all or a portion of the vector, or transient or inheritable maintenance of the vector as an extrachromosomal element. Thus, the term includes cloning, and expression vehicles, as well as integrating vectors.

An "expression cassette" includes any nucleic acid construct capable of directing the expression of a gene/coding sequence of interest, which is operably linked to a promoter of the expression cassette. Such cassettes can be constructed into a "vector," "vector construct," "expression vector," or "gene transfer vector," in order to transfer the expression cassette into target cells. Thus, the term includes cloning and expression vehicles, as well as viral vectors.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local algorithm of Smith and Waterman, *Advances in Applied Mathematics*, 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986).

An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). Another method of establishing percent identity in the context of the present invention is to use the MPSRCH package of programs copyrighted by the University of Edinburgh, developed by John F. Collins and Shane S. Sturrok, and distributed by Intelli-Genetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

Two nucleic acids, or two polypeptide sequences are "substantially identical" to each other when the sequences exhibit at least about 80%-85%, at least about 85%-90%, at least about 90%-95%, or at least about 95%-98% sequence identity over a defined length of the molecules, as determined using the methods above. As used herein, substantially identical also refers to sequences showing complete identity to the specified nucleic acid or polypeptide sequence.

As used herein, the terms "homologous", "homology" and "regions of homology" refer to regions (sites) where two nucleic acids share at least partial complementarity. A region of homology may span only a portion of the sequences or the entirety of the sequences. For example, DNA sequences that are homologous can be identified in a Southern hybridization experiment under, for example, stringent conditions, as defined for that particular system. Defining appropriate hybridization conditions is within the skill of the art. See, e.g., Sambrook and Russel, *Molecular Cloning: A Laboratory Manual* Third Edition, (2001) Cold Spring Harbor Laboratory Press, Cold Spring Harbor, N.Y.

A first polynucleotide is "derived from" a second polynucleotide if it has the same or substantially the same nucleotide sequence as a region of the second polynucleotide, its cDNA, complements thereof, or if it displays sequence identity as described above. This term is not meant to require or imply the polynucleotide must be obtained from the origin cited (although such is encompassed), but rather can be made by any suitable method.

A first polypeptide (or peptide) is "derived from" a second polypeptide (or peptide) if it is (i) encoded by a first polynucleotide derived from a second polynucleotide, or (ii) displays sequence identity to the second polypeptides as described above. This term is not meant to require or imply the polypeptide must be obtained from the origin cited (although such is encompassed), but rather can be made by any suitable method.

The terms "discrete entities", "discrete entity" and the like are used herein to refer to objects, such as droplets, including multiple emulsions (such as double emulsions), wells, compartments and containers capable of encapsulating and/or containing one or more molecular targets as described herein and/or one or more barcodes or unique molecular identifiers as described herein. Discrete entities as used or generated in connection with the subject methods, devices, and/or systems may be sphere shaped or they may have any other suitable shape, e.g., an ovular or oblong shape. Discrete entities as described herein may include a liquid phase and/or a solid phase material. In some embodiments, discrete entities according to the present disclosure include a gel material. In some embodiments, the subject discrete entities have a dimension, e.g., a diameter, of or about 1.0 µm to 1000 µm, inclusive, such as 1.0 µm to 750 µm, 1.0 µm to 500 µm, 1.0 µm to 100 µm, 1.0 µm to 10 µm, or 1.0 µm to 5 µm, inclusive. In some embodiments, discrete entities as described herein have a dimension, e.g., diameter, of or about 1.0 µm to 5 µm, 5 µm to 10 µm, 10 µm to 100 µm, 100 µm to 500 µm, 500 µm to 750 µm, or 750 µm to 1000 µm, inclusive. Furthermore, in some embodiments, discrete entities as described herein have a volume ranging from about 1 fL to 1 nL, inclusive, such as from 1 fL to 100 pL, 1 fL to 10 pL, 1 fL to 1 pL, 1 fL to 100 fL, or 1 fL to 10 fL, inclusive. In some embodiments, discrete entities as described herein have a volume of 1 fL to 10 fL, 10 fL to 100 fL, 100 fL to 1 pL, 1 pL to 10 pL, 10 pL to 100 pL or 100 pL to 1 nL, inclusive. In addition, discrete entities as described herein may have a size and/or shape such that they may be produced in, on, or by a microfluidic device and/or flowed from or applied by a microfluidic device.

In some embodiments, the discrete entities as described herein are droplets. The terms "drop," "droplet," and "microdroplet" are used interchangeably herein, to refer to small, generally spherically structures, containing at least a first fluid phase, e.g., an aqueous phase (e.g., water), bounded by a second fluid phase (e.g., oil) which is immiscible with the first fluid phase. In some embodiments, droplets according to the present disclosure may contain a first fluid phase, e.g., oil, bounded by a second immiscible fluid phase, e.g. an aqueous phase fluid (e.g., water). In some embodiments, the second fluid phase will be an immiscible phase carrier fluid. Thus droplets according to the present disclosure may be provided as aqueous-in-oil emulsions or oil-in-aqueous emulsions. Droplets may be sized and/or shaped as described herein for discrete entities. For example, droplets according to the present disclosure generally range from 1 µm to 1000 µm, inclusive, in diameter. Droplets according to the present disclosure may be used to encapsulate cells, nucleic acids (e.g., DNA), enzymes, reagents, and a variety of other components. The term droplet may be used to refer to a droplet produced in, on, or by a microfluidic device and/or flowed from or applied by a microfluidic device.

As used herein, the term "carrier fluid" refers to a fluid configured or selected to contain one or more discrete entities, e.g., droplets, as described herein. A carrier fluid may include one or more substances and may have one or more properties, e.g., viscosity, which allow it to be flowed through a microfluidic device or a portion thereof, such as a delivery orifice. In some embodiments, carrier fluids include, for example: oil or water, and may be in a liquid or gas phase. Suitable carrier fluids are described in greater detail herein.

As used in the claims, the term "comprising", which is synonymous with "including", "containing", and "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, and/or ingredient not specifically recited. For example, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. With respect to the terms "comprising", "consisting essentially of", and "consisting of", where one of these three terms is used herein, the presently disclosed subject matter can include the use of either of the other two terms.

Methods

As summarized above, the present disclosure provides microfluidic methods for barcoding nucleic acid target molecules to be analyzed, e.g., via nucleic acid sequencing techniques. Also provided are microfluidic, droplet-based methods of preparing nucleic acid barcodes for use in various barcoding applications. The methods described herein facilitate high-throughput sequencing of nucleic acid target molecules as well as single cell or single virus genomic, transcriptomic, and/or proteomic analysis/profiling.

Methods for Making Barcodes

The present disclosure provides a variety of methods for the preparation of nucleic acid barcodes sequences and/or unique molecular identifiers (UMI)s, which may in turn be used to label one or more molecular targets of interest, e.g., one or more nucleic acids of interest.

Cell Barcodes:

In some embodiments of the present disclosure, cells can be used to deliver barcodes to discrete entities, e.g., droplets. For example, in some methods of the present disclosure, a plurality of discrete entities containing cell lysates is provided. The nucleic acids in the lysates may be barcoded so as to enable their sequencing while allowing for the identification of which nucleic acids originated from which droplet and, thus, from single cells. To accomplish this, barcodes that are unique to each cell may be introduced into the discrete entities. There are a variety of methods which may be used to accomplish this goal. One such method is to introduce a cell into the droplet, wherein the barcode is expressed in the cell, for example, as a high copy number plasmid. This serves to increase the starting concentration of the barcode so that it can be more easily integrated into the sequences of the cell nucleic acids. A suitable plasmid may be, e.g., from about 1 kb to about 3 kb in size.

Using cells to deliver barcodes has a number of advantages. For example, to produce more barcode-containing cells for use, a library of barcode-containing cells need only be grown up to increase the size of the population. To create the barcode-containing cells, one can generate a library of barcodes synthetically as single molecule randomers, and then clone these into, for example, plasmids. The plasmids can then be introduced into a host cell, such as *E. coli*, and amplified by growing the cells.

Another advantage of cell barcodes is that the cells, being discrete objects, can be controllably encapsulated into discrete entities, e.g., droplets, using, for example, inertial ordering. For example cells, such as yeast or *E. coli*, can be flowed through a channel at high speeds, causing inertial effects to become important and the inertial ordering of the cells in the channel, and thereby producing a periodic spacing of cells. The periodicity of the cell flow can then be matched by the periodicity of the droplet generation of a droplet maker, enabling efficient encapsulation of the barcode-containing cells in droplets. This process can be combined with paired coalescence of droplets containing lysates to, for example, add a barcode to a droplet containing cell lysate with high efficiency.

Accordingly, in some embodiments the present disclosure provides a method of introducing multiple copies of a nucleic acid barcode sequence into a discrete entity, wherein the method includes: (a) encapsulating a plurality of nucleic acid target molecules in a discrete entity; (b) introducing into the discrete entity a cell including multiple copies of a nucleic acid barcode sequence; (c) lysing the cell to release the multiple copies of the nucleic acid barcode sequence in the discrete entity; and (d) subjecting the discrete entity to conditions sufficient for enzymatic incorporation of the nucleic acid barcode sequence into the plurality of nucleic acid target molecules or amplification products thereof.

In other embodiments, the present disclosure provides a method of introducing multiple copies of a nucleic acid barcode sequence into a discrete entity, wherein the method includes: (a) encapsulating a plurality of nucleic acid target molecules in a first discrete entity; (b) encapsulating a cell in a second discrete entity, wherein the cell includes multiple copies of a nucleic acid barcode sequence; (c) merging the first and second discrete entities; and (d) subjecting the merged discrete entities to conditions sufficient for enzymatic incorporation of the nucleic acid barcode sequence into the plurality of nucleic acid target molecules or amplification products thereof.

In one such embodiment, the second discrete entity is a microdroplet and the step of encapsulating the cell in the second discrete entity includes (e) flowing a plurality of cells through a channel of a microfluidic device, the microfluidic device including a droplet generator in fluid communication with the channel, under conditions sufficient to effect inertial ordering of the cells in the channel, thereby providing periodic injection of the cells into the droplet generator; and (f) matching the periodicity of the injection with the periodicity of droplet generation of the droplet generator, thereby encapsulating individual cells in individual microdroplets using the droplet generator.

Bead Barcodes:

In some embodiments of the present disclosure it may be advantageous to introduce barcodes into discrete entities, e.g., microdroplets, on the surface of a bead, such as a solid polymer bead or a hydrogel bead. These beads can be synthesized using a variety of techniques. For example, using a mix-split technique, beads with many copies of the same, random barcode sequence can be synthesized. This can be accomplished by, for example, creating a plurality of beads including sites on which DNA can be synthesized. The beads can be divided into four collections and each mixed with a buffer that will add a base to it, such as an A, T, G, or C. By dividing the population into four subpopulations, each subpopulation can have one of the bases added to its surface. This reaction can be accomplished in such a way that only a single base is added and no further bases are added. The beads from all four subpopulations can be combined and mixed together, and divided into four populations a second time. In this division step, the beads from the previous four populations may be mixed together randomly. They can then be added to the four different solutions, adding another, random base on the surface of each bead. This process can be repeated to generate sequences on the surface of the bead of a length approximately equal to the number of times that the population is split and mixed. If this was done 10 times, for example, the result would be a population of beads in which each bead has many copies of the same random 10-base sequence synthesized on its surface. The sequence on each bead would be determined by the particular sequence of reactors it ended up in through each mix-spit cycle.

Unique molecular identifiers (UMIs) can also be added to the molecules on the bead surfaces by, for example, a PCR hybridization and extension with primers that have a random UMI sequence. This would permit every individual barcode on a given bead's surface to have a unique identifier, so that bias in the rates at which different molecules are amplified during generation of a sequencing library can be partly corrected by disregarding and/or aggregating duplicated UMIs in quantitation.

With a hard bead, like a polystyrene bead, most of the oligo synthesis will be confined to the surface of the bead. However, hydrogel beads, like polyacrylamide, agarose, alginate, etc., can also be used, with the advantage that they are porous, permitting the oligos to be synthesized even within the bulk of the beads. These porous beads have the benefit of permitting a much larger number of oligos to be synthesized on/and or in the bead, which may be advantageous for applications that require large numbers of target molecules to be labeled with the barcodes or to control the stoichiometry of the barcode concentration in the subsequent reactions.

Another advantage of hydrogels and other polymer beads is that they can be induced to melt or dissolve by changing environmental conditions. For example, with beads made of low melting point agarose, it is possible to melt the agarose beads in a droplet that is heated above the melting point of the hydrogel, which may happen during thermal cycling for PCR. This has the advantage of allowing the barcodes to mix into the bulk of the droplet, which may enhance the efficiency of the barcoding reaction. Additionally, discrete entities, e.g., droplets, that contain the beads can be sorted based on whether they contain a specific number of beads, such as 0, 1, 2, etc., beads. This is advantageous because it can be used, for example, to generate a plurality of discrete entities in which nearly every discrete entity contains the exact number of desired beads, such as one bead. For example, when barcoding cellular nucleic acids, one bead may be paired with one cell or cell lysate in a discrete entity, e.g., a droplet.

Where the encapsulation of cells is achieved using random encapsulation techniques, only certain discrete entities, e.g., droplets, will contain a single cell while, since the same is true for the beads, only certain discrete entities will contain a single bead. The probability of obtaining a discrete entity that has exactly one cell and one bead then becomes the probability of encapsulating one cell and one bead in the same discrete entity, which can often be low. This can greatly reduce the efficiency of the process that generates the barcoded molecular targets, e.g. cellular nucleic acids. By sorting to ensure that only discrete entities containing a bead are used to encapsulate cells, the efficiency of the pairing can be increased significantly.

Another advantage of the use of beads is that they can enable enrichment of specific nucleic acids out of the discrete entities, e.g., droplets, or avoid issues associated with the need to change reaction buffers due to inhibition of the reactions, such as, for example, cell lysate inhibition of PCR. For example, using beads with barcodes and also a sequence that can hybridize to the target nucleic acids, such as a poly T sequence that can anneal to the poly A tails of mRNA transcripts, it is possible to hybridize to the transcripts and potentially remove them from the lysate while keeping all the transcripts originating from each cell on a single, associated bead. Since the beads are small, this process can be performed on many single cells in parallel.

Alternatively, if a more complex reaction is performed with the beads involving multiple reactions, some of which may be inhibited while others are not, the beads can also be valuable. For example, if the goal is to perform an RT-PCR to barcode single cell transcriptomes, then the beads can be used to hybridize to the mRNA of the cell in a discrete entity, e.g., a droplet. The reverse transcriptase reaction can then be performed in the discrete entity to extend the mRNA sequences onto the barcodes on the beads, thereby labeling them with the barcodes. If the PCR that follows is inhibited in the discrete entity in the high concentration of cell lysate, the discrete entity can be ruptured and the beads collected and removed from the lysate. The barcoded transcripts attached to the bead can then be subjected to additional PCR in a single tube and in optimal buffers, overcoming inhibition since lysate is no longer present, but also ensuring that the transcript products are barcoded, since the amplicons are generated from cDNA molecules on the bead sequence that have the barcode attached to them.

Yet another advantage of using beads this way is that the same bead library can be stored after use and used again to produce another library for sequencing. This is facilitated by the fact that the beads are solid and can be removed from the buffer they are currently in and introduced into another buffer such as, for example, removed from a storage buffer designed to preserve the beads and their attached nucleic acids, and introduced into an amplification buffer to enable PCR generation of amplicons for sequencing.

Accordingly, in some embodiments the present disclosure provides a method of introducing multiple copies of a nucleic acid barcode sequence into a discrete entity, wherein the method includes: (a) encapsulating a plurality of nucleic acid target molecules in a discrete entity; (b) introducing into the discrete entity a porous bead including multiple copies of a nucleic acid barcode sequence, wherein the multiple copies of the nucleic acid barcode sequence are distributed at least in part on surfaces defined by one or more pores of the porous bead; and (c) subjecting the discrete entity to conditions sufficient for enzymatic incorporation of the nucleic acid barcode sequence into the plurality of nucleic acid target molecules or amplification products thereof. This method could also be performed using a non-porous bead, wherein the multiple copies of the nucleic acid barcode sequence are distributed on the surface of the non-porous bead, e.g., bound to the non-porous bead via a nucleic acid binding molecule.

In other embodiments, the present disclosure provides a method of introducing multiple copies of a nucleic acid barcode sequence into a discrete entity, wherein the method includes: (a) encapsulating a plurality of nucleic acid target molecules in a first discrete entity; (b) encapsulating a bead in a second discrete entity, wherein the second discrete entity is a microdroplet and the bead includes multiple copies of a nucleic acid barcode sequence on a surface thereof, and wherein the step of encapsulating the bead in the second discrete entity includes (i) flowing a plurality of beads through a channel of a microfluidic device, the microfluidic device including a droplet generator in fluid communication with the channel, under conditions sufficient to effect inertial ordering of the beads in the channel, thereby providing periodic injection of the beads into the droplet generator; and (ii) matching the periodicity of the injection with the periodicity of droplet generation of the droplet generator, thereby encapsulating individual beads in individual microdroplets using the droplet generator; (c) merging the first and second discrete entities; and (d) subjecting the merged discrete entities to conditions sufficient for enzymatic incorporation of the nucleic acid barcode sequence into the plurality of nucleic acid target molecules or amplification products thereof.

In other embodiments, the present disclosure provides a method of introducing multiple copies of a nucleic acid barcode sequence into a discrete entity, wherein the method includes: (a) encapsulating a plurality of nucleic acid target molecules in a discrete entity; (b) introducing into the discrete entity a bead including multiple copies of a nucleic acid barcode sequence on a surface thereof, wherein each copy of the nucleic acid barcode sequence includes a unique molecular identifier (UMI) attached thereto; and (c) subjecting the discrete entity to conditions sufficient for enzymatic incorporation of the nucleic acid barcode sequence into the plurality of nucleic acid target molecules or amplification products thereof.

In other embodiments, the present disclosure provides a method of introducing multiple copies of a nucleic acid barcode sequence into a discrete entity, wherein the method includes: (a) encapsulating a plurality of nucleic acid target molecules in a first discrete entity; (b) encapsulating a bead in a second discrete entity, wherein the second discrete entity is a microdroplet and the bead includes multiple copies of a nucleic acid barcode sequence on a surface thereof, and wherein the step of encapsulating the bead in the second discrete entities includes (i) flowing a plurality of beads through a channel of a microfluidic device, the microfluidic device including a droplet generator in fluid communication with the channel, (ii) encapsulating one or more beads in one or more discrete entities produced by the droplet generator, and (iii) sorting the one or more discrete entities produced by the droplet generator to remove discrete entities which do not include one or more beads; (c) merging the first and second discrete entities; and (d) subjecting the merged discrete entities to conditions sufficient for enzymatic incorporation of the nucleic acid barcode sequence into the plurality of nucleic acid target molecules or amplification products thereof.

Single Stranded Barcodes:

In some embodiments the present disclosure provides methods of making and/or using single-stranded barcodes. These barcodes can be generated using a number of techniques. For example, they can be generated by obtaining a plurality of DNA barcode molecules in which the sequences of the different molecules are at least partially different. These molecules can then be amplified so as to produce single stranded copies using, for instance, asymmetric PCR. Alternatively, the barcode molecules can be circularized and then subjected to rolling circle amplification. This will yield a product molecule in which the original DNA barcoded is concatenated numerous times as a single long molecule. The benefit of this is that the long string of barcode copies is a single molecule that can be flowed through a device, e.g., a microfluidic device allowing it to be encapsulated individually in discrete entities, e.g., droplets, yet the barcode sequence exits at far greater than a single copy.

In some embodiments, circular barcode DNA containing a barcode sequence flanked by any number of constant sequences can be obtained by circularizing linear DNA. Primers that anneal to any constant sequence can initiate rolling circle amplification by the use of a strand displacing polymerase (such as Phi29 polymerase), generating long linear concatemers of barcode DNA. The linear concatemers represent single molecules that contain multiple copies of the same barcode, and can be used to introduce high copy barcodes into discrete entities, e.g., droplets.

Accordingly, in some embodiments the present disclosure provides a method for preparing single stranded barcodes, wherein the method includes: (a) encapsulating a plurality of nucleic acid target molecules in a discrete entity; (b) introducing a circular nucleic acid molecule including a nucleic acid barcode sequence into the discrete entity; (c) subjecting the discrete entity to conditions sufficient for rolling circle amplification of the nucleic acid barcode sequence, such that a concatemer of the nucleic acid barcode sequence is produced; and (d) subjecting the discrete entity to conditions sufficient for enzymatic incorporation of the nucleic acid barcode sequence into the plurality of nucleic acid target molecules or amplification products thereof.

In other embodiments, the present disclosure provides a method for preparing single stranded barcodes, wherein the method includes: (a) encapsulating a plurality of nucleic acid target molecules in a discrete entity; (b) introducing a DNA molecule including a nucleic acid barcode sequence into the discrete entity; (c) subjecting the discrete entity to conditions sufficient for amplification via Transcription Chain Reaction (TCR) of the nucleic acid barcode sequence, such that a plurality of single stranded copies of the nucleic acid barcode sequence are produced; and (d) subjecting the discrete entity to conditions sufficient for enzymatic incorporation of the nucleic acid barcode sequence into the plurality of nucleic acid target molecules or amplification products thereof.

In other embodiments, the present disclosure provides a method for preparing single stranded barcodes, wherein the method includes: (a) encapsulating a plurality of nucleic acid target molecules in a discrete entity; (b) introducing a DNA molecule including a nucleic acid barcode sequence into the discrete entity; (c) subjecting the discrete entity to conditions sufficient for amplification via rolling circle Transcription Chain Reaction (rcTCR) of the nucleic acid barcode sequence, such that a plurality of single stranded copies of the nucleic acid barcode sequence are produced; and (d) subjecting the discrete entity to conditions sufficient for enzymatic incorporation of the nucleic acid barcode sequence into the plurality of nucleic acid target molecules or amplification products thereof.

Digital PCR:

One way to produce barcodes for use in reactions, e.g., reactions occurring in discrete entities, e.g., droplets, is using digital PCR. In this approach, individual DNA barcode sequences are encapsulated in discrete entities at limiting dilution, such that a fraction of discrete entities contain no molecules and, normally, a much smaller fraction contain single molecules. Reagents sufficient for amplification are also included in the discrete entity and the discrete entities incubated under conditions sufficient to induce amplification such as, for example, thermal cycling for PCR. The amplification fills each droplet with many copies of the original molecule. This library can be used directly or, if desired, sorted using active or passive means to discard empty discrete entities.

An embodiment of a barcode library generation method is depicted generally in FIG. 1. A library of synthesized barcodes with a random (NNNNNNN region or any variation of random bases) can be encapsulated in drops so that most drops contain one or no barcodes. The single barcodes within drops are amplified by using the universal sequences as a priming site. Exemplary nucleic acid amplification methods that can be used to amplify the single barcodes include: PCR, strand displacement amplification, rolling circle amplification, helicase dependent isothermal amplification, recombinase based PCR (twistamp), and loop mediated amplification (LAMP).

To use the barcode discrete entity library, the discrete entities in the library can be combined with the molecular targets, e.g., nucleic acids, intended for barcoding and subjected to a barcoding reaction. The benefit of amplifying the barcodes prior to introducing them to the molecular targets is that their concentration can be greatly increased, making the subsequent barcoding reactions more efficient in some instances. For example, with an unamplified barcode, many cycles of PCR may be necessary to amplify the barcode and then allow its attachment to target nucleic acids when using a splicing by overlap extension approach. This large amount of amplification can degrade reagents before linkage occurs, resulting in inefficiency, and also necessitate additional thermal cycling, which can produce amplification bias. In addition to PCR, which requires thermal cycling, isothermal methods can also be used, such as, for example Loop-mediated isothermal amplification (LAMP), multiple displacement amplification (MDA), multiple annealing and looping-based amplification cycles (MALBAC), etc. The discrete entities, e.g., droplets, containing the barcodes can also be solidified, generating gel particles filled with barcode molecules. The molecules can be attached to the gels using covalent or non-covalent interactions, permitting the gel beads to be dispersed in an aqueous solvent, or attached to the surface of a bead in the discrete entity.

Accordingly, in some embodiments the present disclosure provides a method of introducing multiple copies of a nucleic acid barcode sequence into a discrete entity, wherein the method includes: (a) encapsulating individual nucleic acid barcode sequences in a population of discrete entities at limiting dilution such that each individual discrete entity of the population of discrete entities statistically contains either zero or one nucleic acid barcode sequence; (b) enzymatically amplifying the nucleic acid barcode sequences in the population of discrete entities to provide a plurality of discrete entities wherein each discrete entity of the plurality of discrete entities includes multiple copies of the individual nucleic acid barcode sequence for that discrete entity; (c) introducing into one or more of the plurality of discrete entities a plurality of nucleic acid target molecules; and (d) subjecting the one or more of the plurality of discrete entities to conditions sufficient for enzymatic incorporation of the nucleic acid barcode sequence into the plurality of nucleic acid target molecules or amplification products thereof.

Combinatorial Library Generation:

A challenge when barcoding certain samples of interest, such as the transcriptomes of cells, is the isolation of a cell together with a barcode sequence in a discrete entity, e.g., a droplet. This allows the barcode sequence to be uniquely associated with the cell so that all sequencing reads containing the barcode are known to originate from the cell. Technically, the challenge is controllably, efficiently, and rapidly creating pairs of individual cells and barcodes. For example, using the bead based method discussed herein; this could necessitate encapsulating one bead and one cell in every droplet. However, since discrete objects such as molecules, beads, cells, etc., are generally encapsulated randomly, the encapsulation statics follow a Poisson distribution, necessitating the generation of many empty and unusable droplets to obtain a small set of droplets that contain a single object. When seeking to achieve the co-encapsulation of two discrete objects, such as a cell and a barcode, the overwhelming majority of droplets generated will be empty or contain a single cell and no barcode, or a single barcode and no cell, neither of which yield the desired data, with a minute fraction containing both a cell and a barcode.

One method for overcoming this inefficiency is to overload the discrete entities, e.g., droplets, so that, for example, every discrete entity with a cell contains multiple barcode sequences and, thus, more cell containing discrete entities yield the desired data. This, however, can create other challenges because, in such a strategy, it is no longer possible to associate each unique barcode sequence with just one cell, leading to inaccuracy in the data. One way to overload the droplets with barcode sequences while also being able to associate each barcode sequence back to one cell is to use a combinatorial bracing approach, in which the barcodes are also barcoded.

For example, rather than a barcode including just a single sequence, it can include two or more sub-sequences that must be connected together using, for example, splicing by overlap extension. The barcode library can then be divided into two, three, etc., different barcode sub-sequences, each of which will exist within the final, conjoined barcode molecule. In this strategy, the concentrations of the different barcode sub-sequences can be set so that a majority of droplets get at least one of each sub-sequence. The final barcode can then be generated by linking all of the sub-sequences into a single barcode molecule that can be amplified and used to label the molecular targets, e.g., nucleic acids, of the cell.

In this approach, the probability of encapsulating a cell and a barcode becomes much higher. For example, if the concentrations of the barcode sub-sequences are set such that ~80% of discrete entities, e.g., droplets, get at least one of each sub-sequence and thus yield a usable barcode, then, assuming that the encapsulation of the cell is uncorrelated with the encapsulation of the barcodes, 80% of cell-containing discrete entities will also get a barcode and yield the desired data. Where unique molecular identifiers are used, this is achieved without having the stitch together different parts of the barcode because, in essence, the UMIs provide a second type of barcode that can be used to associate different cell barcodes together.

For example, suppose that three barcode sequences are encapsulated in a droplet with a single cell and that UMIs are attached to its cDNA products. These cDNA products would, often, be barcoded with the cell barcodes in the next step using a linkage reaction, such that each cDNA is amplified and its amplicons labeled with one of the barcode molecules in the droplet, the one used being selected at random. If one sequences the nucleic acids from all droplets and the data is grouped by UMI, one will find that each UMI groups together, for example three barcode sequences, the ones that were co-encapsulated in the initial droplet. This then informs the analyzer of the data that these three barcodes should be treated as a single barcode group corresponding to one droplet/cell and, now, rather than grouping simply by unique barcode sequences, the data is grouped by the expanded set of barcode sequences. Thus, in this approach, the UMI grouping is first used to identify the barcode groups that corresponds to each cell and then the barcode groups are used to group all sequence reads for each cell. Some barcode groups may include just one barcode, while others may include, for example, one, two, three, etc., barcode sequences, depending on how many unique barcode sequences were introduced into the encapsulating droplet prior to the barcoding linkage reaction. A similar bioinformatic algorithm can be used in the alternative approach in which the barcodes include a series of linked sub-sequences, grouping first by one sub-sequence to identify all other subsequences it is associated with, and then using the expanded set of subsequences to group the single cell or discrete entity data.

Accordingly, in some embodiments the present disclosure provides a method of preparing a nucleic acid barcode library, wherein the method includes: (a) encapsulating in a population of discrete entities (i) a plurality of first nucleic acid molecules, each of the first nucleic acid molecules including a first nucleic acid barcode sub-sequence and a first linkage sequence, and (i) a plurality of second nucleic acid molecules, each of the second nucleic acid molecules including a second nucleic acid barcode sub-sequence and a second linkage sequence, wherein the encapsulating is performed such that at least about 10%, e.g., at least about 20%, at least about 30%, at least about 40%, at least about 50%, at least about 60%, at least about 70% or more of the discrete entities of the population of discrete entities include at least one of the first nucleic acid molecules and at least one of the second nucleic acid molecules; and (b) subjecting the discrete entities to conditions sufficient for enzymatic linkage and/or amplification, such that, for discrete entities including at least one of the first nucleic acid molecules and at least one of the second nucleic acid molecules, linkage and/or amplification products including the sequences of both the first and second nucleic acid molecules are produced, providing composite nucleic acid barcode molecules. It should be noted that the above linkage and/or amplification may occur at the same time as linkage of the composite nucleic acid barcode molecules to a target nucleic acid molecule or the incorporation of the composite nucleic acid barcode molecules into an amplification product of the target nucleic acid molecule.

In other embodiments, the present disclosure provides a method for barcoding nucleic acid target molecules, wherein the method includes: (a) encapsulating a plurality of nucleic acid target molecules in a discrete entity; (b) introducing a plurality of unique molecular identifier (UMI) molecules into the discrete entity; (c) subjecting the discrete entity to conditions sufficient for enzymatic incorporation of a unique UMI molecule sequence into each of a plurality of the plurality of nucleic acid target molecules or an amplification product thereof (thereby providing a plurality of uniquely labeled nucleic acids); (d) introducing a plurality of different nucleic acid barcode sequences into the discrete entity; and (e) subjecting the discrete entity to conditions sufficient for enzymatic incorporation of one of the plurality of barcode sequences into each of the plurality of nucleic acid target molecules or amplification products thereof or amplification products of the amplification products thereof. In some embodiments, UMIs may be incorporated into a plurality of the plurality of nucleic acid target molecules prior to encapsulation. In some embodiments, a UMI and a nucleic acid barcode sequence which both label a particular nucleic acid are not directly connected to each other. For example, a UMI may label one end of a nucleic acid while a nucleic acid barcode sequence labels the other end of the nucleic acid. In some embodiments, rather than introducing the UMIs and nucleic acid barcode sequences serially, they may be added contemporaneously, e.g., following encapsulation of the nucleic acid target molecules in a discrete entity.

Methods for Linking Barcodes to Nucleic Acid Targets

The present disclosure provides a variety of methods for the attachment of nucleic acid barcode sequences to nucleic acid target molecules and/or amplification products thereof.

Linking Barcodes to Nucleic Acid Targets:

One objective of the barcoding strategy of this disclosure is to enable independent sequence reads to be associated with one another via a barcode which relates reads that originated from molecules that existed within the same discrete entity, e.g., droplet, e.g., such as from the same cell from the same droplet. Important to this concept is a methodology for attaching barcodes to target nucleic acids in a droplet, whether they originate from the fragments of molecules, the amplified products of molecules, or even cells or viruses.

There are numerous techniques that can be used to attach barcodes to the nucleic acids within a discrete entity. For example, the target nucleic acids may or may not be first amplified and fragmented into shorter pieces. The molecules can be combined with discrete entities, e.g., droplets, containing the barcodes. The barcodes can then be attached to the molecules using, for example, splicing by overlap extension. In this approach, the initial target molecules can have "adaptor" sequences added, which are molecules of a known sequence to which primers can be synthesized.

When combined with the barcodes, primers can be used that are complementary to the adaptor sequences and the barcode sequences, such that the product amplicons of both target nucleic acids and barcodes can anneal to one another and, via an extension reaction such as DNA polymerization, be extended onto one another, generating a double-stranded product including the target nucleic acids attached to the barcode sequence.

Alternatively, the primers that amplify that target can themselves be barcoded so that, upon annealing and extending onto the target, the amplicon produced has the barcode sequence incorporated into it. This can be applied with a number of amplification strategies, including specific amplification with PCR or non-specific amplification with, for example, MDA.

An alternative enzymatic reaction that can be used to attach barcodes to nucleic acids is ligation, including blunt or sticky end ligation. In this approach, the DNA barcodes are incubated with the nucleic acid targets and ligase enzyme, resulting in the ligation of the barcode to the targets. The ends of the nucleic acids can be modified as needed for ligation by a number of techniques, including by using adaptors introduced with ligase or fragments to enable greater control over the number of barcodes added to the end of the molecule.

Yet another approach for adding the barcodes to the target is to introduce them directly with a transposase or with a combination of enzymes, such as a non-specific endonuclease or combination of non-specific endonucleases (e.g., Fragmentase®) and ligase. For example, in this approach, barcodes can be synthesized that are compatible with a transposase. The transposase can then fragment the target molecules and add the barcodes to the ends of the fragment molecules, performing all steps of the reaction in one reaction. This is elegant and straightforward, but has the challenge of requiring the generation of barcodes that are compatible with the enzyme. A combination of Fragmentase® and ligase can also be used, wherein the Fragmentase® to fragment the nucleic acids to a size suitable for sequencing, and the ligase used to attach the barcodes to the fragment ends.

Accordingly, in some embodiments the present disclosure provides a method for barcoding nucleic acid target molecules, wherein the method includes: (a) introducing into a discrete entity (i) a nucleic acid target molecule, (ii) a nucleic acid barcode sequence, (iii) a first set of primers configured to amplify a sequence of the nucleic acid target molecule, (iv) a second set of primers configured to amplify a sequence of the nucleic acid barcode sequence, wherein one of the first set of primers includes a sequence which is at least partially complementary to a sequence of one of the second set of primers, and (v) an enzymatic amplification reagent; (b) subjecting the discrete entity to conditions sufficient for enzymatic amplification of a sequence of the nucleic acid target molecule and a sequence of the nucleic acid barcode sequence, wherein amplification products having regions of partial sequence homology are produced; and (c) subjecting the discrete entity to conditions sufficient for complementary regions of sequences of the amplification products to hybridize and for the hybridized sequences to be enzymatically extended, thereby providing a product including the amplified sequence of the nucleic acid target molecule and the amplified sequence of the nucleic acid barcode sequence.

In other embodiments, the present disclosure provides a method for barcoding nucleic acid target molecules, wherein the method includes: (a) introducing into a discrete entity (i) a plurality of nucleic acid target molecules, (ii) a plurality of nucleic acid barcode sequences, (iii) first primer sets configured to amplify sequences of the plurality of nucleic acid target molecules, (iv) second primer sets configured to amplify sequences of the plurality of nucleic acid barcode sequences, wherein the first primer sets and the second primer sets include sequences which are at least partially complementary, and (v) an enzymatic amplification reagent; (b) subjecting the discrete entity to conditions sufficient for enzymatic amplification of sequences of the plurality of nucleic acid target molecules and sequences of the plurality of nucleic acid barcode sequences, wherein amplification products having regions of partial sequence homology are produced; and (c) subjecting the discrete entity to conditions sufficient for complementary regions of sequences of the amplification products to hybridize and for the hybridized sequences to be enzymatically extended, thereby providing a plurality of products, each including an amplified sequence of one of the plurality of target nucleic molecules and an amplified sequences of one of the plurality of nucleic acid barcode sequences.

In other embodiments, the present disclosure provides a method for barcoding nucleic acid target molecules, wherein the method includes: (a) generating a library of nucleic acid barcode primers, wherein each nucleic acid barcode primer in the library includes a first sequence sufficient to anneal to a nucleic acid target molecule and a second sequence including a nucleic acid barcode sequence; (b) combining in each of a plurality of discrete entities one or more nucleic acid barcode primers selected from the library and one or more nucleic acid target molecules, wherein the one or more primers selected from the library for inclusion in each discrete entity includes one or more primers with a first sequence sufficient to anneal to one or more of the nucleic acid target molecules in that discrete entity; and (c) enzymatically amplifying one or more of the nucleic acid target molecules in each discrete entity using one or more of the nucleic acid barcode primers in that discrete entity, such that amplification products including a sequence of one of the one or more nucleic acid target molecules and a nucleic acid barcode sequence are produced.

In other embodiments, the present disclosure provides a method for barcoding nucleic acid target molecules, wherein the method includes: (a) generating a library of nucleic acid barcode sequences; (b) combining in each of a plurality of discrete entities one or more nucleic acid barcode sequences selected from the library and one or more nucleic acid target molecules; and (c) enzymatically fragmenting the one or more nucleic acid target molecules in each discrete entity and enzymatically incorporating one or more of the one or more nucleic acid barcode sequences in each discrete entity into fragments of the one or more target nucleic acid molecules or amplification products thereof in that discrete entity.

In other embodiments, the present disclosure provides a method for barcoding nucleic acid target molecules, wherein the method includes: (a) generating a library of nucleic acid barcode sequences; (b) combining in each of a plurality of discrete entities one or more nucleic acid barcode sequences selected from the library and one or more nucleic acid target molecules; and (c) enzymatically ligating the one or more nucleic acid target molecules in each discrete entity to one or more nucleic acid barcode sequences in that discrete entity.

Figure 2:
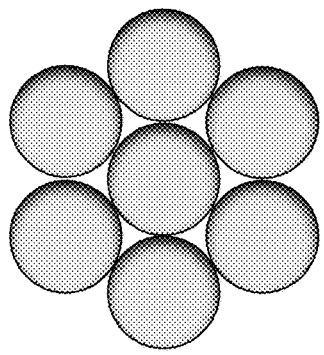
FIG. 2 provides a schematic depicting a method of barcoding nucleic acids isolated from single cells.
Figure 2:
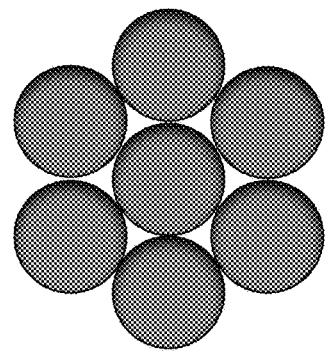
Figure 2:
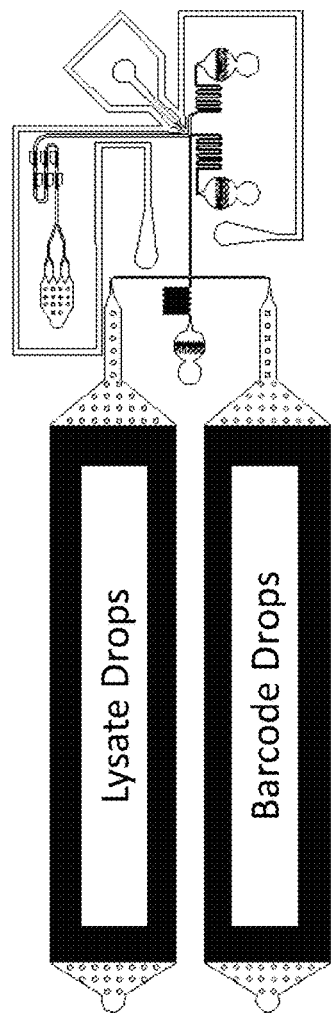
Figure 2:
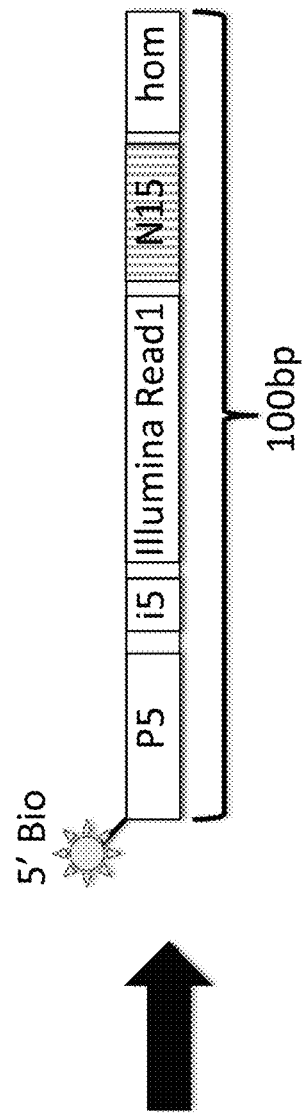
Figure 3:
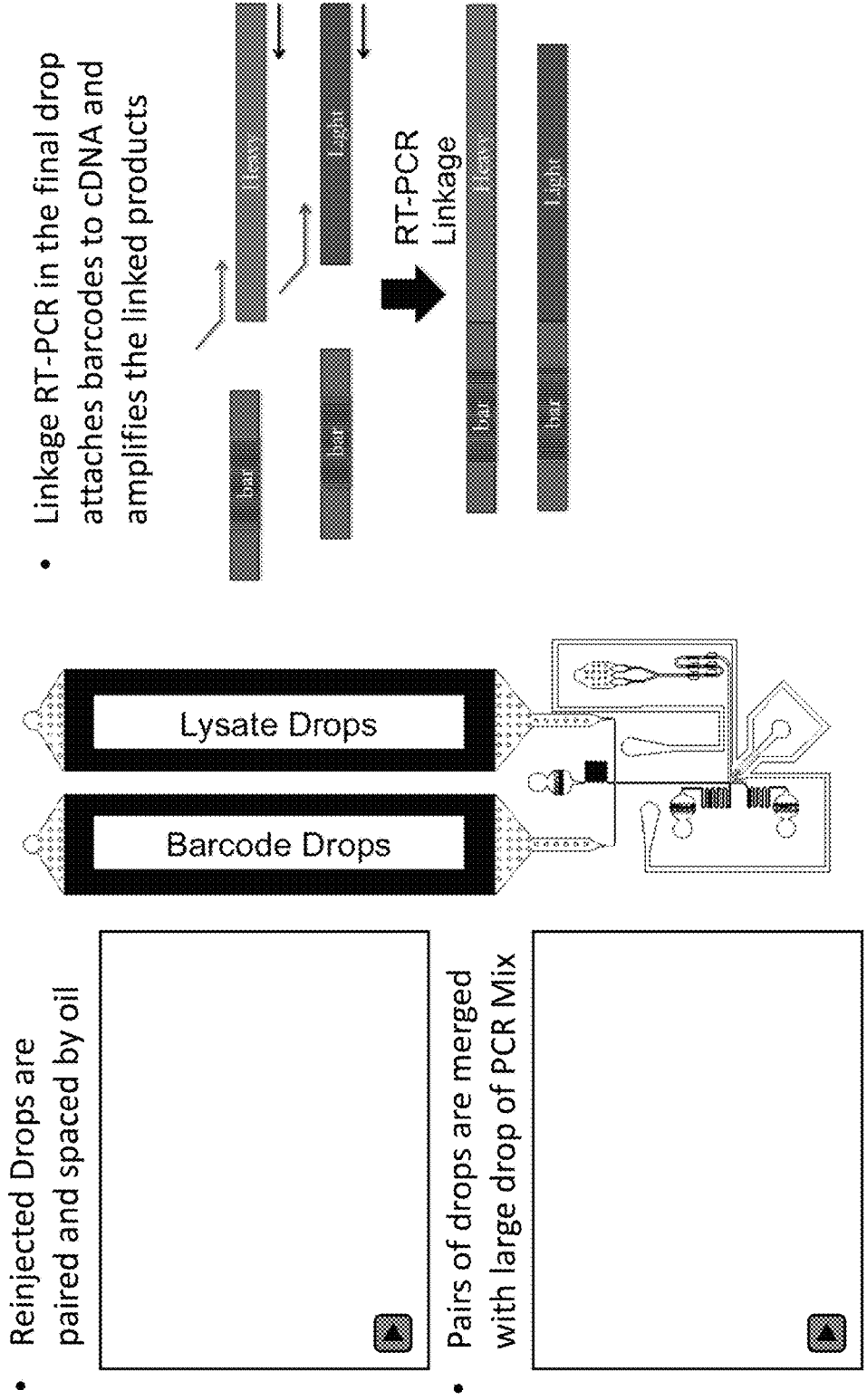
FIG. 3 provides a schematic and images of a microfluidic device configured to pair and merge cell lysate containing microdroplets and nucleic acid barcode containing droplets. Merger with PCR reagent containing microdroplets is also depicted.
Figure 4:
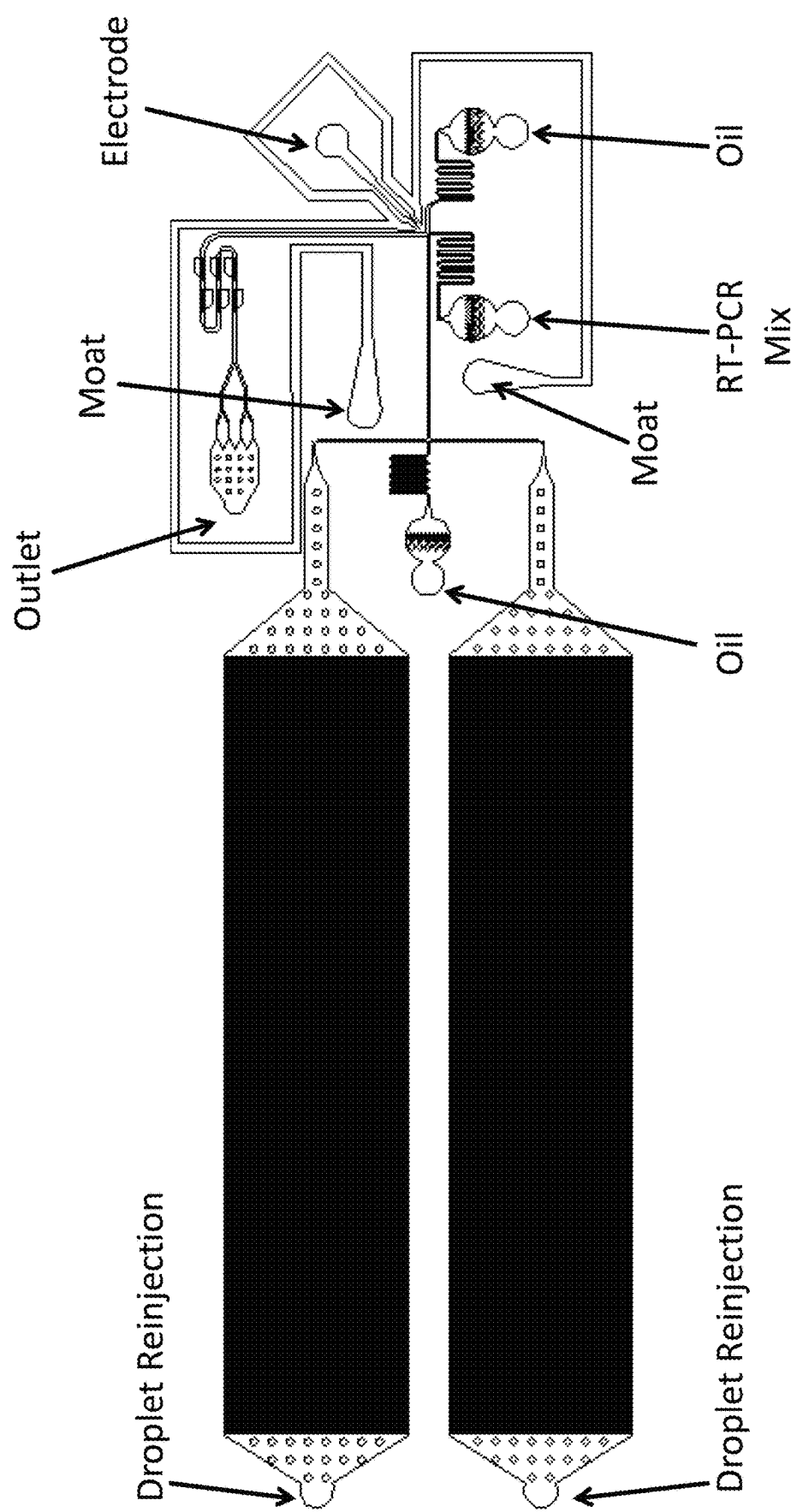
FIG. 4 provides a more detailed schematic of the microfluidic device depicted in FIGS. 2-3 and various features thereof.

An exemplary embodiment is now described with reference to FIGS. 2-4 which depict a single cell barcoding device and method. (1) A first set of microdroplets is prepared, wherein each microdroplet includes cell lysate derived from a single cell, e.g., as a result of treatment with proteinase K (PK). (2) A second set of microdroplets is prepared, wherein each microdroplet includes multiple copies of a unique nucleic acid barcode sequence. (3) A schematic of a microfluidic device which can be used to merge pairs of lysate containing microdroplets and barcode containing microdroplets along with RT-PCR reagents. A more detailed schematic of the microfluidic device is provided in FIG. 4. As shown in FIG. 3, microdroplets are paired and spaced by a carrier fluid, e.g., oil, and merged with a larger drop containing RT-PCR reagents. Linkage RT-PCR is performed in the final merged drops to attach barcodes to cDNA and amplify the linked products. A detailed schematic of the microfluidic device is provided in FIG. 4, in which droplet reinjection features, a liquid electrode, moat, and the reservoirs for the spacing carrier fluid, e.g., oil, and RT-PCR reagents are identified. The microfluidic device utilizes a moat salt solution (to generate the field gradient used for dielectrophoretic deflection and to limit stray fields that can cause unintended droplet merger).

Methods for Manipulating Microdroplets

Split-Merge Method:

One aspect of the present disclosure is a workflow that allows for the combining of cells with barcodes in discrete entities while also permitting the execution of reactions in the discrete entities. A challenge to accomplishing this is that cell lysate may be a potent inhibitor of certain reactions, such as PCR, necessitating steps to overcome this inhibitory effect. One method for accomplishing this is to use a two-step procedure in which the cell lysate is digested with proteases to degrade compounds that might interfere with the reaction, and dilution is used to dilute compounds to an acceptable level. This can be accomplished using a number of methods. For example, one method is to merge droplets containing cell lysates with significantly larger droplets to achieve, for example, a significant dilution of the cell lysate in the final droplet. A challenge with this approach, however, is that the large droplet that is formed may be less stable with regard to the handling or temperature cycling required for downstream reactions, such as PCR. In addition, the volume of reagent required to generate the larger droplets is proportional to the number of droplets generated and their volume; large droplets thus require more total reagent, making the process more demanding on the available resources.

One way to enhance stability is to merge the lysate-containing droplets with larger droplets, mix the contents, and then split a portion off of the large, mixed droplet for the steps that follow. However, this approach may still use a large amount of the reagent to generate a larger droplet. An alternative to this approach that can achieve the same dilution is to split the lysate-containing droplet (or a droplet containing any other suitable material) first and then merge the split portion with a reagent droplet that is, for example, approximately the same size as the lysate droplet before it was split. By way of example, a lysate-containing droplet may be split to provide a plurality of droplets having approximately 10% of the volume of the lysate-containing droplet. These reduced-volume droplets may then be merged with reagent droplets having approximately 90% of the volume of the original lysate-containing drop to provide an approximately 10× dilution.

Accordingly, in some embodiments the present disclosure provides a method for manipulating microdroplets, wherein the method includes: (a) generating a first plurality of microdroplets and a second plurality of microdroplets; (b) flowing the first plurality of microdroplets in a channel of a microfluidic device; (c) splitting each of the first plurality of microdroplets to provide a plurality of reduced-volume microdroplets; (d) merging each of the plurality of reduced volume microdroplets with a microdroplet of the second plurality of microdroplets, wherein the microdroplets of the second plurality of microdroplets each have a volume that is approximately equal to or less than that of the first plurality of microdroplets.

In some embodiments, the first and/or second plurality of microdroplets has diameter of from about 5 µm to about 200 µm, e.g., from about 15 µm to about 150 µm, or from about 15 µm to about 50 µm.

Merging Multiple Microdroplets:

In some embodiments of the present disclosure it may be desirable to merge several droplets together, as opposed to just pairs of droplets. This can be achieved by introducing the different droplet types into a microfluidic device from separate inlets in such a way that the droplets flow into a single, joined channel. The droplets can be induced to flow as groups of the different droplet types. This can be accomplished, for example, by joining the outlets of the channels from which the different types are introduced into a single channel, such that the flow of one droplet partly impedes the flow of the droplet in an adjacent channel. After the first droplet enters into the joined channel, the second droplet is able to flow in after it, causing the droplets to be injected into the joined channel as an alternating stream. This concept can be extended to larger numbers of droplets, such as three or more droplets. The droplets can also be induced to flow as groups by making the different droplet types different sizes, which causes the smaller droplets to "catch up" to the larger droplets and naturally form groups. They can then be merged by applying an electric field or using the merger geometries described herein. Alternatively, the pairs of droplets can be flowed alongside another droplet, such as a larger droplet, and merged with it. They can also be merged with a stream, such as a liquid jet which can then be induced to break into smaller droplets, if desired. Droplet-stream merger and droplet-jet merger are discussed in greater detail below.

Accordingly, in some embodiments the present disclosure provides a method for merging two or more microdroplets, wherein the method includes: (a) introducing two or more populations of microdroplets into a flow channel of a microfluidic device, (i) wherein the flow channel includes a microdroplet merger section associated with one or more electrodes or one or more portions of one or more electrodes configured to apply an electric field in the microdroplet merger section of the flow channel, (ii) wherein the two or more populations of microdroplets are introduced into the flow channel at a single junction from two or more separate inlet channels, respectively, and (iii) wherein the two or more populations of microdroplets are introduced into the flow channel such that the microdroplet inputs from each inlet channel at least partially synchronize due to hydrodynamic effects, resulting in the ejection of spaced groups of microdroplets, in which at least some of the spaced groups of microdroplets include a microdroplet from each of the two or more populations of microdroplets; (b) flowing the spaced groups of microdroplets into the microdroplet merger section; and (c) merging microdroplets within a spaced group by applying an electric field in the microdroplet merger section of the flow channel using the one or more electrodes or the one or more portions of the one or more electrodes.

Drop-Stream/Drop-Jet Combination:

In some embodiments the present disclosure provides a method for merging two or more liquids, wherein the method includes: (a) introducing a first liquid into a flow channel of a microfluidic device as a stream at least partially in contact with an immiscible phase liquid; (b) introducing a microdroplet including a second liquid into the flow channel; (c) merging the microdroplet into the stream, thereby combining the first and second liquids; and (d) inducing the stream including the combined first and second liquids to break into individual microdroplets including the combined first and second liquids.

In some embodiments of the above method, the flow channel includes a microdroplet merger section associated with one or more electrodes or one or more portions of one or more electrodes configured to apply an electric field in the microdroplet merger section of the flow channel, and the method includes applying the electric filed in the microdroplet merger section of the flow channel to merge the microdroplet into the stream.

Figure 5:
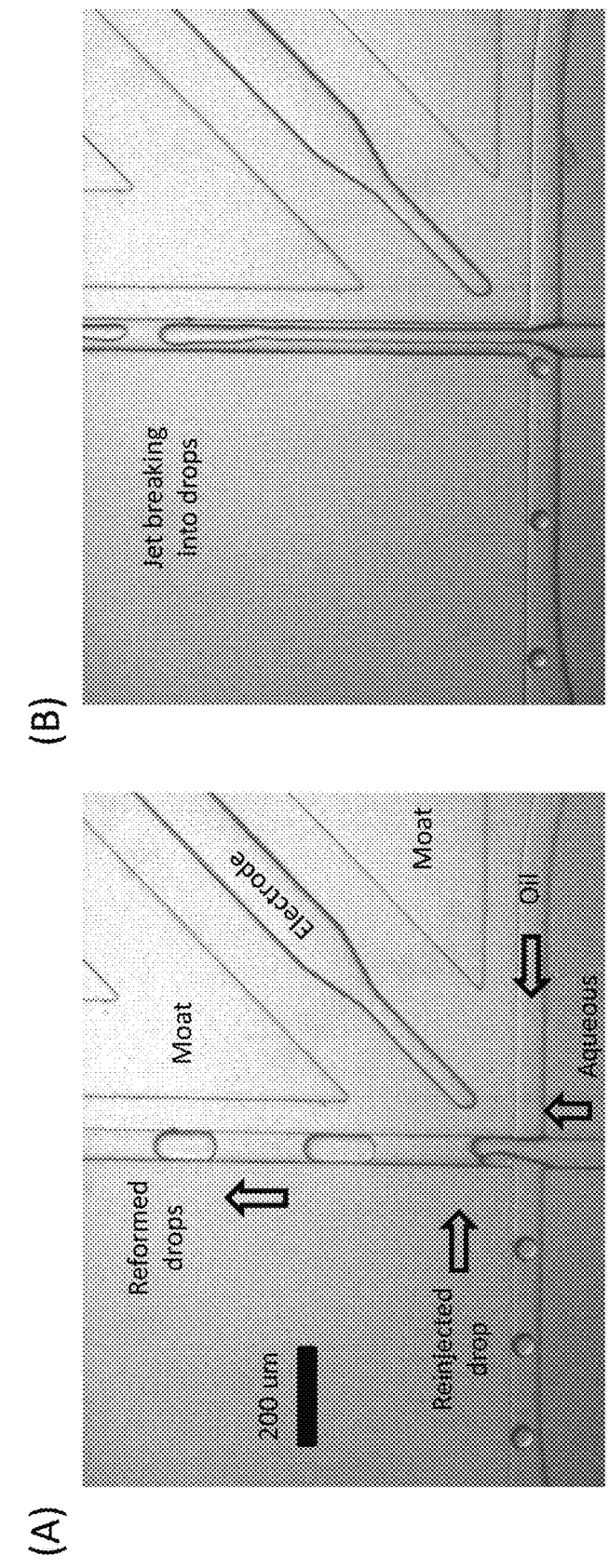
FIG. 5 provides images of a microfluidic device configured for use in drop-stream combination methods. (A) Reinjected drops travel down one of the oil side-channels of a symmetric flow-focus drop-maker and electrocoalesce with the aqueous phase before drop generation. (B) Drops are similarly joined under jetting conditions with a jetting drop maker.

In some embodiments of the above method, the first liquid is introduced into the flow channel under dripping conditions. In other embodiments, the first liquid is introduced into the flow channel under jetting conditions. Examples of these embodiments are provided in FIG. 5, Panels A and B, respectively.

Generally, the dripping-jetting transition is governed by the applicable viscosity ratio, capillary number, Weber number and Reynolds number. For example, a viscosity ratio of approximately 1, a Reynolds number of <1, a Weber number of <1, and a capillary number of <1 will provide for droplet forming conditions. Deviation from the above conditions tends to result in jetting or stable co-flow. See, for example, Nunes et al. *J Phys D Appl Phys.* 2013 Mar. 20; 46(11): 114002 and Utada et al. *Phys. Rev. Lett.* 99, 094502, the disclosure of each of which is incorporated by reference herein for all purposes.

Figure 6:
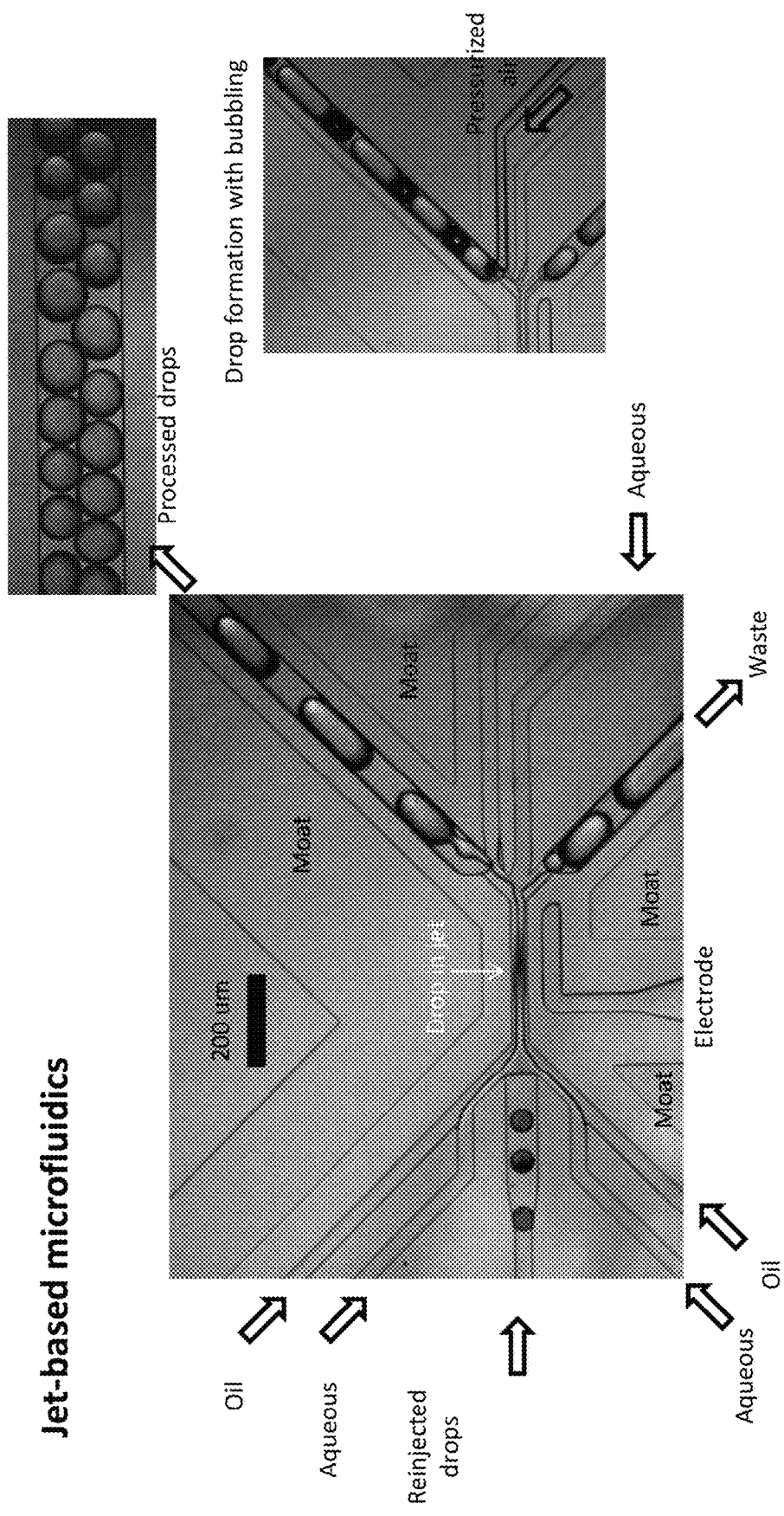
FIG. 6 provides images of a microfluidic device configured for processing of small volumes of fluid using jet-based microfluidics. Droplets are reinjected and electrocoalesced with a aqueous-in-oil jet. The drop fluid remains as a bolus and can be split, diluted, and created as a drop later.

An example of an additional embodiment, which may be utilized to process small volumes of liquid, is depicted in FIG. 6. As shown, droplets are reinjected and merged, e.g., via electrocoalescence, with a liquid jet at least partially in contact with an immiscible phase liquid, e.g., an aqueous-in-oil jet. The drop liquid remains as a bolus and can be split, diluted and/or reformed as a droplet subsequent to the merger. It should be noted that the concept and implementation of droplet-jet merger has wide applicability in the field of liquid handling, including applications other than those relating to barcoding and the related analysis methods as described herein.

Single-Cell Transcriptome Analysis and Sequencing

To sequence the transcriptomes of individual cells a variety of workflows can be used. In one workflow, reagents sufficient for cDNA synthesis and amplification of the cell transcriptome, such as SMART™ reagents (available from Clontech Laboratories, Palo Alto, Calif.—see, e.g., Zhu et al., BioTechniques 30:892-897 (2001)), can be introduced into a droplets containing cell lysate together with reagents for barcoding. Then, by thermally cycling the droplets, the reactions can be performed in the same step, resulting in cDNA synthesis of the mRNA transcriptomes, their amplification, and tagging of the ends of the amplification products with barcodes using, for example, splicing by overlap extension PCR (SOEing PCR).

This is a relatively straightforward workflow that can be performed on a small number of devices, or potentially a single device, and provides information about the ends of the transcripts, which is useful for expression profiling. This approach is referred to herein as "SMARTOne" because all reactions for the cDNA synthesis, amplification, and barcoding are performed in one step. Alternatively, the cDNA synthesis, which relies on reverse transcriptase, can be performed in one step, and then reagents can be added to perform the amplification and barcoding in later steps. Allowing these reactions to be performed in different steps, allows for the modification of buffers after the individual steps, which could be valuable for optimizing the reactions to obtain the most accurate data. This method is referred to herein as "SMART-2Step".

Both of the described methods provide sequencing reads for the ends of the mRNA transcripts. If it is desirable to obtain the full transcript sequence, then there are also several options. One option is to obtain the barcoded transcripts from the previously described approaches and sequence them with a long molecule sequencing technology such as, for example, the PACBIO RS II sequencer, Pacific Biosciences, Menlo Park, Calif. Alternatively, the long molecule sequencing method described herein can also be used for this purpose. Both of these methods have the advantage of not only providing reads which relate splice variation, but also allow the reconstitution of full length individual transcript molecules.

An alternative approach is to perform fragmentation and barcoding as follows. The cell mRNA is reverse transcribed into cDNA and amplified in one step, referred to herein as "SMART-Tag", or in two steps, in which cDNA synthesis occurs first and reagents sufficient for amplification are added in a second step, referred to herein as "SMART-Tag-2Step". The amplified molecules are then subjected to fragmentation using any suitable method/reagents, for example, Fragmentase® or transposase, and barcodes are then introduced with any of the previously described methods, such as ligation or SOEing using adaptors that are inserted during, for example, fragmentation with transposase. In addition, the target molecules can be labeled with unique molecular identifiers (UMIs) before, during, or after the cDNA synthesis step. These UMIs are substantially distinct from one another and label the molecules, allowing for more accurate transcript counting by taking advantage of the UMI diversity.

Yet another approach is to target specific transcripts for sequencing, which can be accomplished using a number of techniques. For example, specific primers can be used to reverse transcribe only certain sequences during the cDNA synthesis or amplification steps, which can then be subjected to barcoding. This can be used to, for example, target the B or T cell receptor genes for sequencing in a cell population, which could be useful for identifying disease biomarkers or therapeutic antibodies. Other combinations can also be selected by multiplexing the primer sets to, for example, correlate the expression and sequences of multiple genes. Viral genes, for example, in HIV infection, can be correlated with the expression of host genes by designing primer sets that barcode only these genes. This has the advantage of providing much simpler data and also allowing the sequencing to be targeted to the genes of interest, which is useful in some applications of the present disclosure.

Accordingly, in some embodiments the present disclosure provides a "SmartOne" method of barcoding and amplifying RNA from single cells, wherein the method includes: (a) encapsulating individual cells in a population of discrete entities at limiting dilution such that each individual discrete entity of the population of discrete entities statistically contains either zero or one cell; (b) lysing the cells to release RNA target molecules within the discrete entities; (c) introducing into each discrete entity a nucleic acid barcode sequence unique to that discrete entity and reagents sufficient for cDNA synthesis and amplification of the resulting cDNA products; and (d) subjecting each discrete entity to conditions sufficient for cDNA synthesis and enzymatic incorporation of the nucleic acid barcode sequence unique to that discrete entity into cDNA amplification products, thereby providing a plurality of discrete entities wherein each discrete entity of the plurality includes cDNA amplification products labeled with a unique nucleic acid barcode sequence relative to the other discrete entities of the plurality.

In some embodiments, the encapsulating, lysing and cDNA synthesis steps are performed in a first microfluidic device and the enzymatic incorporation, e.g., via SOEing PCR, is performed in a second microfluidic device, providing a "SMART-2Step" method.

In other embodiments, the present disclosure provides a "SmartOne" method of barcoding and amplifying RNA from single cells, wherein the method includes: (a) providing a population of discrete entities, each discrete entity of the population of discrete entities including cell lysate originating from a single cell; (b) introducing into each discrete entity a nucleic acid barcode sequence unique to that discrete entity and reagents sufficient for cDNA synthesis and amplification of the resulting cDNA products; and (c) subjecting each discrete entity to conditions sufficient for cDNA synthesis and enzymatic incorporation of the nucleic acid barcode sequence unique to that discrete entity into cDNA amplification products, thereby providing a plurality of discrete entities wherein each discrete entity of the plurality includes cDNA amplification products labeled with a unique nucleic acid barcode sequence relative to the other discrete entities of the plurality.

In some embodiments, the cDNA synthesis steps are performed in a first microfluidic device and the enzymatic incorporation is performed in a second microfluidic device, providing a "SMART-2Step" method.

In some embodiments, the above methods include introducing into each discrete entity reagents sufficient for the enzymatic incorporation of a nucleic acid molecule including a unique molecular identifier (UMI) into each cDNA sequence, wherein the conditions sufficient for enzymatic incorporation of the nucleic acid barcode sequence unique to that discrete entity into cDNA amplification products are sufficient for enzymatic incorporation of the nucleic acid molecule including a unique molecular identifier into each cDNA sequence. Such reagents may include, e.g., a template switching oligo including a degenerate sequence.

The nucleic acid barcode sequences and/or the UMIs utilized in these methods may be prepared and/or introduced according to any of the methods described herein. In addition, any of the microfluidic devices or features thereof described herein may be utilized in connection with these methods.

In other embodiments, the present disclosure provides a "SMART-Tag" method of barcoding and amplifying RNA from single cells, wherein the method includes: (a) encapsulating individual cells in a population of discrete entities at limiting dilution such that each individual discrete entity of the population of discrete entities statistically contains either zero or one cell; (b) lysing the cells to release RNA target molecules within the discrete entities; (c) introducing into each discrete entity reagents sufficient for cDNA synthesis and amplification of the resulting cDNA products, and subjecting each discrete entity to conditions sufficient for cDNA synthesis and amplification of the resulting cDNA products; (d) introducing into each discrete entity reagents sufficient for fragmentation of the amplified cDNA products, and subjecting each discrete entity to conditions sufficient for fragmentation of the amplified cDNA products; and (e) introducing into each discrete entity a nucleic acid barcode sequence unique to that discrete entity and reagents sufficient for enzymatic incorporation of the nucleic acid barcode sequence into the fragmented cDNA products, and subjecting each discrete entity to conditions sufficient for enzymatic incorporation of the nucleic acid barcode sequence into the fragmented cDNA products.

In some embodiments, step (c) is performed in two different steps and/or using two different devices, a first step in which reagents sufficient for cDNA synthesis are introduced and each discrete entity is subjected to conditions sufficient for cDNA synthesis, and a second step in which reagents sufficient for amplification of the resulting cDNA products are introduced and each discrete entity is subjected to conditions sufficient for amplification of the resulting cDNA products, providing a "SMART-Tag-2Step". In another "SMART-Tag-2Step" method, step (e) includes introducing the discrete entities from step (d) into a microfluidic device, introducing discrete entities including the nucleic acid barcode sequences into the microfluidic device, and merging the discrete entities to provide discrete entities of increased volume.

In other embodiments, the present disclosure provides a "SMART-Tag" method of barcoding and amplifying RNA from single cells, wherein the method includes: (a) providing a population of discrete entities, each discrete entity of the population of discrete entities including cell lysate originating from a single cell; (b) introducing into each discrete entity reagents sufficient for cDNA synthesis and amplification of the resulting cDNA products, and subjecting each discrete entity to conditions sufficient for cDNA synthesis and amplification of the resulting cDNA products; (c) introducing into each discrete entity reagents sufficient for fragmentation of the amplified cDNA products, and subjecting each discrete entity to conditions sufficient for fragmentation of the amplified cDNA products; and (d) introducing into each discrete entity a nucleic acid barcode sequence unique to that discrete entity and reagents sufficient for enzymatic incorporation of the nucleic acid barcode sequence into the fragmented cDNA products, and subjecting each discrete entity to conditions sufficient for enzymatic incorporation of the nucleic acid barcode sequence into the fragmented cDNA products.

In some embodiments, step (b) is performed in two different steps and/or using two different devices, a first step in which the reagents sufficient for cDNA synthesis are introduced and each discrete entity is subjected to conditions sufficient for cDNA synthesis, and a second step in which the reagents sufficient for amplification of the resulting cDNA products are introduced and each discrete entity is subjected to conditions sufficient for amplification of the resulting cDNA products, providing a "SMART-Tag-2Step". In another "SMART-Tag-2Step" method, step (d) includes introducing the discrete entities from step (c) into a microfluidic device, introducing discrete entities including the nucleic acid barcode sequences into the microfluidic device, and merging the discrete entities to provide discrete entities of increased volume.

The methods described thus far for barcoding nucleic acids in cells utilize, for the most part, homogenous, liquid phase reactions where all constituents in the reaction are soluble in the droplet compartments. However, another approach that may be valuable in certain embodiments is the use of a solid-phase support, such as a bead. For example, one or more solid supports can be coated with oligos designed to hybridize to nucleic acid target molecules and can be encapsulated in droplets and incubated under conditions that allow for hybridization of the nucleic acid target molecules to the surface of the solid support. Additional reactions may or may not be performed, such as removing the solid support from the droplet or performing reverse transcriptase or polymerase extension of the hybridized molecules onto the oligos attached to the solid support.

The molecules in the droplets can be the result of cDNA synthesis and/or a fragmentation reaction, and the sequences that hybridize to the beads can be, for example, adaptors added by a transposase or ligase. Alternatively, fragmentation can be performed on the solid support after hybridization and/or extension has occurred, removing all but the bound ends of the target nucleic acids.

Solid supports can also be used to barcode nucleic acid targets. In this approach, beads can be generated that, alternatively or in addition to being coated in a capture sequence, can be coated with a nucleic acid barcode sequence and/or UMI. The beads can then be incubated with the nucleic acid targets under conditions sufficient for hybridization and/or extension, thereby transferring the sequences in the droplet to the surface of the bead. Sequencing libraries can be prepared from the beads by, for example, amplifying nucleic acids off of the beads, including their barcodes and UMIs, and performing library preparation reactions on the products. Fragmentation can also be performed on the beads, if desired, to release cleaved products from the beads.

Accordingly, in some embodiments the present disclosure provides a method of preparing cDNA for sequencing, wherein the method includes: (a) fragmenting cDNA into a plurality of fragments, the plurality of fragments including 5' ends, 3' ends, and internal fragments; (b) encapsulating the plurality of fragments in one or more discrete entities along with a solid support; (c) reversibly immobilizing the 5' ends and/or 3' ends on the solid support; (d) separating the internal fragments from the 5' ends and/or 3' ends reversibly immobilized on the solid support; and (e) releasing the 5' ends and/or 3' ends reversibly immobilized on the solid support. The cDNA may be generated from mRNA originating from a single cell, wherein each cDNA includes a nucleic acid barcode sequence incorporated into the 5' ends and/or 3' ends which is unique to the cell from which the mRNA originated. In addition, each cDNA may include a unique molecular identifier (UMI) incorporated into the 5' ends and/or 3' ends.

In other embodiments, the present disclosure provides a method of preparing barcoded nucleic acids for sequencing, wherein the method includes: (a) encapsulating in a discrete entity a plurality of nucleic acid target molecules and a plurality of beads, wherein each of the plurality of beads includes a nucleic acid barcode sequence, a unique molecular identifier (UMI), and a nucleic acid capture sequence designed to hybridize to one of the plurality of nucleic acid target molecules; (b) subjecting the discrete entity to conditions sufficient for hybridization of the one or more nucleic acid target molecules and the nucleic acid capture sequence; and (c) recovering the plurality of beads from the discrete entity for subsequent analysis. In some embodiments, the method includes enzymatically incorporating one of the nucleic acid barcode sequences or an amplification product thereof into each of the plurality of target nucleic acid molecules or an amplification product thereof. In some embodiments, the method includes enzymatically extending each of the plurality of nucleic acid target molecules onto one of the nucleic acid barcode sequences so as to generate chimeric molecules including the nucleic acid barcode sequence or a sequence complementary thereto and at least a portion of the sequence of the nucleic acid target molecules.

Single-Cell Genome Analysis and Sequencing

Amplification for Deep Sequencing of Nucleic Acids:

In some embodiments, the methods of the present disclosure can be used to deeply sequence molecules, including long single molecules originating from the nucleic acids of single cells. To accomplish this, it may often be desirable to amplify the molecules so that, upon fragmentation and barcoding, there are multiple copies of each region of the original molecule in the fragmented products, permitting multifold sequencing of each region, which can enable the collection of accurate data that averages out source error.

An approach for amplifying the target nucleic acids includes encapsulating the targets, often, but not always, as individual molecules, in compartments such as microfluidic droplets. Reagents sufficient for amplification may also be included in the droplets, such as enzymes necessary for thermal cycled amplification, including thermostable polymerases, or isothermal amplification, such as polymerases for multiple-displacement amplification. Other, less common forms of amplification may also be applied, such as amplification using DNA-dependent RNA polymerases to create multiple copies of RNA from the original DNA target which themselves can be converted back into DNA, resulting in, in essence, amplification of the target. Living organisms can also be used to amplify the target by, for example, transforming the targets into the organism which can then be allowed or induced to copy the targets with or without replication of the organisms. The degree of amplification may also be controlled by modulating the concentration of the amplification reagents to achieve a desired level of amplification. In some instances, this is useful for fine tuning of the reactions in which the amplified products are used.

Suitable amplification methods for use with the disclosed methods may include, e.g., DNA polymerase PCR, RecA-mediated recombination PCR, helicase displacement PCR, and/or strand displacement based template amplification methods, including, but not limited to Multiple Displacement Amplification (MDA), Multiple Annealing and Looping-Based Amplification Cycles (MALBEC), rolling circle amplification, nick-displacement amplification, and Loop-Mediated Isothermal Amplification (LAMP).

Accordingly, in some embodiments the present disclosure provides a method for producing compartmentalized, amplified target libraries for barcode-based sequencing, wherein the method includes (a) encapsulating a plurality of nucleic acid target molecules in a plurality of discrete entities with reagents sufficient for the enzymatic amplification of the nucleic acid target molecules; (b) subjecting the discrete entities to conditions sufficient for enzymatic amplification of the nucleic acid target molecules, providing amplification products; (c) fragmenting the amplification products; and (d) incorporating nucleic acid barcode sequences into the fragmented amplification products.

In some embodiments, the plurality of nucleic acid target molecules are encapsulated in the plurality of discrete entities at limiting dilution such that each individual discrete entity of the plurality statistically contains either zero or one nucleic acid target molecule.

The target nucleic acids which may be analyzed via these methods may be relatively long, such as greater than 1 kb in length, e.g., greater than 10 kb in length, greater than 100 kb in length or greater than 1000 kb in length. In some embodiments, the target nucleic acids which may be analyzed via these methods have a length of between about 1 kb and 1000 kb, e.g., between about 10 kb and 500 kb, or between about 10 kb and 100 kb.

In-Droplet Fragmentation:

Another important step in deeply sequencing long molecules via the disclosed methods may be fragmentation of the nucleic acids to a length that permits their sequencing with existing platforms, which often have limited read length. Fragmentation can be achieved in a variety of ways and can be applied to either amplified or non-amplified nucleic acid targets. For example, enzymes capable of fragmenting DNA such as Fragmentase® or other nucleases can be included in a discrete entity and the discrete entity subjected to conditions sufficient for fragmentation. Suitable enzymes capable of fragmenting DNA may include, e.g., DNAse I, micrococcal nuclease, DNAse III, and any other nuclease that results in fragmented DNA, including nucleases with sequence specific catalysis. Alternatively, chemical methods can be used, such as the inclusion of acids, reactive oxygen species, etc. Organisms that degrade DNA can also be used by including them in the compartment with the nucleic acids. Physical methods, such as shear generated by flow of the nucleic acids, in or not contained in compartments, or in hydrodynamic jets, can also be used. Other methods can also be used that perform multiple operations on the nucleic acids including fragmentation. For example, transposons can be used to insert or attach sequences into the nucleic acids, often fragmenting them in the process.

Accordingly, in some embodiments the present disclosure provides a method for fragmenting and barcoding nucleic acid target molecules, wherein the method includes (a) encapsulating a plurality of nucleic acid target molecules or amplification products thereof in a plurality of discrete entities; (b) subjecting the discrete entities to conditions sufficient for fragmentation of the nucleic acid target molecules or amplification products thereof to provide fragmented nucleic acid target molecules or amplification products thereof; (c) incorporating nucleic acid barcode sequences into the fragmented nucleic acid target molecules or amplification products thereof, wherein the nucleic acid barcode sequences identify each fragment into which the nucleic acid barcode sequence is incorporated as originating from a single discrete entity, a single cell, or a single organism.

In some embodiments, the subjecting includes fragmenting the nucleic acid target molecules or amplification products thereof by the application of UV light.

In some embodiments, the method includes, prior to the subjecting, incorporating one or more enzymatic cleavage sites into the nucleic acid target molecules or amplification products thereof, e.g., one or more enzymatic cleavage sites including a dUTP.

In some embodiments, the subjecting includes fragmenting the nucleic acid target molecules or amplification products thereof through the application of a force, such as a shear force induced by the hydrodynamic flow of the nucleic acid target molecules or amplification products thereof through a microfluidic channel, a microfluidic jet, or a microfluidic junction in a microfluidic device.

In some embodiments, the subjecting includes fragmenting the nucleic acid target molecules or amplification products thereof via transposon insertion, e.g., using Tn5 transposon, Mu transposon, or any other suitable transposon known in the art.

Characterizing Copy Number Variation in Cells:

In some embodiments, the present disclosure provides a method of characterizing copy number variation in cells. For example, in some embodiments, the present disclosure provides a method for characterizing copy number variation in cells, wherein the method includes (a) isolating single cells in discrete entities; (b) fragmenting cellular nucleic acids in the discrete entities; (c) incorporating unique molecular identifiers (UMI)s into the fragmented cellular nucleic acids; (d) sequencing the fragmented cellular nucleic acids; and (e) using the UMIs to infer the copy number of specific sequences in the cellular nucleic acids.

Linking Barcodes for Deep Sequencing:

An important step in the deep sequencing workflow is linking barcodes to nucleic acids, whether amplified and fragmented or not, so that molecules that were at one point in the same discrete entity, e.g., microdroplet, because they originated from the same molecule, virus, or cell, for example as separate chromosomes or genomic segments, can be associated with one another by computationally sorting reads by barcode. Barcode linkage can be accomplished using a variety of techniques, including using a ligase such as T4 ligase, T7 ligase, *E. coli* ligase, Taq DNA ligase, an RNA ligase, etc., or direct transposon insertion and fragmentation. Recombination methods with integrases, recombinases, lipases, etc., can also be used, which can effect strand exchange between barcoded DNA and fragment DNA.

Another method which can be powerful is overlap extension PCR (SOEing PCR), which can be used to spice the barcodes and fragments together in amplification products. This can be achieved, for example, by using a first set of primers configured to amplify a sequence of the fragments and a second set of primers configured to amplify a sequence of the nucleic acid barcode sequence, wherein one of the first set of primers includes a sequence which is at least partially complementary to a sequence of one of the second set of primers. The primers, fragments and nucleic acid barcode sequences can then be subjected to conditions sufficient for enzymatic amplification of a sequence of the fragments and a sequence of the nucleic acid barcode sequence, wherein amplification products having regions of partial sequence homology are produced. The reaction mixture can then be subjected to conditions sufficient for complementary regions of sequences of the amplification products to hybridize and for the hybridized sequences to be enzymatically extended, thereby providing a product including the amplified sequence of the fragment and the amplified sequence of the nucleic acid barcode sequence.

Accordingly, in some embodiments the present disclosure provides a method for attaching barcodes to fragmented nucleic acids or amplification products thereof, wherein the method includes (a) combining in a plurality of discrete entities, e.g., microdroplets, a plurality of fragmented nucleic acid target molecules, nucleic acid barcode sequences, and reagents sufficient for the incorporation of the nucleic acid barcode sequences into the fragmented nucleic acid target molecules or amplification products thereof; and (b) subjecting the plurality of discrete entities to conditions sufficient for incorporation of the nucleic acid barcode sequences into the fragmented nucleic acid target molecules or amplification products thereof, wherein the nucleic acid barcode sequences identify each fragment or amplification product thereof into which the nucleic acid barcode sequence is incorporated as originating from a single discrete entity, a single cell or a single organism.

Single-Cell/Single-Molecule Next Generation Sequencing (NGS) Workflow:

A goal of the nucleic acid deep sequencing technology described herein is to enable the amplification, fragmentation, and barcoding of target nucleic acids in discrete entities, e.g., microdroplets, or series of discrete entities that permit the sequencing reads originating from specific molecules to be associated with one another. Aspects of this approach may involve, as described herein, isolation, amplification, fragmentation, and barcode linkage of the target nucleic acids. However, different steps can be included or omitted as needed to optimize the process for the target application. For example, if the amplification step is omitted, then the nucleic acids will only be present for the fragmentation step at their unamplified copy number. This means that if there is any inefficiency in the fragmentation and barcoding process, there may be portions of the original nucleic acids that do not get barcoded and, thus, gaps in the sequencing of these regions.

In other embodiments, fragmentation and barcode addition can be performed in a single step, for example, using a transposase, or in two steps, in which a fragmenting technique, for example, using Fragmentase®, is followed by barcode addition with, for example, ligase or overlap extension PCR. Amplification can be implemented in a discrete entity, e.g., a microdroplet, using a variety of techniques that result in physically unattached products, such as PCR. Alternatively, amplification can be accomplished prior to isolation in the compartment but may require that the amplified products remain attached. This can be accomplished, for example, by preforming rolling circle amplification which yields a single, long concatenated molecule of the original nucleic acids, or a technique like multiple displacement amplification, which can produce single fractal-like nuclei of the amplified targets.

Amplification can also be achieved with techniques like emulsion PCR, which can be used to coat a bead with the amplification products. The beads may then be encapsulated into the discrete entities, e.g., microdroplets, as single, entities including many copies of the same set of nucleic acid targets, permitting the next steps in the barcoding reaction to occur.

The microfluidic devices that perform these operations can include architecture which facilitates one or more of droplet generation, droplet merger, stream merger, picoinjection, sorting, etc. Barcodes may be introduced by encapsulating single molecules, which may then be amplified, by merging droplets containing many copies of a starting set of molecules, and/or by encapsulating entities including the barcodes, such as cells or beads made of plastic or gel coated or impregnated with the barcode. The barcodes can be isolated with the templates prior to, simultaneous with, or subsequent to fragmentation, if fragmentation is utilized.

Barcode addition can then be achieved using any number of techniques, including splicing PCR, ligation, etc. The approach may be applied to single molecules or collections of molecules in the same discrete entity, e.g., microdroplet, such as, for example, segments of viral genomes or chromosomes from single cells. The combinatorial barcoding strategies described herein can also be used to achieve efficient loading of the barcodes.

Sorting may be used to discard discrete entities, e.g., droplets, devoid of target or barcode using active or passive means. For example, amplification of target nucleic acids may change the physical properties of the encapsulating compartment, such as its size, shape, viscosity, surface tension, etc., any of which may enable passive separation of filled from empty droplets. Alternatively, or in addition, active sorting may be applied by triggering sorting based on changes in measurable properties of the compartments post amplification, such as a fluorescent signal produced by staining with intercalating dyes, e.g., SYBR® green.

Whichever of the aforementioned methods is used, and whether the steps of amplification, sorting, fragmentation, and barcoding are implemented, or one or more of these steps is omitted, an important aspects of some embodiments of the disclosed methods is the sequencing of short, barcoded reads using available sequencing technologies and the subsequent aggregation of reads by the barcodes to simplify analysis and enable the recovery of single cell, virus, molecule, etc., data. This aggregates all sequences that were encapsulated within the same discrete entity, e.g., microdroplet, and, thus, originated from the same collection of nucleic acids. In certain instances, this may facilitate manipulation, assembly, and analysis of the nucleic acids, particularly when the nucleic acids in the sample contain sequence similarity for regions longer than the read length of the sequencer, preventing unique assembly of the starting molecules.

With the methods described herein, while the reads themselves may span short distances, the barcodes can be used to aggregates large numbers of reads spanning very long distances, permitting unique reassembly in which conventional methods fail. Moreover, this can be used to associate molecules that are related to one another but not physically connected. For example, certain viruses have segmented genomes including physically disconnected molecules, making it difficult with conventional short read sequencing to associate sets of these disconnected molecules together, since the segments from different viruses in the sample are able to mix upon lysis of the viruses during sequencing preparation. However, using the methods described herein, viruses can be isolated, lysed, and their genome segments barcoded so that, even if physically detached, they can be associated together. This is valuable for studying various aspects of viral biology, such as population diversity and evolution. Similar strategies apply to analyzing the nucleic acids of other biologicals systems that have variation, including microbes, stem cells, cancer cells, etc.

Figure 7:
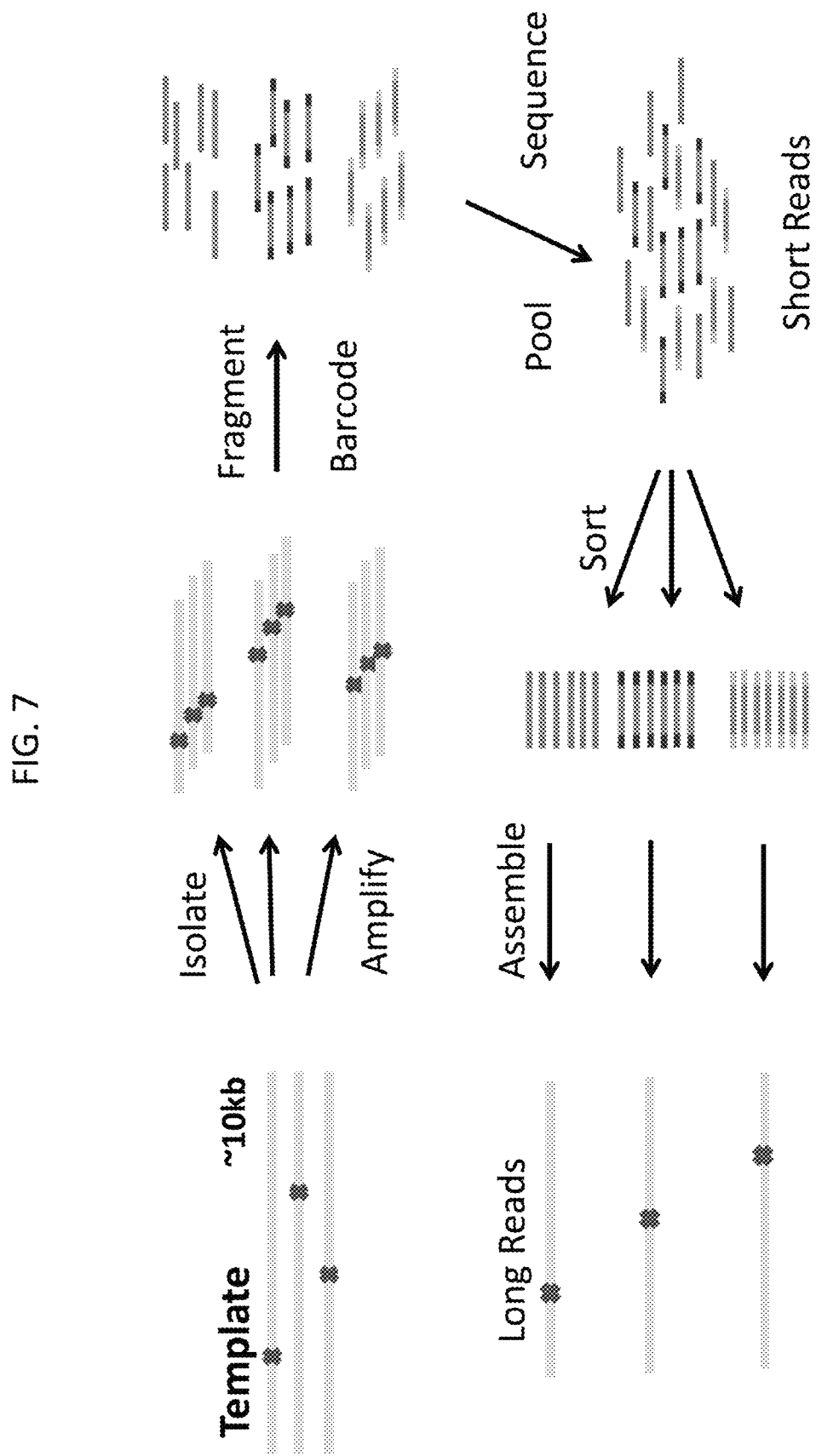
FIG. 7 provides a schematic depicting an exemplary method for barcoding and analyzing template DNA. Template DNA is physically isolated and amplified, then each group of amplicons are fragmented and uniquely barcoded. The fragments can be sequenced on a short read sequencer, and then bioinformatically sorted based on their barcodes. Long reads are reconstructed from short reads that contain the same barcode.

An exemplary method for barcoding and analyzing template DNA is now described with reference to FIG. 7. Template DNA is physically isolated and amplified, then each group of amplicons are fragmented and uniquely barcoded. The fragments can be sequenced on a short read sequencer, and then bioinformatically sorted based on their barcodes. Long reads are reconstructed from short reads that contain the same barcode.

Figure 8:
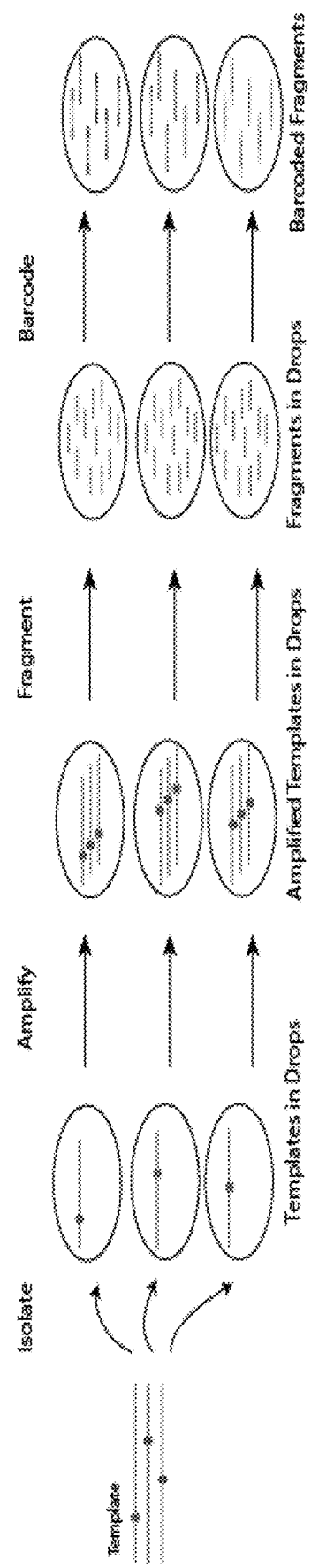
FIG. 8 provides a schematic depicting an exemplary method in which single nucleic acid molecules are isolated and barcoded at high throughput. Single molecules are isolated by encapsulation into droplets. They can then be amplified within these droplets to generate clonal populations of these molecules. They are then fragmented and barcoded within these droplets, so that each droplet contains fragments that derive from the same single molecules and are uniquely barcoded.

FIG. 8 illustrates a method in which single nucleic acid molecules are isolated and barcoded at high throughput. Single molecules are isolated by encapsulation into droplets. They can then be amplified within these droplets to generate clonal populations of these molecules. They are then fragmented and barcoded within these droplets, so that each droplet contains fragments that derive from the same single molecules and are uniquely barcoded.

Fragmentation of DNA can be achieved using Fragmentase® (NEB), Transposon Insertion (Nextera), non-specific DNA endonuclease such as DNAseI, or incorporation of modified bases during amplification and cleavage using DNA repair enzymes, such as dUTP incorporation during amplification and specific cleavage using EndoV and uracil glycosylase. Hydrodynamic shearing can also be used to fragment DNA.

Accordingly, in some embodiments the present disclosure provides a method of sequencing nucleic acids which includes both amplifying and fragmenting steps, wherein the method includes: (a) encapsulating a plurality of nucleic acid target molecules in a plurality of discrete entities; (b) enzymatically amplifying the nucleic acid target molecules to provide first amplification products; (c) fragmenting the first amplification products to provide fragmented first amplification products; (d) incorporating nucleic acid barcode sequences into the fragmented first amplification products or second amplification products amplified from the fragmented first amplification products; (e) sequencing the fragmented first amplification products having nucleic acid barcode sequences incorporated therein, or the second amplification products having nucleic acid barcode sequences incorporated therein; and (f) using the nucleic acid barcode sequences to group sequencing reads for members of the fragmented first amplification products or members of the second amplification products that were, at one time, present in the same discrete entity.

In other embodiments, the present disclosure provides a method of sequencing nucleic acids which includes a fragmenting step, wherein the method includes: (a) encapsulating a plurality of nucleic acid target molecules in a plurality of discrete entities; (b) fragmenting the plurality of nucleic acid target molecules to provide fragmented nucleic acid target molecules; (c) incorporating nucleic acid barcode sequences into the fragmented nucleic acid target molecules or amplification products amplified from the fragmented nucleic acid target molecules; (d) sequencing the fragmented nucleic acid target molecules having nucleic acid barcode sequences incorporated therein or the amplification products having nucleic acid barcode sequences incorporated therein; and (e) using the nucleic acid barcode sequences to group sequencing reads for members of the fragmented nucleic acid target molecules or members of the amplification products that were, at one time, present in the same discrete entity.

In other embodiments, the present disclosure provides a method of sequencing nucleic acids which includes an amplifying step, wherein the method includes: (a) encapsulating a plurality of nucleic acid target molecules in a plurality of discrete entities; (b) enzymatically amplifying the nucleic acid target molecules in the plurality of discrete entities to provide first amplification products; (c) incorporating nucleic acid barcode sequences into the first amplification products or second amplification products amplified from the first amplification products; (d) sequencing the first amplification products having nucleic acid barcode sequences incorporated therein, or the second amplification products having nucleic acid barcode sequences incorporated therein; and (e) using the nucleic acid barcode sequences to group sequencing reads for members of the first amplification products or members of the second amplification products that were, at one time, present in the same discrete entity.

Two-Step Single Molecule Deep Sequencing Workflow:

As discussed above, in some embodiments, the methods and/or devices described herein can be used to deeply sequence a plurality of "long" DNA molecules, e.g., DNA molecules which are from about 1 kb to about 1000 kb in length, e.g., from about 1 kb to about 500 kb or from about 10 kb to about 100 kb. In some embodiments, this is achieved by encapsulating the target molecules in droplets in one microfluidic step and amplifying them. Then reagents sufficient for fragmentation and barcoding are added to those droplets in a second microfluidic step and incubated. Additional reagents sufficient for incorporating barcodes into the fragments and amplifying the fragments are added in a third step. This process thus requires three microfluidic steps and the execution of an in-droplet amplification of the target molecules.

In some instances, it may be desirable to reduce the number of steps required to achieve a similar goal without performing in droplet amplification. This can be accomplished using an alternative workflow in which the target molecules are first labeled with UMI sequences and amplified in bulk prior to any droplet or microfluidic encapsulation. This generates many copies of each target molecule containing the same, unique UMI of the parent molecule from which it was copied. This plurality of sequences can then be encapsulated in discrete entities, such as droplets, so that, for example, there are 10 molecules per compartment. Prior to, simultaneously with, or after encapsulation of the target molecules, reagents sufficient for fragmentation and adaptor addition can be added to the discrete entities. Following encapsulation of the target molecules the discrete entities can be incubated so as to enable fragmentation and adaptor addition reactions to occur.

Exemplary reagents include those provided in the Nextera DNA Sample Prep Kit, available from Illumina, Inc., San Diego, Calif., and/or enzymes such as Fragmentase® and ligase. For example, each discrete entity, e.g., droplet, could include 10 different target molecules on average, each of which could be a distinct sequence and labeled with a different UMI. Each of these molecules may also be a copy of an original molecule to which the UMI had been attached, the other copies being encapsulated in different discrete entities, e.g., droplets. After fragmentation and adaptor ligation, reagents sufficient for droplet barcoding and amplification can be added and the discrete entities incubated as necessary to add barcodes to the fragments and amplify the barcoded products. All molecules can then be recovered, pooled, subjected to additional processing as necessary, and sequenced.

During the bioinformatic analysis of the sequence library, the sequences of the original targets can be re-assembled using the following exemplary algorithm. First, all sequences that contain a particular UMI can be assembled into a set of sequences. Within this set are the fragmented sequences of the target molecule that had the original UMI. Since copies of these target sequences would, in general, be encapsulated in different droplets, these sequences may have different droplet barcodes. The other sequences in this set would be those of the fragments of the molecules that happened to be co-encapsulated with the target sequence. However, since co-encapsulation is random, these sequences will appear rarely in the set when grouped by UMI, while the sequences that appear more frequently and have barcodes indicating that they were in different droplets are likely to correspond to different copies of the same original target. The most frequent sequences in the library can then be used to reassemble the target sequence. This process can then be repeated for all other UMIs, eventually reassembling each individual target.

This technique has a number of strengths. It should allow even very similar sequences to be differentiated from one another and reassembled. For example, suppose that two sequences A and A' differ by two bases separated by 3 kb, and that the targets are 10 kb long. When the sequences are grouped by UMI to recover all sequences corresponding to A, then in the set of grouped sequences most will contain the bases at this position corresponding to A. If many targets are encapsulated per droplet, this process may fail if A and A' include a large portion of the sequences in the library, but provided that the library is diverse, this grouping should recover sequences that correspond to the target sequence since co-encapsulation of A and A' is random and a rare event in a large library of diverse, target sequences. If the library has low diversity, then a possible solution is to lower the number of molecules encapsulated per droplet to less than 1, such that the majority of droplets contain 1 or 0 molecules. In this case, since co-encapsulation is rare, grouping by UMIs will recover primarily the sequences of A, leading to unambiguous reassembly.

This approach is also high throughput. In some embodiments of the previously described method, the target molecules are encapsulated at less than 1 molecule per droplet, meaning that most droplets are empty. This means that most droplets, all of which have to be processed and thus require instrument run time, do not yield useful data. By contrast, in this method, the use of UMIs allows the droplets to be "overloaded" during the target encapsulation step encapsulating, for example, 10 molecules per droplet on average. This ensures that nearly every droplet provides usable sequence data, providing a higher effective throughput. It can also be accomplished using only two microfluidic steps, the step of molecule encapsulation and fragmentation, and the step of barcode addition and amplification of barcoded products. With the use of other bulk amplification methods, the lengths of the molecules that can be analyzed by this method may be as large as megabases in length.

Accordingly, in some embodiments the present disclosure provides a method for barcoding nucleic acid target molecules, wherein the method includes: (a) attaching a unique molecular identifier (UMI) molecule to each of a plurality of nucleic acid target molecules to provide UMI-labeled nucleic acid target molecules; (b) enzymatically amplifying the UMI-labeled nucleic acid target molecules to provide amplification products including the sequences of the UMI-labeled nucleic acid target molecules; (c) encapsulating the amplification products in a plurality of discrete entities, e.g., at one molecule or less per discrete entity; (d) fragmenting the amplification products in the plurality of discrete entities; (e) attaching nucleic acid barcode sequences to the fragmented amplification products, wherein the nucleic acid barcode sequences in each discrete entity relate the fragmented amplification products to the discrete entity in which the fragmented amplification products are encapsulated; (f) releasing from the discrete entities the fragmented amplification products including nucleic acid barcode sequences attached thereto; (g) sequencing the fragmented amplification products; and (h) bioinformatically reassembling the fragmented amplification products using the sequences of the UMIs and the nucleic acid barcodes sequences to provide the sequence of the nucleic acid target molecules from which the amplification products originated. It should be noted that during reassembly fragments or amplification products thereof which include a barcode, but which do not contain a UMI may be associated with fragments having the same barcode which do contain a UMI to identify fragments originating from the same droplet and thus the same molecule.

Thus, for example, if one starts with a reaction vessel containing a plurality of 5 kb DNA molecules, each of which is different and all of which are to be sequenced in their entirety, a UMI may be attached to the end of each of the plurality of 5 kb molecules in the reaction vessel. This may be done in a bulk step prior to encapsulation in droplets. The DNA molecules may then be amplified in bulk, thereby creating many copies of each target-UMI hybrid created previously. This produces a reaction vessel containing a plurality of 5 kb molecules, in which each 5 kb molecule has a UMI, and in which each of those molecules is present in many copies in the reaction vessel.

Each of those molecules can now be individually encapsulated in droplets. The encapsulated droplets can then be fragmented and adaptors can be attached to the ends of the fragment of each molecule in each droplet. This means that, for example, if each 5 kb target was fragmented into 100 pieces 50 bp each, then one would have in each droplet 100 pieces of DNA.

Nucleic acid barcode sequences can now be attached to the 100 fragments in each droplet via the adaptors, such that the nucleic acid barcode sequence is the same for all 100 fragments in a given droplet, but different between droplets.

The nucleic acids from the droplets can then be pooled, sequences and bioinformatically reassembled. Where a given droplet contains gaps with respect to the reassembled sequence, sequences from different droplets can be spliced together based on UMI to build a new, consensus sequence that has all the gaps filled in.

Proteomics Through Deep Sequencing

In some embodiments, the present disclosure provides barcoding methods which can be used to characterize proteins and/or epitopes present in one or more biological samples.

Oligonucleotide-Conjugated Affinity Reagents:

In some embodiments, individual cells, for example, are isolated in discrete entities, e.g., droplets. These cells may be lysed and their nucleic acids barcoded. This process can be performed on a large number of single cells in discrete entities with unique barcode sequences enabling subsequent deconvolution of mixed sequence reads by barcode to obtain single cell information. This strategy, in essence, provides a way to group together nucleic acids originating from large numbers of single cells. Generally, in the embodiments described so far, the nucleic acids have been assumed to originate from the cells themselves, but alternative embodiments permit the barcoding of nucleic acids that are foreign to a cell but, nevertheless, may be associated with the cell in a functional way.

For example, affinity reagents such as antibodies can be conjugated with nucleic acid labels, e.g., oligonucleotides including barcodes, which can be used to identify antibody type, e.g., the target specificity of an antibody. These reagents can then be used to bind to the proteins within or on cells, thereby associating the nucleic acids carried by the affinity reagents to the cells to which they are bound. These cells can then be processed through a barcoding workflow as described herein to attach barcodes to the nucleic acid labels on the affinity reagents. Techniques of library preparation, sequencing, and bioinformatics may then be used to group the sequences according to cell/discrete entity barcodes. Any suitable affinity reagent that can bind to or recognize a biological sample or portion or component thereof, such as a protein, a molecule, or complexes thereof, may be utilized in connection with these methods.

The affinity reagents may be labeled with nucleic acid sequences that relates their identity, e.g., the target specificity of the antibodies, permitting their detection and quantitation using the barcoding and sequencing methods described herein. Suitable nucleic acid labels can include DNA, RNA, and nucleic acid analogues such as LNA, XNA, etc., for example.

The affinity reagents can include, for example, antibodies, antibody fragments, Fabs, scFvs, peptides, drugs, etc. or combinations thereof. The affinity reagents, e.g., antibodies, can be expressed by one or more organisms or provided using a biological synthesis technique, such as phage, mRNA, or ribosome display. The affinity reagents may also be generated via chemical or biochemical means, such as by chemical linkage using N-Hydroxysuccinimide (NETS), click chemistry, or streptavidin-biotin interaction, for example.

The oligo-affinity reagent conjugates can also be generated by attaching oligos to affinity reagents and hybridizing, ligating, and/or extending via polymerase, etc., additional oligos to the previously conjugated oligos. An advantage of affinity reagent labeling with nucleic acids is that it permits highly multiplexed analysis of biological samples. For example, large mixtures of antibodies or binding reagents recognizing a variety of targets in a sample can be mixed together, each labeled with its own nucleic acid sequence. This cocktail can then be reacted to the sample and subjected to a barcoding workflow as described herein to recover information about which reagents bound, their quantity, and how this varies among the different entities in the sample, such as among single cells.

The above approach can be applied to a variety of molecular targets, including samples including one or more of cells, peptides, proteins, macromolecules, macromolecular complexes, etc. The sample can be subjected to conventional processing for analysis, such as fixation and permeabilization, aiding binding of the affinity reagents. To obtain highly accurate quantitation, the unique molecular identifier (UMI) techniques described herein can also be used so that affinity reagent molecules are counted accurately. This can be accomplished in a number of ways, including by synthesizing UMIs onto the labels attached to each affinity reagent before, during, or after conjugation, or by attaching the UMIs microfluidically when the reagents are used.

Similar methods of generating the barcodes, for example, using combinatorial barcode techniques as applied to single cell sequencing and described herein, are applicable to the affinity reagent technique. These techniques enable the analysis of proteins and/or epitopes in a variety of biological samples to perform, for example, mapping of epitopes or post translational modifications in proteins and other entities or performing single cell proteomics. For example, using the methods described herein, it is possible to generate a library of labeled affinity reagents that detect an epitope in all proteins in the proteome of an organism, label those epitopes with the reagents, and apply the barcoding and sequencing techniques described herein to detect and accurately quantitate the labels associated with these epitopes.

Accordingly, in some embodiments the present disclosure provides a method for detecting target molecules, wherein the method includes: (a) labeling each of a plurality of affinity reagents specific for a molecular target with an oligonucleotide including a first nucleic acid barcode sequence, wherein the first nucleic acid barcode sequence identifies the target-specificity of the affinity reagent labeled by the oligonucleotide; (b) contacting the plurality of affinity reagents with a plurality of molecular targets under conditions sufficient for specific binding of the plurality of affinity reagents to their specific molecular targets, when present; (c) encapsulating the plurality of affinity reagents bound to their specific molecular targets, when present, in a plurality of discrete entities, with a plurality of second nucleic acid barcode sequences, wherein the second nucleic acid barcode sequences encapsulated in each discrete entity uniquely identify the discrete entity in which they are encapsulated; (d) incorporating the second nucleic acid barcode sequences into the oligonucleotides including the first nucleic acid barcode sequences or amplification products thereof; (e) sequencing the oligonucleotides including the first nucleic acid barcode sequences or the amplification products thereof; and (f) using the first and second nucleic acid barcode sequences to identify and/or quantitate affinity reagents that were, at one time, present in the same discrete entity.

In some embodiments of the above method, each of the plurality of affinity reagents and/or each oligonucleotide including a first nucleic acid barcode sequence includes a unique molecular identifier (UMI), which uniquely identifies each of the affinity reagents and/or each of the oligonucleotides including a first nucleic acid barcode sequence, respectively.

Single cell proteomics: The extremely high throughput nature of the methods described herein allows proteomic analysis to be performed on thousands to millions of single cells, providing a scalable means by which to characterize the proteomes of large numbers of single cells. Other methods such as, for example, mass cytometry, which use affinity reagents labeled with mass-spectrometry readable tags, are limited in the number of tags that they can create and the sensitivity of the method, since the mass-spec readout is unable to detect proteins that are present at low levels. Flow cytometry and fluorescence methods may, in some instances, provide higher sensitivity, but these are severely limited with respect to multiplexing since it is only possible to uniquely label tens or, at most, hundreds of affinity reagent probes with fluorescent dyes. By contrast, the methods described herein are effectively unlimited with respect to the number of unique nucleic acids labels that can be generated. For example, for a 15mer, the number of possible permutations of label is $4^{15}$, which provides more than enough sequences to label an affinity reagent targeting every protein in most organismal proteomes. Moreover, particularly with the implementation of UMIs, the sensitivity of the method is unparalleled, since even a single affinity reagent, and its accompanying label, can be amplified using, for example, PCR to produce sufficient nucleic acid copies for sequence analysis and detection. The use of UMIs allows massive amplification of rare reagents while still enabling accurate quantitation, since bias generated during the amplification can be corrected using the UMI information.

Accordingly, in some embodiments the present disclosure provides a method of barcoding and amplifying oligonucleotide-conjugated affinity reagents, wherein the method includes: (a) contacting a biological material, e.g., the product of a fixed cell, with a plurality of affinity reagents, each specific for a molecular target, under conditions sufficient for specific binding of the affinity reagents to their respective molecular targets, when present in the biological material, wherein each of the affinity reagents includes an oligonucleotide conjugated thereto; (b) encapsulating the biological material in a plurality of first discrete entities; (c) providing a plurality of second discrete entities including nucleic acid barcode sequences; (d) using a microfluidic device to combine in a discrete entity contents of one of the plurality of first discrete entities, contents of one of the plurality of second discrete entities, and reagents sufficient for incorporation of one of the nucleic acid barcode sequences into one of the oligonucleotides conjugated to the affinity reagents or amplification products thereof; and (e) subjecting the discrete entity including the combined contents of one of the plurality of first discrete entities and one of the plurality of second discrete entities to conditions sufficient for the incorporation of one of the nucleic acid barcode sequences into one of the oligonucleotides conjugated to the affinity reagents or amplification products thereof.

In some embodiments of the above method, the method includes a step of incorporating a unique molecular identifier (UMI) into the oligonucleotide-conjugated affinity reagents.

In other embodiments, the present disclosure provides a method of barcoding and amplifying oligonucleotide-conjugated affinity reagents, wherein the method includes: (a) contacting a plurality of cells with a plurality of affinity reagents, each specific for a molecular target, under conditions sufficient for specific binding of the affinity reagents to their respective molecular targets, when present in the cells, wherein each of the affinity reagents includes an oligonucleotide conjugated thereto; (b) encapsulating and lysing the cells in a plurality of first discrete entities; (c) providing a plurality of second discrete entities including nucleic acid barcode sequences; (d) using a microfluidic device to combine in a discrete entity contents of one of the plurality of first discrete entities, contents of one of the plurality of second discrete entities, and reagents sufficient for incorporation of one of the nucleic acid barcode sequences into one of the oligonucleotides conjugated to the affinity reagents and amplification thereof; and (e) subjecting the discrete entity including the combined contents of one of the plurality of first discrete entities and one of the plurality of second discrete entities to conditions sufficient for the incorporation of one of the nucleic acid barcode sequences into one of the oligonucleotides conjugated to the affinity reagents and amplification thereof.

In some embodiments of the above method, the method includes a step of incorporating a unique molecular identifier (UMI) into the oligonucleotide-conjugated affinity reagents.

Protein-protein interactions: The affinity reagent barcoding techniques described herein can be used to detect and quantitate protein-protein interactions. For example, proteins that interact can be labeled with nucleic acid sequences and reacted with one another. If the proteins interact by, for example, binding one another, their associated labels are localized to the bound complex, whereas proteins that do not interact will remain unbound from one another. The sample can then be isolated in discrete entities, such as microfluidic droplets, and subjected to fusion PCR or barcoding of the nucleic acid labels. In the case that proteins interact, a given barcode group will contain nucleic acids including the labels of both interacting proteins, since those nucleic acids would have ended up in the same compartment and been barcoded by the same barcode sequence.

In contrast, proteins that do not interact will statistically end up in different compartments and, thus, will not cluster into the same barcode group post sequencing. This permits identification of which proteins interact by clustering the data according to barcode and detecting all affinity reagent labels in the group. A purification step can also be implemented to remove unbound affinity reagents prior to isolation in discrete entities, which discards sequences that yield no interaction data. Alternatively, using the fusion approach, such as pairwise fusions post-encapsulation, amplification can be used to selectively amplify fused products, effectively diluting away unfused molecules and enriching for fusions, making the sequencing more efficient for detecting interacting proteins.

Accordingly, in some embodiments the present disclosure provides a method for linking and amplifying nucleic acids conjugated to proteins, wherein the method includes: (a) incubating a population of nucleic acid barcode sequence-conjugated proteins under conditions sufficient for a plurality of the proteins to interact, bringing the nucleic acid barcode sequences on the interacting proteins in proximity to each other; (b) encapsulating the population of nucleic acid barcode sequence-conjugated proteins in a plurality of discrete entities such that interacting proteins are co-encapsulated, if present; (c) using a microfluidic device to combine in a discrete entity contents of one of the plurality of first discrete entities and reagents sufficient for amplification and linkage of the nucleic acid barcode sequences on the interacting proteins, if present; and (d) subjecting the discrete entity to conditions sufficient for the amplification and linkage of the nucleic acid barcode sequences on the interacting proteins, if present.

In other embodiments, the present disclosure provides a method for identifying protein-protein interactions with barcoding, wherein the method includes: (a) incubating a population of nucleic acid barcode sequence-conjugated proteins under conditions sufficient for a plurality of the proteins to interact, bringing the nucleic acid barcode sequences on the interacting proteins in proximity to each other; (b) encapsulating the population of nucleic acid barcode sequence-conjugated proteins in a plurality of discrete entities such that interacting proteins are co-encapsulated, if present; (c) using a microfluidic device to combine in a discrete entity contents of one of the plurality of first discrete entities and reagents sufficient for incorporation of second nucleic acid barcode sequences into the nucleic acid barcode sequences on the interacting proteins, if present, or amplification products thereof; and (d) subjecting the discrete entity to conditions sufficient for incorporation of second nucleic acid barcode sequences into the nucleic acid barcode sequences on the interacting proteins or amplification products thereof, if present.

The population of nucleic acid barcode sequence-conjugated proteins utilized in the above methods may be generated using any suitable method known in the art, e.g., phage display, ribosome display, and/or mRNA display.

Epitope and PTM Mapping Alternative to Immunoprecipitation:

Methods disclosed herein allow for the detection of epitopes, post-translational modifications (PTM)s, splice variations, etc., in proteins, e.g., single molecules, and protein complexes. For example, using methods described herein, a sample including proteins with different PTMs or epitopes can be incubated with nucleic acid labeled affinity reagents such that the reagents bind to the PTMs or epitopes on the molecules. This labels the molecules in the sample with a collection of affinity reagents which relate the epitopes present on the molecules. The bound complexes can then be subjected to isolation, barcoding, and sequencing processes described herein to map which epitopes or PTMs are present on each individual molecule in the sample.

In addition to individual proteins, these methods can be applied to macromolecular complexes, such as, for example, a ribosome, to detect which epitopes are present in the complexes. Such methods can also be used to also determine variation in purportedly similar complexes. One method for accomplishing this uses an immunoprecipitation "pull down" strategy in which the complexes are subjected to binding by an affinity reagent, such as an antibody, and the antibodies used to enrich the complexes from the sample by binding them to a solid support and removing the bound samples. However, performing this pull down process repeatedly for different epitopes is labor intensive and involves an inevitable loses of material. By contrast, using the techniques described herein, the complexes can be reacted with a cocktail of affinity reagents detecting the different epitopes suspected to be present in the entities, and then subjected to a barcoding workflow as described herein to determine which epitopes are present in each simple. Purification strategies, such as a pull down, can also be used to enrich for complexes and bound affinity reagents prior to sequencing.

Accordingly, in some embodiments the present disclosure provides a method of determining the epitopes present in a molecule, a molecular complex and/or structure, wherein the method includes: (a) contacting a plurality of molecules, molecular complexes and/or structures with a plurality of affinity reagents, each specific for an epitope, under conditions sufficient for specific binding of the affinity reagents to their respective epitopes, when present in the molecules, molecular complexes and/or structures, wherein each of the affinity reagents includes a first nucleic acid barcode sequence conjugated thereto which identifies the epitope specificity of the affinity reagent; (b) encapsulating in discrete entities molecules, molecular complexes and/or structures which are specifically bound to one or more of the affinity reagents; (c) incorporating a second nucleic acid barcode sequence into the first nucleic acid barcode sequences or amplification products thereof, wherein the second nucleic acid barcode sequence uniquely identifies the discrete entities; and (d) sequencing the first nucleic acid barcode sequences or amplification products thereof including the second nucleic acid barcode sequence to identify the epitopes present on the molecules, molecular complexes and/or structures.

UMIs for Proteomics:

The power of unique molecular identifiers (UMI)s in connection with the methods described herein are that they allow a sample including nucleic acids to be subjected to significant amplification, which may induce bias in the fraction of resulting molecules of each type in the sample post amplification, while still being able to accurately assess the original fraction of each type. This may be important for transcriptome amplification, for example, because the transcriptomes of single cells generally require significant amplification to yield sufficient nucleic acids for sequencing, and such amplification is likely to bias and thereby skew transcriptome counts. However, by incorporating UMIs, the biased counts can be corrected.

A similar strategy can be applied to the affinity reagent methods described herein. In this case, rather than attaching UMIs to the nucleic acids originating in the cell, such as the cells' genomic fragments or mRNA transcripts, the UMIs can be attached to the labels of the affinity reagents, thereby labeling every affinity reagent complex with a unique identifier that allows it to be amplified significantly and yet counted only once. The incorporation of a UMI into an affinity reagent can be accomplished at multiple steps in the process, including when the affinity reagent label is made, so that it is naturally incorporated into the affinity reagent during a conjugation or expression step, or during microfluidic processing. For example, affinity reagents can be bound to the entities in a sample and isolated and, post isolation, UMIs for each molecule and barcodes for each discrete entity can be attached to barcode labels on the affinity reagents, such that most label molecules on the affinity reagents are labeled with UMIs of distinct sequence, while all affinity reagents within a given discrete entity are labeled with the same or a similar nucleic acid barcode sequence. As in other instances in which UMIs are useful, they can be used in this instance to correct quantitation data for each affinity reagent type that may be skewed by, for example, sequencing or library preparation procedures. This is useful for enabling highly accurate quantitation of cellular proteins in a proteome, particular for quantizing single cell proteomes which yield small amounts of total nucleic acids and require substantial amplification.

Accordingly, in some embodiments the present disclosure provides a method for determining the number of affinity reagents in a sample, wherein the method includes: (a) contacting a sample suspected of containing one or more molecular targets with a plurality of affinity reagents, wherein each of the affinity reagents is specific for a molecular target and includes an oligonucleotide including a nucleic acid barcode sequence which identifies the specificity of the affinity reagent, wherein one or both of the affinity reagent and the oligonucleotide includes a unique molecular identifier (UMI) which uniquely identifies each of the plurality of affinity reagents; and (b) using the UMI to determine the number of affinity reagents in the sample.

In some embodiments of the above method, the method includes a step of amplifying the nucleic acid barcode sequences, wherein the UMIs are used to correct for amplification bias.

FACS, Fluidigm Based Barcoding of Antibody Labeled Cells:

Described herein are processes for barcoding nucleic acids associated with entities in biological samples, such as cells, to enable a sequencing readout to obtain single cell information from a large population. As described herein, similar concepts can be applied to entities such as proteins and protein complexes. The processes described herein are generally geared towards relatively high throughput microfluidic techniques, such as droplet based microfluidic techniques, but may also be applicable to lower throughout methods. For example, the approach for barcoding nucleic acids for single cell transcriptomics or single cell proteomics, can be applied to a FACS based isolation approach in which cells are isolated in wells and subjected to barcoding and sequencing preparation.

Alternatively, microfluidic systems, like the Fluidigm C1™ platform, can be used to capture, isolate, and prepare nucleic acids from single cells for barcoding and sequencing analysis. Ultimately, the method of cell manipulation, while important, can be selected to best suit the needs of the experiment, with high throughput droplet methods being particularly well-suited of analyzing large numbers (thousand to millions) of single cells for transcriptomic, genomic, and/or proteomic analysis.

Accordingly, in some embodiments the present disclosure provides a method of barcoding labeled affinity reagents, wherein the method includes: (a) contacting a sample containing one or more molecular targets with a plurality of affinity reagents, wherein each of the affinity reagents is specific for a molecular target and includes an oligonucleotide including a first nucleic acid barcode sequence which identifies the specificity of the affinity reagent; (b) isolating the one or more molecular targets from the sample; (c) incorporating a second nucleic acid barcode sequence into the oligonucleotide or amplification products thereof, wherein the second nucleic acid barcode sequence uniquely identifies affinity reagents isolated with the one or more molecular targets; and (d) sequencing the oligonucleotide or amplification products thereof having the second nucleic acid barcode sequence incorporated therein to identify which of the plurality of affinity reagents bound to one of the one or more molecular targets in the sample.

In some embodiments of the above method, the isolating includes a step of dispensing individual cells into individual wells. In other embodiments, of the above method, the isolating step includes a step of isolating individual cells using a microfluidic cell capture device.

Single Cell Genetic Modification/Interaction Profiling

A valuable application of the technologies described herein is their use for identifying genetic modifications and determining the effects of genetic modifications/interactions.

Genetic Modifications/Interactions:

In this application, populations of cells can be generated in which genes have been manipulated in various ways such as, for example, using a transposase to insert fragments into the genomes of cells or using, for example, a CRISPR-Cas system to edit or regulate the expression of genes. These techniques can be used, for example to insert sequences such as barcodes, into or nearby the genes that are to be edited or regulated, and repeated, for example, to affect the function of multiple genes within cells. Depending on the interactions of these genes and their impact on cell processes, some cells in the population may behave differently than others, for example, growing more or less rapidly in a particular environment or medium. The challenge then is to determine which modifications have been made in the cells and to correlate them with cell properties, which can be accomplished using the methods described herein. For example, the cells from a modified sample can be subjected to the barcoding and/or fusion workflows described herein to selectively amplify the sequences that are inserted into the cell nucleic acids and/or genome. These amplicons, which may relate the type and location of the modification, can then be fused and/or barcoded with a unique cell barcode. This process can be repeated on large numbers of cells isolated in different discrete entities, such as microfluidic droplets, using different barcodes or fusions that are unique to each cell. The nucleic acids from all discrete entities can then be recovered and subjected to sequence analysis to obtained information to determine which modifications are present in a particular cell. If the sample is sorted or otherwise enriched prior to this step, for example, to recover cells that grow rapidly in a specific environment, then the sequences that are obtained from the use of the method will be known to impact cell properties in this environment, providing information about how these genes contribute to cell properties.

Accordingly, in some embodiments the present disclosure provides a method for identifying genetic modifications in one or more cells, wherein the method includes: (a) introducing one or more genetic modifications into a plurality of cells; (b) identifying one or more cellular phenotypes resulting from the introduction of the one or more genetic modifications into the plurality of cells; (c) isolating each of the cells in a discrete entity and selectively amplifying one or more regions of DNA including the one or more genetic modifications; (d) incorporating a nucleic acid barcode sequence into the amplified DNA including the one or more genetic modifications or amplification products thereof, wherein the nucleic acid barcode sequence identifies the one or more genetic modifications as originating from a single cell; (e) sequencing the amplified DNA including the one or more genetic modifications or amplification products thereof to identify the one or more genetic modifications in the cells having the one or more cellular phenotypes.

Multiplexing Genome, Transcriptome, and Proteome Analysis for Single Cells:

The methods described herein, such as the single cell genomic, transcriptomic, and proteomic sequencing methods, can be used in combination to obtain multiple kinds of information from each cell. For example, as a non-limiting example, a plurality of cells can be labeled with affinity reagents labeled with nucleic acids. These cells can then be subjected to a barcoding workflow in which they are isolated in droplets, lysed, and their mRNA copied to cDNA and barcoded and/or amplified. Simultaneously with, before, or after this step, the nucleic acid labels attached to the affinity reagents can also be barcoded using the same or a different barcode. If the same barcode is used for the cDNA and affinity reagents labels, then all data can be sorted by the one barcode, aggregating all reads for a given cell that correspond to the transcript sequences and the affinity reagent sequences. Moreover, since the affinity reagent sequences can be designed and constructed synthetically, if desired, it is possible to easily differentiate reads pertaining to transcriptomes from reads pertaining to the affinity reagents. This particular embodiment provides, for example, highly detailed information about a single cell's transcriptome and proteome simultaneously, which should be valuable for a broad array of biological studies. Moreover, the use of UMIs on both forms of nucleic acid permits highly accurate quantitation of the levels of each of the transcripts and affinity reagents in the sample, which is also of great value.

Single cell genomic information can also be added to the data by using, for example, the single cell genomic sequencing methods described herein. For example, in a non-limiting embodiment, cells labeled with affinity reagents can be subjected to a workflow in which the cells are isolated, lysed, and their genomes subjected to amplification. The cell transcriptomes can also be subjected to, for example, cDNA synthesis and amplification prior to, simultaneously with, or after the genomic amplification step. A fragmentation step can be used to fragment the genomic and cDNA material into smaller fragments that have adaptor sequences on the ends which may, for example, be the same sequences as the ones used for amplification of the affinity reagent sequences. Barcodes can then be incorporated into the nucleic acids of the three different types of material, labeling, simultaneously or in different reaction steps, the nucleic acids of the different types. The resulting material can be subjected to library preparation, purification, etc., and sequenced. This can be performed on large numbers of cells in parallel and the data subjected to barcode clustering to aggregate all reads associated with a given cell. In such a methodology, it may be important to choose the correct sequencing capability so as to enable the decreased level of sequence depth of the different forms of information to still yield useful data, since such a process produce large amounts of sequence information for each cell and since large numbers of total cells may be analyzed.

Accordingly, in some embodiments the present disclosure provides a method for barcoding and amplifying oligonucleotide-conjugated affinity reagents and RNA from single cells, wherein the method includes: (a) contacting a plurality of cells with a plurality of affinity reagents, wherein each of the affinity reagents is specific for a molecular target and includes an oligonucleotide including a first nucleic acid barcode sequence which identifies the specificity of the affinity reagent; (b) encapsulating the plurality of cells in discrete entities such that each discrete entity includes not more than one cell; (c) lysing the plurality of cells in the discrete entities; and (d) introducing into the discrete entities containing the lysed cells second nucleic acid barcode sequences and reagents sufficient for reverse transcription of RNA, barcoding and amplification of cDNA products, and incorporation of the second nucleic acid barcode sequences into the oligonucleotides including a first nucleic acid barcode sequence or amplification products thereof.

In other embodiments, the present disclosure provides a method for barcoding and amplifying oligonucleotide-conjugated affinity reagents and RNA from single cells, wherein the method includes: (a) contacting a plurality of cells with a plurality of affinity reagents, wherein each of the affinity reagents is specific for a molecular target and includes an oligonucleotide including a first nucleic acid barcode sequence which identifies the specificity of the affinity reagent; (b) encapsulating the plurality of cells in a plurality of first discrete entities such that each first discrete entity includes not more than one cell; (c) lysing the plurality of cells in the first discrete entities; (d) providing a plurality of second nucleic acid barcode sequences in a plurality of second discrete entities; (e) combining each of the first discrete entities with one of the second discrete entities to form a third discrete entity in a first microfluidic device, wherein the third discrete entity includes reagents sufficient for reverse transcription of RNA into cDNA products; and (f) utilizing a second microfluidic device to introduce into the third discrete entities reagents sufficient for barcoding and amplification of the cDNA products and incorporation of the second nucleic acid barcode sequences into the oligonucleotides including a first nucleic acid barcode sequence or amplification products thereof.

In some embodiments of the above methods, the methods includes a step of incorporating unique molecular identifiers (UMIs) into RNA molecules of the lysed cells. Alternatively, or in addition, the oligonucleotides including a first nucleic acid barcode sequence each include a UMI.

Microfluidic Autoimmunoprofiling:

In addition to correlating information within a single entity, the methods described herein can be used to correlate information within the entity with information originating foreign to the entity. For example, in one embodiment, the invention can be used to identify the epitopes bound by immune cells, such as B or T cells. In this embodiment, for example, a plurality of epitopes that may be bound by the B cells can be expressed using a display technology, such as ribosome, mRNA, or phage display. The epitopes can then be reacted with the B cells such that, if a particular B cell receptor binds one or more of the epitopes, the two are conjoined. The bound complexes can then be encapsulated in discrete entities, e.g., microdroplets, and subjected to, for example, the fusion or barcoding methods described herein. This can be used, for example, to link the sequences coding for the epitope to the sequences coding for the B cell receptor, or to link each of them to mutual barcode sequences.

Whichever method is used, the molecules can be sequenced and the pairs that interact detected by, either, reading sequences that are fused together or, alternatively, by clustering reads by barcodes, which then contain reads coding for the epitopes and reads coding for the receptor. This is very useful for screening large libraries of molecules which may interact with other large libraries of molecules to detect a large set of interactions. Such interactions are currently costly to detect since they often require each of the different possible interacting molecules to be isolated in single reactors for testing. By contrast, using the methods described herein, all interactions can be tested in a single reactor, if desired, and the barcoding/sequencing methods used to detect the interaction information. Washes can also be incorporated, if desired, to remove weakly bound epitopes and, generally, to control for the strength of the interactions that are obtained. Similar approaches can also be applied to detect other entities foreign to, for example, a cell or virus such as, for example, a viral sequence residing in a host cell.

Accordingly, in some embodiments the present disclosure provides a method for detecting epitopes bound by one or more cells, wherein the method includes: (a) contacting a plurality of cells with a plurality of epitopes, wherein the epitopes are labeled with nucleic acid barcode sequences and/or UMIs identifying the epitopes, (b) isolating the cells and any bound epitopes in discrete entities; (c) fusing nucleic acids encoding the epitope-bound cellular polypeptides with nucleic acids encoding the epitopes to which polypeptides are bound; (d) identifying which epitopes are bound by which polypeptides by detecting the sequences of the fused nucleic acids.

The labeled epitopes may include polypeptides or other biomolecules expressed by mRNA, ribosome, phage or other display technologies.

As an alternative to fusing the epitope encoding sequence to the cellular polypeptide encoding sequence to which the epitope binds, the two sequences may be linked with a nuclei acid barcode sequence, permitting detection of interacting epitopes and polypeptides by clustering the sequence data according to the nucleic acid barcode sequence.

One or more UMIs may be incorporated to obtain more accurate quantitation of the epitope-polypeptide interactions.

One or more purification steps may be utilized to remove unbound epitopes prior to isolation and fusion and/or barcoding.

Library Preparation, Analysis, Storage, and Reuse
Bead-Based Library Prep:

In some embodiments the present disclosure provides a method of preparing barcoded DNA for sequencing, wherein the method includes: (a) fragmenting DNA into a plurality of fragments, the plurality of fragments including 5' ends, 3' ends, and internal fragments; (b) encapsulating the plurality of fragments in one or more discrete entities, e.g., microdroplets, along with a solid support, such as a bead (e.g., a magnetic bead); (c) reversibly immobilizing the 5' ends and/or 3' ends on the solid support; (d) separating the internal fragments from the 5' ends and/or 3' ends reversibly immobilized on the solid support; and (e) releasing the 5' ends and/or 3' ends reversibly immobilized on the solid support.

The fragmenting may be accomplished using any suitable method, such as physical shearing and/or enzymatic fragmentation with one or more enzymes, and may occur before or after reversibly immobilizing the 5' ends and/or 3' ends of the DNA on the solid support.

In some embodiments, the method includes a step of subjecting the 5' ends and/or 3' ends reversibly immobilized on the solid support to enzymatic modification, such as restriction digestion, ligation, and/or polyadenylation.

Computational Sorting of Reads:

In some embodiments, the present disclosure provides a method for grouping sequencing reads using barcodes, wherein the method includes: (a) sequencing a plurality of nucleic acid molecules including nucleic acid barcode sequences to provide sequencing reads, wherein the plurality of nucleic acid molecules includes nucleic acid molecules originating from the same and different discrete entities; (b) grouping the sequencing reads by nucleic acid barcode sequence using a Hamming or Levenshtein distance criterion; (c) using the sequences of one or more additional barcodes or unique molecular identifiers (UMI)s incorporated into the sequencing reads to statistically determine barcode groups that originated from the same discrete entity; (d) combining reads for barcode groups that originated from the same discrete entity; and (e) removing the barcode portion of each sequencing read and using the remaining portion for further analysis.

Reuse and Storage of Libraries:

The barcoded molecular libraries described herein, e.g., a barcoded cDNA library produced using methods described herein, can be used to generate several nucleic acid samples for sequencing. For example, the barcoded molecules, whether obtained from single cell genomes, transcriptomes, or bound affinity reagents, can include nucleic acids sequences labeled with barcodes. Known primer sequences may be provided flanking these barcodes sequences. This permits the sample to be amplified, e.g., via PCR, to continually produce more samples for sequencing. An advantage of this is that libraries that are constructed can be stored and recovered at a later time to generate additional sequencing libraries. This could be valuable when a sample must be re-visited to obtain more detailed information or in which a first analysis yields new knowledge that motivates additional, follow-on analyses. Combined with the enrichment strategies described in this invention, this could be valuable for analyzing at great depth interesting subpopulations in a large, heterogeneous population.

Moreover, using bead-based methods as described herein, washing steps can also be incorporated, if desired. For example, barcoded nucleic acids attached to beads using one or more of the methods described herein can be purified from a solution by selecting for the beads using, for example, a magnetic force to isolate magnetic beads. This permits washing of the sample to recover purified nucleic acids, aiding in additional processing. Additionally, primers labeled with molecules, such as biotin, can be used to amplify barcoded nucleic acids such that the biotin is incorporated into the affixed products. The resulting amplicons can be isolated via attachment to purification beads coated in, for example, streptavidin. Additional steps of purification based on size selection and the like may be performed. This allows the non-bead based approaches to be used to generate barcoded nucleic acid libraries which can then be attached to beads for purification purposes.

Accordingly, in some embodiments the present disclosure provides a method for preparing a sequence library from a library of barcoded nucleic acids, wherein the method includes: (a) generating a first library of barcoded nucleic acids; (b) preparing a sequencing library from the first library; (c) storing the first library; and (d) preparing a second sequencing library from the first library. In some embodiments of the method, the first library includes nucleic acids attached to a solid support, e.g, one or more beads, which may be sorted by one or more of fluorescence-activated cell sorting (FACS), PCR-activated cell sorting (PACS), or magnetic-activated cell sorting (MACS).

In some embodiments, the first library is purified for storage and/or additional processing by amplifying the nucleic acids of the library with labeled primers, e.g., biotin labeled primers, and isolating the amplified products with an affinity reagent, e.g., streptavidin, having specific binding affinity for the label of the labeled primers.

Targeted Sequence Library Generation Using MACS, PACS, PAS, or Dial-Out PCR:

In certain applications of the present disclosure, it is desirable to sequence specific subpopulations of nucleic acids corresponding to specific barcode groups more deeply than others. This can be accomplished using the methods described herein to, for example, perform a first sequence analysis of a library in which the sequencing is not targeted at particular nucleic acids. Because large numbers of barcode groups may exist, the coverage for a given barcode group may not be sufficient to sequence that group's nucleic acids in the desired depth. The broad and shallow sequencing of the library can then be clustered by barcode and the barcode groups analyzed to detect interesting subpopulations and their barcodes.

For example, using shallow transcriptome sequencing, the phenotypes of different cells may be identified with some degree of certainty in a mixed population of different cell phenotypes. The barcode sequences of the interesting cells can then be used as a means to selectively enrich the nucleic acids from this group for deep sequencing, thereby focusing the sequencing on the groups of interest. This can be accomplished in a number of ways. For example, fluorescent probes with sequences complementary to the barcodes can be generated that hybridize to the nucleic acids of the target barcodes, making them fluorescent. They can then be sorted using, for example, flow cytometry. This is greatly aided by having the barcodes bound to beads so that each bead has many copies of the same barcode, making it easier to detect with a flow cytometer.

Alternatively, a method like PCR-Activated Sorting in microfluidic droplets can be used to sort single molecules or beads with desired barcode sequences. Another alternative is to label probes with sequences complementary to the target barcodes with, for example, biotin, so that they can be enriched with, for example, streptavidin coated magnetic beads. Yet another approach is to apply a technique known as dial-out PCR in which primers specific to the barcode groups of interest are generated and used as priming sequences for amplification. They can then be used to selectively amplify the target groups out of the mixed, barcoded library.

Accordingly, in some embodiments the present disclosure provides a method for preparing a sequence library from a library of barcoded nucleic acids, wherein the method includes: (a) generating a library of barcoded nucleic acids, wherein the library includes sequences of nucleic acid molecules originating from a plurality of cells; (b) obtaining sequence information from the library; (c) using the sequence information to design primers capable of selectively amplifying barcoded nucleic acids including sequences originating from specific cells; and (d) selectively amplifying and analyzing the barcoded nucleic acids including sequences originating from specific cells. In some embodiments, the primers capable of selectively amplifying barcoded nucleic acids including sequences originating from specific cells include nucleic acid barcode sequences obtained from the previous analysis of the library of barcoded nucleic acids or sequences complementary thereto.

In other embodiments, the present disclosure provides a method for analyzing a barcoded sequence library, wherein the method includes: (a) generating a library of barcoded nucleic acids; (b) sequencing, at a first coverage depth, the library to obtain information about a plurality of barcode groups in the library; (c) analyzing the information about the plurality of barcode groups in the library to identify a subset of barcode groups for sequencing at a second, deeper coverage depth; and (d) enriching for the nucleic acids of the subset of barcode groups to produce a targeted library for sequencing at the second, deeper coverage depth.

In some embodiments of the above method, the subset of barcode groups are bound to one or more beads, and the enriching includes hybridizing labeled probes complementary to a known barcode of one of the subset of barcode groups and sorting the beads using the labeled probes. In other embodiments of the above method, the enriching includes utilizing primers that hybridize to specific barcodes sequences in the subset of barcode groups to perform PCR-activated sorting in microfluidic droplets thereby sorting the nucleic acids of the subset of barcode groups.

Applications

The ability to analyze the genomes, transcriptomes, and proteomes of large numbers of cells, separately or simultaneously, using the methods described herein, is valuable for a broad array of applications. The methods are particularly useful for analyzing systems composed of heterogeneous entities, like tissues or populations of stem cells.

Tissue Analysis:

The methods describe herein can be used to analyze heterogeneous blood cells, or the different cells that compose healthy tissues, e.g., kidney, liver, brain, etc. They are also useful for studying diseased tissues, such as tumors. For example the method can be applied to so called "liquid tumors" such as the cells that include blood cancers, or solid tumors, in which the tumors can be disaggregated using enzymatic techniques and then the cells of the tumor subjected to genomic, transcriptomic, and/or proteomic analysis with methods described herein.

The methods of the present disclosure can be used to obtain genomic sequences or haplotypes from single cancer cells, and the related transcriptomic and proteomic analysis methods can be used to follow the flow of information from the encoding genome to its modification in the phenotype and dysregulation of the pathways of the cancer cells. Due to the intrinsically high throughput nature of the invention, making it possible to analyze millions of single cells, the disclosed methods are particularly suited to aid in understanding heterogeneity in tumors and the nature and mechanisms of cancer.

Similar techniques can also be applied to studying antibody and T-cell receptor repertoires, as well as other repertoires in organisms that exhibit diversity. For example, the splicing and/or barcoding methods described herein can be used to link or group the nucleic acids coding for antibody or T cell receptor chains so that they can be sequenced as pairs. This would be valuable for identifying potent antibodies that may be the source of or targets for therapies for diseases ranging from viral and bacterial infection to autoimmune disorders, such as rheumatoid arthritis.

Steps, Components and Procedures for Use in Connection with the Disclosed Methods A variety of steps, components, reagents and procedures may be used to implement various aspects of the disclosed methods. Non-limiting examples of such steps, components, reagents and procedures are provided below.

Types of Discrete Entities:

The composition and nature of the discrete entities, e.g., microdroplets, prepared and or utilized in connection with the disclosed methods may vary. For example, in some embodiments, a discrete entity may include one cell and not more than one cell. In other embodiments, a discrete entity may include a plurality of cells, i.e., two or more cells. In some aspects, discrete entities according to the present disclosure may include a nucleic acid or a plurality of nucleic acids. In some embodiments, as discussed herein, discrete entities may include one or more solid and/or gel materials, such as one or more polymers.

In some embodiments, a surfactant may be used to stabilize the discrete entities, e.g., microdroplets. Accordingly, a microdroplet may involve a surfactant stabilized emulsion. Any convenient surfactant that allows for the desired reactions to be performed in the discrete entities, e.g., microdroplets, may be used. In other aspects, a discrete entity, e.g., a microdroplet, is not stabilized by surfactants or particles.

The surfactant used depends on a number of factors such as the oil and aqueous phases (or other suitable immiscible phases, e.g., any suitable hydrophobic and hydrophilic phases) used for the emulsions. For example, when using aqueous droplets in a fluorocarbon oil, the surfactant may have a hydrophilic block (PEG-PPO) and a hydrophobic fluorinated block (Krytox® FSH). If, however, the oil was switched to be a hydrocarbon oil, for example, the surfactant would instead be chosen so that it had a hydrophobic hydrocarbon block, like the surfactant ABIL EM90. In selecting a surfactant, desirable properties that may be considered in choosing the surfactant may include one or more of the following: (1) the surfactant has low viscosity; (2) the surfactant is immiscible with the polymer used to construct the device, and thus it doesn't swell the device; (3) biocompatibility; (4) the assay reagents are not soluble in the surfactant; (5) the surfactant exhibits favorable gas solubility, in that it allows gases to come in and out; (6) the surfactant has a boiling point higher than the temperature used for PCR (e.g., 95° C.); (7) the emulsion stability; (8) that the surfactant stabilizes drops of the desired size; (9) that the surfactant is soluble in the carrier phase and not in the droplet phase; (10) that the surfactant has limited fluorescence properties; and (11) that the surfactant remains soluble in the carrier phase over a range of temperatures.

Other surfactants can also be envisioned, including ionic surfactants. Other additives can also be included in the oil to stabilize the discrete entities, e.g., microdroplets, including polymers that increase discrete entity, e.g., droplet, stability at temperatures above 35° C.

The discrete entities, e.g., microdroplets, described herein may be prepared as emulsions, e.g., as an aqueous phase fluid dispersed in an immiscible phase carrier fluid (e.g., a fluorocarbon oil or a hydrocarbon oil) or vice versa. The nature of the microfluidic channel (or a coating thereon), e.g., hydrophilic or hydrophobic, may be selected so as to be compatible with the type of emulsion being utilized at a particular point in a microfluidic work flow.

Emulsions may be generated using microfluidic devices as described in greater detail below. Microfluidic devices can form emulsions made up of droplets that are extremely uniform in size. The microdroplet generation process may be accomplished by pumping two immiscible fluids, such as oil and water, into a junction. The junction shape, fluid properties (viscosity, interfacial tension, etc.), and flow rates influence the properties of the microdroplets generated but, for a relatively wide range of properties, microdroplets of controlled, uniform size can be generated using methods like T-junctions and flow focusing. To vary microdroplet size, the flow rates of the immiscible liquids may be varied since, for T-junction and flow focus methodologies over a certain range of properties, microdroplet size depends on total flow rate and the ratio of the two fluid flow rates. To generate an emulsion with microfluidic methods, the two fluids are normally loaded into two inlet reservoirs (syringes, pressure tubes) and then pressurized as needed to generate the desired flow rates (using syringe pumps, pressure regulators, gravity, etc.). This pumps the fluids through the device at the desired flow rates, thus generating microdroplet of the desired size and rate.

In some embodiments, microdroplets are generated using a droplet maker as described in PCT Publication No. WO 2014/028378, the disclosure of which is incorporated by reference herein in its entirety and for all purposes.

Adding Reagents to Discrete Entities:

In practicing the subject methods, a number of reagents may be added to, i.e., incorporated into and/or encapsulated by, the discrete entities, e.g., microdroplets, in one or more steps (e.g., about 2, about 3, about 4, or about 5 or more steps). Such reagents may include, for example, amplification reagents, such as Polymerase Chain Reaction (PCR) reagents. The methods of adding reagents to the discrete entities, e.g., microdroplets, may vary in a number of ways. Approaches of interest include, but are not limited to, those described by Ahn, et al., Appl. Phys. Lett. 88, 264105 (2006); Priest, et al., Appl. Phys. Lett. 89, 134101 (2006); Abate, et al., PNAS, Nov. 9, 2010 vol. 107 no. 45 19163-19166; and Song, et al., Anal. Chem., 2006, 78 (14), pp 4839-4849; the disclosures of which are incorporated herein by reference.

For instance, a reagent may be added to a discrete entity, e.g., microdroplet, by a method involving merging a discrete entity, e.g., a microdroplet, with a second discrete entity, e.g., microdroplet, which contains the reagent(s). The reagent(s) that are contained in the second discrete entity may be added by any convenient methods, specifically including those described herein. This second discrete entity may be merged with the first discrete entity to create a discrete entity, e.g., a microdroplet, which includes the contents of both the first discrete entity and the second discrete entity.

In some embodiments, merging of discrete entities, e.g., droplets, is accomplished using a microfluidic device including a concatemerized merger architecture as described in greater detail below.

One or more reagents may also, or instead, be added using techniques such as droplet coalescence, or picoinjection. In droplet coalescence, a target drop (i.e., the microdroplet) may be flowed alongside a microdroplet containing the reagent(s) to be added to the microdroplet. The two microdroplets may be flowed such that they are in contact with each other, but not touching other microdroplets. These drops may then be passed through electrodes or other aspects for applying an electrical field, wherein the electric field may destabilize the microdroplets such that they are merged together.

Reagents may also, or instead, be added using picoinjection. In this approach, a target drop (i.e., the microdroplet) may be flowed past a channel containing the reagent(s) to be added, wherein the reagent(s) are at an elevated pressure. Due to the presence of the surfactants, however, in the absence of an electric field, the microdroplet will flow past without being injected, because surfactants coating the microdroplet may prevent the fluid(s) from entering. However, if an electric field is applied to the microdroplet as it passes the injector, fluid containing the reagent(s) will be injected into the microdroplet. The amount of reagent added to the microdroplet may be controlled by several different parameters, such as by adjusting the injection pressure and the velocity of the flowing drops, by switching the electric field on and off, and the like.

In various aspects, one or more reagents may also, or instead, be added to a microdroplet by a method that does not rely on merging two droplets together or on injecting liquid into a drop. Rather, one or more reagents may be added to a microdroplet by a method involving the steps of emulsifying a reagent into a stream of very small drops, and merging these small drops with a target microdroplet. Such methods shall be referred to herein as "reagent addition through multiple-drop coalescence." These methods take advantage of the fact that due to the small size of the drops to be added compared to that of the target drops, the small drops will flow faster than the target drops and collect behind them. The collection can then be merged by, for example, applying an electric field. This approach can also, or instead, be used to add multiple reagents to a microdroplet by using several co-flowing streams of small drops of different fluids. To enable effective merger of the tiny and target drops, it is important to make the tiny drops smaller than the channel containing the target drops, and also to make the distance between the channel injecting the target drops from the electrodes applying the electric field sufficiently long so as to give the tiny drops time to "catch up" to the target drops. If this channel is too short, not all tiny drops will merge with the target drop and adding less reagent than desired. To a certain degree, this can be compensated for by increasing the magnitude of the electric field, which tends to allow drops that are farther apart to merge. In addition to making the tiny drops on the same microfluidic device, they can also, or instead, be made offline using another microfluidic drop maker or through homogenization and then injecting them into the device containing the target drops.

Accordingly, in some embodiments a reagent is added to a microdroplet by a method involving emulsifying the reagent into a stream of droplets, wherein the droplets are smaller than the size of the microdroplet; flowing the droplets together with the microdroplet; and merging a droplet with the microdroplet. The diameter of the droplets contained in the stream of droplets may vary ranging from about 75% or less than that of the diameter of the microdroplet, e.g., the diameter of the flowing droplets is about 75% or less than that of the diameter of the microdroplet, about 50% or less than that of the diameter of the microdroplet, about 25% or less than that of the diameter of the microdroplet, about 15% or less than that of the diameter of the microdroplet, about 10% or less than that of the diameter of the microdroplet, about 5% or less than that of the diameter of the microdroplet, or about 2% or less than that of the diameter of the microdroplet. In certain aspects, a plurality of flowing droplets may be merged with the microdroplet, such as 2 or more droplets, 3 or more, 4 or more, or 5 or more. Such merging may be achieved in a variety of ways, including but not limited to by applying an electric field, wherein the electric field is effective to merge the flowing droplet with the microdroplet.

A reagent, in another aspect, is added to a drop (e.g., a microdroplet) formed at an earlier time by enveloping the drop to which the reagent is be added (i.e., the "target drop") inside a drop containing the reagent to be added (the "target reagent"). In certain embodiments such a method is carried out by first encapsulating the target drop in a shell of a suitable hydrophobic phase, e.g., oil, to form a double emulsion. The double emulsion is then encapsulated by a drop containing the target reagent to form a triple emulsion. To combine the target drop with the drop containing the target reagent, the double emulsion is then burst open using any suitable method, including, but not limited to, applying an electric field, adding chemicals that destabilizes the droplet interface, flowing the triple emulsion through constrictions and other microfluidic geometries, applying mechanical agitation or ultrasound, increasing or reducing temperature, or by encapsulating magnetic particles in the drops that can rupture the double emulsion interface when pulled by a magnetic field.

Sorting:

In practicing the methods of the present disclosure, one or more sorting steps may be employed. Sorting approaches of interest include, by are not necessarily limited to, approaches that involve the use of one or more sorters, e.g., sorters of a microfluidic device, which employ microfluidic valves, membrane valves, bifurcating channels, surface acoustic waves, and/or dielectrophoresis. Sorting approaches which may be utilized in connection with the disclosed methods, systems and devices also include those described by Agresti, et al., PNAS vol. 107, no 9, 4004-4009; and those described in PCT Publication No. WO 2014/028378, the disclosure of each of which is incorporated by reference herein in its entirety and for all purposes. A population, e.g., a population of discrete entities, may be enriched by sorting, in that a population containing a mix of members having or not having a desired property may be enriched by removing those members that do not have the desired property, thereby producing an enriched population having the desired property.

In various embodiments, the subject methods include scanning, e.g., optically scanning one or more discrete entities, e.g., microdroplets, to facilitate sorting of the discrete entities. As such, in some embodiments, microfluidic devices or portions thereof, e.g., sorters, include one or more detectors, e.g., optical scanners. A variety of suitable optical scanners are known in the art. Such optical scanners may include, e.g., one or more optical fibers for applying excitation energy to one or more discrete entities. In some embodiments, a suitable optical scanner utilizes a laser light source directed into the back of an objective, and focused onto a microfluidic channel through which droplets flow, e.g., to excite fluorescent dyes within one or more discrete entities. Scanning one more discrete entities may allow one or more properties, e.g., size, shape, composition, of the scanned entities to be determined. Sorting may, in turn, be carried out based on the one or more properties. For example, sorting may be based on results obtained from an optical scan of one or more discrete entities.

Properties of discrete entities which may be detected include, but are not limited to, the size, viscosity, mass, buoyancy, surface tension, electrical conductivity, charge, magnetism, and/or presence or absence of one or more components, e.g., one or more detectable labels (e.g., one or more fluorescent labels). In certain aspects, sorting may be based at least in part upon the presence or absence of one or more cells in the microdroplet, e.g., one or more detectably labeled cells. In certain aspects, sorting may be based at least in part based upon the detection of the presence or absence of PCR amplification products.

Sorting may be applied at any suitable point in the disclosed methods. Moreover, two or more sorting steps may be applied to a population of discrete entities or types thereof, e.g., microdroplets, e.g., about 2 or more sorting steps, about 3 or more, about 4 or more, or about 5 or more, etc. When a plurality of sorting steps is applied, the steps may be substantially identical or different in one or more ways (e.g., sorting based upon a different property, sorting using a different technique, and the like).

Moreover, discrete entities, e.g., droplets, may be purified prior to, or after, any sorting step. In one embodiment a droplet may be purified as follows: a majority of the fluid in the drop is replaced it with a purified solution, without removing any discrete reagents that may be encapsulated in the drop, such a cells or beads. The microdroplet is first injected with a solution to dilute any impurities within it. The diluted microdroplet is then flowed through a microfluidic channel on which an electric field is being applied using electrodes. Due to the dielectrophoretic forces generated by the field, as the cells or other discrete reagents pass through the field they will be displaced in the flow. The drops are then split, so that all the objects end up in one microdroplet. Accordingly, the initial microdroplet has been purified, in that the contaminants may be removed while the presence and/or concentration of discrete reagents, such as beads or cells, which may be encapsulated within the droplet, are maintained in the resulting microdroplet.

Microdroplets may be sorted based on one or more properties. Properties of interest include, but are not limited to, the size, viscosity, mass, buoyancy, surface tension, electrical conductivity, charge, magnetism, and/or presence or absence of one or more components, e.g., one or more detectable labels. In certain aspects, sorting may be based at least in part upon the presence or absence of one or more cells in the microdroplet, e.g., one or more detectably labeled cells. In certain aspects, sorting may be based at least in part based upon the detection of the presence or absence of PCR amplification products.

Sorting may be employed, for example, to remove discrete entities, e.g., microdroplets, in which no cells are present. Encapsulation may result in one or more discrete entities, e.g., microdroplets, including a majority of the discrete entities, e.g., microdroplets, in which no cell is present. If such empty drops were left in the system, they would be processed as any other drop, during which reagents and time would be wasted. To achieve the highest speed and efficiency, these empty drops may be removed with droplet sorting. For example, a drop maker may operate close to the dripping-to-jetting transition such that, in the absence of a cell, drops of a first size, e.g., 8 μm, are formed; by contrast, when a cell is present the disturbance created in the flow will trigger the breakup of the jet, forming drops of a second size, e.g., 25 μm in diameter. The device may thus produce a bi-disperse population of empty drops of a first size, e.g., 8 μm, and single-cell containing drops of a second size, e.g., 25 μm, which may then be sorted by size using, e.g., a hydrodynamic sorter to recover only the, single-cell containing drops of the second, e.g., larger, size.

Sorters of the subject embodiments may be active or passive sorters. Passive sorters of interest include hydrodynamic sorters, which sort discrete entities, e.g., microdroplets, into different channels according to size, based on the different ways in which small and large drops travel through the microfluidic channels. Also of interest are bulk sorters, a simple example of which is a tube containing drops of different mass in a gravitational field. By centrifuging, agitating, and/or shaking the tube, lighter drops that are more buoyant will naturally migrate to the top of the container. Drops that have magnetic properties could be sorted in a similar process, except by applying a magnetic field to the container, towards which drops with magnetic properties will naturally migrate according to the magnitude of those properties. A passive sorter as used in the subject methods may also involve relatively large channels that will sort large numbers of drops simultaneously based on their flow properties. Additionally, in some embodiments, sorting is carried out via activation of one or more valves, e.g., microfluidic valves.

Picoinjection can also be used to change the electrical properties of the drops. This could be used, for example, to change the conductivity of the drops by adding ions, which could then be used to sort them, for example, using dielectrophoresis. Alternatively, picoinjection can also be used to charge the drops. This could be achieved by injecting a fluid into the drops that is charged, so that after injection, the drops would be charged. This would produce a collection of drops in which some were charged and others not, and the charged drops could then be extracted by flowing them through a region of electric field, which will deflect them based on their charge amount. By injecting different amounts of liquid by modulating the piocoinjection, or by modulating the voltage to inject different charges for affixed injection volume, the final charge on the drops could be adjusted, to produce drops with different charge. These would then be deflected by different amounts in the electric field region, allowing them to be sorted into different containers.

Encapsulation and/or Lysis of Cells:

According to some embodiments of the subject methods, cells may be recovered from a subject using any convenient method, e.g., by applying a needle and/or a syringe. The biological sample may then be processed to remove components other than cells using, for example, processing steps such as centrifugation, filtration, and the like.

Each cell in the biological sample, or a subset thereof, may then be encapsulated into a discrete entity, e.g., a droplet, using a microfluidic device. Methods and devices which may be utilized in the encapsulating of a component from a biological sample are described in PCT Publication No. WO 2014/028378, the disclosure of which is incorporated by reference herein in its entirety and for all purposes. Encapsulation approaches of interest also include, but are not limited to, hydrodynamically-triggered drop formation and those described by Link, et al., *Phys. Rev. Lett.* 92, 054503 (2004), the disclosure of which is incorporated herein by reference. Other methods of encapsulating cells into droplets may also be applied. Where desired, the cells may be stained with one or more antibodies and/or probes prior to encapsulating them into drops.

One or more lysing agents may also be added to the discrete entities, e.g., droplets, containing a cell, under conditions in which the cell(s) may be caused to burst, thereby releasing their genomes. The lysing agents may be added after the cells are encapsulated into discrete entities, e.g., microdroplets. Any convenient lysing agent may be employed, such as proteinase K or cytotoxins. In particular embodiments, cells may be co-encapsulated in drops with lysis buffer containing detergents such as Triton X100 and/or proteinase K. The specific conditions in which the cell(s) may be caused to burst will vary depending on the specific lysing agent used. For example, if proteinase K is incorporated as a lysing agent, the discrete entities, e.g., droplets, may be heated to about 37-60° C. for about 20 min to lyse the cells and to allow the proteinase K to digest cellular proteins, after which they may be heated to about 95° C. for about 5-10 min to deactivate the proteinase K.

In certain aspects, cell lysis may also, or instead, rely on techniques that do not involve addition of lysing agent. For example, lysis may be achieved by mechanical techniques that may employ various geometric features to effect piercing, shearing, abrading, etc. of cells. Other types of mechanical breakage such as acoustic techniques may also be used. Further, thermal energy can also be used to lyse cells. Any convenient methods of effecting cell lysis may be employed in the methods described herein.

PCR:

As described above, in practicing the subject methods, a PCR-based assay, e.g., quantitative PCR (qPCR), may be used to detect the presence of certain nucleic acids, e.g., genes, of interest, present in discrete entities or one or more components thereof, e.g., cells encapsulated therein. Such assays can be applied to discrete entities within a microfluidic device or a portion thereof or any other suitable location. The conditions of such PCR-based assays may include detecting nucleic acid amplification over time and may vary in one or more ways.

For instance, the number of PCR primers that may be added to a microdroplet may vary. The term "primer" may refer to more than one primer and may refer to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include, e.g., the presence of four different deoxyribonucleoside triphosphates and a polymerization-inducing agent such as DNA polymerase or reverse transcriptase, in a suitable buffer ("buffer" which includes substituents which are cofactors, or which affect pH, ionic strength, etc.), and at a suitable temperature. The primer may be single-stranded for maximum efficiency in amplification.

The complement of a nucleic acid sequence as used herein may refer to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases. Duplex stability can be determined by empirically considering a number of variables including, for example, the length of the oligonucleotide, percent concentration of cytosine and guanine bases in the oligonucleotide, ionic strength, and incidence of mismatched base pairs.

The number of PCR primers that may be added to a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

Such primers may contain primers for one or more nucleic acid of interest, e.g. one or more genes of interest. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

Such primers and/or reagents may be added to a discrete entity, e.g., a microdroplet, in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent. In some embodiments, the discrete entity, e.g., a microdroplet, may be subjected to a dilution step and/or enzyme inactivation step prior to the addition of the PCR reagents. Exemplary embodiments of such methods are described in PCT Publication No. WO 2014/028378, the disclosure of which is incorporated by reference herein in its entirety and for all purposes.

Once primers have been added to a discrete entity, e.g., a microdroplet, the discrete entity, e.g., a microdroplet, may be incubated under conditions allowing for PCR. The discrete entity, e.g., a microdroplet, may be incubated on the same microfluidic device as was used to add the primer(s), or may be incubated on a separate device. In certain embodiments, incubating the discrete entity, e.g., a microdroplet, under conditions allowing for PCR amplification is performed on the same microfluidic device used to encapsulate the cells and/or lyse the cells. Incubating the microdroplets may take a variety of forms. In certain aspects, the drops containing the PCR mix may be flowed through a channel that incubates the droplets under conditions effective for PCR. Flowing the microdroplets through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the drops move through such zones, their temperature cycles, as needed for PCR. The precise number of zones, and the respective temperature of each zone, may be determined to achieve the desired PCR amplification.

In other embodiments, incubating the microdroplets may involve the use of a "Megadroplet Array", for example as described in PCT Publication No. WO 2014/028378, the disclosure of which is incorporated by reference herein in its entirety and for all purposes. In such a device, an array of hundreds, thousands, or millions of traps indented into a channel (e.g., a PDMS channel) sit above a thermal system. The channel may be pressurized, thereby preventing gas from escaping. The height of the microfluidic channel is smaller than the diameter of the discrete entities, e.g., drops, causing discrete entities to adopt a flattened pancake shape. When a discrete entity flows over an unoccupied indentation, it adopts a lower, more energetically favorable, radius of curvature, leading to a force that pulls the discrete entity entirely into the trap. By flowing discrete entities as a close pack, it is ensured that all traps on the array are occupied. The entire device may be thermal cycled using a heater.

In certain aspects, the heater includes a Peltier plate, heat sink, and control computer. The Peltier plate allows for the heating or cooling of the chip above or below room temperature by controlling the applied current. To ensure controlled and reproducible temperature, a computer may monitor the temperature of the array using integrated temperature probes, and may adjust the applied current to heat and cool as needed. A metallic (e.g. copper) plate allows for uniform application of heat and dissipation of excess heat during cooling cycles, enabling cooling from about 95° C. to about 60° C. in under about one minute.

Methods of the disclosure may also include introducing one or more probes to the microdroplet. As used herein with respect to nucleic acids, the term "probe" refers to a labeled oligonucleotide which forms a duplex structure with a sequence in the target nucleic acid, due to complementarity of at least one sequence in the probe with a sequence in the target region. Probes of interest include, but are not limited to, TaqMan® probes (e.g., as described in Holland, P. M.; Abramson, R. D.; Watson, R.; Gelfand, D. H. (1991). "Detection of specific polymerase chain reaction product by utilizing the 5'----3' exonuclease activity of *Thermus aquaticus* DNA polymerase". PNAS, 88 (16): 7276-7280).

In some embodiments of the subject methods, an RT-PCR based assay is used to detect the presence of certain transcripts of interest, e.g., oncogene(s), present in cells. In such embodiments, reverse transcriptase and any other reagents necessary for cDNA synthesis are added to the discrete entity, e.g., microdroplet, in addition to the reagents used to carry out PCR described herein (collectively referred to as the "RT-PCR reagents"). The RT-PCR reagents are added to the discrete entity, e.g., microdroplet, using any of the methods described herein. Once reagents for RT-PCR have been added to a discrete entity, e.g., microdroplet, the microdroplet may be incubated under conditions allowing for reverse transcription followed by conditions allowing for PCR as described herein. The microdroplet may be incubated on the same microfluidic device as was used to add the RT-PCR reagents, or may be incubated on a separate device. In certain embodiments, incubating the microdroplet under conditions allowing for RT-PCR is performed on the same microfluidic device used to encapsulate the cells and lyse the cells.

In certain embodiments, the reagents added to the microdroplet for RT-PCR or PCR further includes a fluorescent DNA probe capable of detecting real-time RT-PCR or PCR products. Any suitable fluorescent DNA probe can be used including, but not limited to SYBR Green, TaqMan®, Molecular Beacons and Scorpion probes. In certain embodiments, the reagents added to the microdroplet include more than one DNA probe, e.g., two fluorescent DNA probes, three fluorescent DNA probes, or four fluorescent DNA probes. The use of multiple fluorescent DNA probes allows for the concurrent measurement of RT-PCR or PCR products in a single reaction.

Furthermore, examples of PCR-based assays of interest which may be employed according to the subject embodiments, include, but are not limited to, quantitative PCR (qPCR), quantitative fluorescent PCR (QF-PCR), multiplex fluorescent PCR (MF-PCR), real time PCR (RT-PCR), single cell PCR, PCR-RFLP/RT-PCR-RFLP, hot start PCR, nested PCR, in situ polony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA).

Multiplexing:

In various aspects of the subject methods, multiple biomarkers may be detected and analyzed for a particular discrete entity or one or more components thereof, e.g., cell(s) encapsulated therein. Biomarkers detected may include, but are not limited to, one or more proteins, transcripts and/or genetic signatures in a cell's genome or combinations thereof. With standard fluorescence based detection, the number of biomarkers that can be simultaneously interrogated may be limited to the number of fluorescent dyes that can be independently visualized within each discrete entity, e.g., microdroplet. Accordingly, the use of nucleic acid barcodes as described herein greatly increases the level of multiplexing which can be achieved using the disclosed methods.

In certain embodiments, the number of biomarkers that can be individually detected within a particular discrete entity, e.g., a microdroplet, can be increased using non-barcode based methods or non-barcode based methods in combination with one or more barcode-based methods described herein. For example, this may be accomplished by segregation of dyes to different parts of the discrete entity, e.g., a microdroplet. In particular embodiments, beads (e.g. LUMINEX® beads) conjugated with dyes and probes (e.g., nucleic acid or antibody probes) may be encapsulated in the discrete entity, e.g., microdroplet to increase the number of biomarkers analyzed. In another embodiment, fluorescence polarization may be used to achieve a greater number of detectable signals for different biomarkers for a single cell. For example, fluorescent dyes may be attached to various probes and the discrete entity, e.g., microdroplet, may be visualized under different polarization conditions. In this way, the same colored dye can be utilized to provide a signal for different probe targets for a single cell. The use of fixed and/or permeabilized cells also may allow for increased levels of multiplexing. For example, labeled antibodies may be used to target protein targets localized to cellular components while labeled PCR and/or RT-PCR products are free within a discrete entity, e.g., microdroplet. This allows for dyes of the same color to be used for antibodies and for amplicons produced by RT-PCR.

Detecting PCR Products:

The manner in which PCR products can be detected according to the subject methods may vary. As discussed herein nucleic acid barcode sequences and UMIs can be used to identify PCR products via sequencing and correct for amplification bias as needed. In addition to detection via sequencing of barcode containing nucleic acids, various non-barcode based detection methods may be utilized in connection with the disclosed methods, including, e.g., the use one or more fluorescent dyes. Such fluorescent dyes may be divided into families, such as fluorescein and its derivatives; rhodamine and its derivatives; cyanine and its derivatives; coumarin and its derivatives; Cascade Blue and its derivatives; *Lucifer* Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa fluor-355, Alexa Fluor 488, Alexa Fluor 532, Alexa Fluor 546, Alexa Fluor-555, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine), carboxy tetramethylrhodamine (TAMRA), carboxy-X-rhodamine (ROX), LIZ, VIC, NED, PET, SYBR, PicoGreen, RiboGreen, and the like. Descriptions of fluorophores and their use, can be found in, among other places, R. Haugland, Handbook of Fluorescent Probes and Research Products, 9th ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va.

In practicing the subject methods, therefore, a component may be detected based upon, for example, a change in fluorescence. In certain aspects, the change in fluorescence is due to fluorescence resonance energy transfer (FRET). In this approach, a special set of primers may be used in which the 5' primer has a quencher dye and the 3' primer has a fluorescent dye. These dyes can be arranged anywhere on the primers, either on the ends or in the middles. Because the primers are complementary, they will exist as duplexes in solution, so that the emission of the fluorescent dye will be quenched by the quencher dye, since they will be in close proximity to one another, causing the solution to appear dark. After PCR, these primers will be incorporated into the long PCR products, and will therefore be far apart from one another. This will allow the fluorescent dye to emit light, causing the solution to become fluorescent. Hence, to detect if a particular target gene is present, one may measure the intensity of the discrete entity, e.g., droplet, at the wavelength of the fluorescent dye. To detect if different target genes, e.g., oncogenes, are present, this would be done with different colored dyes for the different primers. This would cause the discrete entity, e.g., droplet, to become fluorescent at all wavelengths corresponding to the primers of the target genes present in the cell.

Devices and Systems

As indicated above, embodiments of the disclosed subject matter employ systems and/or devices including microfluidic devices. Devices of the subject disclosure include all those described above in association with the subject methods. Microfluidic devices of this disclosure may be characterized in various ways.

In some aspects, for example, microfluidic systems and/or devices are provided which include one or more discrete entity makers, e.g., droplet makers, configured to generate discrete entities, e.g., droplets, as described herein, and/or one or more flow channels. In some aspects, the one or more flow channels are operably connected, e.g., fluidically connected, to the one or more droplet makers and/or are configured to receive one or more droplets therefrom. By "operably connected" and "operably coupled", as used herein, is meant connected in a specific way (e.g., in a manner allowing fluid, e.g., water, to move and/or electric power to be transmitted) that allows a disclosed system or device and its various components to operate effectively in the manner described herein.

As noted above, microfluidic devices may include one or more flow channels, e.g., flow channels which discrete entities may pass into, out of, and/or through. In certain embodiments, flow channels are one or more "micro" channel. Such channels may have at least one cross-sectional dimension on the order of a millimeter or smaller (e.g., less than or equal to about 1 millimeter). For certain applications, this dimension may be adjusted; in some embodiments the at least one cross-sectional dimension is about 500 micrometers or less. In some embodiments, the cross-sectional dimension is about 100 micrometers or less, or about 10 micrometers or less, and sometimes about 1 micrometer or less. A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here. Note that microchannels employed in this disclosure may have two dimensions that are grossly disproportionate—e.g., a rectangular cross-section having a height of about 100-200 micrometers and a width on the order or a centimeter or more. Of course, certain devices may employ channels in which the two or more axes are very similar or even identical in size (e.g., channels having a square or circular cross-section).

Microfluidic devices, in some embodiments of this disclosure, are fabricated using microfabrication technology. Such technology may be employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. Aspects of microfluidic devices include the presence of one or more fluid flow paths, e.g., channels, having dimensions as discussed herein. A microfluidics "system" may include one or more microfluidic devices and associated fluidic connections, electrical connections, control/logic features, etc.

Systems may also include one or more of: (a) a temperature control module for controlling the temperature of one or more portions of the subject devices and/or discrete entities therein and which is operably connected to the microfluidic device(s), (b) a detection means, i.e., a detector, e.g., an optical imager, operably connected to the microfluidic device(s), (c) an incubator, e.g., a cell incubator, operably connected to the microfluidic device(s), and (d) a sequencer operably connected to the microfluidic device(s). The subject systems may also include one or more conveyor configured to move, e.g., convey, a substrate from a first discrete entity, e.g., droplet, receiving position to one or more of (a)-(d).

The subject devices and systems, include one or more sorter for sorting discrete entities, e.g., droplets, into one or more flow channels. Such a sorter may sort and distribute discrete entities, e.g., droplets, based on one or more characteristics of the discrete entities including composition, size, shape, buoyancy, or other characteristics.

Aspects of the devices also include one or more detection means i.e., a detector, e.g., an optical imager, configured for detecting the presence of one or more discrete entities, e.g., droplets, or one or more characteristics thereof, including their composition. In some embodiments, detection means are configured to recognize one or more components of one or more discrete entities, e.g., discrete entities, in one or more flow channel.

In various embodiments, microfluidic devices of this disclosure provide a continuous flow of a fluid medium. Fluid flowing through a channel in a microfluidic device exhibits many unique properties. Typically, the dimensionless Reynolds number is extremely low, resulting in flow that always remains laminar. Further, in this regime, two fluids joining will not easily mix, and diffusion alone may drive the mixing of two compounds.

In addition, the subject devices, in some embodiments, include one or more temperature and/or pressure control module. Such a module may be capable of modulating temperature and/or pressure of a carrier fluid in one or more flow channels of a device. More specifically, a temperature control module may be one or more thermal cycler.

Various features and examples of microfluidic device components suitable for use in connection with the disclosed methods, devices and systems will now be described.

Substrates:

According to the subject disclosure, substrates used in microfluidic devices and/or systems are the supports in which the necessary elements for fluid transport are provided. The basic structure of a substrate may be monolithic, laminated, or otherwise sectioned. Substrates may include one or more flow channels, such as microchannels serving as conduits for molecular libraries and/or reagents. They may also include input ports, output ports, and/or features to assist in flow control.

In certain embodiments, the substrate choice may be dependent on the application and design of the device. Substrate materials may be chosen for their compatibility with a variety of operating conditions. Limitations in microfabrication processes for a given material are also relevant considerations in choosing a suitable substrate. Useful substrate materials which may be employed with the subject disclosure include, e.g., glass, polymers, silicon, metal, ceramics, and/or combinations thereof.

The subject devices, in some embodiments, include one or more polymers. Polymers are useful materials for microfluidic devices because they are amenable to both cost effective and high volume production. Polymers, including polymers for use in accordance with the subject disclosure, can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated device of this disclosure are polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidic devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Surface Treatments and Coatings:

Surface modification may be useful for controlling the functional mechanics (e.g., flow control) of a microfluidic device and may be applied according to the subject disclosure. For example, it may be useful to keep fluidic species from adsorbing to channel walls or for attaching antibodies to the surface for detection of biological components.

Polymer devices in particular tend to be hydrophobic, and thus loading of the channels may be difficult. The hydrophobic nature of polymer surfaces may also make it difficult to control electroosmotic flow (EOF). One technique for coating polymer surface according to the subject disclosure is the application of polyelectrolyte multilayers (PEM) to channel surfaces. PEM involves filling the channel successively with alternating solutions of positive and negative polyelectrolytes allowing for multilayers to form electrostatic bonds. Although the layers typically do not bond to the channel surfaces, they may completely cover the channels even after long-term storage. Another technique for applying a hydrophilic layer on polymer surfaces according to the subject disclosure involves the UV grafting of polymers to the surface of the channels. First grafting sites, radicals, are created at the surface by exposing the surface to UV irradiation while simultaneously exposing the device to a monomer solution. The monomers react to form a polymer covalently bonded at the reaction site.

In some embodiments, glass channels according to the subject disclosure, generally have high levels of surface charge, thereby causing proteins to adsorb and possibly hindering separation processes. In some situations, the disclosure includes applying a polydimethylsiloxane (PDMS) and/or surfactant coating to the glass channels. Other polymers that may be employed to retard surface adsorption include polyacrylamide, glycol groups, polysiloxanes, glyceroglycidoxypropyl, poly(ethyleneglycol) and hydroxyethylated poly(ethyleneimine). Furthermore, subject electroosmotic devices may include a coating bearing a charge that is adjustable in magnitude by manipulating conditions inside of the device (e.g. pH). The direction of the flow can also be selected based on the coating since the coating can either be positively or negatively charged.

Specialized coatings can also be applied according to this disclosure to immobilize certain species on the channel surface—this process is called "functionalizing the surface." For example, a polymethylmethacrylate (PMMA) surface may be coated with amines to facilitate attachment of a variety of functional groups or targets. Alternatively, PMMA surfaces can be rendered hydrophilic through an oxygen plasma treatment process.

Microfluidic Elements:

Microfluidic systems and devices according to the subject disclosure can contain one or more flow channels (such as microchannels), valves, pumps, reactors, mixers and other/or components. Some of these components and their general structures and dimensions are discussed below.

Various types of valves can be applied for flow control in microfluidic devices of this disclosure. These include, but are not limited to passive valves and check valves (membrane, flap, bivalvular, leakage, etc.). Flow rate through these valves are dependent on various physical features of the valve such as surface area, size of flow channel, valve material, etc. Valves also have associated operational and manufacturing advantages/disadvantages that may be taken into consideration during design of a microfluidic device.

Embodiments of the subject devices include one or more micropumps. Micropumps, as with other microfluidic components, are subjected to manufacturing constraints. Typical considerations in pump design include treatment of bubbles, clogs, and durability. Micropumps which may be included in the subject devices include, but are not limited to electric equivalent pumps, fixed-stroke microdisplacement, peristaltic micromembrane and/or pumps with integrated check valves.

Macrodevices rely on turbulent forces such as shaking and stirring to mix reagents. In comparison, such turbulent forces are not practically attainable in microdevices, such as those of the present disclosure, and instead mixing in microfluidic devices is generally accomplished through diffusion. Since mixing through diffusion can be slow and inefficient, microstructures, such as those employed with the disclosed subject matter, are often designed to enhance the mixing process. These structures manipulate fluids in a way that increases interfacial surface area between the fluid regions, thereby speeding up diffusion. In certain embodiments, microfluidic mixers are employed. Such mixers may be provided upstream from, and in some cases integrated with, a microfluidic separation device and/or a sorter, of this disclosure.

In some embodiments, the devices and systems of the present disclosure include micromixers. Micromixers may be classified into two general categories: active mixers and passive mixers. Active mixers work by exerting active control over flow regions (e.g. varying pressure gradients, electric charges, etc.). Passive mixers do not require inputted energy and use only "fluid dynamics" (e.g. pressure) to drive fluid flow at a constant rate. One example of a passive mixer involves stacking two flow streams on top of one another separated by a plate. The flow streams are contacted with each other once the separation plate is removed. The stacking of the two liquids increases contact area and decreases diffusion length, thereby enhancing the diffusion process. Mixing and reaction devices can be connected to heat transfer systems if heat management is needed. As with macro-heat exchangers, micro-heat exchanges can either have co-current, counter-current, or cross-flow flow schemes. Microfluidic devices may have channel widths and depths between about 10 µm and about 10 cm. One channel structure includes a long main separation channel, and three shorter "offshoot" side channels terminating in either a buffer, sample, or waste reservoir. The separation channel can be several centimeters long, and the three side channels usually are only a few millimeters in length. Of course, the actual length, cross-sectional area, shape, and branch design of a microfluidic device depends on the application as well other design considerations such as throughput (which depends on flow resistance), velocity profile, residence time, etc.

Microfluidic devices described herein may include one or more electric field generators to perform certain steps of the methods described herein, including, but not limited to, picoinjection, droplet coalescence, selective droplet fusion, and droplet sorting. In certain embodiments, the electric fields are generated using metal electrodes. In particular embodiments, electric fields are generated using liquid electrodes. In certain embodiments, liquid electrodes include liquid electrode channels filled with a conducting liquid (e.g. salt water or buffer) and situated at positions in the microfluidic device where an electric field is desired. In particular embodiments, the liquid electrodes are energized using a power supply or high voltage amplifier. In some embodiments, the liquid electrode channel includes an inlet port so that a conducting liquid can be added to the liquid electrode channel. Such conducting liquid may be added to the liquid electrode channel, for example, by connecting a tube filled with the liquid to the inlet port and applying pressure. In particular embodiments, the liquid electrode channel also includes an outlet port for releasing conducting liquid from the channel. In particular embodiments, the liquid electrodes are used in picoinjection, droplet coalescence, selective droplet fusion, and/or droplet sorting aspects of a microfluidic device described herein. Liquid electrodes may find use, for example, where a material to be injected via application of an electric field is not charged.

In certain embodiments, the width of one or more of the microchannels of the microfluidic device (e.g., input microchannel, pairing mircochannel, pioinjection microchannel, and/or a flow channel upstream or downstream of one or more of these channels) is 100 microns or less, e.g., 90 microns or less, 80 microns or less, 70 microns or less, 60 microns or less, 50 microns or less, e.g., 45 microns or less, 40 microns or less, 39 microns or less, 38 microns or less, 37 microns or less, 36 microns or less, 35 microns or less 34 microns or less, 33 microns or less, 32 microns or less, 31 microns or less, 30 microns or less, 29 microns or less, 28 microns or less, 27 microns or less, 26 microns or less, 25 microns or less, 20 microns or less, 15 microns or less, or 10 microns or less. In some embodiments, the width of one or more of the above microchannels is from about 10 microns to about 15 microns, from about 15 microns to about 20 microns, from about 20 microns to about 25 microns, from about 25 microns to about 30 microns, from about 30 microns to about 35 microns, from about 35 microns to about 40 microns, from about 40 microns to about 45 microns, or from about 45 microns to about 50 microns, from about 50 microns to about 60 microns, from about 60 microns to about 70 microns, from about 70 microns to about 80 microns, from about 80 microns to about 90 microns, or from about 90 microns to about 100 microns. Additional descriptions of various microchannel structures and features which may be utilized in connection with the disclosed methods and devices are provided in PCT Publication No. WO 2014/028378, the disclosure of which is incorporated by reference herein in its entirety and for all purposes.

Concatemerized Merger Architecture: In some embodiments, droplet merger may be utilized in the disclosed methods relating to the barcoding of molecular targets, e.g., nucleic acids. For example, when barcoding the transcriptomes of single cells, droplets containing cell lysate may be merged with droplets containing reagents and barcodes. Normally, droplet merging is achieved by flowing the droplets to be merged into a channel such that they pair, and then applying an electric field to merge the pairs into combined droplets. However, the probability that the pair merges is often less than one so that, for a single merger attempt, some droplets are not merged.

Figure 9:
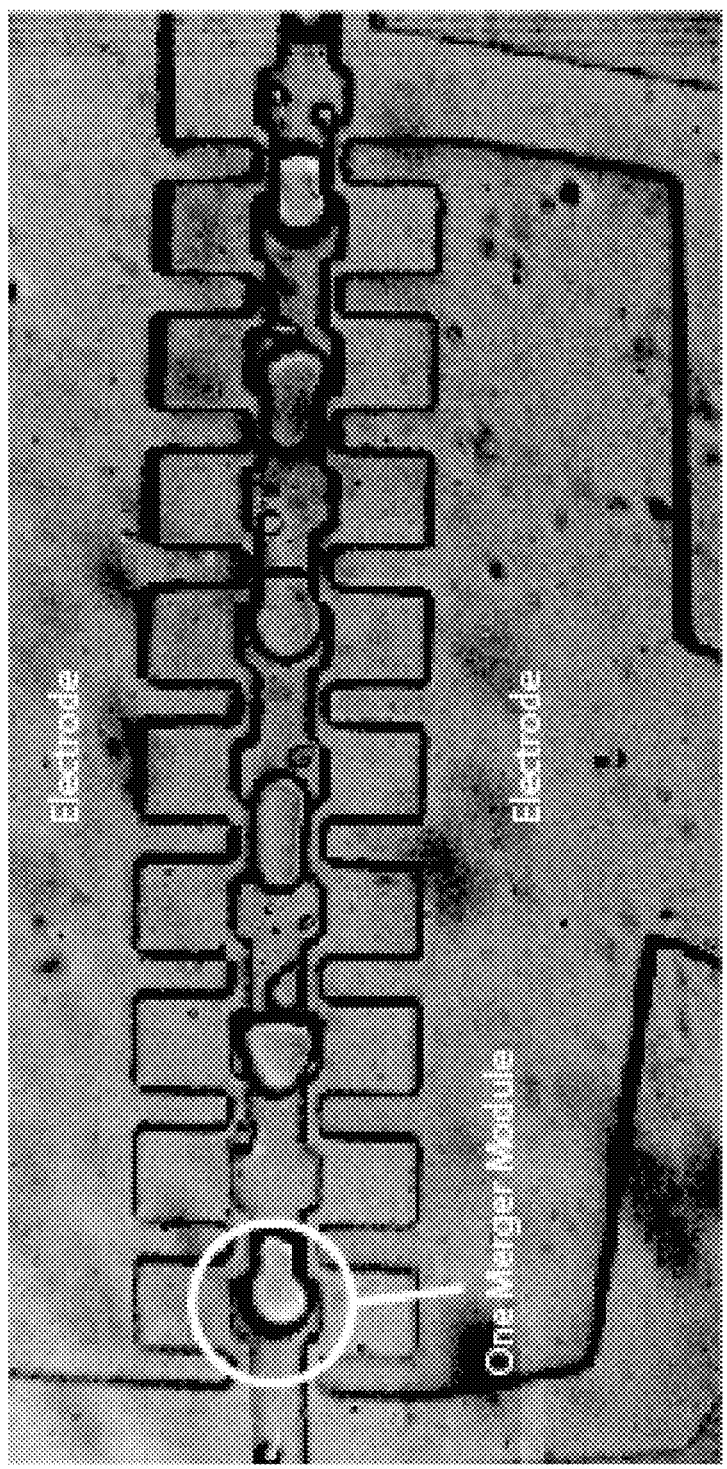
FIG. 9 provides an image of an exemplary microfluidic device including a concatemerized merger architecture including 10 droplet merger structures connected in series.

To address this challenge, a device may be utilized that merges droplets by flowing them into channels with constrictions and expansions. The constrictions are designed to be smaller than the droplets, which causes them, as they flow from the wide part of the channel to the constriction, to change shape and be compressed, which appears to increase the probability of merger. In addition, several of these expansion compression geometries may be utilized in series, providing multiple opportunities for the droplets to merge. An electric field can be applied using different types of electrodes, such as metal electrodes, solder electrodes, and/or liquid electrodes including channels filled with conducting liquid. An exemplary microfluidic device including a concatemerized merger architecture including 10 droplet merger structures connected in series is provided in FIG. 9.

Accordingly, in some embodiments, the present disclosure provides a microfluidic device including a flow channel including a microdroplet merger section including a plurality of channel geometry features in series, wherein each channel geometry feature is associated with one or more electrodes or one or more portions of one or more electrodes configured to apply an electric field in the channel in proximity to the channel geometry feature. In some embodiments, each of the plurality of channel geometry features includes a channel constriction, expansion, bend, or a combination thereof. In some embodiments, each of the plurality of channel geometry features includes a channel constriction, wherein each of the channel constrictions is followed by or preceded by a channel expansion. A channel constriction as described herein can be a decrease in the channel width or height relative to the channel width or height upstream or downstream of the droplet merger section. A channel expansion can be an increase in the channel width or height relative to a constriction as described above.

A droplet merger section as described above, may include any suitable number of channel geometry features, e.g., a constriction and/or expansion, in series. For example, in some embodiments, a merger section includes from 2 to 100, such as from 2 to 5, 2 to 10, 2 to 20, 2 to 30, 2 to 40, 2 to 50, 2 to 60, 2 to 70, 2 to 80, or 2 to 90 channel geometry features, e.g., a constriction and/or expansion, in series. In some embodiments, a merger section includes from 2 to 5, 5 to 10, 10 to 20, 20 to 30, 30 to 40, 40 to 50, 50 to 60, 60 to 70, 70 to 80, 80 to 90, or 90 to 100 channel geometry features, e.g., a constriction and/or expansion, in series.

In some embodiments, each channel geometry feature is positioned in proximity to a first electrode or portion thereof and a second electrode or portion thereof, wherein the first electrode or portion thereof and the second electrode or portion thereof are positioned in a facing relationship on either side of the flow channel.

Fan-Male Mixer:

It is often desirable to mix the contents of one or more droplets. For example, after merging groups of droplets, it is often desirable to mix the contents of the merged droplets. For example, when merging lysate droplets with reagent, it may be desirable to mix the fluids before the droplets are split, otherwise the daughter droplets that are generated will have different concentrations of the fluids. Mixing can be achieved by rapidly flowing droplets down a zigzag channel. However, for certain fluids and viscosities, this approach can be ineffective because the friction of the walls on the droplets does not lead to much flow in the droplets, so that fluids do not mix.

Another method for enhancing mixing in droplets is to flow the droplets though a channel with offshoots, referred to herein as a "fan-blade mixer". In this device, a channel is outfitted with offshoots that are shorter than the height of the channel. Often, the offshoots are designed to be longer than the droplets, but too short for the droplets to flow into. When a droplet passes a blade, the carrier vehicle, e.g., oil, which is unobstructed, flows into the fan blade, creating a cross-current in the carrier fluid in the channel containing the droplet. This cross-current can cause similar currents within the droplet, leading to mixing. As the droplet passes the end of the blade, the carrier vehicle that flowed into the blade flows back into the channel, creating another cross-flow in the opposite direction that again enhances mixing. The droplets are prevented from flowing into the blade because, to do so, they would need to deform and adopt an energetically-unfavorable shape. For certain flow regimes and fluid properties, e.g., at capillary numbers less than 1 (e.g., less than 0.1) this causes the droplets to remain primarily in the main channel, so that primarily oil flows into the blades. To enhance mixing further many fan blades can be added down the length of the channel, providing many opportunities for the effect to mix the contents of the droplets. Without intending to be bound by any particular theory, it is believed that as the drops pass a fan blade, they experience a shear force generated by the inflow of carrier vehicle, e.g., oil, to the fan blade. When capillary number is low, the interfacial tension of the droplet is able to resist this shear and prevent the drop from moving significantly into the fan blade. However, when the capillary number is larger, viscous effects can overcome interfacial tension and the shear generated by the inflow of carrier vehicle can be sufficient to pull a larger portion of the droplet into the fan blade.

For suitable operation, the capillary number should be neither too high nor too low. If too high, the droplet may flow into the fan blade and, possibly, break into pieces. If too low, the inner contents of the droplet may not be adequately mixed. In some embodiments, a capillary number of approximately 0.01 is preferred.

Accordingly, in some embodiments the present disclosure provides a microfluidic device, wherein the microfluidic device includes: (a) a flow channel including a microdroplet mixing section including one or more off-shoot channels in fluid communication with the flow channel, wherein the one or more off-shoot channels are angled between 10° and 170° relative to the centerline of the flow channel, wherein the one or more off-shoot channels have a height which is less than the height of the flow channel and less than the diameter of a droplet to be flowed through the flow channel (e.g., the diameter of a discrete entity or microdroplet as described herein), and wherein the one or more off-shoot channels are configured such that a microdroplet, when flowed through the flow channel in a carrier fluid, is exposed to cross-flow generated as the carrier fluid flows into and out of the one or more off-shoot channels, and wherein the cross-flow is sufficient to generate a flow in the microdroplet that mixes the contents of the microdroplet.

In some embodiments, the one or more off-shoot channels are angled between 45° and 135° relative to the centerline of the flow channel, e.g., between about 50° and about 130°, between about 55° and about 125°, between about 60° and about 120°, between about 65° and about 115°, between about 70" and about 110°, between about 75° and about 100°, between about 80° and about 95°, e.g., about 90°.

In some embodiments, the microdroplet mixing section includes multiple off-shoot channels positioned along the length of the flow channel such that a microdroplet, when flowed through the flow channel in a carrier fluid, is exposed to multiple cross-flows.

Figure 15:
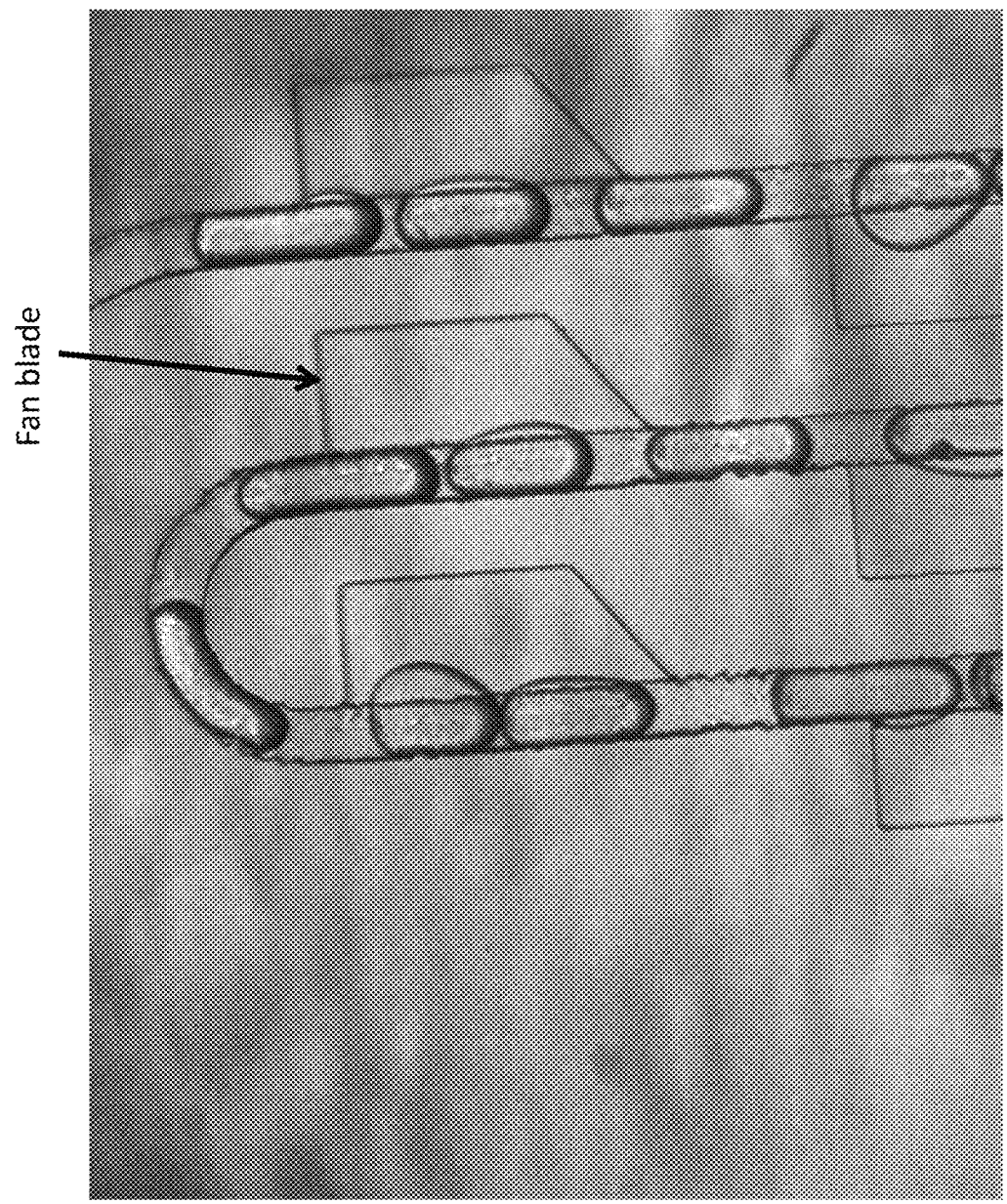
FIG. 15 provides an image of a fan-blade mixer which may be utilized in connection with the methods and devices described herein.

In some embodiments, the width of the one or more off-shoot channels is greater than the diameter of a microdroplet (e.g., the diameter of a discrete entity or microdroplet as described herein) to be flowed through the flow channel. An exemplary embodiment of a fan-blade mixer is shown in FIG. 15. As shown in FIG. 15, a microfluidic device channel may be configured to include multiple "fan-blades" which extend from the main flow channel. In addition, as shown in FIG. 15, such "fan-blades" may alternate in a spaced-apart relationship, with a first "fan-blade" on one side of the channel and a second "fan-blade" on an opposite side of the channel. Such "fan-blades" may alternate along a length of a flow channel, e.g., along the length of an S-shaped mixing channel.

Methods of Fabrication:

According to the disclosed embodiments, microfabrication processes differ depending on the type of materials used in the substrate and/or the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition):

According to embodiments of the disclosed subject matter, a combination of lithography, etching and/or deposition techniques may be used to make microcanals and microcavities out of glass, silicon and other "hard" materials. Technologies based on the above techniques may be applied in fabrication of devices in the scale of 0.1-500 micrometers.

Microfabrication techniques based on semiconductor fabrication processes are generally carried out in a clean room. The quality of the clean room is classified by the number of particles<4 µm in size in a cubic inch. Typical clean room classes for MEMS microfabrication may be 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 µm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate— area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 µm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features are usually sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used may have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100° C.

Polymers/Plastics:

A variety of techniques may be employed for micromachining plastic substrates in accordance with the subject embodiments. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In microinjection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is suited for microchannels between about 5 μm and 500 μm. Specific properties of PDMS make it suitable for microfluidic purposes. Such properties include:
1) It is optically clear which allows for visualization of the flows.
2) PDMS, when mixed with a proper amount of reticulating agent, has elastomeric qualities that facilitates keeping microfluidic connections "watertight."
3) Valves and pumps using membranes can be made with PDMS because of its elasticity.
4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma.
5) PDMS is permeable to gas. Filling of the channel with liquids is facilitated even when there are air bubbles in the canal because the air bubbles are forced out of the material. Additionally, PDMS is also permeable to non polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180° C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials, such as stainless steel, make durable mold inserts and can be micromachined to form structures down to the 10-μm range. Various other micromachining techniques for microfabrication exist including μ-Electro Discharge Machining (μ-EDM), μ-milling, focused ion beam milling. μ-EDM allows the fabrication of 3-dimensional structures in conducting materials. In μ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices must be closed up before they can become functional. Common problems in the bonding process for microfluidic devices include the blocking of channels and changes in the physical parameters of the channels. Lamination is one method used to seal plastic microfluidic devices. In one lamination process, a PET foil (about 30 µm) coated with a melting adhesive layer (typically 5-10 µm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65° C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

One nucleic acid amplification technique described herein is a polymerase chain reaction (PCR). However, in certain embodiments, non-PCR amplification techniques may be employed such as various isothermal nucleic acid amplification techniques; e.g., real-time strand displacement amplification (SDA), rolling-circle amplification (RCA) and multiple-displacement amplification (MDA).

Regarding PCR amplification modules, it will be necessary to provide to such modules at least the building blocks for amplifying nucleic acids (e.g., ample concentrations of four nucleotides), primers, polymerase (e.g., Taq), and appropriate temperature control programs). The polymerase and nucleotide building blocks may be provided in a buffer solution provided via an external port to the amplification module or from an upstream source. In certain embodiments, the buffer stream provided to the sorting module contains some of all the raw materials for nucleic acid amplification. For PCR in particular, precise temperature control of the reacting mixture is extremely important in order to achieve high reaction efficiency. One method of on-chip thermal control is Joule heating in which electrodes are used to heat the fluid inside the module at defined locations. The fluid conductivity may be used as a temperature feedback for power control.

In certain aspects, the discrete entities, e.g., microdroplets, containing the PCR mix may be flowed through a channel that incubates the discrete entities under conditions effective for PCR. Flowing the discrete entities through a channel may involve a channel that snakes over various temperature zones maintained at temperatures effective for PCR. Such channels may, for example, cycle over two or more temperature zones, wherein at least one zone is maintained at about 65° C. and at least one zone is maintained at about 95° C. As the discrete entities move through such zones, their temperature cycles, as needed for PCR. The precise number of zones, and the respective temperature of each zone, may be readily determined by those of skill in the art to achieve the desired PCR amplification.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-443 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A method of introducing multiple copies of a nucleic acid barcode sequence into a discrete entity, the method including:
    encapsulating a plurality of nucleic acid target molecules in a discrete entity;
    introducing into the discrete entity a cell including multiple copies of a nucleic acid barcode sequence;
    lysing the cell to release the multiple copies of the nucleic acid barcode sequence in the discrete entity; and
    subjecting the discrete entity to conditions sufficient for enzymatic incorporation of the nucleic acid barcode sequence into the plurality of nucleic acid target molecules or amplification products thereof
2. The method of 1, wherein the cell is a bacterial cell.
3. The method of 1, wherein the cell is a fungal cell.
4. The method of any one of 1-3, wherein the cell includes multiple plasmids, each plasmid including the nucleic acid barcode sequence.
5. The method of any one of 1-4, wherein the subjecting includes introducing polymerase extension reagents and/or polymerase amplification reagents into the discrete entity.
6. The method of any one of 1-5, including lysing a target cell to provide the plurality of nucleic acid target molecules.
7. The method of any one of 1-6, wherein the cell including multiple copies of the nucleic acid barcode sequence is selected from a library of nucleic acid barcode-containing cells.
8. The method of 7, wherein each cell in the library includes multiple copies of a single nucleic acid barcode sequence.
9. The method of any one of 1-8, wherein the method includes preparing the library of nucleic acid barcode-containing cells by
    generating a library of nucleic acid barcode sequences;
    incorporating individual nucleic acid barcode sequences from the library of nucleic acid barcode sequences into individual cells; and
    subjecting the individual cells to conditions sufficient for the generation of multiple copies of the individual nucleic acid barcode sequences in the individual cells.

10. The method of any one of 1-9, wherein the method includes
    releasing from the discrete entity the plurality of nucleic acid target molecules or amplification products thereof including the nucleic acid barcode sequence;
    sequencing the nucleic acid molecules released from the discrete entity; and
    identifying the sequenced nucleic acid molecules as originating from the discrete entity based on the presence of the nucleic acid barcode sequence.
11. The method of any one of 1-10, wherein the plurality of nucleic acid target molecules in the discrete entity originate from a single cell.
12. The method of any one of 1-11, wherein the discrete entity is a microdroplet.
13. A method of introducing multiple copies of a nucleic acid barcode sequence into a discrete entity, the method including:
    encapsulating a plurality of nucleic acid target molecules in a first discrete entity;
    encapsulating a cell in a second discrete entity, wherein the cell includes multiple copies of a nucleic acid barcode sequence;
    merging the first and second discrete entities; and
    subjecting the merged discrete entities to conditions sufficient for enzymatic incorporation of the nucleic acid barcode sequence into the plurality of nucleic acid target molecules or amplification products thereof
14. The method of 13, wherein the cell is a bacterial cell.
15. The method of 13, wherein the cell is a fungal cell.
16. The method of any one of 13-15, wherein the cell includes multiple plasmids, each plasmid including the nucleic acid barcode sequence.
17. The method of any one of 13-16, wherein the subjecting includes introducing polymerase extension reagents and/or polymerase amplification reagents into the first discrete entity.
18. The method of any one of 13-17, including lysing a target cell to provide the plurality of nucleic acid target molecules.
19. The method of any one of 13-18, wherein the second discrete entity is a microdroplet and the step of encapsulating the cell in the second discrete entity includes
    flowing a plurality of cells through a channel of a microfluidic device, the microfluidic device including a droplet generator in fluid communication with the channel, under conditions sufficient to effect inertial ordering of the cells in the channel, thereby providing periodic injection of the cells into the droplet generator; and
    matching the periodicity of the injection with the periodicity of droplet generation of the droplet generator, thereby encapsulating individual cells in individual microdroplets using the droplet generator.
20. The method of any one of 13-19, wherein the cell including multiple copies of the nucleic acid barcode sequence is selected from a library of nucleic acid barcode-containing cells.
21. The method of 20, wherein each cell in the library includes multiple copies of a single nucleic acid barcode sequence.
22. The method of any one of 20-21, wherein the method includes preparing the library of nucleic acid barcode-containing cells by
    generating a library of nucleic acid barcode sequences;
    incorporating individual nucleic acid barcode sequences from the library of nucleic acid barcode sequences into individual cells; and
    subjecting the individual cells to conditions sufficient for the generation of multiple copies of the individual nucleic acid barcode sequences in the individual cells.
23. The method of any one of 13-22, wherein the method includes
    releasing from the first discrete entity the plurality of nucleic acid molecules or amplification products thereof including the nucleic acid barcode sequence;
    sequencing the nucleic acid molecules released from the first discrete entity; and
    identifying the sequenced nucleic acid molecules as originating from the first discrete entity based on the presence of the nucleic acid barcode sequence.
24. The method of any one of 13-23, wherein the plurality of nucleic acid target molecules in the first discrete entity originate from a single cell.
25. The method of any one of 13-24, wherein the first and second discrete entities are microdroplets.
26. A method of introducing multiple copies of a nucleic acid barcode sequence into a discrete entity, the method including:
    encapsulating a plurality of nucleic acid target molecules in a discrete entity;
    introducing into the discrete entity a porous bead including multiple copies of a nucleic acid barcode sequence, wherein the multiple copies of the nucleic acid barcode sequence are distributed at least in part on surfaces defined by one or more pores of the porous bead; and
    subjecting the discrete entity to conditions sufficient for enzymatic incorporation of the nucleic acid barcode sequence into the plurality of nucleic acid target molecules or amplification products thereof
27. The method of 26, wherein the subjecting includes introducing polymerase extension reagents and/or polymerase amplification reagents into the discrete entity.
28. The method of 26 or 27, including lysing a target cell to provide the plurality of nucleic acid target molecules.
29. The method of any one of 26-28, wherein the porous bead including multiple copies of the nucleic acid barcode sequence is selected from a library of nucleic acid barcode-containing porous beads.
30. The method of 29, wherein each porous bead in the library includes multiple copies of a single nucleic acid barcode sequence.
31. The method of any one of 26-30, wherein the method includes
    releasing from the discrete entity the plurality of nucleic acid molecules or amplification products thereof including the nucleic acid barcode sequence;
    sequencing the nucleic acid molecules released from the discrete entity; and
    identifying the sequenced nucleic acid molecules as originating from the discrete entity based on the presence of the nucleic acid barcode sequence.
32. The method of any one of 26-31, wherein the plurality of nucleic acid target molecules in the discrete entity originate from a single cell.

33. The method of any one of 26-32, including exposing the porous bead to a temperature above the melting point of the bead for a time sufficient to result in melting of the porous bead and release of the multiple copies of a nucleic acid barcode sequence.

34. The method of any one of 26-33, wherein the discrete entity is a microdroplet.

35. A method of introducing multiple copies of a nucleic acid barcode sequence into a discrete entity, the method including:
    encapsulating a plurality of nucleic acid target molecules in a first discrete entity;
    encapsulating a bead in a second discrete entity, wherein the second discrete entity is a microdroplet and the bead includes multiple copies of a nucleic acid barcode sequence on a surface thereof, and wherein the step of encapsulating the bead in the second discrete entity includes
        flowing a plurality of beads through a channel of a microfluidic device, the microfluidic device including a droplet generator in fluid communication with the channel, under conditions sufficient to effect inertial ordering of the beads in the channel, thereby providing approximately periodic injection of the beads into the droplet generator; and
        approximately matching the periodicity of the injection with the periodicity of droplet generation of the droplet generator, thereby encapsulating individual beads in individual microdroplets using the droplet generator;
    merging the first and second discrete entities; and
    subjecting the merged discrete entities to conditions sufficient for enzymatic incorporation of the nucleic acid barcode sequence into the plurality of nucleic acid target molecules or amplification products thereof 36. The method of 35, wherein the subjecting includes introducing polymerase extension reagents and/or polymerase amplification reagents into the first discrete entity.

37. The method of 35 or 36, including lysing a target cell to provide the plurality of nucleic acid target molecules.

38. The method of any one of 35-37, wherein the bead including multiple copies of the nucleic acid barcode sequence on a surface thereof is selected from a library of nucleic acid barcode-containing beads.

39. The method of 38, wherein each bead in the library includes multiple copies of a single nucleic acid barcode sequence.

40. The method of any one of 35-39, wherein the method includes
    releasing from the first discrete entity the plurality of nucleic acid molecules or amplification products thereof including the nucleic acid barcode sequence;
    sequencing the nucleic acid molecules released from the first discrete entity; and
    identifying the sequenced nucleic acid molecules as originating from the first discrete entity based on the presence of the nucleic acid barcode sequence.

41. The method of any one of 35-40, wherein the plurality of nucleic acid target molecules in the first discrete entity originate from a single cell.

42. The method of any one of 35-41, wherein the first and second discrete entities are microdroplets.

43. A method of introducing multiple copies of a nucleic acid barcode sequence into a discrete entity, the method including:
    encapsulating a plurality of nucleic acid target molecules in a discrete entity;
    incorporating a unique molecular identifier (UMI) into each of the plurality of nucleic acid target molecules prior to or subsequent to the encapsulating;
    introducing into the discrete entity a bead including multiple copies of a nucleic acid barcode sequence on a surface thereof and
    subjecting the discrete entity to conditions sufficient for enzymatic incorporation of the nucleic acid barcode sequence into the plurality of nucleic acid target molecules or amplification products thereof 44. The method of 43, wherein the subjecting includes introducing polymerase extension reagents and/or polymerase amplification reagents into the discrete entity.

45. The method of 43 or 44, including lysing a target cell to provide the plurality of nucleic acid target molecules.

46. The method of any one of 43-45, wherein the bead including multiple copies of the nucleic acid barcode sequence is selected from a library of nucleic acid barcode-containing beads.

47. The method of 46, wherein each bead in the library includes multiple copies of a single nucleic acid barcode sequence.

48. The method of any one of 43-47, wherein the method includes
    amplifying the plurality of nucleic acid molecules including the nucleic acid barcode sequence;
    releasing from the discrete entity the plurality of nucleic acid molecules or amplification products thereof including the nucleic acid barcode sequence;
    sequencing the nucleic acid molecules released from the discrete entity;
    correcting for amplification bias by aggregating sequencing reads for duplicate UMIs; and
    identifying the sequenced nucleic acid molecules as originating from the discrete entity based on the presence of the nucleic acid barcode sequence.

49. The method of any one of 43-48, wherein the plurality of nucleic acid target molecules in the discrete entity originate from a single cell.

50. The method of any one of 43-49, wherein the bead is a porous bead and the multiple copies of the nucleic acid barcode sequence are distributed at least in part on surfaces defined by one or more pores of the porous bead.

51. The method of any one of 43-50, wherein the discrete entity is a microdroplet.

52. A method of introducing multiple copies of a nucleic acid barcode sequence into a discrete entity, the method including:
    encapsulating a plurality of nucleic acid target molecules in a first discrete entity;
    encapsulating a bead in a second discrete entity, wherein the second discrete entity is a microdroplet and the bead includes multiple copies of a nucleic acid barcode sequence on a surface thereof, and wherein the step of encapsulating the bead in the second discrete entities includes
        flowing a plurality of beads through a channel of a microfluidic device, the microfluidic device including a droplet generator in fluid communication with the channel, encapsulating one or more beads in one or more discrete entities produced by the droplet generator, and
sorting the one or more discrete entities produced by the droplet generator to remove discrete entities which do not include one or more beads;
merging the first and second discrete entities; and
subjecting the merged discrete entities to conditions sufficient for enzymatic incorporation of the nucleic acid barcode sequence into the plurality of nucleic acid target molecules or amplification products thereof
53. The method of 52, wherein the subjecting includes introducing polymerase extension reagents and/or polymerase amplification reagents into the first discrete entity.
54. The method of 52 or 53, including lysing a target cell to provide the plurality of nucleic acid target molecules.
55. The method of any one of 52-54, wherein the bead including multiple copies of the nucleic acid barcode sequence on a surface thereof is selected from a library of nucleic acid barcode-containing beads.
56. The method of 55, wherein each bead in the library includes multiple copies of a single nucleic acid barcode sequence.
57. The method of any one of 52-56, wherein the method includes
releasing from the first discrete entity the plurality of nucleic acid molecules or amplification products thereof including the nucleic acid barcode sequence;
sequencing nucleic acid molecules released from the first discrete entity; and
identifying the sequenced nucleic acid molecules as originating from the first discrete entity based on the presence of the nucleic acid barcode sequence.
58. The method of any one of 52-57, wherein the plurality of nucleic acid target molecules in the first discrete entity originate from a single cell.
59. The method of any one of 52-58, wherein the first and second discrete entities are microdroplets.
60. A method for preparing single stranded barcodes, the method including:
encapsulating a plurality of nucleic acid target molecules in a discrete entity;
introducing a circular nucleic acid molecule including a nucleic acid barcode sequence into the discrete entity;
subjecting the discrete entity to conditions sufficient for rolling circle amplification of the nucleic acid barcode sequence, such that a concatemer of the nucleic acid barcode sequence is produced; and
subjecting the discrete entity to conditions sufficient for enzymatic incorporation of the nucleic acid barcode sequence into the plurality of nucleic acid target molecules or amplification products thereof
61. The method of 60, wherein subjecting the discrete entity to conditions sufficient for enzymatic incorporation of the nucleic acid barcode sequence into the plurality of nucleic acid targets molecules or amplification products thereof includes introducing polymerase extension reagents and/or polymerase amplification reagents into the discrete entity.
62. The method of 60 or 61, including lysing a target cell to provide the plurality of nucleic acid target molecules.
63. The method of any one of 60-62, wherein the circular nucleic acid molecule including a nucleic acid barcode sequence is selected from a library of circular nucleic acid molecules including a nucleic acid barcode sequence.
64. The method of any one of 60-63, wherein the discrete entity is a microdroplet.
65. A method for preparing single stranded barcodes, the method including:
encapsulating a plurality of nucleic acid target molecules in a discrete entity;
introducing a DNA molecule including a nucleic acid barcode sequence into the discrete entity;
subjecting the discrete entity to conditions sufficient for amplification via Transcription Chain Reaction (TCR) of the nucleic acid barcode sequence, such that a plurality of single stranded copies of the nucleic acid barcode sequence are produced; and
subjecting the discrete entity to conditions sufficient for enzymatic incorporation of the nucleic acid barcode sequence into the plurality of nucleic acid target molecules or amplification products thereof
66. The method of 65, wherein subjecting the discrete entity to conditions sufficient for enzymatic incorporation of the nucleic acid barcode sequence into the plurality of nucleic acid targets molecules or amplification products thereof includes introducing polymerase extension reagents and/or polymerase amplification reagents into the discrete entity.
67. The method of 65 or 66, including lysing a target cell to provide the plurality of nucleic acid target molecules.
68. The method of any one of 65-67, wherein the discrete entity is a microdroplet.
69. A method for preparing single stranded barcodes, the method including:
encapsulating a plurality of nucleic acid target molecules in a discrete entity;
introducing a DNA molecule including a nucleic acid barcode sequence into the discrete entity;
subjecting the discrete entity to conditions sufficient for amplification via rolling circle Transcription Chain Reaction (rcTCR) of the nucleic acid barcode sequence, such that a plurality of single stranded copies of the nucleic acid barcode sequence are produced; and
subjecting the discrete entity to conditions sufficient for enzymatic incorporation of the nucleic acid barcode sequence into the plurality of nucleic acid target molecules or amplification products thereof
70. The method of 69, wherein subjecting the discrete entity to conditions sufficient for enzymatic incorporation of the nucleic acid barcode sequence into the plurality of nucleic acid target molecules or amplification products thereof includes introducing polymerase extension reagents and/or polymerase amplification reagents into the discrete entity.
71. The method of 69 or 70, including lysing a target cell to provide the plurality of nucleic acid target molecules.
72. The method of any one of 69-71, wherein the discrete entity is a microdroplet.
73. A method introducing multiple copies of a nucleic acid barcode sequence into a discrete entity, the method including:
encapsulating individual nucleic acid barcode sequences in a population of discrete entities at limiting dilution such that each individual discrete entity of the
population of discrete entities statistically contains either zero or one nucleic acid barcode sequence;

enzymatically amplifying the nucleic acid barcode sequences in the population of discrete entities to provide a plurality of discrete entities wherein each discrete entity of the plurality of discrete entities includes multiple copies of the individual nucleic acid barcode sequence for that discrete entity;

introducing into one or more of the plurality of discrete entities a plurality of nucleic acid target molecules; and subjecting the one or more of the plurality of discrete entities to conditions sufficient for enzymatic incorporation of the nucleic acid barcode sequence into the plurality of nucleic acid target molecules or amplification products thereof 74. The method of 73, including sorting the population of discrete entities prior to the introducing to remove discrete entities not including a nucleic acid barcode sequence.

75. The method of 73 or 74, wherein the subjecting includes introducing polymerase extension reagents and/or polymerase amplification reagents into the discrete entity.

76. The method of any one of 73-75, including lysing a target cell to provide the plurality of nucleic acid target molecules.

77. The method of any one of 73-76, wherein the discrete entity is a microdroplet.

78. A method of preparing a nucleic acid barcode library, the method including:

encapsulating in a population of discrete entities
  a plurality of first nucleic acid molecules, each of the first nucleic acid molecules including a first nucleic acid barcode sub-sequence and a first linkage sequence, and
  a plurality of second nucleic acid molecules, each of the second nucleic acid molecules including a second nucleic acid barcode sub-sequence and a second linkage sequence, wherein the encapsulating is performed such that at least about 50% of the discrete entities of the population of discrete entities include at least one of the first nucleic acid molecules and at least one of the second nucleic acid molecules; and subjecting the discrete entities to conditions sufficient for enzymatic linkage and/or amplification, such that, for discrete entities including at least one of the first nucleic acid molecules and at least one of the second nucleic acid molecules, linkage and/or amplification products including the sequences of both the first and second nucleic acid molecules are produced, providing composite nucleic acid barcode molecules.

79. The method of 78, wherein the subjecting includes subjecting the discrete entities to conditions sufficient for enzymatic ligation of the first and second linkage sequences.

80. The method of 78, wherein the first and second linkage sequences are at least partially complementary.

81. The method of 78, including:

introducing into discrete entities including at least one composite nucleic acid barcode molecule a plurality of nucleic acid target molecules; and subjecting the discrete entities including a plurality of nucleic acid target molecules and at least one composite nucleic acid barcode molecule to conditions sufficient for enzymatic incorporation of the sequence of the composite nucleic acid barcode molecule into the plurality of nucleic acid target molecules or amplification products thereof.

82. The method of 81, including:

releasing from the discrete entities the plurality of nucleic acid molecules or amplification products thereof including the composite nucleic acid barcode sequence;

sequencing the nucleic acid molecules released from the discrete entities; and identifying the sequenced nucleic acid molecules as originating from a particular discrete entity based on the sequence of the composite nucleic acid barcode sequence.

83. The method of any one of 78-82, wherein the conditions sufficient for enzymatic linkage and/or amplification are conditions sufficient for linkage PCR.

84. The method of any one of 78-83, wherein the discrete entities are microdroplets.

85. A method for barcoding nucleic acid target molecules, the method including:

encapsulating a plurality of nucleic acid target molecules in a discrete entity;

introducing a plurality of unique molecular identifier (UMI) molecules into the discrete entity;

subjecting the discrete entity to conditions sufficient for enzymatic incorporation of a unique UMI molecule sequence into each of a plurality of the plurality of nucleic acid target molecules or an amplification product thereof;

introducing a plurality of different nucleic acid barcode sequences into the discrete entity; and subjecting the discrete entity to conditions sufficient for enzymatic incorporation of one of the plurality of barcode sequences into each of the plurality of nucleic acid target molecules or amplification products thereof or amplification products of the amplification products thereof.

86. The method of 85, including:

releasing from the discrete entity the plurality of nucleic acid molecules or amplification products thereof or amplification products of the amplification products thereof including the sequence of one of the UMIs and one of the barcodes;

sequencing the nucleic acid molecules released from the discrete entities; and identifying the sequenced nucleic acid molecules as originating from a particular discrete entity based on the combination of the sequence of the UMI and the barcode.

87. The method of 85 or 86, wherein the discrete entities are microdroplets.

88. A method for barcoding nucleic acid target molecules, the method including:

attaching a unique molecular identifier (UMI) molecule to each of a plurality of nucleic acid target molecules to provide UMI-labeled nucleic acid target molecules;

enzymatically amplifying the UMI-labeled nucleic acid target molecules to provide amplification products including the sequences of the UMI-labeled nucleic acid target molecules;

encapsulating the amplification products in a plurality of discrete entities;

fragmenting the amplification products in the plurality of discrete entities;

attaching nucleic acid barcode sequences to the fragmented amplification products, wherein the nucleic acid barcode sequences in each discrete entity relate the fragmented amplification products to the discrete entity in which the fragmented amplification products are encapsulated;

releasing from the discrete entities the fragmented amplification products including nucleic acid barcode sequences attached thereto;

sequencing the fragmented amplification products; and bioinformatically reassembling the fragmented amplification products using the sequences of the UMIs and the nucleic acid barcodes sequences to provide the sequence of the nucleic acid target molecules from which the amplification products originated.

89. The method of 88, wherein encapsulating the amplification products in a plurality of discrete entities includes encapsulating the amplification products at limiting dilution in a population of discrete entities such that each of the individual discrete entities of the population of discrete entities contains either zero or one amplification product.

90. The method of 88, wherein amplification products originating from two or more nucleic acid target molecules are encapsulated in the plurality of discrete entities.

91. The method of any one of 88-90, wherein the nucleic acid barcode sequences are generated according to a method as described in one of 78-80.

92. The method of any one of 88-91, wherein the enzymatically amplifying includes enzymatically amplifying via Polymerase Chain Reaction (PCR), Multiple Displacement Amplification (MDA), or Multiple Annealing and Looping-Based Amplification Cycles (MALBAC).

93. The method of any one of 88-92, wherein the bioinformatically reassembling includes computationally grouping by UMI, sequence reads obtained from the sequencing to identify subsets of molecules that occur with similar sequence in different discrete entities and thereby generate an expanded set of sequences that can be used to generate a greater than 1× coverage of the target molecule.

94. The method of any one of 88-93, wherein the attaching of a UMI molecule to each of the plurality of nucleic acid target molecules and the enzymatically amplifying occurs in a reactor, the encapsulating of the amplification products in a plurality of discrete entities occurs in a first microfluidic device, and the attaching of the nucleic acid barcode sequences to the fragmented amplification products occurs in a second microfluidic device.

95. The method of any one of 88-90, wherein the discrete entities are microdroplets.

96. A method for barcoding nucleic acid target molecules, the method including:
introducing into a discrete entity
a nucleic acid target molecule,
a nucleic acid barcode sequence,
a first set of primers configured to amplify a sequence of the nucleic acid target molecule,
a second set of primers configured to amplify a sequence of the nucleic acid barcode sequence, wherein one of the first set of primers includes a sequence which is at least partially complementary to a sequence of one of the second set of primers, and
an enzymatic amplification reagent;

subjecting the discrete entity to conditions sufficient for enzymatic amplification of a sequence of the nucleic acid target molecule and a sequence of the nucleic acid barcode sequence, wherein amplification products having regions of partial sequence homology are produced; and subjecting the discrete entity to conditions sufficient for complementary regions of sequences of the amplification products to hybridize and for the hybridized sequences to be enzymatically extended, thereby providing a product including the amplified sequence of the nucleic acid target molecule and the amplified sequence of the nucleic acid barcode sequence.

97. The method of 96, wherein the introducing includes introducing a plurality of nucleic acid target molecules into the discrete entity.

98. The method of 97, wherein the plurality of nucleic acid target molecules includes nucleic acid target molecules including different sequences.

99. The method of 96, wherein the introducing includes introducing a plurality of nucleic acid barcode sequences into the discrete entity.

100. The method of 99, wherein the plurality of nucleic acid barcode sequences includes nucleic acid barcode sequences including different sequences.

101. The method of any one of 96-100, wherein subjecting the discrete entity to conditions sufficient for enzymatic amplification includes subjecting the discrete entity to thermal cycling.

102. The method of any one of 96-100, wherein subjecting the discrete entity to conditions sufficient for enzymatic amplification includes subjecting the discrete entity to isothermal amplification conditions.

103. The method of any one of 96-102, wherein the method includes incorporating adaptor sequences into the nucleic acid target molecule, and wherein the first set of primers are at least partially complementary to the adaptor sequences.

104. The method of any one of 96-103, wherein the discrete entity is a microdroplet.

105. A method for barcoding nucleic acid target molecules, the method including:
introducing into a discrete entity
a plurality of nucleic acid target molecules,
a plurality of nucleic acid barcode sequences,
first primer sets configured to amplify sequences of the plurality of nucleic acid target molecules,
second primer sets configured to amplify sequences of the plurality of nucleic acid barcode sequences, wherein the first primer sets and the second primer sets include sequences which are at least partially complementary, and
an enzymatic amplification reagent;

subjecting the discrete entity to conditions sufficient for enzymatic amplification of sequences of the plurality of nucleic acid target molecules and sequences of the plurality of nucleic acid barcode sequences, wherein amplification products having regions of partial sequence homology are produced; and subjecting the discrete entity to conditions sufficient for complementary regions of sequences of the amplification products to hybridize and for the hybridized sequences to be enzymatically extended, thereby providing a plurality of products, each including an amplified sequence of one of the plurality of target nucleic molecules and an amplified sequences of one of the plurality of nucleic acid barcode sequences.

106. The method of 105, wherein the plurality of nucleic acid target molecules includes nucleic acid target molecules including different sequences.

107. The method of 105 or 106, wherein the plurality of nucleic acid barcode sequences includes nucleic acid barcode sequences including different sequences.

108. The method of any one of 105-107, wherein subjecting the discrete entity to conditions sufficient for enzymatic amplification includes subjecting the discrete entity to thermal cycling.

109. The method of any one of 105-107, wherein subjecting the discrete entity to conditions sufficient for enzymatic amplification includes subjecting the discrete entity to isothermal amplification conditions.

110. The method of any one of 105-109, wherein the method includes incorporating adaptor sequences into each of the nucleic acid target molecules, and wherein each of the primers of the first primer sets is at least partially complementary to one of the adaptor sequences.

111. The method of any one of 105-110, wherein the discrete entity is a microdroplet.

112. A method for barcoding nucleic acid target molecules, the method including:
generating a library of nucleic acid barcode primers, wherein each nucleic acid barcode primer in the library includes a first sequence sufficient to anneal to a nucleic acid target molecule and a second sequence including a nucleic acid barcode sequence;
combining in each of a plurality of discrete entities one or more nucleic acid barcode primers selected from the library and one or more nucleic acid target molecules, wherein the one or more primers selected from the library for inclusion in each discrete entity includes one or more primers with a first sequence sufficient to anneal to one or more of the nucleic acid target molecules in that discrete entity; and
enzymatically amplifying one or more of the nucleic acid target molecules in each discrete entity using one or more of the nucleic acid barcode primers in that discrete entity,
such that amplification products including a sequence of one of the one or more nucleic acid target molecules and a nucleic acid barcode sequence are produced.

113. The method of 112, wherein the method includes incorporating adaptor sequences into the one or more nucleic acid target molecules, and wherein the one or more primers selected from the library for inclusion in each discrete entity includes one or more primers with a first sequence sufficient to anneal to one or more of the adaptor sequences.

114. The method of 112 or 113, wherein the one or more nucleic acid target molecules are a plurality of nucleic acid target molecules including different sequences.

115. The method of any one of 112-114, wherein each of the plurality of discrete entities includes nucleic acid target molecules including different sequences relative to other discrete entities of the plurality.

116. The method of any one of 112-115, wherein the one or more nucleic acid barcode primers selected from the library are a plurality of nucleic acid barcode primers including different sequences.

117. The method of any one of 112-116, wherein each of the plurality of discrete entities includes nucleic acid barcode primers including different sequences relative to other discrete entities of the plurality.

118. The method of any one of 112-117, wherein the enzymatically amplifying includes subjecting the plurality of discrete entities to thermal cycling.

119. The method of any one of 112-117, wherein the enzymatically amplifying includes subjecting the plurality of discrete entities to isothermal amplification conditions.

120. The method of any one of 112-119, wherein the discrete entities are microdroplets.

121. A method for barcoding nucleic acid target molecules, the method including:
generating a library of nucleic acid barcode sequences;
combining in each of a plurality of discrete entities one or more nucleic acid barcode sequences selected from the library and one or more nucleic acid target molecules; and
enzymatically fragmenting the one or more nucleic acid target molecules in each discrete entity and enzymatically incorporating one or more of the one or more nucleic acid barcode sequences in each discrete entity into fragments of the one or more target nucleic acid molecules or amplification products thereof in that discrete entity.

122. The method of 121, wherein the method includes incorporating adaptor sequences into the one or more nucleic acid target molecules.

123. The method of 121 or 122, wherein the one or more nucleic acid target molecules are a plurality of nucleic acid target molecules including different sequences.

124. The method of any one of 121-123, wherein each of the plurality of discrete entities includes nucleic acid target molecules including different sequences relative to other discrete entities of the plurality.

125. The method of any one of 121-124, wherein the one or more nucleic acid barcode sequences selected from the library are a plurality of nucleic acid barcode sequences including different sequences.

126. The method of any one of 121-125, wherein each of the plurality of discrete entities includes nucleic acid barcode sequences including different sequences relative to other discrete entities of the plurality.

127. The method of any one of 121-125, wherein the enzymatically fragmenting and/or incorporating steps utilize one or more of the following enzymes: a transposase, a Fragmentase®, a ligase, a polymerase, and a reverse transcriptase.

128. The method of any one of 121-125, wherein the enzymatically fragmenting and/or incorporating steps utilize an integrase or a recombinase.

129. The method of any one of 121-128, wherein the discrete entities are microdroplets.

130. A method for barcoding nucleic acid target molecules, the method including:
generating a library of nucleic acid barcode sequences;
combining in each of a plurality of discrete entities one or more nucleic acid barcode sequences selected from the library and one or more nucleic acid target molecules; and
enzymatically ligating the one or more nucleic acid target molecules in each discrete entity to one or more nucleic acid barcode sequences in that discrete entity.

131. The method of 130, wherein the method includes incorporating adaptor sequences into the one or more nucleic acid target molecules prior to enzymatically ligating.

132. The method of 130 or 131, wherein the one or more nucleic acid target molecules are a plurality of nucleic acid target molecules including different sequences.

133. The method of any one of 130-132, wherein each of the plurality of discrete entities includes nucleic acid target molecules including different sequences relative to other discrete entities of the plurality.

134. The method of any one of 130-132, wherein the one or more nucleic acid barcode sequences selected from the library are a plurality of nucleic acid barcode sequences including different sequences.

135. The method of any one of 130-132, wherein each of the plurality of discrete entities includes nucleic acid barcode sequences including different sequences relative to other discrete entities of the plurality.

136. The method of any one of 130-135, wherein the discrete entities are microdroplets.

137. A method for manipulating microdroplets, the method including:
generating a first plurality of microdroplets and a second plurality of microdroplets;
flowing the first plurality of microdroplets in a channel of a microfluidic device;
splitting each of the first plurality of microdroplets to provide a plurality of reduced-volume microdroplets;
merging each of the plurality of reduced volume microdroplets with a microdroplet of the second plurality of microdroplets, wherein the microdroplets of the second plurality of microdroplets each have a volume that is approximately equal to or less than that of the first plurality of microdroplets.

138. The method of 137, wherein the channel of the microfluidic device includes a droplet splitting architecture.

139. The method of 138, wherein the droplet splitting architecture includes a serial bisection architecture.

140. The method of any one of 137-139, wherein each of the first plurality of microdroplets includes a cell lysate.

141. The method of 140, wherein the method includes lysing a cell in each of the first plurality of microdroplets to provide the cell lysate.

142. The method of any one of 137 to 141, wherein the microdroplets of the second plurality of microdroplets each include one or more reagents configured to facilitate one or more reactions with one or more components of the cell lysate.

143. The method of 142, wherein the one or more reagents include one or more PCR reagents and/or one or more RT-PCR reagents.

144. A microfluidic device including:
a flow channel including a microdroplet merger section including a plurality of channel geometry features in series, wherein each channel geometry feature is associated with one or more electrodes or one or more portions of one or more electrodes configured to apply an electric field in the channel in proximity to the channel geometry feature.

145. The microfluidic device of 144, wherein each of the plurality of channel geometry features includes a channel constriction, expansion, bend, or a combination thereof.

146. The microfluidic device of 145, wherein each of the plurality of channel geometry features includes a channel constriction, and wherein each of the channel constrictions is followed by or preceded by a channel expansion.

147. The microfluidic device of 145 or 146, wherein each constriction is a decrease the channel width or height relative to the channel width or height upstream or downstream of the droplet merger section.

148. The microfluidic device of 147, wherein each channel expansion is an increase in the channel width or height relative to a constriction as set forth in 148.

149. The microfluidic device of any one of 144-148, wherein droplet merger section includes from 2 to 20 of the channel geometry features in series.

150. The microfluidic device of 149, wherein droplet merger section includes from 2 to 10 of the channel geometry features in series.

151. The microfluidic device of 150, wherein droplet merger section includes from 2 to 5 of the channel geometry features in series.

152. The microfluidic device of any one of 144-151, wherein the one or more electrodes are liquid electrodes.

153. The microfluidic device of any one of 144-152, wherein each channel geometry feature is associated with a first electrode or portion thereof and a second electrode or portion thereof, wherein the first electrode or portion thereof and the second electrode or portion thereof are positioned in a facing relationship on either side of the flow channel.

154. A method of merging microdroplets using the microfluidic device of any one of 144-153, wherein the method includes
flowing two or more microdroplets through the microdroplet merger section of the flow channel of the microfluidic device of any one of 144-153, such that the two more microdroplets are positioned in proximity to one of the channel geometry features; and
merging the two or more microdroplets in proximity to one of the channel geometry features via application of an electric field using the one or more electrodes or the one or more portions of the one or more electrodes associated with the channel geometry feature.

155. The method of 154, wherein one of the two or more microdroplets includes a cell lysate.

156. The method of 154, wherein one of the two or more microdroplets includes one or more nucleic acid barcode sequences.

157. A method for merging two or more microdroplets, the method including:
introducing two or more populations of microdroplets into a flow channel of a microfluidic device,
wherein the flow channel includes a microdroplet merger section associated with one or more electrodes or one or more portions of one or more electrodes configured to apply an electric field in the microdroplet merger section of the flow channel,
wherein the two or more populations of microdroplets are introduced into the flow channel at a single junction from two or more separate inlet channels, respectively, and
wherein the two or more populations of microdroplets are introduced into the flow channel such that the microdroplet inputs from each inlet channel at least partially synchronize due to hydrodynamic effects, resulting in the ejection of spaced groups of microdroplets, in which at least some of the spaced groups of microdroplets include a microdroplet from each of the two or more populations of microdroplets;

flowing the spaced groups of microdroplets into the microdroplet merger section; and merging microdroplets within a spaced group by applying an electric field in the microdroplet merger section of the flow channel using the one or more electrodes or the one or more portions of the one or more electrodes.

158. The method of 157, wherein three or more populations of microdroplets are introduced into the flow channel at a single junction from three or more separate inlet channels, respectively, and wherein the three or more populations of microdroplets are introduced into the flow channel such that the microdroplet inputs from each inlet channel at least partially synchronize due to hydrodynamic effects, resulting in the ejection of spaced groups of microdroplets, in which at least some of the spaced groups of microdroplets include a microdroplet from each of the three or more populations of microdroplets.

159. A method for merging two or more liquids, the method including:

introducing a first liquid into a flow channel of a microfluidic device as a stream at least partially in contact with an immiscible phase liquid;

introducing a microdroplet including a second liquid into the flow channel;

merging the microdroplet into the stream, thereby combining the first and second liquids; and inducing the stream including the combined first and second liquids to break into individual microdroplets including the combined first and second liquids.

160. The method of 159, wherein the flow channel includes a microdroplet merger section associated with one or more electrodes or one or more portions of one or more electrodes configured to apply an electric field in the microdroplet merger section of the flow channel, and wherein the method includes applying the electric filed in the microdroplet merger section of the flow channel to merge the microdroplet into the stream.

161. The method of 159 or 160, wherein the first liquid is introduced into the flow channel under dripping conditions.

162. The method of 159 or 160, wherein the first liquid is introduced into the flow channel under jetting conditions.

163. The method of any one of 159-162, wherein the method includes merging multiple microdroplets into the stream prior to inducing the stream to break into individual microdroplets.

164. The method of any one of 159-162, wherein the method includes introducing a second microdroplets including a third liquid into the flow channel, and wherein the inducing includes inducing the stream to break into a plurality of individual microdroplets prior to merging the second microdroplet into the stream.

165. The method of 164 wherein the second and third liquids are the same.

166. The method of any one of 159-162, wherein the method includes introducing one or more additional liquids into the flow channel as either streams or droplets.

167. A microfluidic device including:

a flow channel including a microdroplet mixing section including one or more off-shoot channels in fluid communication with the flow channel, wherein the one or more off-shoot channels are angled between 10° and 170° relative to the centerline of the flow channel, wherein the one or more off-shoot channels have a height which is less than the height of the flow channel and less than the diameter of a droplet to be flowed through the flow channel, and wherein the one or more off-shoot channels are configured such that a microdroplet, when flowed through the flow channel in a carrier fluid, is exposed to cross-flow generated as the carrier fluid flows into and out of the one or more off-shoot channels, and wherein the cross-flow is sufficient to generate a flow in the microdroplet that mixes the contents of the microdroplet.

168. The microfluidic device of 167, wherein the one or more off-shoot channels are angled between 45° and 135° relative to the centerline of the flow channel.

169. The microfluidic device of 168, wherein the one or more off-shoot channels are angled at about 90° relative to the centerline of the flow channel.

170. The microfluidic device of any one of 167-169, wherein the microdroplet mixing section includes multiple off-shoot channels positioned along the length of the flow channel such that a microdroplet, when flowed through the flow channel in a carrier fluid, is exposed to multiple cross-flows.

171. The microfluidic device of any one of 167-170, wherein the width of the one or more off-shoot channels is greater than the diameter of a microdroplet to be flowed through the flow channel.

172. A method of mixing the contents of one or more microdroplets using the microfluidic device of any one of 167-171, wherein the method includes flowing one or more microdroplets in a carrier fluid through the microdroplet mixing section of the flow channel of the microfluidic device of any one of 167-171, wherein the one or more microdroplets are exposed to cross-flow generated as the carrier fluid flows into and out of the one or more off-shoot channels, and wherein the cross-flow is sufficient to generate a flow in the microdroplet that mixes the contents of the one or more microdroplets.

173. A method of barcoding and amplifying RNA from single cells, the method including:

encapsulating individual cells in a population of discrete entities at limiting dilution such that each individual discrete entity of the population of discrete entities statistically contains either zero or one cell;

lysing the cells to release RNA target molecules within the discrete entities;

introducing into each discrete entity a nucleic acid barcode sequence unique to that discrete entity and reagents sufficient for cDNA synthesis and amplification of the resulting cDNA products; and subjecting each discrete entity to conditions sufficient for cDNA synthesis and enzymatic incorporation of the nucleic acid barcode sequence unique to that discrete entity into cDNA amplification products, thereby providing a plurality of discrete entities wherein each discrete entity of the plurality includes cDNA amplification products labeled with a unique nucleic acid barcode sequence relative to the other discrete entities of the plurality.

174. The method of 173, including introducing into each discrete entity reagents sufficient for the enzymatic incorporation of a nucleic acid molecule including a unique molecular identifier (UMI) into each cDNA sequence, wherein the conditions sufficient for enzymatic incorporation of the nucleic acid barcode sequence unique to that discrete entity into cDNA amplification products are sufficient for enzymatic incorporation of the nucleic acid molecule including a unique molecular identifier into each cDNA sequence.

175. The method of 174, wherein the reagents sufficient for the enzymatic incorporation of a nucleic acid molecule including a unique molecular identifier into each cDNA sequence include a template switching oligo including a degenerate sequence.

176. The method of any one of 173-175, wherein the discrete entities are microdroplets.

177. The method of any one of 173-176, wherein the nucleic acid barcode sequences or the UMIs are prepared or introduced according to any one of 1-95.

178. The method of any one of 173-176, wherein the nucleic acid barcode sequences or the UMIs are prepared or introduced according to any one of 96-120 or 130-136.

179. The method of any one of 173-176, wherein the introducing is according to any one of 137-139 or 154-166.

180. The method of any one of 173-176, wherein the method is performed at least in part using a microfluidic device as set forth in any one of 144-153.

181. The method of any one of 173-176, wherein the components of the discrete entities are mixed using a microfluidic device as set forth in any one of 167-172.

182. The method of any one of 173-181, wherein neither the introducing nor the subjecting step occurs in the presence of a bead.

183. The method of any one of 173-182, wherein the amplification is performed using oligonucleotide primers containing a ligand, e.g., a biotin or thiol moiety.

184. The method of any one of 173-183, wherein the encapsulating, lysing and cDNA synthesis steps are performed in a first microfluidic device and the enzymatic incorporation is performed in a second microfluidic device.

185. The method of 184, wherein the enzymatic incorporation includes SOEing PCR.

186. A method of barcoding and amplifying RNA from single cells, the method including:
providing a population of discrete entities, each discrete entity of the population of discrete entities including cell lysate originating from a single cell;
introducing into each discrete entity a nucleic acid barcode sequence unique to that discrete entity and reagents sufficient for cDNA synthesis and amplification of the resulting cDNA products; and
subjecting each discrete entity to conditions sufficient for cDNA synthesis and enzymatic incorporation of the nucleic acid barcode sequence unique to that discrete entity into cDNA amplification products, thereby providing a plurality of discrete entities wherein each discrete entity of the plurality includes cDNA amplification products labeled with a unique nucleic acid barcode sequence relative to the other discrete entities of the plurality.

187. The method of 186, including introducing into each discrete entity reagents sufficient for the enzymatic incorporation of a nucleic acid molecule including a unique molecular identifier (UMI) into each cDNA sequence, wherein the conditions sufficient for enzymatic incorporation of the nucleic acid barcode sequence unique to that discrete entity into cDNA amplification products are sufficient for enzymatic incorporation of the nucleic acid molecule including a unique molecular identifier into each cDNA sequence.

188. The method of 187, wherein the reagents sufficient for the enzymatic incorporation of a nucleic acid molecule including a unique molecular identifier into each cDNA sequence include a template switching oligo including a degenerate sequence.

189. The method of any one of 186-188, wherein the discrete entities are microdroplets.

190. The method of any one of 186-189, wherein the nucleic acid barcode sequences or the UMIs are prepared or introduced according to any one of 1-95.

191. The method of any one of 186-189, wherein the nucleic acid barcode sequences or the UMIs are prepared or introduced according to any one of 96-120 or 130-136.

192. The method of any one of 186-189, wherein the introducing is according to any one of 137-139 or 154-166.

193. The method of any one of 186-189, wherein the method is performed at least in part using a microfluidic device as set forth in any one of 144-153.

194. The method of any one of 186-189, wherein the components of the discrete entities are mixed using a microfluidic device as set forth in any one of 167-172.

195. The method of any one of 186-194, wherein neither the introducing nor the subjecting step occurs in the presence of a bead.

196. The method of any one of 186-195, wherein the amplification is performed using oligonucleotide primers containing a ligand, e.g., a biotin or thiol moiety.

197. The method of any one of 186-196, wherein the cDNA synthesis steps are performed in a first microfluidic device and the enzymatic incorporation is performed in a second microfluidic device.

198. The method of 197, wherein the enzymatic incorporation includes SOEing PCR.

199. A method of barcoding and amplifying RNA from single cells, the method including:
(a) encapsulating individual cells in a population of discrete entities at limiting dilution such that each individual discrete entity of the population of discrete entities statistically contains either zero or one cell;
(b) lysing the cells to release RNA target molecules within the discrete entities;
(c) introducing into each discrete entity reagents sufficient for cDNA synthesis and amplification of the resulting cDNA products, and subjecting each discrete entity to conditions sufficient for cDNA synthesis and amplification of the resulting cDNA products;
(d) introducing into each discrete entity reagents sufficient for fragmentation of the amplified cDNA products, and subjecting each discrete entity to conditions sufficient for fragmentation of the amplified cDNA products; and
(e) introducing into each discrete entity a nucleic acid barcode sequence unique to that discrete entity and reagents sufficient for enzymatic incorporation of the nucleic acid barcode sequence into the fragmented cDNA products, and subjecting each discrete entity to conditions sufficient for enzymatic incorporation of the nucleic acid barcode sequence into the fragmented cDNA products.

200. The method of 199, wherein steps (a), (b) and/or (c) are performed in a first microfluidic device, step (d) is performed in a second microfluidic device, and step (e) is performed in a third microfluidic device.

201. The method of 199, wherein steps (a), (b), (c), (d) and (e) are performed in a single microfluidic device.

202. The method of any one of 199-201, including introducing into each discrete entity reagents sufficient for the enzymatic incorporation of a nucleic acid molecule including a unique molecular identifier (UMI) into each mRNA, cDNA, or amplification product thereof, and subjecting each discrete entity to conditions sufficient for enzymatic incorporation of the nucleic acid molecule including a unique molecular identifier (UMI) into each mRNA, cDNA, or amplification product thereof 203. The method of 202, wherein the reagents sufficient for the enzymatic incorporation of a nucleic acid molecule including a unique molecular identifier include a template switching oligo including a degenerate sequence.

204. The method of any one of 199-203, wherein the discrete entities are microdroplets.

205. The method of any one of 199-204, wherein the nucleic acid barcode sequences or the UMIs are prepared or introduced according to any one of 1-95.

206. The method of any one of 199-204, wherein the nucleic acid barcode sequences or the UMIs are prepared or introduced according to any one of 96-120 or 130-136.

207. The method of any one of 199-204, wherein one or more of the introducing steps are according to any one of 137-139 or 154-166.

208. The method of any one of 199-204, wherein the method is performed at least in part using a microfluidic device as set forth in any one of 144-153.

209. The method of any one of 199-204, wherein the components of the discrete entities are mixed using a microfluidic device as set forth in any one of 167-172.

210. The method of any one of 199-204, wherein introducing reagents sufficient for fragmentation and introducing and enzymatically incorporating a nucleic acid barcode sequence are performed according to the method set forth in any one of 121-129.

211. The method of any one of 199-210, wherein neither the introducing nor the subjecting steps occur in the presence of a bead.

212. The method of any one of 199-211, wherein step (c) is performed in two different steps, a first step in which the reagents sufficient for cDNA synthesis are introduced and each discrete entity is subjected to conditions sufficient for cDNA synthesis, and a second step in which the reagents sufficient for amplification of the resulting cDNA products are introduced and each discrete entity is subjected to conditions sufficient for amplification of the resulting cDNA products.

213. The method of any one of 199-211, wherein step (e) includes introducing the discrete entities from step (d) into a microfluidic device, introducing discrete entities including the nucleic acid barcode sequences into the microfluidic device, and merging the discrete entities to provide discrete entities of increased volume.

214. The method of any one of 199-212, wherein the enzymatic incorporation includes SOEing PCR.

215. A method of barcoding and amplifying RNA from single cells, the method including:
(a) providing a population of discrete entities, each discrete entity of the population of discrete entities including cell lysate originating from a single cell;
(b) introducing into each discrete entity reagents sufficient for cDNA synthesis and amplification of the resulting cDNA products, and subjecting each discrete entity to conditions sufficient for cDNA synthesis and amplification of the resulting cDNA products;
(c) introducing into each discrete entity reagents sufficient for fragmentation of the amplified cDNA products, and subjecting each discrete entity to conditions sufficient for fragmentation of the amplified cDNA products; and
(d) introducing into each discrete entity a nucleic acid barcode sequence unique to that discrete entity and reagents sufficient for enzymatic incorporation of the nucleic acid barcode sequence into the fragmented cDNA products, and subjecting each discrete entity to conditions sufficient for enzymatic incorporation of the nucleic acid barcode sequence into the fragmented cDNA products.

216. The method of 215, wherein steps (a) and/or (b) are performed in a first microfluidic device, step (c) is performed in a second microfluidic device, and step (d) is performed in a third microfluidic device.

217. The method of 215, wherein steps (a), (b), (c), and (d) are performed in a single microfluidic device.

218. The method of any one of 215-217, including introducing into each discrete entity reagents sufficient for the enzymatic incorporation of a nucleic acid molecule including a unique molecular identifier (UMI) into each mRNA, cDNA, or amplification product thereof, and subjecting each discrete entity to conditions sufficient for enzymatic incorporation of the nucleic acid molecule including a unique molecular identifier (UMI) into each mRNA, cDNA, or amplification product thereof.

219. The method of 218, wherein the reagents sufficient for the enzymatic incorporation of a nucleic acid molecule including a unique molecular identifier include a template switching oligo including a degenerate sequence.

220. The method of any one of 215-219, wherein the discrete entities are microdroplets.

221. The method of any one of 215-220, wherein the nucleic acid barcode sequences or the UMIs are prepared or introduced according to any one of 1-95.

222. The method of any one of 215-220, wherein the nucleic acid barcode sequences or the UMIs are prepared or introduced according to any one of 96-120 or 130-136.

223. The method of any one of 215-220, wherein one or more of the introducing steps are according to any one of 137-139 or 154-166.

224. The method of any one of 215-220, wherein the method is performed at least in part using a microfluidic device as set forth in any one of 144-153.

225. The method of any one of 215-220, wherein the components of the discrete entities are mixed using a microfluidic device as set forth in any one of 167-172.

226. The method of any one of 215-220, wherein introducing reagents sufficient for fragmentation and introducing and enzymatically incorporating a nucleic acid barcode sequence are performed according to the method set forth in any one of 121-129.

227. The method of any one of 215-226, wherein neither the introducing nor the subjecting steps occur in the presence of a bead.

228. The method of any one of 199-227, wherein step (b) is performed in two different steps, a first step in which the reagents sufficient for cDNA synthesis are introduced and each discrete entity is subjected to conditions sufficient for cDNA synthesis, and a second step in which the reagents sufficient for amplification of the resulting cDNA products are introduced and each discrete entity is subjected to conditions sufficient for amplification of the resulting cDNA products.

229. The method of any one of 199-227, wherein step (d) includes introducing the discrete entities from step (c) into a microfluidic device, introducing discrete entities including the nucleic acid barcode sequences into the microfluidic device, and merging the discrete entities to provide discrete entities of increased volume.

230. The method of any one of 199-228, wherein the enzymatic incorporation includes SOEing PCR.

231. A method of preparing cDNA for sequencing, the method including:
fragmenting cDNA into a plurality of fragments, the plurality of fragments including 5' ends, 3' ends, and internal fragments;
encapsulating the plurality of fragments in one or more discrete entities along with a solid support;
reversibly immobilizing the 5' ends and/or 3' ends on the solid support;
separating the internal fragments from the 5' ends and/or 3' ends reversibly immobilized on the solid support; and
releasing the 5' ends and/or 3' ends reversibly immobilized on the solid support.

232. The method of 231, wherein the cDNA is generated from mRNA originating from a single cell, and wherein each cDNA includes a nucleic acid barcode sequence incorporated into the 5' ends and/or 3' ends which is unique to the cell from which the mRNA originated.

233. The method of 231 or 232, wherein each cDNA includes a unique molecular identifier (UMI) incorporated into the 5' ends and/or 3' ends.

234. The method of 231, wherein the cDNA is a product of the method of any one of 173-197.

235. The method of any one of 231-234, wherein the fragmenting includes physical shearing.

236. The method of any one of 231-235, wherein the fragmenting includes enzymatic fragmentation with one or more enzymes.

237. The method of any one of 231-236, wherein the 5' ends and/or 3' ends include a ligand and reversibly immobilizing the 5' ends and/or 3' ends on the solid support includes specifically binding the ligand to a receptor for the ligand immobilized on the solid support.

238. The method of any one of 231-237, wherein the solid support is a bead.

239. The method of 238, wherein the bead is a magnetic bead.

240. The method of any one of 231-239, including subjecting the 5' ends and/or 3' ends reversibly immobilized on the solid support to enzymatic modification.

241. The method of 240, wherein the enzymatic modification is selected from restriction digestion, ligation, and polyadenylation.

242. The method of any one of 231-241, wherein the fragmenting occurs after reversibly immobilizing the 5' ends and/or 3' ends of the cDNA on the solid support.

243. The method of any one of 231-242, wherein the one or more discrete entities are microdroplets.

244. A method of preparing barcoded nucleic acids for sequencing, the method including:
encapsulating in a discrete entity a plurality of nucleic acid target molecules and a plurality of beads, wherein each of the plurality of beads includes a nucleic acid barcode sequence, a unique molecular identifier (UMI), and a nucleic acid capture sequence designed to hybridize to one of the plurality of nucleic acid target molecules;
subjecting the discrete entity to conditions sufficient for hybridization of the one or more nucleic acid target molecules and the nucleic acid capture sequence; and
recovering the plurality of beads from the discrete entity for subsequent analysis.

245. The method of 244, including enzymatically incorporating one of the nucleic acid barcode sequences or an amplification product thereof into each of the plurality of target nucleic acid molecules or an amplification product thereof.

246. The method of 244, including enzymatically extending each of the plurality of nucleic acid target molecules onto one of the nucleic acid barcode sequences so as to generate chimeric molecules including the nucleic acid barcode sequence or a sequence complementary thereto and at least a portion of the sequence of the nucleic acid target molecules.

247. The method of any one of 244-246, wherein the recovering includes sorting the beads by one or more of fluorescence-activated cell sorting (FACS), PCR-activated cell sorting (PACS), or magnetic-activated cell sorting (MACS).

248. The method of any one of 244-247, wherein the nucleic acid target molecules includes cellular DNA, RNA, or nucleic acids which were associated with a cell via affinity reagents.

249. The method of any one of 244-248, including enzymatically amplifying the nucleic acid target molecules from the beads.

250. The method of any one of 244-249, including removing the nucleic acid target molecules from the beads.

251. The method of any one of 244-250, including sequencing the nucleic acid target molecules or portions thereof, or sequencing amplification products of the nucleic acid target molecules or portions thereof.

252. The method of any one of 244-251, wherein the discrete entity is a microdroplet.

253. A method for producing compartmentalized, amplified target libraries for barcode-based sequencing, the method including:
encapsulating a plurality of nucleic acid target molecules in a plurality of discrete entities with reagents sufficient for the enzymatic amplification of the nucleic acid target molecules;
subjecting the discrete entities to conditions sufficient for enzymatic amplification of the nucleic acid target molecules, providing amplification products;
fragmenting the amplification products; and
incorporating nucleic acid barcode sequences into the fragmented amplification products.

254. The method of 253, wherein the discrete entities are microdroplets.
255. The method of 253 or 254, wherein the reagents sufficient for the enzymatic amplification of the nucleic acid target molecules include one or more enzymes selected from a DNA polymerase, RecA protein, and a helicase.
256. The method of any one of 253-255, wherein subjecting the discrete entities to conditions sufficient for enzymatic amplification of the nucleic acid target molecules includes thermalcycling the discrete entities.
257. The method of any one of 253-256, wherein the nucleic acid target molecules are DNA molecules, and wherein an RNA intermediate is used to amplify the nucleic acid target molecules.
258. The method of any one of 253-257, wherein the nucleic acid target molecules are amplified in one or more organisms.
259. The method of any one of 253-258, including modulating the reagents or conditions so as to modulating the degree of amplification of the nucleic acid target molecules.
260. The method of any one of 253-259, wherein the plurality of nucleic acid target molecules are encapsulated in the plurality of discrete entities at limiting dilution such that each individual discrete entity of the plurality statistically contains either zero or one nucleic acid target molecule.
261. The method of any one of 253-260, including attaching the amplification products to one or more solid supports either before or after the fragmenting.
262. The method of 261, wherein the one or more solid supports are one or more beads.
263. The method of any one of 253-262, wherein the nucleic acid target molecules are greater than 10 kilobases in length.
264. The method of 263, wherein the nucleic acid target molecules are greater than 100 kilobases in length.
265. The method of 264, wherein the nucleic acid target molecules are greater than 1 megabase in length.
266. A method for fragmenting and barcoding nucleic acid target molecules, the method including:
    encapsulating a plurality of nucleic acid target molecules or amplification products thereof in a plurality of discrete entities;
    subjecting the discrete entities to conditions sufficient for fragmentation of the nucleic acid target molecules or amplification products thereof to provide fragmented nucleic acid target molecules or amplification products thereof;
    incorporating nucleic acid barcode sequences into the fragmented nucleic acid target molecules or amplification products thereof, wherein the nucleic acid barcode sequences identify each fragment into which the nucleic acid barcode sequence is incorporated as originating from a single discrete entity, a single cell, or a single organism.
267. The method of 266, wherein the subjecting includes enzymatically fragmenting the nucleic acid target molecules or amplification products thereof.
268. The method of 266, wherein the subjecting includes fragmenting the nucleic acid target molecules or amplification products thereof using physical or chemical means.
269. The method of 266, wherein the subjecting includes fragmenting the nucleic acid target molecules or amplification products thereof by the application of UV light.
270. The method of 266, including, prior to the subjecting, incorporating one or more enzymatic cleavage sites into the nucleic acid target molecules or amplification products thereof.
271. The method of 270, wherein the one or more enzymatic cleavage sites includes a dUTP.
272. The method of 266, wherein the subjecting includes fragmenting the nucleic acid target molecules or amplification products thereof through the application of a force.
273. The method of 272, wherein the force is a shear force induced by the hydrodynamic flow of the nucleic acid target molecules or amplification products thereof through a microfluidic channel, a microfluidic jet, or a microfluidic junction in a microfluidic device.
274. The method of 266, wherein the subjecting includes fragmenting the nucleic acid target molecules or amplification products thereof via transposon insertion.
275. The method of 266, wherein the subjecting includes fragmenting the nucleic acid target molecules or amplification products thereof using a nucleic acid-fragmenting microorganism.
276. The method of any one of 266-275, wherein the discrete entities are microdroplets.
277. The method of any one of 266-276, wherein the nucleic acid target molecules are greater than 10 kilobases in length.
278. The method of 277, wherein the nucleic acid target molecules are greater than 100 kilobases in length.
279. The method of 278, wherein the nucleic acid target molecules are greater than 1 megabase in length.
280. A method for characterizing copy number variation in cells, the method including:
    isolating single cells in discrete entities;
    fragmenting cellular nucleic acids in the discrete entities;
    incorporating unique molecular identifiers (UMI)s into the fragmented cellular nucleic acids;
    sequencing the fragmented cellular nucleic acids; and
    using the UMIs to infer the copy number of specific sequences in the cellular nucleic acids.
281. The method of 280, wherein the cellular nucleic acids include genomic DNA.
282. The method of 280 or 281, wherein the cellular nucleic acids include RNA.
283. The method of any one of 280-282, wherein a population of cells is subjected to the isolating, fragmenting, incorporating, and sequencing steps.
284. The method of any one of 280-283, wherein the discrete entities are microdroplets.
285. The method of any one of 280-284, including incorporating into the cellular nucleic acids a nucleic acid barcode sequence unique to each cell and/or each discrete entity.
286. The method of any one of 280-285, wherein the sequencing produces sequencing reads which include a UMI and/or a nucleic acid barcode sequence.
287. A method for attaching barcodes to fragmented nucleic acids or amplification products thereof, the method including:
    combining in a plurality of discrete entities a plurality of fragmented nucleic acid target molecules, nucleic acid barcode sequences, and reagents sufficient for the incorporation of the nucleic acid barcode sequences into the fragmented nucleic acid target molecules or amplification products thereof; and subjecting the plurality of discrete entities to conditions sufficient for incorporation of the nucleic acid barcode sequences into the fragmented nucleic acid target molecules or amplification products thereof, wherein the nucleic acid barcode sequences identify each fragment or amplification product thereof into which the nucleic acid barcode sequence is incorporated as originating from a single discrete entity, a single cell or a single organism.

288. The method of 287, wherein the subjecting does not occur in the presence of a bead.

289. The method of 287 or 288, wherein the reagents include a ligase.

290. The method of 287 or 288, wherein the reagents include one or more enzymes selected from an integrase, a recombinase, and a flippase.

291. The method of 287 or 288, wherein the incorporation includes SOEing PCR.

292. The method of any one of 287-291, wherein the discrete entities are microdroplets.

293. A method of sequencing nucleic acids, including:
encapsulating a plurality of nucleic acid target molecules in a plurality of discrete entities;
enzymatically amplifying the nucleic acid target molecules to provide first amplification products;
fragmenting the first amplification products to provide fragmented first amplification products;
incorporating nucleic acid barcode sequences into the fragmented first amplification products or second amplification products amplified from the fragmented first amplification products;
sequencing the fragmented first amplification products having nucleic acid barcode sequences incorporated therein, or the second amplification products having nucleic acid barcode sequences incorporated therein; and
using the nucleic acid barcode sequences to group sequencing reads for members of the fragmented first amplification products or members of the second amplification products that were, at one time, present in the same discrete entity.

294. The method of 293, wherein the enzymatically amplifying occurs prior to the encapsulating.

295. The method of 293 or 294, wherein the discrete entities are microdroplets.

296. The method of 295, wherein the incorporating includes merging each of the plurality of discrete entities with a microdroplet including a nucleic acid barcode sequence.

297. The method of 295, wherein the incorporating includes encapsulating in each of the plurality of discrete entities a cell including the nucleic acid barcode sequence.

298. The method of any one of 293-297, wherein the fragmenting and incorporating steps are performed as a single step utilizing a transposon.

299. The method of any one of 293-298, wherein one or more of the discrete entities includes a plurality of different nucleic acid target molecules and/or a plurality of different nucleic acid barcode sequences, and wherein the method includes bioinformatically analyzing mixed sequencing reads resulting from the sequencing to obtain sequence information for the individual nucleic acid target molecules.

300. The method of any one of 293-299, including lysing one or more cells or viruses to obtain the plurality of nucleic acid target molecules.

301. The method of 300, wherein the lysing occurs in the plurality of discrete entities.

302. The method of any one of 293-301, wherein the nucleic acid target molecules in each of the plurality of discrete entities originate from a single cell.

303. The method of any one of 293-301, wherein the nucleic acid target molecules in each of the plurality of discrete entities originate from a single molecule.

304. The method of any one of 293-303, including incorporating a unique molecular identifier (UMI) into one or more of the nucleic acid target molecules, first amplification products, fragmented first amplification products, and second amplification products.

305. A method of sequencing nucleic acids, including:
encapsulating a plurality of nucleic acid target molecules in a plurality of discrete entities;
fragmenting the plurality of nucleic acid target molecules to provide fragmented nucleic acid target molecules;
incorporating nucleic acid barcode sequences into the fragmented nucleic acid target molecules or amplification products amplified from the fragmented nucleic acid target molecules;
sequencing the fragmented nucleic acid target molecules having nucleic acid barcode sequences incorporated therein or the amplification products having nucleic acid barcode sequences incorporated therein; and
using the nucleic acid barcode sequences to group sequencing reads for members of the fragmented nucleic acid target molecules or members of the amplification products that were, at one time, present in the same discrete entity.

306. The method of 305, wherein the discrete entities are microdroplets.

307. The method of 306, wherein the incorporating includes merging each of the plurality of discrete entities with a microdroplet including a nucleic acid barcode sequence.

308. The method of 306, wherein the discrete entities are microdroplets, and the incorporating includes encapsulating in each of the plurality of discrete entities a cell including the nucleic acid barcode sequence.

309. The method of any one of 305-308, wherein the fragmenting and incorporating steps are performed as a single step utilizing a transposon.

310. The method of any one of 305-309, wherein one or more of the discrete entities includes a plurality of different nucleic acid target molecules and/or a plurality of different nucleic acid barcode sequences, and wherein the method includes bioinformatically analyzing mixed sequencing reads resulting from the sequencing to obtain sequence information for the individual nucleic acid target molecules.

311. The method of any one of 305-310, including lysing one or more cells or viruses to obtain the plurality of nucleic acid target molecules.

312. The method of 311, wherein the lysing occurs in the plurality of discrete entities.

313. The method of any one of 305-312, wherein the nucleic acid target molecules in each of the plurality of discrete entities originate from a single cell.

314. The method of any one of 305-312, wherein the nucleic acid target molecules in each of the plurality of discrete entities originate from a single molecule.

315. The method of any one of 305-314, including incorporating a unique molecular identifier (UMI) into one or more of the nucleic acid target molecules, the fragmented nucleic acid target molecules, and the amplification products.

316. A method of sequencing nucleic acids, including:
    encapsulating a plurality of nucleic acid target molecules in a plurality of discrete entities;
    enzymatically amplifying the nucleic acid target molecules in the plurality of discrete entities to provide first amplification products;
    incorporating nucleic acid barcode sequences into the first amplification products or second amplification products amplified from the first amplification products;
    sequencing the first amplification products having nucleic acid barcode sequences incorporated therein, or the second amplification products having nucleic acid barcode sequences incorporated therein; and
    using the nucleic acid barcode sequences to group sequencing reads for members of the first amplification products or members of the second amplification products that were, at one time, present in the same discrete entity.
317. The method of 316, wherein the enzymatically amplifying occurs prior to the encapsulating.
318. The method of 316 or 317, wherein the discrete entities are microdroplets.
319. The method of 318, wherein the incorporating includes merging each of the plurality of discrete entities with a microdroplet including a nucleic acid barcode sequence.
320. The method of 318, wherein the incorporating includes encapsulating in each of the plurality of discrete entities a cell including the nucleic acid barcode sequence.
321. The method of any one of 316-320, wherein one or more of the discrete entities includes a plurality of different nucleic acid target molecules and/or a plurality of different nucleic acid barcode sequences, and wherein the method includes bioinformatically analyzing mixed sequencing reads resulting from the sequencing to obtain sequence information for the individual nucleic acid target molecules.
322. The method of any one of 316-321, including lysing one or more cells or viruses to obtain the plurality of nucleic acid target molecules.
323. The method of 322, wherein the lysing occurs in the plurality of discrete entities.
324. The method of any one of 316-323, wherein the nucleic acid target molecules in each of the plurality of discrete entities originate from a single cell.
325. The method of any one of 316-323, wherein the nucleic acid target molecules in each of the plurality of discrete entities originate from a single molecule.
326. The method of any one of 316-325, including incorporating a unique molecular identifier (UMI) into one or more of the nucleic acid target molecules, first amplification products, and second amplification products.
327. A method for detecting target molecules, the method including:
    labeling each of a plurality of affinity reagents specific for a molecular target with an oligonucleotide including a first nucleic acid barcode sequence, wherein the first nucleic acid barcode sequence identifies the target-specificity of the affinity reagent labeled by the oligonucleotide;
    contacting the plurality of affinity reagents with a plurality of molecular targets under conditions sufficient for specific binding of the plurality of affinity reagents to their specific molecular targets, when present;
    encapsulating the plurality of affinity reagents bound to their specific molecular targets, when present, in a plurality of discrete entities, with a plurality of second nucleic acid barcode sequences, wherein the second nucleic acid barcode sequences encapsulated in each discrete entity uniquely identify the discrete entity in which they are encapsulated;
    incorporating the second nucleic acid barcode sequences into the oligonucleotides including the first nucleic acid barcode sequences or amplification products thereof;
    sequencing the oligonucleotides including the first nucleic acid barcode sequences or the amplification products thereof; and
    using the first and second nucleic acid barcode sequences to identify and/or quantitate affinity reagents that were, at one time, present in the same discrete entity.
328. The method of 327, wherein the plurality of affinity reagents includes affinity reagents specific for different molecular targets.
329. The method of 327 or 328, wherein the molecular targets are included by cells.
330. The method of 329, wherein the cells are encapsulated in the discrete entities at limiting dilution such that each individual discrete entity of the plurality of discrete entities statistically contains either zero or one cell.
331. The method of 329 or 330, wherein the molecular targets are bound to or associated with a surface of one or more of the cells.
332. The method of any one of 327-331, wherein the affinity reagents are antibodies.
333. The method of any one of 327-332, wherein the oligonucleotide includes DNA or an analogue thereof.
334. The method of any one of 327-332, wherein the oligonucleotide includes RNA or an analogue thereof
335. The method of any one of 327-332, wherein each of the plurality of affinity reagents and/or each oligonucleotide including a first nucleic acid barcode sequence includes a unique molecular identifier (UMI), which uniquely identifies each of the affinity reagents and/or each of the oligonucleotides including a first nucleic acid barcode sequence, respectively.
336. The method of any one of 327-335, wherein the plurality of affinity reagents are generated using one or more of phage display, ribosome display, and mRNA display.
337. The method of any one of 327-336, wherein the oligonucleotides used to label the plurality of affinity agents are attached to the affinity agents via one or more of covalent, ionic, and hydrophobic interactions.
338. The method of any one of 327-336, wherein the discrete entities are microdroplets.
339. A method of barcoding and amplifying oligonucleotide-conjugated affinity reagents, the method including:
    contacting a biological material with a plurality of affinity reagents, each specific for a molecular target, under conditions sufficient for specific binding of the affinity reagents to their respective molecular targets, when present in the biological material, wherein each of the affinity reagents includes an oligonucleotide conjugated thereto;
encapsulating the biological material in a plurality of first discrete entities;
providing a plurality of second discrete entities including nucleic acid barcode sequences;
using a microfluidic device to combine in a discrete entity contents of one of the plurality of first discrete entities, contents of one of the plurality of second discrete entities, and reagents sufficient for incorporation of one of the nucleic acid barcode sequences into one of the oligonucleotides conjugated to the affinity reagents or amplification products thereof; and
subjecting the discrete entity including the combined contents of one of the plurality of first discrete entities and one of the plurality of second discrete entities to conditions sufficient for the incorporation of one of the nucleic acid barcode sequences into one of the oligonucleotides conjugated to the affinity reagents or amplification products thereof 340. The method of 339, wherein the biological material is the product of a fixed cell.

341. The method of 339 or 340, wherein the affinity reagents are antibodies.

342. The method of any one of 339-341, including incorporating a unique molecular identifier (UMI) into the oligonucleotide-conjugated affinity reagents.

343. The method of any one of 339-342, wherein the discrete entities are microdroplets.

344. The method of any one of 339-343, wherein the nucleic acid barcode sequences or the UMIs are prepared or incorporated according to any one of 1-95.

345. The method of any one of 339-343, wherein the nucleic acid barcode sequences or the UMIs are prepared or incorporated according to any one of 96-120 or 130-136.

346. The method of any one of 339-343, wherein the incorporation is according to any one of 137-139 or 154-166.

347. The method of any one of 339-343, wherein the method is performed at least in part using a microfluidic device as set forth in any one of 144-153.

348. A method of barcoding and amplifying oligonucleotide-conjugated affinity reagents, the method including:
contacting a plurality of cells with a plurality of affinity reagents, each specific for a molecular target, under conditions sufficient for specific binding of the affinity reagents to their respective molecular targets, when present in the cells, wherein each of the affinity reagents includes an oligonucleotide conjugated thereto;
encapsulating and lysing the cells in a plurality of first discrete entities;
providing a plurality of second discrete entities including nucleic acid barcode sequences;
using a microfluidic device to combine in a discrete entity contents of one of the plurality of first discrete entities, contents of one of the plurality of second discrete entities, and reagents sufficient for incorporation of one of the nucleic acid barcode sequences into one of the oligonucleotides conjugated to the affinity reagents and amplification thereof; and
subjecting the discrete entity including the combined contents of one of the plurality of first discrete entities and one of the plurality of second discrete entities to conditions sufficient for the incorporation of one of the nucleic acid barcode sequences into one of the oligonucleotides conjugated to the affinity reagents and amplification thereof 349. The method of 348, wherein the cells are encapsulated in the first discrete entities such that not more than one cell is present in each of the first discrete entities.

350. The method of 348 or 349, wherein the affinity reagents are antibodies.

351. The method of any one of 348-350, including incorporating a unique molecular identifier (UMI) into the oligonucleotide-conjugated affinity reagents.

352. The method of any one of 348-351, wherein the discrete entities are microdroplets.

353. The method of any one of 348-352, wherein the nucleic acid barcode sequences or the UMIs are prepared or incorporated according to any one of 1-95.

354. The method of any one of 348-352, wherein the nucleic acid barcode sequences or the UMIs are prepared or incorporated according to any one of 96-120 or 130-136.

355. The method of any one of 348-352, wherein the incorporation is according to any one of 137-139 or 154-166.

356. The method of any one of 348-352, wherein the method is performed at least in part using a microfluidic device as set forth in any one of 144-153.

357. A method for linking and amplifying nucleic acids conjugated to proteins, the method including:
incubating a population of nucleic acid barcode sequence-conjugated proteins under conditions sufficient for a plurality of the proteins to interact, bringing the nucleic acid barcode sequences on the interacting proteins in proximity to each other;
encapsulating the population of nucleic acid barcode sequence-conjugated proteins in a plurality of discrete entities such that interacting proteins are co-encapsulated, if present;
using a microfluidic device to combine in a discrete entity contents of one of the plurality of first discrete entities and reagents sufficient for amplification and linkage of the nucleic acid barcode sequences on the interacting proteins, if present; and
subjecting the discrete entity to conditions sufficient for the amplification and linkage of the nucleic acid barcode sequences on the interacting proteins, if present.

358. The method of 357, wherein the population is prepared using one or more of phage display, ribosome display, and mRNA display.

359. The method of any one of 357-358, wherein the discrete entities are microdroplets.

360. The method of any one of 357-359, wherein the method is performed at least in part using a microfluidic device as set forth in any one of 144-153.

361. The method of any one of 357-360, in which a purification step is used to remove non-interacting proteins prior to encapsulation.

362. The method of any one of 357-361, including identifying interacting proteins relative to non-interacting proteins based on the number of unique amplification products present in a discrete entity.

363. The method of any one of 357-362, wherein the interaction is a specific binding interaction.

364. A method for identifying protein-protein interactions with barcoding, the method including:
incubating a population of nucleic acid barcode sequence-conjugated proteins under conditions sufficient for a plurality of the proteins to interact, bringing the nucleic acid barcode sequences on the interacting proteins in proximity to each other;
encapsulating the population of nucleic acid barcode sequence-conjugated proteins in a plurality of discrete entities such that interacting proteins are co-encapsulated, if present;
using a microfluidic device to combine in a discrete entity contents of one of the plurality of first discrete entities and reagents sufficient for incorporation of second nucleic acid barcode sequences into the nucleic acid barcode sequences on the interacting proteins, if present, or amplification products thereof; and
subjecting the discrete entity to conditions sufficient for incorporation of second nucleic acid barcode sequences into the nucleic acid barcode sequences on the interacting proteins or amplification products thereof, if present.

365. The method of 364, wherein the population is prepared using one or more of phage display, ribosome display, and mRNA display.

366. The method of any one of 364-365, wherein the discrete entities are microdroplets.

367. The method of any one of 364-366, wherein the method is performed at least in part using a microfluidic device as set forth in any one of 144-153.

368. The method of any one of 364-367 in which a purification step is used to remove non-interacting proteins prior to encapsulation.

369. The method of any one of 364-368, including identifying interacting proteins relative to non-interacting proteins based on the number of unique second nucleic acid barcode sequences or amplification products thereof in a discrete entity.

370. The method of any one of 364-369, wherein the interaction is a specific binding interaction.

371. A method of determining the epitopes present in a molecule, a molecular complex and/or structure, the method including:
contacting a plurality of molecules, molecular complexes and/or structures with a plurality of affinity reagents, each specific for an epitope, under conditions sufficient for specific binding of the affinity reagents to their respective epitopes, when present in the molecules, molecular complexes and/or structures, wherein each of the affinity reagents includes a first nucleic acid barcode sequence conjugated thereto which identifies the epitope specificity of the affinity reagent;
encapsulating in discrete entities molecules, molecular complexes and/or structures which are specifically bound to one or more of the affinity reagents;
incorporating a second nucleic acid barcode sequence into the first nucleic acid barcode sequences or amplification products thereof, wherein the second nucleic acid barcode sequence uniquely identifies the discrete entities; and
sequencing the first nucleic acid barcode sequences or amplification products thereof including the second nucleic acid barcode sequence to identify the epitopes present on the molecules, molecular complexes and/or structures.

372. The method of 371, wherein the epitopes include post-translational modifications or splice variations.

373. The method of 371 or 372, including enriching for affinity reagents specifically bound to one or more epitopes using immunoprecipitation prior to barcoding or sequencing.

374. The method of any one of 371-373, wherein the affinity reagents are antibodies.

375. The method of any one of 371-374, wherein the discrete entities are microdroplets.

376. A method for determining the number of affinity reagents in a sample, the method including:
contacting a sample suspected of containing one or more molecular targets with a plurality of affinity reagents, wherein each of the affinity reagents is specific for a molecular target and includes an oligonucleotide including a nucleic acid barcode sequence which identifies the specificity of the affinity reagent, wherein one or both of the affinity reagent and the oligonucleotide includes a unique molecular identifier (UMI) which uniquely identifies each of the plurality of affinity reagents; and
using the UMI to determine the number of affinity reagents in the sample.

377. The method of 376, including amplifying the nucleic acid barcode sequences, wherein the UMIs are used to correct for amplification bias.

378. The method of 377, wherein the amplifying is performed in one or more microdroplets.

379. The method of any one of 376-378, wherein the affinity reagents are not antibodies.

380. A method of barcoding labeled affinity reagents, the method including:
contacting a sample containing one or more molecular targets with a plurality of affinity reagents, wherein each of the affinity reagents is specific for a molecular target and includes an oligonucleotide including a first nucleic acid barcode sequence which identifies the specificity of the affinity reagent;
isolating the one or more molecular targets from the sample;
incorporating a second nucleic acid barcode sequence into the oligonucleotide or amplification products thereof, wherein the second nucleic acid barcode sequence uniquely identifies affinity reagents isolated with the one or more molecular targets; and
sequencing the oligonucleotide or amplification products thereof having the second nucleic acid barcode sequence incorporated therein to identify which of the plurality of affinity reagents bound to one of the one or more molecular targets in the sample.

381. The method of 380, wherein the one or more molecular targets are included by one or more cells.

382. The method of 381, wherein the isolating includes dispensing individual cells into individual wells.

383. The method of 381, wherein the isolating includes isolating individual cells using a microfluidic cell capture device.

384. A method for identifying genetic modifications in one or more cells, the method including:
introducing one or more genetic modifications into a plurality of cells;
identifying one or more cellular phenotypes resulting from the introduction of the one or more genetic modifications into the plurality of cells;

isolating each of the cells in a discrete entity and selectively amplifying one or more regions of DNA including the one or more genetic modifications;

incorporating a nucleic acid barcode sequence into the amplified DNA including the one or more genetic modifications or amplification products thereof, wherein the nucleic acid barcode sequence identifies the one or more genetic modifications as originating from a single cell;

sequencing the amplified DNA including the one or more genetic modifications or amplification products thereof to identify the one or more genetic modifications in the cells having the one or more cellular phenotypes.

385. The method of 384, wherein the selectively amplifying and incorporating are performed using SOEing PCR.

386. The method of any one of 384-385, wherein the discrete entities are microdroplets.

387. The method of any one of 384-386, wherein the method is performed at least in part using a microfluidic device as set forth in any one of 144-153.

388. A method for barcoding and amplifying oligonucleotide-conjugated affinity reagents and RNA from single cells, the method including:

contacting a plurality of cells with a plurality of affinity reagents, wherein each of the affinity reagents is specific for a molecular target and includes an oligonucleotide including a first nucleic acid barcode sequence which identifies the specificity of the affinity reagent;

encapsulating the plurality of cells in discrete entities such that each discrete entity includes not more than one cell;

lysing the plurality of cells in the discrete entities; and introducing into the discrete entities containing the lysed cells second nucleic acid barcode sequences and reagents sufficient for reverse transcription of RNA, barcoding and amplification of cDNA products, and incorporation of the second nucleic acid barcode sequences into the oligonucleotides including a first nucleic acid barcode sequence or amplification products thereof.

389. The method of 388, including incorporating unique molecular identifiers (UMI)s into RNA molecules of the lysed cells.

390. The method of 388 or 389, wherein the oligonucleotides including a first nucleic acid barcode sequence each include a unique molecular identifiers (UMI).

391. The method of any one of 388-390, wherein the discrete entities are microdroplets.

392. The method of any one of 388-391, wherein the nucleic acid barcode sequences or the UMIs are prepared or introduced according to any one of 1-95.

393. The method of any one of 388-391, wherein the nucleic acid barcode sequences or the UMIs are prepared or introduced according to any one of 96-120 or 130-136.

394. The method of any one of 388-391, wherein the introducing is according to any one of 137-139 or 154-166.

395. The method of any one of 388-391, wherein the method is performed at least in part using a microfluidic device as set forth in any one of 144-153.

396. The method of any one of 388-391, wherein the components of the discrete entities are mixed using a microfluidic device as set forth in any one of 167-172.

397. The method of any one of 388-391, wherein the amplification is performed using oligonucleotide primers containing a ligand, e.g., a biotin or thiol moiety.

398. The method of any one of 388-397, wherein the affinity reagents are antibodies.

399. A method for barcoding and amplifying oligonucleotide-conjugated affinity reagents and RNA from single cells, the method including:

contacting a plurality of cells with a plurality of affinity reagents, wherein each of the affinity reagents is specific for a molecular target and includes an oligonucleotide including a first nucleic acid barcode sequence which identifies the specificity of the affinity reagent;

encapsulating the plurality of cells in a plurality of first discrete entities such that each first discrete entity includes not more than one cell;

lysing the plurality of cells in the first discrete entities;

providing a plurality of second nucleic acid barcode sequences in a plurality of second discrete entities;

combining each of the first discrete entities with one of the second discrete entities to form a third discrete entity in a first microfluidic device, wherein the third discrete entity includes reagents sufficient for reverse transcription of RNA into cDNA products; and utilizing a second microfluidic device to introduce into the third discrete entities reagents sufficient for barcoding and amplification of the cDNA products and incorporation of the second nucleic acid barcode sequences into the oligonucleotides including a first nucleic acid barcode sequence or amplification products thereof 400. The method of 399, including incorporating unique molecular identifiers (UMI)s into RNA molecules of the lysed cells.

401. The method of 399 or 400, wherein the first and second microfluidic devices are different.

402. The method of 399 or 400, wherein the first and second microfluidic devices are different.

403. The method of 399 or 400, wherein the oligonucleotides including a first nucleic acid barcode sequence each include a unique molecular identifiers (UMI).

404. The method of any one of 399-390, wherein the discrete entities are microdroplets.

405. The method of any one of 399-404, wherein the nucleic acid barcode sequences or the UMIs are prepared or introduced according to any one of 1-95.

406. The method of any one of 399-404, wherein the nucleic acid barcode sequences or the UMIs are prepared or introduced according to any one of 96-120 or 130-136.

407. The method of any one of 399-404, wherein the introducing is according to any one of 137-139 or 154-166.

408. The method of any one of 399-404, wherein the method is performed at least in part using a microfluidic device as set forth in any one of 144-153.

409. The method of any one of 399-404, wherein the components of the discrete entities are mixed using a microfluidic device as set forth in any one of 167-172.

410. The method of any one of 399-404, wherein the amplification is performed using oligonucleotide primers containing a ligand, e.g., a biotin or thiol moiety.

411. The method of any one of 399-410, wherein the affinity reagents are antibodies.

412. A method of preparing barcoded DNA for sequencing, the method including:
fragmenting DNA into a plurality of fragments, the plurality of fragments including 5' ends, 3' ends, and internal fragments;
encapsulating the plurality of fragments in one or more discrete entities along with a solid support;
reversibly immobilizing the 5' ends and/or 3' ends on the solid support;
separating the internal fragments from the 5' ends and/or 3' ends reversibly immobilized on the solid support; and
releasing the 5' ends and/or 3' ends reversibly immobilized on the solid support.

413. The method of 412, wherein the fragmenting includes physical shearing.

414. The method of 412, wherein the fragmenting includes enzymatic fragmentation with one or more enzymes.

415. The method of any one of 412-414, wherein the solid support is a bead.

416. The method of 415, wherein the bead is a magnetic bead.

417. The method of any one of 412-416, including subjecting the 5' ends and/or 3' ends reversibly immobilized on the solid support to enzymatic modification.

418. The method of 417, wherein the enzymatic modification is selected from restriction digestion, ligation, and polyadenylation.

419. The method of any one of 412-418, wherein the fragmenting occurs after reversibly immobilizing the 5' ends and/or 3' ends of the DNA on the solid support.

420. The method of any one of 412-419, wherein the one or more discrete entities are microdroplets.

421. A method for grouping sequencing reads using barcodes, the method including:
sequencing a plurality of nucleic acid molecules including nucleic acid barcode sequences to provide sequencing reads, wherein the plurality of nucleic acid molecules includes nucleic acid molecules originating from the same and different discrete entities;
grouping the sequencing reads by nucleic acid barcode sequence using a Hamming or Levenshtein distance criterion;
using the sequences of one or more additional barcodes or unique molecular identifiers (UMI)s incorporated into the sequencing reads to statistically determine barcode groups that originated from the same discrete entity;
combining reads for barcode groups that originated from the same discrete entity; and
removing the barcode portion of each sequencing read and using the remaining portion for further analysis.

422. A method for preparing a sequence library from a library of barcoded nucleic acids, the method including:
generating a first library of barcoded nucleic acids;
preparing a sequencing library from the first library;
storing the first library; and
preparing a second sequencing library from the first library.

423. The method of 422, wherein the first library includes soluble nucleic acids.

424. The method of 422, wherein the first library includes nucleic acids attached to a solid support.

425. The method of 424, wherein the solid support includes one or more beads.

426. The method of any one of 422-425, including sorting the beads by one or more of fluorescence-activated cell sorting (FACS), PCR-activated cell sorting (PACS), or magnetic-activated cell sorting (MACS).

427. The method of any one of 422-426, wherein the first library is purified for storage and/or additional processing by amplifying the nucleic acids of the library with labeled primers and isolating the amplified products with an affinity reagent having specific binding affinity for the label of the labeled primers.

428. The method of 427, wherein the label is biotin and the affinity reagent is streptavidin.

429. The method of 428, wherein the streptavidin is coated on one or more beads.

430. A method for preparing a sequence library from a library of barcoded nucleic acids, the method including:
generating a library of barcoded nucleic acids, wherein the library includes sequences of nucleic acid molecules originating from a plurality of cells;
obtaining sequence information from the library;
using the sequence information to design primers capable of selectively amplifying barcoded nucleic acids including sequences originating from specific cells; and
selectively amplifying and analyzing the barcoded nucleic acids including sequences originating from specific cells.

431. The method of 430, wherein the primers capable of selectively amplifying barcoded nucleic acids including sequences originating from specific cells include nucleic acid barcode sequences obtained from the previous analysis of the library of barcoded nucleic acids or sequences complementary thereto.

432. A method for analyzing a barcoded sequence library, the method including:
generating a library of barcoded nucleic acids;
sequencing, at a first coverage depth, the library to obtain information about a plurality of barcode groups in the library;
analyzing the information about the plurality of barcode groups in the library to identify a subset of barcode groups for sequencing at a second deeper coverage depth; and
enriching for the nucleic acids of the subset of barcode groups to produce a targeted library for sequencing at the second deeper coverage depth.

433. The method of 432, wherein nucleic acids of the subset of barcode groups are bound to one or more beads, and wherein the enriching includes hybridizing labeled probes complementary to a known barcode of one of the subset of barcode groups and sorting the beads using the labeled probes.

434. The method of 433, wherein the sorting is via Fluorescence Activated Cell Sorting (FACS).

435. The method of 432, wherein the enriching includes utilizing primers that hybridize to specific barcodes sequences in the subset of barcode groups to perform PCR-activated sorting in microfluidic droplets thereby sorting the nucleic acids of the subset of barcode groups.

436. The method of 435, wherein nucleic acids of the subset of barcode groups are bound to one or more beads.

437. The method of 432, wherein the enriching includes utilizing primers that hybridize to specific barcodes sequences in the subset of barcode groups, and amplifying nucleic acids of the subset of barcode groups using the primers.

438. A method for analyzing tissues, the method including:
disaggretating a tissue into a plurality of cells or cell aggregates;
using one or more of the methods and or devices of 1-437 to analyze the genomes, transcriptomes, and/or proteomes of the plurality of cells or cell aggregates to obtain information about the heterogeneity or homogeneity of the tissue.

439. The method of 438, wherein the tissue includes a solid tissue.

440. The method of 439, wherein the solid tissue is selected from lung, heart, kidney, and tumor tissue.

441. The method of 439, wherein the tissue includes suspended cells or cell aggregates.

442. The method of 441, wherein the suspended cells or cell aggregates include blood cells, cell culture cells, and/or stem cells.

443. A method for combinatorial barcoding of nucleic acids, the method including:
encapsulating a nucleic acid target molecule in a discrete entity;
introducing into the discrete entity reagents sufficient for fragmentation of the nucleic acid target molecule and incorporation of a nucleic acid barcode sequence into the fragments, wherein the reagents include a plurality of unique nucleic acid barcode sequences;
incubating the discrete entities to fragment the nucleic acid target molecule and incorporate a first one of the plurality of unique nucleic acid barcode sequences into a first fragment and a second one of the unique nucleic acid barcode sequences into a second fragment.

EXAMPLES

Figure 10:
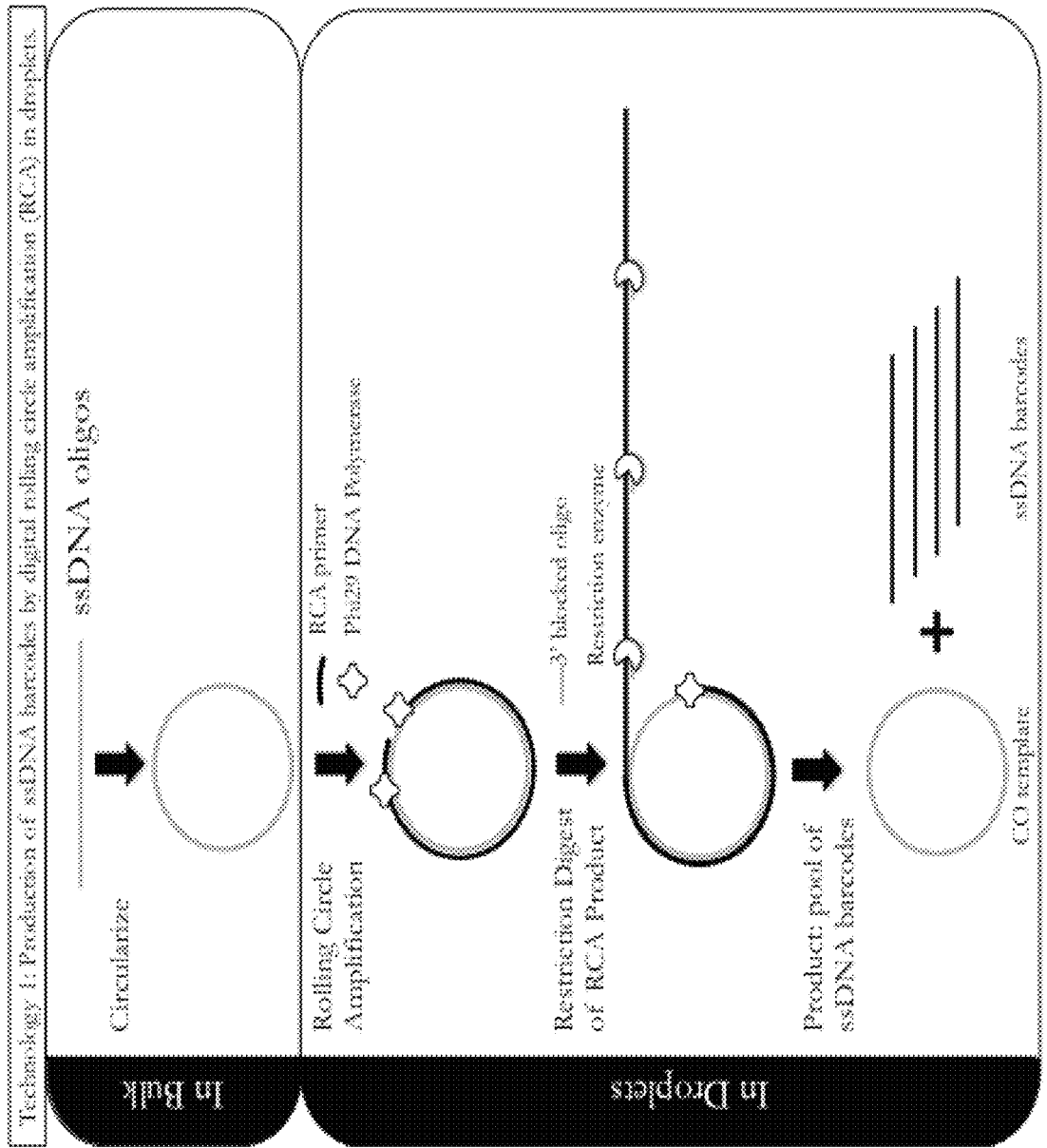
FIG. 10 provides a schematic illustrating steps in a method of preparing ssDNA barcodes by digital rolling circle amplification (RCA) in droplets.

Example 1 (Prophetic): Production of ssDNA Barcodes by Digital Rolling Circle Amplification (RCA) in Droplets A pool of ssDNA oligonucelotides containing a portion of sequential or non-sequential degenerate bases in addition to conserved sequences are first circularized by CircLigase and digested with exonuclease to remove uncircularized oligos. Circularized oligos (COs) are then encapsulated in droplets by limiting dilution with a DNA polymerase such as Phi29X (or similar) and reagents necessary for rolling circle amplification (RCA). In addition to RCA reagents, a restriction enzyme and a 3' blocked oligo of known homology to the CO are included such that hybridization of the oligo with the RCA product reconstitutes a dsDNA structure recognized by the restriction enzyme. During incubation in droplets, amplification and digestion happen concurrently and/or sequentially such that the product is a pool of predominantly linear ssDNA with sequence homology to the CO. This process is depicted schematically in FIG. 10.

Materials/Methods:
ssDNA oligos up to 150 bp are commercially synthesized and contain at least a sequence that serves as a primer binding site for RCA in addition to one or more of the following:

(a) A portion of sequential or non-sequential degenerate bases (barcode);
(b) A sequence that serves as a primer binding site which reconstitutes a dsDNA structure recognized by a restriction endonuclease;
(c) One or more bases modified by methylation;
(d) One or more bases which are locked nucleic acids;
(e) Other sequences important for molecular biology assays including:
  a. A poly A sequence, such that poly T barcodes can be used as reverse transcription primers,
  b. A portion of known sequence suitable for primer binding for PCR or ligation chain reaction (LCR),
  c. A portion of known homology used as a recognition sequence for loading into a Tn5 transposase, ssDNA oligos are incubated with CircLigase II from Epicentre in standard reaction buffers to circularize the oligos. Uncircularized oligos are digested by exonuclease treatment and the circularized oligos are purified by standard methods. Circularized ssDNA is encapsulated in droplets with reagents necessary for rolling circle amplification and restriction digestion. Reagents include:

(a) A suitable buffer such as Phi29 reaction buffer (NEB) or CutSmart Buffer (NEB);
(b) Bovine serum albumin (BSA);
(c) A DNA polymerase such as Phi29 or similar polymerase suitable for isothermal RCA;
(d) dNTP's;
(e) A restriction endonuclease;
(f) An oligo with homology to the circularized ssDNA that serves as a primer for DNA synthesis;
(g) An oligo with homology to the circularized ssDNA that reconstitutes a dsDNA sequence recognized by a restriction endonuclease. This oligo can be modified in the following ways:
  a. Incorporation of a 3' modification to block DNA synthesis, such as dideoxy bases, a 3' spacer, or locked nucleic acids,
  b. Incorporation of a 3'/5' fluorophore and/or a 3'/5' quencher to monitor cleavage; and
(h) An oligo with homology to the circularized ssDNA that reconstitutes a functional dsDNA element for loading into a Tn5 transposase.

Reactions are incubated at 30° C. for at least 60 minutes, followed by incubation at 37° C. or higher for at least 15 minutes. Optionally, the temperature can be increased to 65° C. for 10 minutes between the two incubations to deactivate Phi29 polymerase.

Alternatively, the process can be done in two separate steps where RCA is done first and then restriction cutting is done second:

(a) Drops are made containing only circularized ssDNA and reagents necessary for RCA. Drops are incubated at 30° C. for at least 60 minutes followed by heating at 65° C. for 10 minutes.
(b) Restriction endonuclease and an oligo to reconstitute the cut site and/or an oligo to reconstitute a Tn5 loading site are picoinjected into each droplet and incubated at 37° C. for at least 15 minutes.

Figure 11:
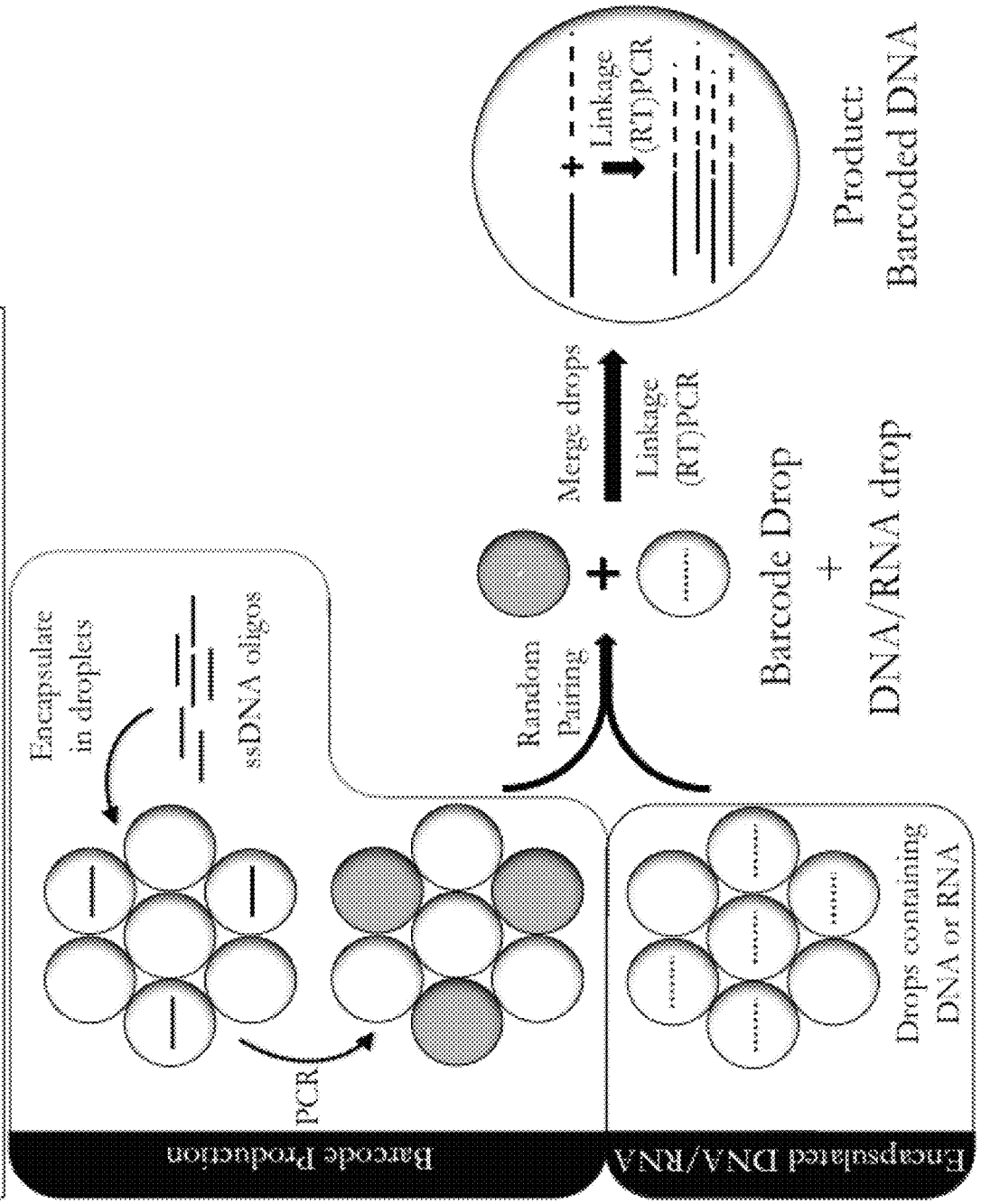
FIG. 11 provides a schematic illustrating steps in a method of preparing dsDNA barcodes by digital PCR in droplets and their use in linkage-PCR.

Example 2 (Prophetic): Production of dsDNA Barcodes by Digital PCR in Droplets and their Use in Linkage-PCR A pool of ssDNA oligonucelotides (barcodes) containing a portion of sequential or non-sequential degenerate bases in addition to at least one conserved sequence are encapsulated in droplets at limiting dilution and amplified by PCR to create dsDNA barcodes. The drop is then merged with another drop containing DNA or RNA nucleic acids and the dsDNA barcodes are spliced onto DNA/RNA of interest by linkage-per or linkage-rtper using primers with homology to the dsDNA barcode. This process is depicted schematically in FIG. 11.

Materials/Methods:

ssDNA oligos up to 100 bp are commercially synthesized and contain at least one or more sequences that serves as primer binding sites for PCR in addition to one or more of the following:
  (a) A portion of sequential or non-sequential degenerate bases (barcode);
  (b) A sequence that serves as a primer binding site which reconstitutes a dsDNA structure recognized by a restriction endonuclease;
  (c) One or more bases modified by methylation;
  (d) One or more bases which are locked nucleic acids;
  (e) One of more bases which are ribonucleotides;
  (f) Other sequences important for molecular biology assays including:
    a. A poly A sequence, such that poly T barcodes can be used as reverse transcription primers,
    b. A portion of known sequence suitable for primer binding for PCR or ligation chain reaction (LCR).

ssDNA oligos are encapsulated in droplets with reagents necessary for PCR, including one more oligos that serve as primers. Primers can contain one or more of the following:
  (a) One or more bases modified by methylation;
  (b) One or more bases which are locked nucleic acids;
  (c) One of more bases which are ribonucleotides;
  (d) 5' Biotinylation.

The products of this PCR reaction are droplets containing dsDNA fragments referred to as barcodes.

Droplets containing PCR amplified barcodes are first paired by microfluidic manipulation with a separate population of drops containing DNA or RNA, which could be derived from single mammalian cells. By "pairing" is meant that populations of drops containing barcodes and drops containing DNA and/or RNA are flowed through a microfluidic device that orders the drops into groups containing a specified ratio of barcode and DNA/RNA drops.

These groups of paired drops are then merged by an electric field with a separate drop that contains standard reagents necessary for reverse transcription and PCR in addition to the following: At least one oligo that serves as a primer for PCR and contains sequence homology with the dsDNA barcodes. The homology should be sufficient to enable Linkage-PCR of the sequence amplified by the primer target with the barcode.

The droplets from the previous step are thermalcycled under standard conditions such that DNA/RNA products within each drop are amplified and linked to dsDNA barcodes present in each drop by Linkage-PCR.

Figure 12:
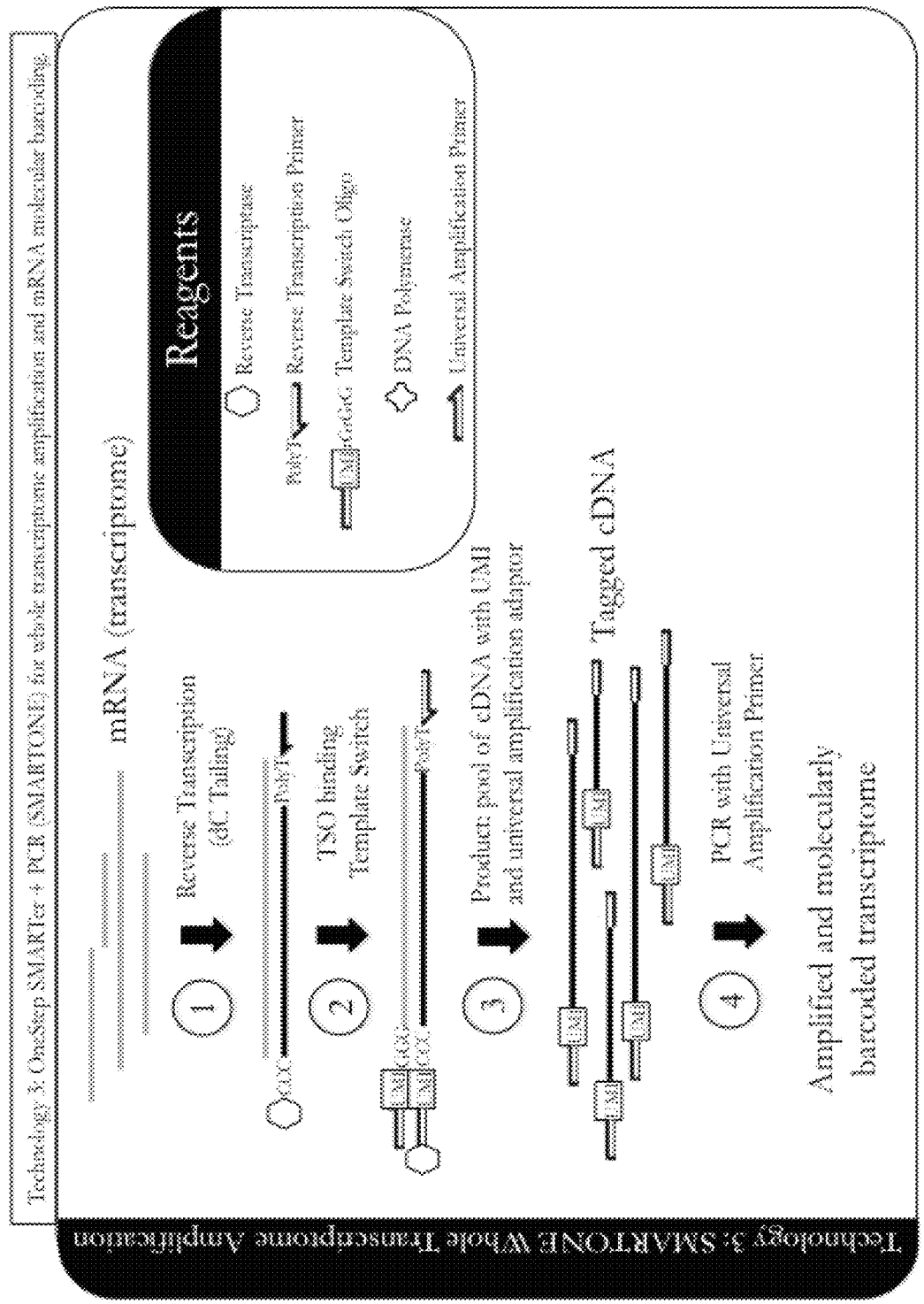
FIG. 12 provides a schematic illustrating steps in a method for whole transcriptome amplification and mRNA barcoding.

Example 3 (Prophetic): OneStep SMARTer+PCR (SMARTONE) for Whole Transcriptome Amplification and mRNA Molecular Barcoding A method for whole transcriptome amplification and mRNA molecular barcoding is described below with reference to FIG. 12. The SMARTer technology takes advantage of the terminal transferase activity of some reverse transcriptases, wherein several cytosine nucleotides are added to the 3' end of cDNA, called a dC tail (1). When a special template switching oligo (TSO) containing riboguanosine or LNA-guanosine at the 3' end is included in the reverse transcription reaction, the oligo will hybridize to the dC tail and serve as an additional template for reverse transcription, causing the cDNA to be elongated and the complementary TSO sequence added to the 3' end. Additionally, a six base pair degenerate sequence is incorporated into the design of the TSO oligo such that each cDNA contains a unique barcode as a result of the template switching mechanism (2), these barcodes are referred to as unique molecular identifiers (UMI). The UMI is used to accurately quantify mRNA copy number in downstream analysis and is very important for transcriptional profiling. Importantly, because the conserved sequence in the TSO oligo is added to all cDNA it can be used as a common priming site for whole transcriptome amplification by PCR(4).

The approach described herein is the consolidated process of SMART and PCR in a one step, one tube reaction, which is referred to as SMARTONE. The consolidated, one step protocol can also be performed inside of microfluidic drops to enable the one step amplification of single cell transcriptomes.

Materials/Methods:

Cell lysate or purified total RNA from one or more cells is mixed with dNTP's and a primer containing at least a poly T sequence in addition to one or more of the following:
  (a) A portion of sequential or non-sequential degenerate bases;
  (b) One or more bases modified by methylation;
  (c) One or more bases which are locked nucleic acids;
  (d) One of more bases which are ribonucleotides;
  (e) 5' Biotinylation;
  (f) Other sequences important for molecular biology assays including:
    a. A portion of known sequence suitable for primer binding for PCR or ligation chain reaction (LCR).

The solution is heated to at least 72° C. for at least 3 minutes.

SMARTONE reagents are introduced into the solution, including:
  (a) A buffered solution of pH 7.0-8.0 consisting of common PCR buffers such as Tris-HCL, Tris-Acetate, etc. at concentrations between 10 mM and 100 mM;
  (b) 100 U to 300 U SuperScriptII Reverse Transcriptase (Invitrogen);
  (c) High Fidelity DNA polymerase;
  (d) KCl at concentrations between 50 and 100 mM;
  (e) MgCl2 at concentrations between 6 and 12 mM;
  (f) dNTP's at between 0.2 and 0.4 uM;
  (g) DTT at between 2.5 and 7.5 mM;
  (h) 10 U RNaseOUT (Invitrogen);
  (i) Betaine at 1M;
  (j) 1 uM template switch oligo (TSO) which includes a known sequence that ends in three or more guanosine bases in addition to one or more of the following features:
    a. A portion of sequential or non-sequential degenerate bases including a unique molecular identifier,
    b. One or more bases modified by methylation,
    c. One or more bases which are locked nucleic acids, especially the 3' most guanosine base,
    d. One of more bases which are ribonucleotides, especially the second and third most 3' guanosine base,
    e. 5' Biotinylation,
    f. Other sequences important for molecular biology assays including:
      i. A portion of known sequence suitable for primer binding for PCR or ligation chain reaction (LCR)

(k) 1 uM of one of more oligo primers with homology to the template switch oligo and/or the poly T reverse transcription primer.

Additionally, performance enhancing agents can be added to the reaction, including:
(a) PEG MW 6000 at concentrations from 0.1% up to 5% w/v;
(b) Tween 20 at concentrations from 0.1% up to 5% v/v; and
(c) BSA at concentrations up to 250 ug/mL.

The reaction is thermalcycled with the following conditions:

TABLE 1

| Cycle | Temperature | Time |
|---|---|---|
| 1 | 42° C. | 60 to 90 min |
| 2-11 | 50° C. | 2 min |
|  | 42° C. | 1 min |
| 12 | 93° C. | 3 min |
| 13-25 | 92° C. | 30 sec |
|  | 58° C. | 30 sec |
|  | 68° C. | 5 min |
| 26 | 68° C. | 6 min |
| 27 | 4° C. | Hold |

Example 4 (Prophetic): Production of Tagmentation Droplet Libraries in Droplets

In this method the method of Example 1, 5, or 6 is used to produce barcodes in drops. However, in this implementation the products are not ssDNA but rather transposons suitable for loading into the Tn5 transposase. Each transposon contains at least a degenerate barcode and a 19 base pair conserved region necessary for transposition in addition to optional sequence. Droplets containing amplified and digested transposons are then merged with droplets containing the Tn5 transposase in a buffer suitable for loading of the transposon into the transposase. This population of droplets is then used in downstream applications to fragment and barcode DNA contained in other droplets.

Materials/Methods:
ssDNA oligos up to 150 bp are commercially synthesized and contain at least a sequence that serves as a primer binding site for RCA and a known sequence used as a recognition sequence for loading into a Tn5 transposase in addition to one or more of the following:
(a) A portion of sequential or non-sequential degenerate bases (barcode);
(b) A sequence that serves as a primer binding site which reconstitutes a dsDNA structure recognized by a restriction endonuclease;
(c) One or more bases modified by methylation;
(d) One or more bases which are locked nucleic acids; and
(e) Other sequences important for molecular biology assays including a portion of known sequence suitable for primer binding for PCR or ligation chain reaction (LCR).

ssDNA oligos are incubated with CircLigase II from Epicentre in standard reaction buffers to circularize the oligos. Uncircularized oligos are digested by exonuclease treatment and the circularized oligos are purified by standard methods.

Circularized ssDNA is encapsulated in droplets with reagents necessary for rolling circle amplification and restriction digestion. Reagents include:

(a) A suitable buffer such as Phi29 reaction buffer (NEB) or CutSmart Buffer (NEB);
(b) BSA;
(c) A DNA polymerase such as Phi29 or similar polymerase suitable for isothermal RCA;
(d) dNTP's;
(e) A restriction endonuclease;
(f) An oligo with homology to the circularized ssDNA that serves as a primer binding site for DNA synthesis;
(g) An oligo with homology to the circularized ssDNA that reconstitutes a dsDNA sequence recognized by a restriction endonuclease. This oligo can be modified in the following ways:
   a. Incorporation of a 3' modification to block DNA synthesis, such as dideoxy bases, a 3' spacer, or locked nucleic acids,
   b. Incorporation of a 3'/5' fluorophore and/or a 3'/5' quencher to monitor cleavage
(h) An oligo with homology to the circularized ssDNA that reconstitutes a functional dsDNA element for loading into a Tn5 transposase.

Reactions are incubated at 30° C. for at least 60 minutes, followed by incubation at 37° C. or higher for at least 15 minutes. Optionally, the temperature can be increased to 65° C. for 10 minutes between the two incubations to deactivate Phi29 polymerase.

Alternatively, the process can be done in two separate steps where RCA is done first and then restriction cutting is done second:
(a) Drops are made containing only circularized ssDNA and reagents necessary for RCA. Drops are incubated at 30° C. for at least 60 minutes followed by heating at 65° C. for 10 minutes.
(b) Restriction endonuclease and an oligo to reconstitute the cut site and/or an oligo to reconstitute a Tn5 loading site are picoinjected into each droplet and incubated at 37° C. for at least 15 minutes.

These drops are picoinjected or merged with a solution containing:
(a) 6 uM Tn5 transposase;
(b) PEG MW 6000 up to 5% w/v;
(c) Tween 20 up to 5% v/v;
(d) BSA at concentrations up to 250 ug/mL; and
(e) Glycerol at concentrations up to 40% v/v.

Figure 13:
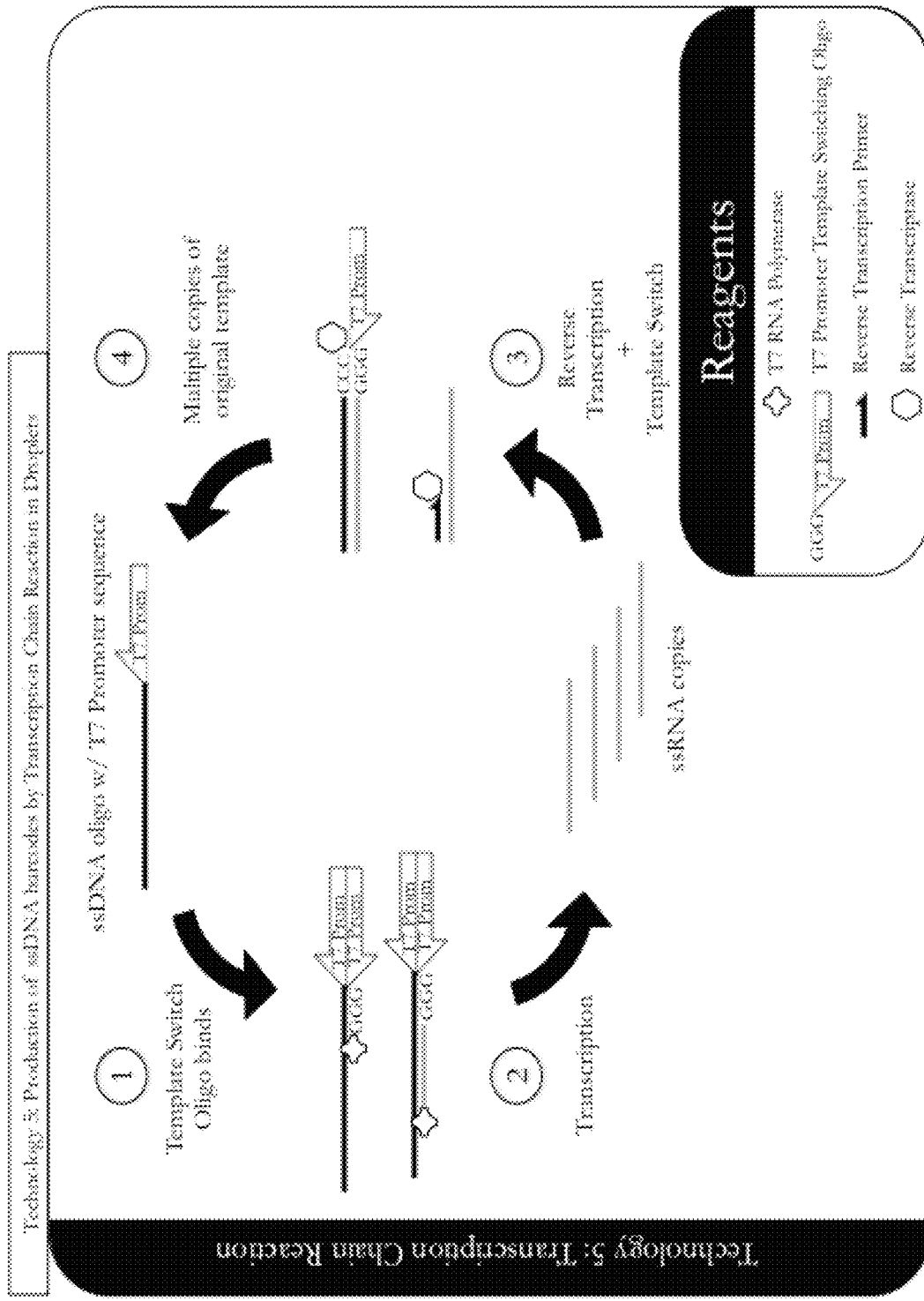
FIG. 13 provides a schematic illustrating steps in a method of preparing ssDNA barcodes by transcription chain reaction (TCR) in droplets.

Example 5 (Prophetic): Production of ssDNA Barcodes by Transcription Chain Reaction (TCR) in Droplets A method for the production of ssDNA barcodes by TCR in droplets is described below with reference to FIG. 13. A pool of ssDNA oligonucelotides containing a portion of sequential or non-sequential degenerate bases in addition to conserved sequences including a T7 RNA polymerase promoter region are encapsulated in drops by limiting dilution along with TCR reagents (1). T7 RNA polymerase first transcribes the complement of the ssDNA oligo to several thousand copies (2). Reverse Transcriptase and a specific reverse transcription primer then convert each RNA copy into cDNA, which is a ssDNA copy of the original barcode. The SMART technology described in Example 3 above is employed to attach the T7 promoter sequence to the end of each cDNA (3), thus allowing it to serve as an addition template for T7 RNA Polymerase mediated transcription. At the end of the process heat or RNase is used to degrade the RNA component leaving only ssDNA copies of the original oligo (4).

Materials/Methods:

ssDNA oligos up to 100 bp are commercially synthesized and contain at least one or more sequences that serve as a transcription initiation site in addition to one or more of the following:
- (a) A portion of sequential or non-sequential degenerate bases (barcode);
- (b) A sequence that serves as a primer binding site which reconstitutes a dsDNA structure recognized by a restriction endonuclease;
- (c) One or more bases modified by methylation;
- (d) One or more bases which are locked nucleic acids;
- (e) One of more bases which are ribonucleotides;
- (f) Other sequences important for molecular biology assays including:
  - a. A poly A sequence, which will result in poly T barcodes to be using as reverse transcription primers,
  - b. A portion of known sequence suitable for primer binding for PCR or ligation chain reaction (LCR).

ssDNA oligos are encapsulated in droplets with reagents necessary for TCR, including:
- (a) An oligo that reconstitutes the dsDNA T7 RNA Polymerase (T7 RNAP) promoter and also serves as a template switch oligo (TSO), which can contain one or more of the following:
  - a. One or more bases modified by methylation,
  - b. One or more bases which are locked nucleic acids, especially the 3' most guanosine base,
  - c. One of more bases which are ribonucleotides, especially the second and third most 3' guanosine base,
  - d. 5' Biotinylation
- (b) T7 RNA polymerase;
- (c) Reverse Transcriptase, such as SuperScript II;
- (d) Deoxyribunucleotides (dNTP's);
- (e) Ribonucleotides (rNTP's);
- (f) Hybridase (Heat Stable RNaseH);
- (g) A restriction endonuclease;
- (h) An oligo with homology to the ssDNA that serves as a primer for cDNA synthesis by reverse transcriptase;
- (i) An oligo with homology to the ssDNA that reconstitutes a dsDNA sequence recognized by a restriction endonuclease. This oligo can be modified in the following ways:
  - a. Incorporation of a 3' modification to block DNA synthesis, such as dideoxy bases, a 3' spacer, or locked nucleic acids,
  - b. Incorporation of a 3'/5' fluorophore and/or a 3'/5' quencher to monitor cleavage;
- (j) An oligo with homology to the ssDNA that reconstitutes a functional dsDNA element for loading into a Tn5 transposase.

Reactions are incubated at 42° C. for at least 60 minutes. Alternatively, the reaction can be thermalcycled as follows:

TABLE 2

| Cycle | Temperature | Time |
| --- | --- | --- |
| 1 | 42° C. | 60 to 90 min |
| 2-11 | 50° C. | 2 min |
|  | 42° C. | 1 min |

Finally, the reaction temperature is raised to 65° C. to allow for RNA degradation. The products of this TCR reaction are droplets containing dsDNA fragments referred to as barcodes. Alternatively, the process can be done in two separate steps where TCR is done first and then restriction cutting is done second.

Figure 14:
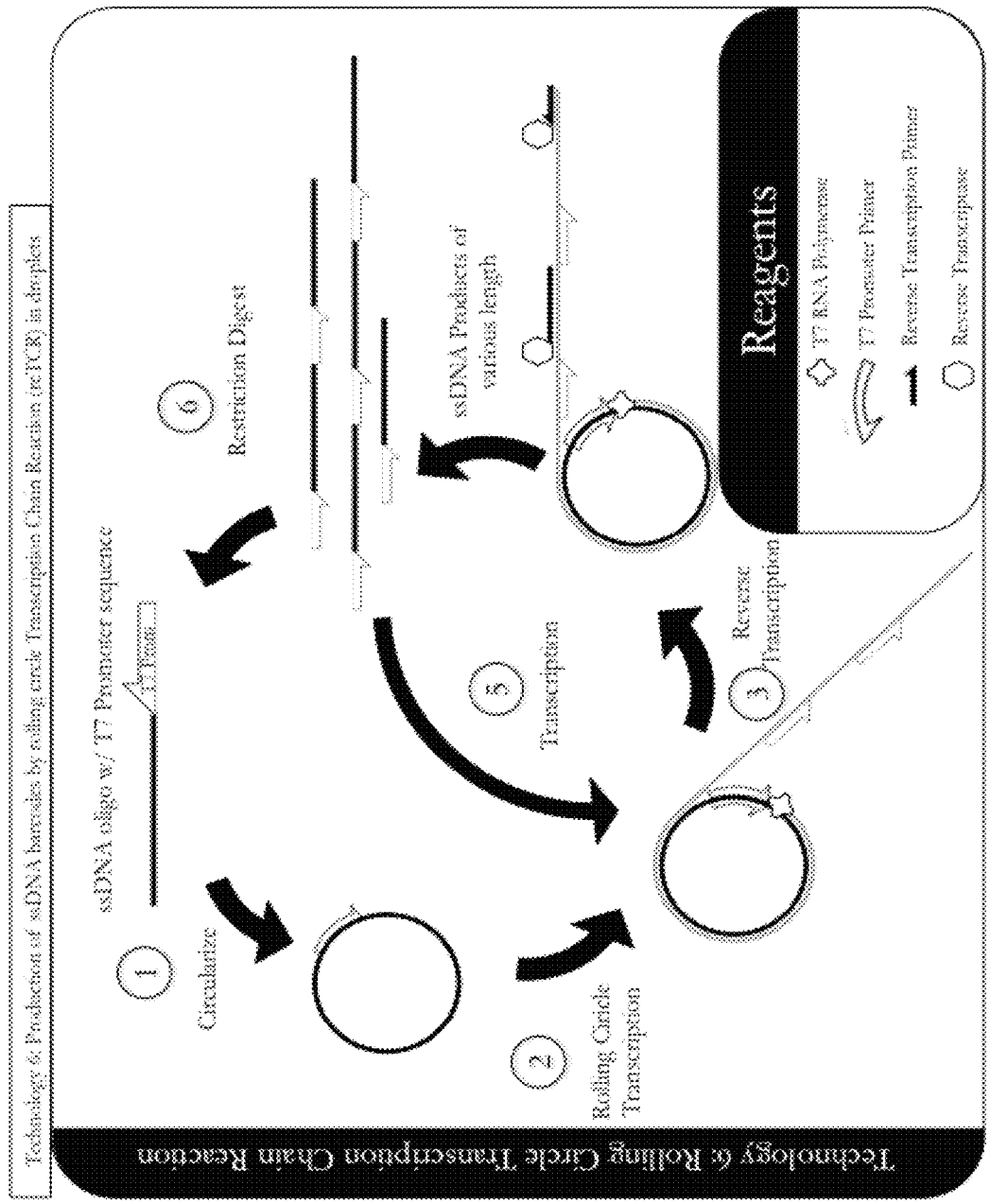
FIG. 14 provides a schematic illustrating steps in a method of preparing ssDNA barcodes by rolling circle transcription chain reaction (rcTCR) in droplets.

Example 6 (Prophetic): Production of ssDNA Barcodes by Rolling Circle Transcription Chain Reaction (rcTCR) in Droplets A method of production of ssDNA barcodes by rolling circle transcription chain reaction (rcTCR) in droplets is described below with reference to FIG. 14.

A pool of ssDNA oligonucelotides containing a portion of sequential or non-sequential degenerate bases in addition to conserved sequences including a T7 RNA polymerase promoter region are first circularized by CircLigase and digested with exonuclease to remove uncircularized oligos (1). Circularized oligos (COs) are then encapsulated in droplets by limiting dilution with rcTCR reagents. T7 RNA polymerase first transcribes the complement of the CO, creating a long linear concatamer including several hundred to several thousand repeats of the CO reverse complement sequence (2). Reverse Transcriptase and a specific reverse transcription primer then reverse transcribe from several sites along the RNA concatmer to produce long strands of ssDNA (3). An additional primer is used to reconstitute the T7 promoter inside these linear ssDNA products to initiate transcription and produce more ssRNA template (5). Finally, heat or RNaseH is used to degrade the RNA components and restriction digestion is used in parallel or sequentially to cleave the long ssDNA into single ssDNA barcodes (6).

Materials/Methods:

ssDNA oligos up to 100 bp are commercially synthesized and contain at least one or more sequences that serve as a transcription initiation site in addition to one or more of the following:
- (a) A portion of sequential or non-sequential degenerate bases (barcode);
- (b) A sequence that serves as a primer binding site which reconstitutes a dsDNA structure recognized by a restriction endonuclease;
- (c) One or more bases modified by methylation;
- (d) One or more bases which are locked nucleic acids;
- (e) One of more bases which are ribonucleotides;
- (f) Other sequences important for molecular biology assays including:
  - a. A poly A sequence, such that poly T barcodes can be used as reverse transcription primers,
  - b. A portion of known sequence suitable for primer binding for PCR or ligation chain reaction (LCR).

ssDNA oligos are incubated with CircLigase II from Epicentre in standard reaction buffers to circularize the oligos. Uncircularized oligos are digested by exonuclease treatment and the circularized oligos are purified by standard methods Circularized ssDNA oligos are encapsulated in droplets with reagents necessary for TCR, including:
- (a) An oligo that reconstitutes the dsDNA T7 RNA Polymerase (T7 RNAP) promoter, which can contain one or more of the following:
  - a. One or more bases modified by methylation,
  - b. One or more bases which are locked nucleic acids,
  - c. One or more bases which are ribonucleotides,
  - d. 5' Biotinylation,
- (b) T7 RNA polymerase;
- (c) Reverse Transcriptase, such as SuperScript II;
- (d) Deoxyribunucleotides (dNTP's);
- (e) Ribonucleotides (rNTP's);

(f) Hybridase (Heat Stable RNaseH);
(g) A restriction endonuclease;
(h) An oligo with homology to the circularized ssDNA that serves as a primer for cDNA synthesis by reverse transcriptase;
(i) An oligo with homology to the circularized ssDNA that reconstitutes a dsDNA sequence recognized by a restriction endonuclease. This oligo can be modified in the following ways:
   a. Incorporation of a 3' modification to block DNA synthesis, such as dideoxy bases, a 3' spacer, or locked nucleic acids,
   b. Incorporation of a 3'/5' fluorophore and/or a 3'/5' quencher to monitor cleavage,
(j) An oligo with homology to the circularized ssDNA that reconstitutes a functional dsDNA element for loading into a Tn5 transposase.

Reactions are incubated at 42° C. for at least 60 minutes. Alternatively, the reaction can be thermalcycled as follows:

TABLE 3

| Cycle | Temperature | Time |
| --- | --- | --- |
| 1 | 42° C. | 60 to 90 min |
| 2-11 | 50° C. | 2 min |
|  | 42° C. | 1 min |

Finally, the reaction temperature is raised to 65° C. to allow for RNA degradation. The products of this TCR reaction are droplets containing dsDNA fragments referred to as barcodes. Alternatively, the process can be done in two separate steps where rcTCR is done first and then restriction cutting is done second.

Example 7 (Prophetic): Implementations

SMARTONE Linkage-PCR:
In this method cellular barcodes are produced according to Example 1 or 2 and spliced onto the 5' and 3' ends of cDNA by the PCR step of SMARTONE (Example 3). In this implementation the incorporation of UMIs in the TSO oligo is used to barcode mRNAs at the molecular level.

cDNA End Tag and Capture (DEToCs):
In this method cellular DNA barcodes are produced by Rolling Circle Amplification (RCA) and used as reverse transcription primers, thus attaching the DNA barcode to each cDNA in a single step.

DeToCs+SMARTONE:
In this method cellular DNA barcodes are produced by Rolling Circle Amplification (RCA) and used as reverse transcription primers, thus attaching the DNA barcode to each cDNA in a single step. Additionally, SMARTONE (Example 3) is used to amplify the barcoded transcriptome, with or without the inclusion of UMIs.

SMARTONE+Transcriptome Tag and Capture:
In this method SMARTONE is used to amplify whole transcriptomes (UMIs optional). Droplets containing whole transcriptomes are then merged with drops containing NextEra reagents and tagmented. These drops are then merged with drops containing cellular barcodes produced according to Example 1 or 2 and Linkage-PCR is used to amplify the tagmented transcriptome using the barcodes as primers.

OneStep Whole Transcriptome Tag and Capture:
In this method tagmentation droplet libraries are made according to Example 4 and merged with drops containing whole transcriptome amplification done using SMARTONE (Example 3).

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Example 8: Fragmentation and Barcoding of Single DNA Templates for Next Generation Sequencing Most genomes comprise millions to billions of base pairs of nucleic acids and, in general, obtaining the maximum amount of information about a genome requires sequencing every base pair and knowing how the bases are connected together on the genomic scale. However, existing sequencing technologies that provide the lowest cost per base also acquire sequences in the form of "short" reads tens to hundreds of base pairs in length. Consequently, when using short read technologies to sequence long molecules or whole genomes, significant bioinformatic analysis is necessary to stitch the short reads into long reads.

When assembling long molecules or genomes from a collection of short reads, the complexity of the assembly scales exponentially with the number of reads in the library since, in general, determining the best assembly is only possible by consulting every read in the library each iteration. Algorithms can be used to perform this process as intelligently and efficiently as possible, but the smaller the reads, the larger the number of reads to test, and the more difficult the assembly. Consequently, technologies for increasing read length can significantly simplify reassembly tasks and enable the recovery of information that is not accessible to short read technologies, such as haplotypes.

Figure 21:
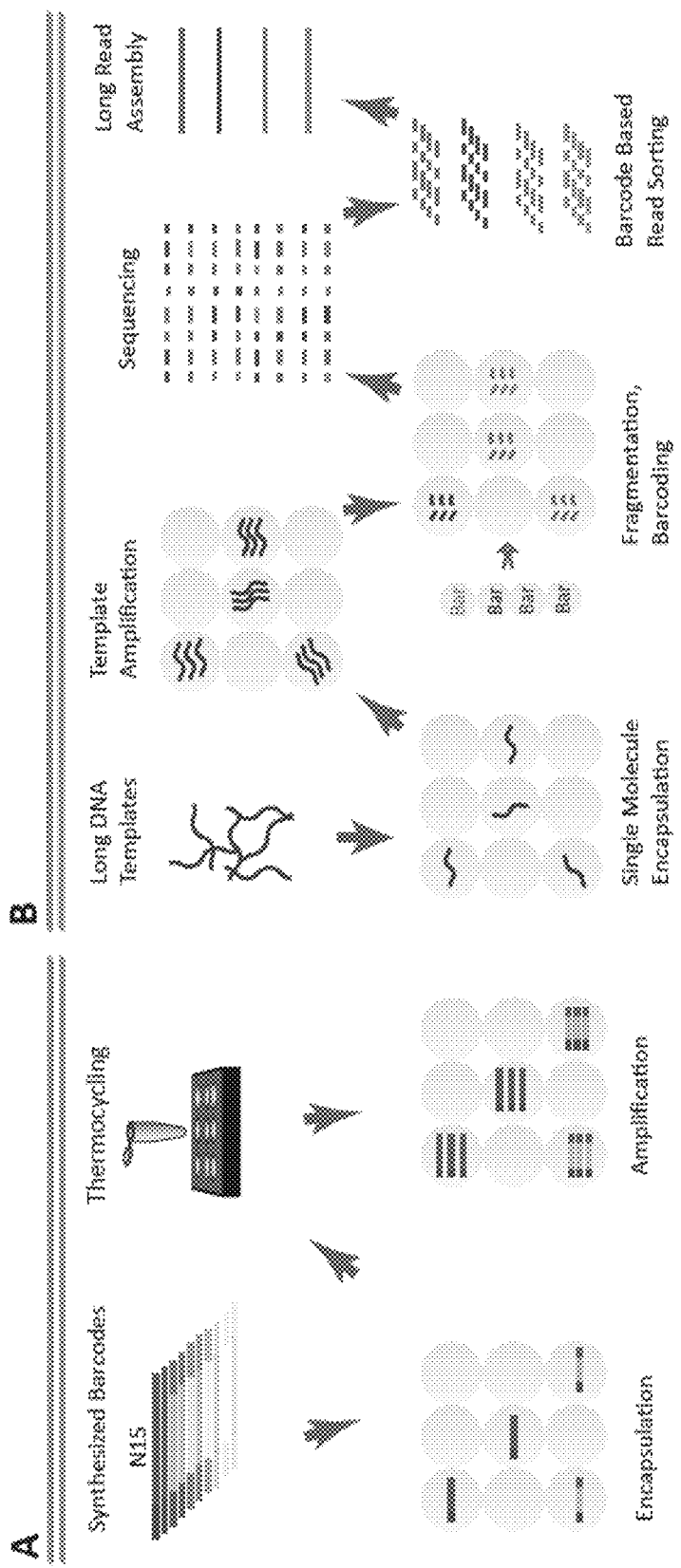
FIG. 21 provides a schematic of a single molecule deep sequencing workflow according to an embodiment of the present disclosure. (A) Barcode molecules are encapsulated in droplets at limiting dilution and amplified, generating an emulsion library that can be used to barcode molecules in droplets. (B) To sequence single long template molecules deeply using the methods described herein, individual molecules are encapsulated in droplets and amplified using, for example, PCR or MDA. The amplified molecules are then fragmented and ligated with adaptors using fragmentase/ligase or, for example, a tagmentation reaction. Barcode droplets are added to the droplets containing the fragmented molecules and then the barcodes spliced onto the fragments using an overlap extension PCR. The short reads are sequenced and sorted by barcode to generate clusters corresponding to the original target molecule, which can then be reassembled.

Described herein is a technology that allows deep sequencing of molecules up to 100 kb in length. In this technology, dubbed single molecule deep sequencing (SMDS), long, individual molecules up to 100 kb are encapsulated in droplets, amplified, fragmented, and barcoded (FIG. 1). By amplifying each molecule in a droplet using PCR or MDA, we create many copies of the single molecule that can be sequenced to create a "deep sequence" cluster that averages over errors in PCR or sequencing. In addition, by fragmenting and barcoding the molecules in droplets, we generate short reads that are sequenceable using available, low-cost technologies, while still having the ability to aggregate reads corresponding to long single molecules without having to rely on assembly algorithms prone to failure (FIG. 21).

Figure 22:
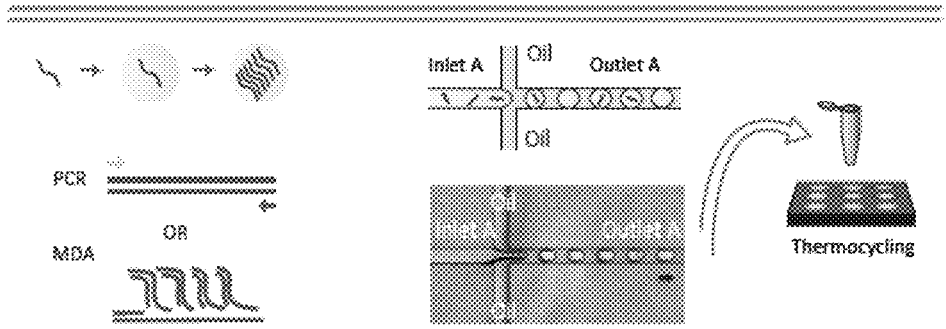
FIG. 22 provides a schematic illustrating the microfluidic steps to perform single molecule deep sequencing in an embodiment of the present disclosure. (Step 1) Encapsulation of the target molecules is accomplished using microfluidic flow focusing followed by thermal cycling of the emulsion. (Step 2) The tagmentation reaction is accomplished using a split-merger device in which the amplified target droplet is introduced, a small portion is split off, and that portion merged with droplets containing the tagmentation reagents. Splitting the template droplets allows one to recover the needed amount of DNA and dilute it to the appropriate concentration of the tagmentation reaction by merging with a target droplet. (Step 3) The amplified and tagmented molecules are barcoded by merging the droplets from Step 2 with newly formed droplets containing the PCR reagents and droplets made in a prior step (not shown) containing amplified barcode. The emulsion is thermocycled, attaching the barcodes to the fragments.
Figure 22:
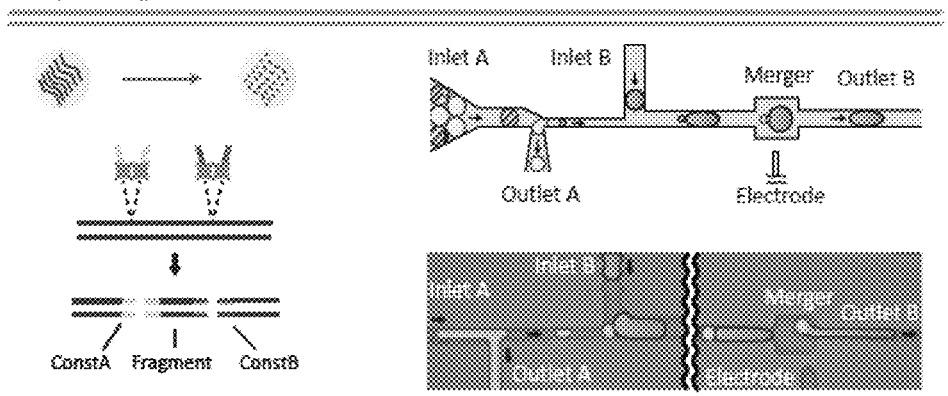
Figure 22:
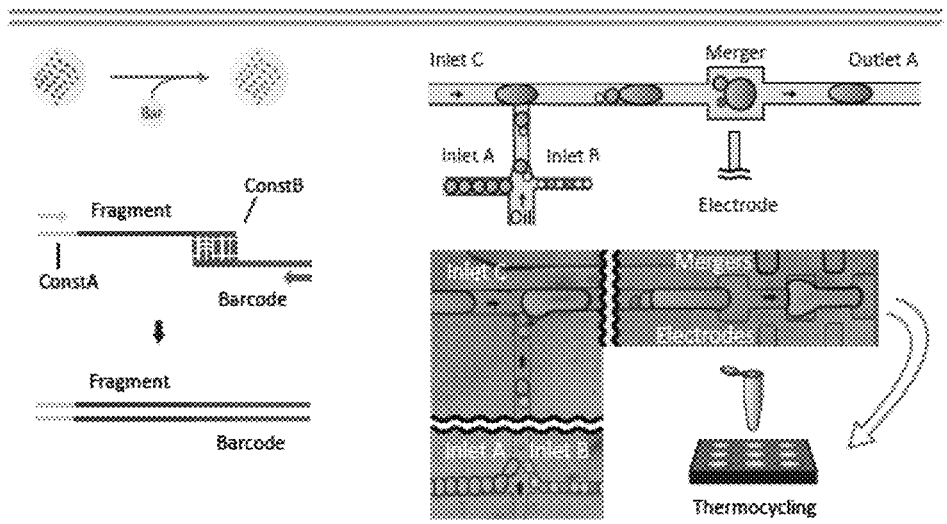

SMDS uses three primary molecular biology steps: (1) digital amplification of single molecules (FIG. 22, Step 1), (2) tagmentation to fragment the molecules and attach universal amplification adaptors (FIG. 22, Step 2) and (3) barcoding with splicing by overlap extension PCR (SOE-PCR) to attach the barcodes to the tagmented fragments (FIG. 22, Step 3). Each of these steps is performed using a separate microfluidic device, a droplet generator for Step 1, a split-merge device for Step 2, and a double droplet merger device for Step 3. In addition, the volumes of the starting droplets, their spit portions, and the droplets they are merged with, are carefully controlled to ensure that the concentrations of the nucleic acids, necessary reagents, and enzymes are at the needed levels to yield an efficient reaction that provides the highest quality data.

Figure 23:
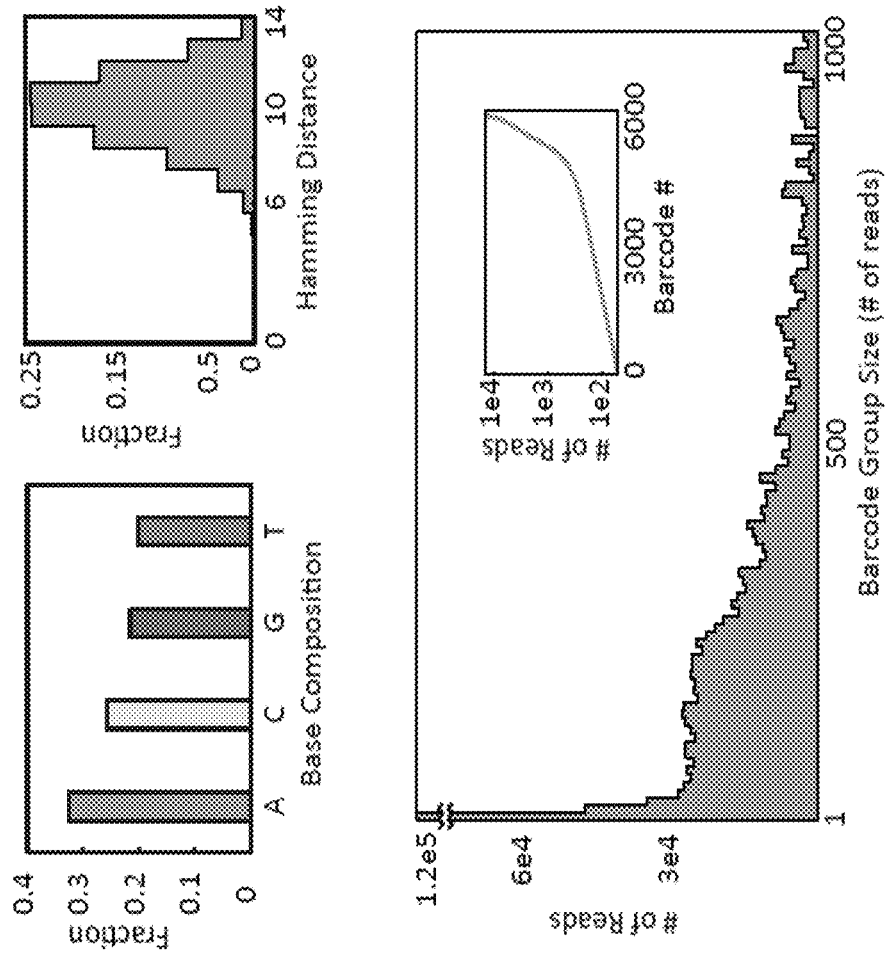
FIG. 23 provides graphs showing the characterization of barcode groups in SMDS. The barcode molecules are synthesized chemically and exhibit a relatively uniform base composition (upper left). The barcode length is selected so that, for the number of barcodes used in the SMDS workflow, the hamming distance between samples barcodes is large, as shown by the histogram of hamming distances, upper-right. This makes it straightforward to identify which barcodes should be clustered into a single group, even if there are imperfect matches due to amplification or sequencing errors. Lower plot shows read counts of barcode groups of different size. For example, a barcode group with one read corresponding to it will have a size of one, x-axis, while the number of read counts of all such 1-read barcode groups comprises the y-axis. The number of reads of each barcode group sorted in ascending order is provided inset.

The data provided by the SMDS platform comes in the form of normal sequence data, except that in addition to the sequences of the fragment molecules, adaptors, etc., there are also sequences for the barcodes added to the molecules in the droplets, which permit unambiguous clustering of all reads corresponding to a single molecule in a droplet. The barcode structure is important since the barcodes are used to correctly cluster the reads into single molecule groups. The barcodes are synthesized chemically (IDT) as a collection of randomers flanked by universal priming sites. The barcode nucleic acid distribution is fairly uniform in the base pair composition, typical of chemical synthesis techniques, FIG. 23, upper left. The barcode sequence comprises ~15 bp, of which there are ~$10^9$ unique permutations. In SMDS, ~100,000 molecules in total are currently sequenced, so that ~0.001% of this space is sampled. This number will increase substantially, but the barcode length can be increased to compensate. As such, the probability that a barcode is used twice is small, although it can happen when sequencing large numbers of molecules. In addition, the low density at which the permutation space is sampled allows for the selection of sequences with maximum hamming distance from one another, FIG. 23, upper right. This ensures that even if a particular barcode sequence has an error in it, it is unlikely to "mutate" into another barcode group and, instead, is much more likely to create a new group including just the one read with the mutated barcode. In addition, it is possible to "adopt" these "orphan" barcodes into clusters by comparing the mutant barcode with all other barcode groups and identifying the one to which it has the highest sequence homology, to which it most likely belongs.

To test the system, SMDS was performed on a sample including many copies of two betaglucosidase variants.

Materials/Methods:

Starting Material—known PCR products of fixed length.

Step I. Encapsulation and Amplification by PCR (1) PCR cocktail (100 μL total)

50 μL Phusion 2× hotstart MM (NEB: M0536)

2 μL primers (10 μM)

X μL templates (to final concentration of 0.003 pM)

4 μL PEG 6000 (50% W/V)

4 μL Tween-20 (50% V/V)

X μL $H_2O$ to final volume of 100 μL (2) The PCR cocktail was loaded into a 30 μm×35 μm flow focus drop maker. The oil pump was run at 600 μL/hr and the aqueous pump was run at 500 μL/hr for ~10 minutes. The emulsion was collected in a PCR tube and thermal cycled: 98° C. 3 min, (98° C. 15 s, 60° C. 20 s, 72° C. 4 min), for 35 cycles.

Step I (Alternative). Amplification by MDA (the following protocol can be used as an alternative to Step 1 above.

(1) Prepare MDA mix (Reagents from Repli-G Single Cell Kit—Qiagen Catalogue 150343)

3 μL D2 Buffer (1:11 DTT and DLB)

4 μL $H_2O$ and Template DNA

Heat to 65° C. for 10 min then add 3 ul μL STOP buffer 14.5 μL polymerase buffer 1 μL polymerase 4.5 μL $H_2O$ (2) Load the cocktail into a 30 μm×35 μm flow focus drop maker. Run oil pump at 600 μL/hr and aqueous pump at 500 μL/hr for ~10 minutes. Collect emulsion in PCR tube and incubate at 30° C. for 6 hours followed by heat kill at 70° C. for 10 min.

Figure 16:
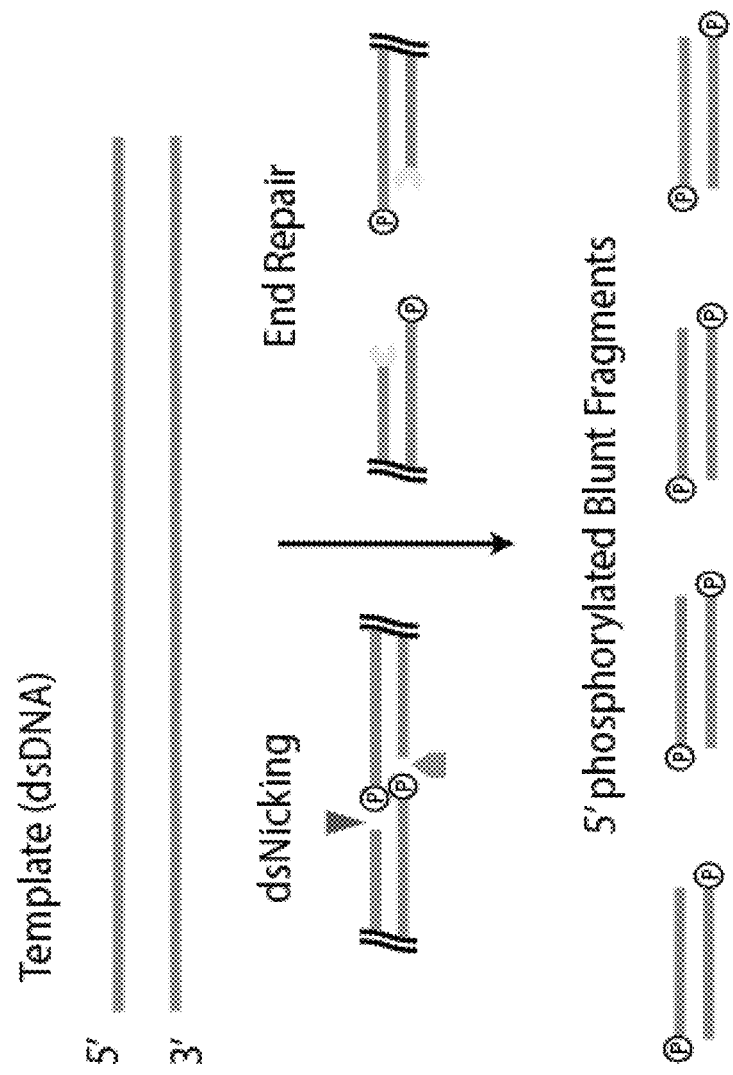
FIG. 16 provides a schematic illustrating a fragmentation step in the method employed in Example 8.

Step II. Fragmentation of Templates in Drops (This step uses enzymes from NEBnext Ion Torrent library preparation kit (E6285)) and is depicted in FIG. 16.

(1) Prepare Fragmentation Cocktail (90 μL)

10 μL Fragmentase Buffer 7.5 μL Fragmentase Enzyme Mix 72.5 μL $H_2O$ (2) The fragmentation cocktail and thermal cycled drops were loaded into a drop merger device and run at Oil: 100 μL/hr, Spacer: 300 μL/hr, Drops: 100 μL/hr, Fragmentase Cocktail: 100 μL/hr. The run took ~50 minutes. The emulsion was collected into PCR tubes and incubate at 25° C. for 15 mins and then 70° C. for 10 mins.

The drop merger device takes ⅒th of the injected drop and merges it with a new drop 9/10th the size of the injected drop to result in new drops that are of the same size.

Run time can be shortened by increasing flow rates.

The collected drops should be approximately the same size as the injected drops, and the total emulsion volume should be ~80-90% of the original.

Figure 17:
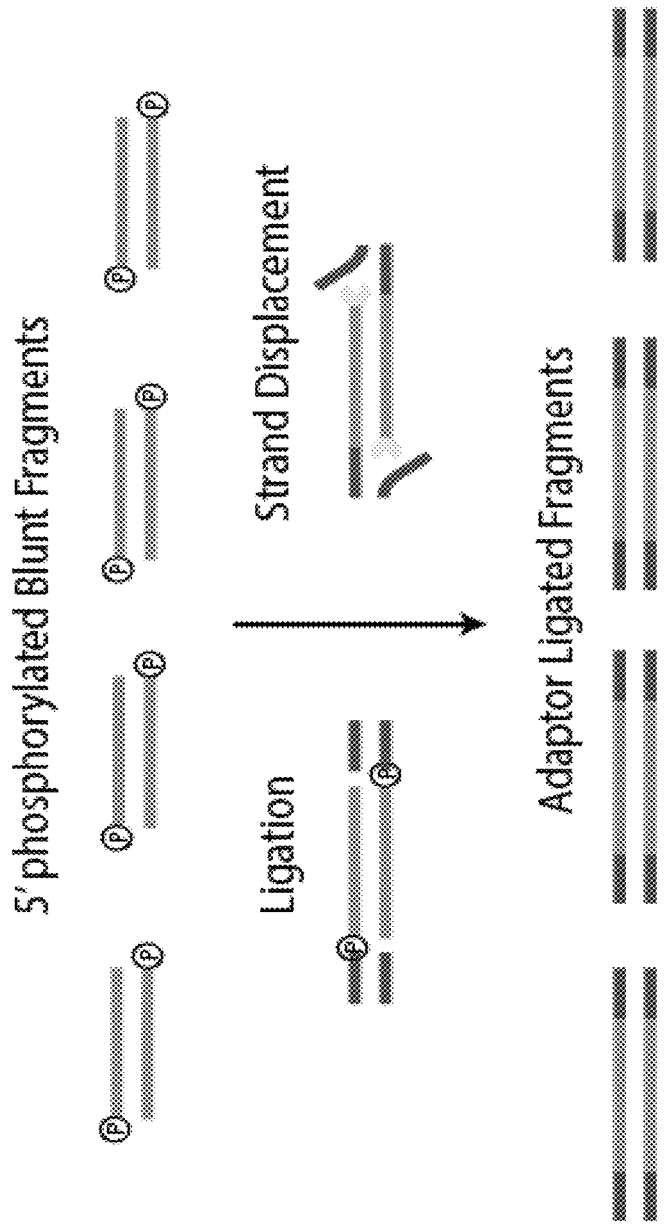
FIG. 17 provides a schematic illustrating a ligation step in the method employed in Example 8.

Step III. Ligation of universal adaptors in drops (Enzymes in this step were from the same kit as step II). This step is depicted schematically in FIG. 17.

(1) Prepare Adaptor Ligation cocktail (90 μL)

10 μL Ligase buffer

4 μL Universal Adaptors (80 μM stock)

10 μL T4 Ligase (Enzyme from Kit, concentration unknown)

2.5 μL Bst Pol (Enzyme from Kit, concentration unknown)

73.5 μL $H_2O$ (2) Drops from Step II were loaded into a syringe and Step II(2) was repeated with the Adaptor Ligation Cocktail. The resulting emulsion was incubated at 25° C. for 15 minutes and 65° C. for 5 minutes. The adaptors included a 3' overhang of two phosphorylthioated bases.

Figure 18:
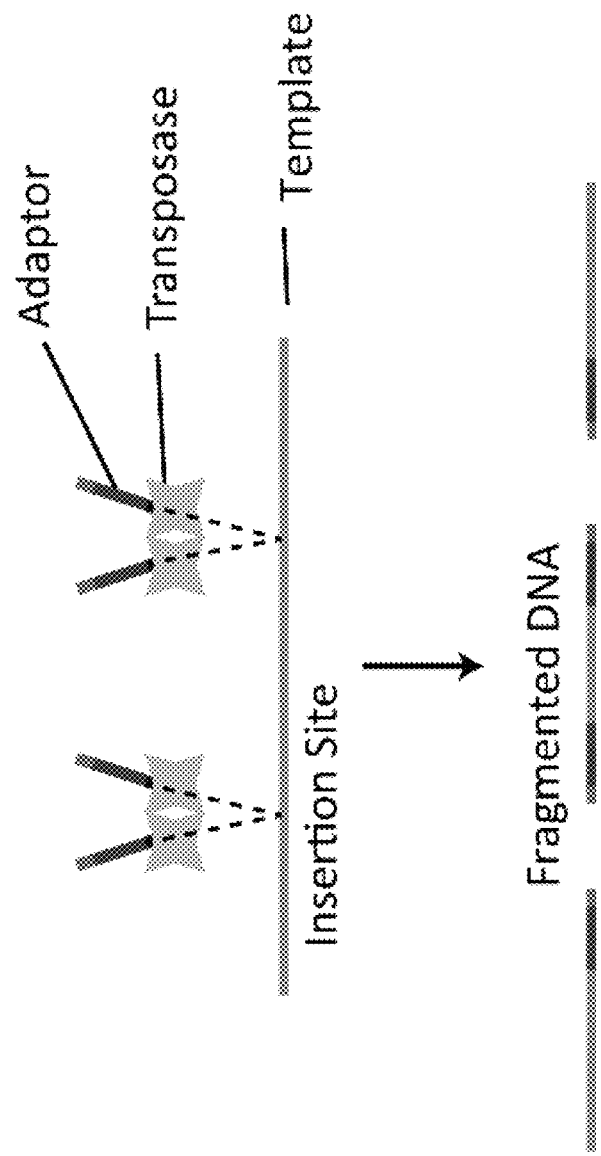
FIG. 18 provides a schematic of an alternative step relative to steps II and III of Example 8.

Step II-III. (Alternative) Tagmentation using Tn5 Transposons. This alternative step/steps is depicted in FIG. 18.

This step uses the hyperactive Tn5 transposons to fragment and add adaptors to the DNA simultaneously (Tagmentation). The Tn5 transposons and adaptors can be attained from Illumina Nextera Kits, or made as described in Adey et al., "Rapid, Low-Input, Low-Bias Construction of Shotgun Fragment Libraries by High-Density in Vitro Transposition" 2010, 11:R119, the disclosure of which is incorporated by reference herein in its entirety and for all purposes.

(1) Prepare Tagmentation master mix (50 μL)

25 μL TD buffer

2 μL PEG 6000 (50% W/V)

2 μL Tween-20 (50% V/V)

16 μL $H_2O$

5 μL Enzyme (2) Load the tagmentation cocktail and thermal cycled drops into the drop merger device and run the device at Oil: 100 μL/hr, Spacer: 300 μL/hr, Drops: 100 μL/hr, Fragmentase Cocktail: 100 μL/hr. The run takes ~50 minutes. Collect the emulsion into PCR tubes and incubate at 55° C. for 10 mins and then 70° C. for 20 mins.

The Drop Merger takes ⅒th of the injected drop and merges it with a new drop 9/10th the size of the injected drop to result in new drops that are of the same size.

Run time can be shortened by increasing flow rates.

The collected drops should be same size as injected drops, and the total emulsion volume should be ~80-90% of the original.

Figure 19:
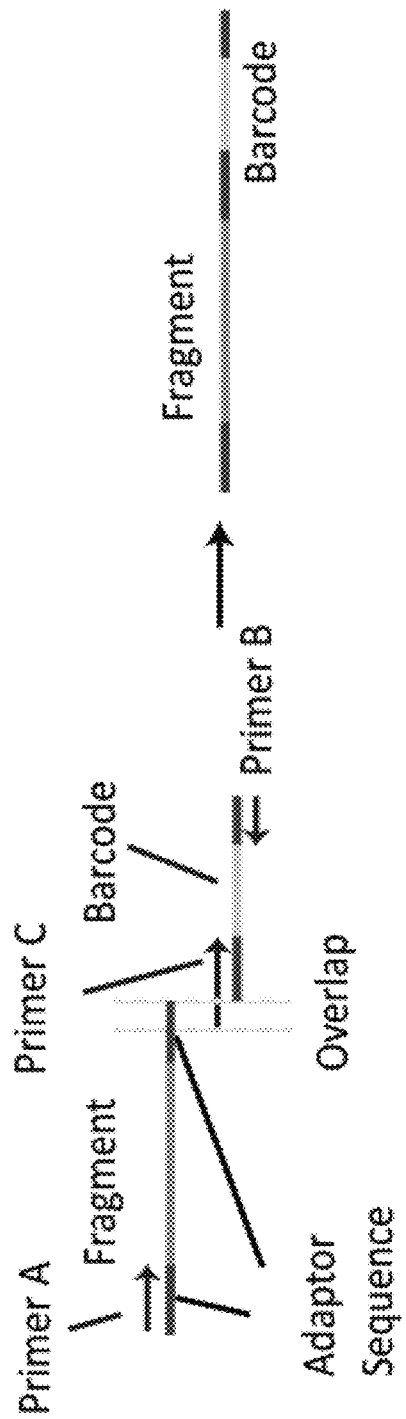
FIG. 19 provides a schematic of a SOE-PCR reaction step as utilized in Example 8.

Step IV. SOE-PCR of Barcodes using Barcode *E. coli* or Barcode Plasmids. This step is depicted schematically in FIG. 19.

(1) Prepare a SOE-PCR cocktail (90 µl)
   50 µL Platinum Multiplex PCR Mastermix (Invitrogen 4464268)
   2 µL primer A (10 µM)
   2 µL primer B (10 µM)
   4 µL primer C (0.1 µM) (optional)
   X µL Barcode Carrying *E. coli* (to 2×106/mL final concentration)
   4 µL PEG 6000 (50% W/V)
   4 µL Tween-20 (50% V/V)
   X µL H2O to 90 µL total volume The barcode library resides on a high-copy number plasmid in *E. coli*. This is used to introduce a higher-than-one copy of barcode into each drop to jump-start the PCR at a higher template count. Using barcode-on-a-plasmid may be optional versus just using a single copy barcode.

(2) Drops from Step III were loaded into a drop merger device and Step III(2) was repeated with SOE-PCR cocktail. The reaction was thermal cycled at 95° C. 5 min, (95° C. 15 s, 60° C. 60 s, 72° C. 60 s), Cycle 22x, 72° C. 5 min.

(3) The emulsion was broken by adding 25 µL 2,2-perfluoro-octanol.

(4) The DNA was purified using a DNA clean-up column.

At this point, the DNA was a mixture of fragments, adaptor ligated fragments, and barcoded fragments. Barcoded fragments contain the necessary sequences to generate clusters on the Illumina flowcells. This DNA mixture can be sent directly to the sequencer.

Step IV (Alternative): SOE-PCR of Barcodes using amplified Barcode drops.

(1) Prepare SOE-PCR Master Mix
   125 µL Platinum Multiplex PCR Mastermix (Invitrogen 4464268)
   5 µL Primer A+C (10 µM)
   5 µL buffer NT from Illumina Catalogue (FC-131-1024)
   5 µL PEG 6000 (50% W/V)
   5 µL Tween-20 (50% V/V)
   5 µL Bst 2.0 Polymerase (NEB Catalogue M0538)
   100 µL $H_{20}$ (2) Load the SOE PCR master mix, barcode drops, and drops from step III into the Double Drop Merger device and run the device at Oil: 700 µL/hr, Spacer: 150 Barcode Drops: 35 µL/hr, Fragmented DNA drops: 70 µL/hr, SOE PCR master mix Cocktail: 600 µL/hr. The run takes ~50 minutes. Collect the emulsion into PCR tubes and thermocyle at 65° C. 5 min, 95° C. 2 min, (95° C. 15 s, 60° C. 60 s, 72° C. 60 s), Cycle 8x, 72° C. 5 min.

(3) Break the emulsion by adding 25 µL 2,2-perfluoro-octanol.

(4) Purify DNA using a DNA clean-up column.

At this point, the DNA is a mixture of fragments, adaptor ligated fragments, and barcoded fragments. Barcoded fragments contain the necessary sequences to generate clusters on the Illumina flowcells. This DNA mixture can be directly sent to the sequencer.

Step V. PCR enrichment for Fragment-Barcode and Size selection for sequencing (1) Prepare Enrichment PCR Cocktail (100 µL)
   50 µL Kapa 2x Hotstart Readymix (KapaBiosystems KK2601)
   1 µL Primer P5 (10 µM)
   1 µL Primer P7 (10 µM) (These are the P5 and P7 sequences from Illumina)
   X µL DNA from Step IV (1 ng total)
   X µL H2O to 100 µL Thermalcycled at 98° C. 3 min, (98° C. 10 s, 60° C. 30 s, 72° C. 45 s), 14 cycles, 72° C. 5 min.

Figure 20:
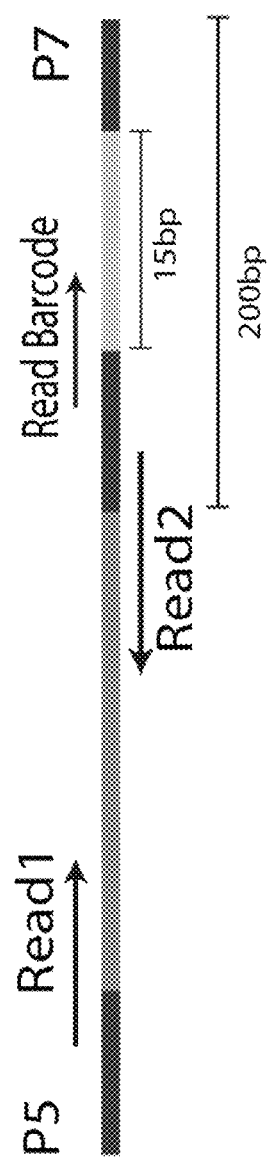
FIG. 20 provides a schematic of a barcodes fragment produced in accordance with Example 8.

(2) Size Selected 400-1000 bp fragments using an Agarose Gel, AmpureXP Beads (or alternatively Pippin Prep) to provide the library ready for sequencing. FIG. 20 provides a schematic of the barcoded fragments.

Results:

To characterize the data produced by SMDS, a histogram was plotted of the number of reads for which a specific barcode group size is observed. For example, due to orphan barcodes, if no adoption is performed, then there will be a large number of barcode groups that correspond to one read. The number of times that these one-read barcode groups are observed is the y-axis value of the plot for an x-axis value of one in FIG. 23. From this plot, it can be seen that, indeed, there are a relatively large number of one-read barcode groups, and that the histograms falls sharply from barcode groups of size 1 to 50. Between 50-250, the number of reads observed belonging to these groups is relatively constant, and then falls off for larger barcode groups. This suggests that there are many large barcode groups that are have not been sampled to saturation and that if more sequencing is performed, more useful data on these large groups can be acquired. The number of reads as a function of the barcode group ID number is plotted in FIG. 23 inset and shows that there is a relatively large variation among barcode groups in the number of reads obtained from them. This can be due partly to natural sampling noise or, additionally, due to bias generated during the process, such that some barcode groups comprise a greater fraction of the total reads in the sample than others and, hence, will always be observed more often.

Figure 24:
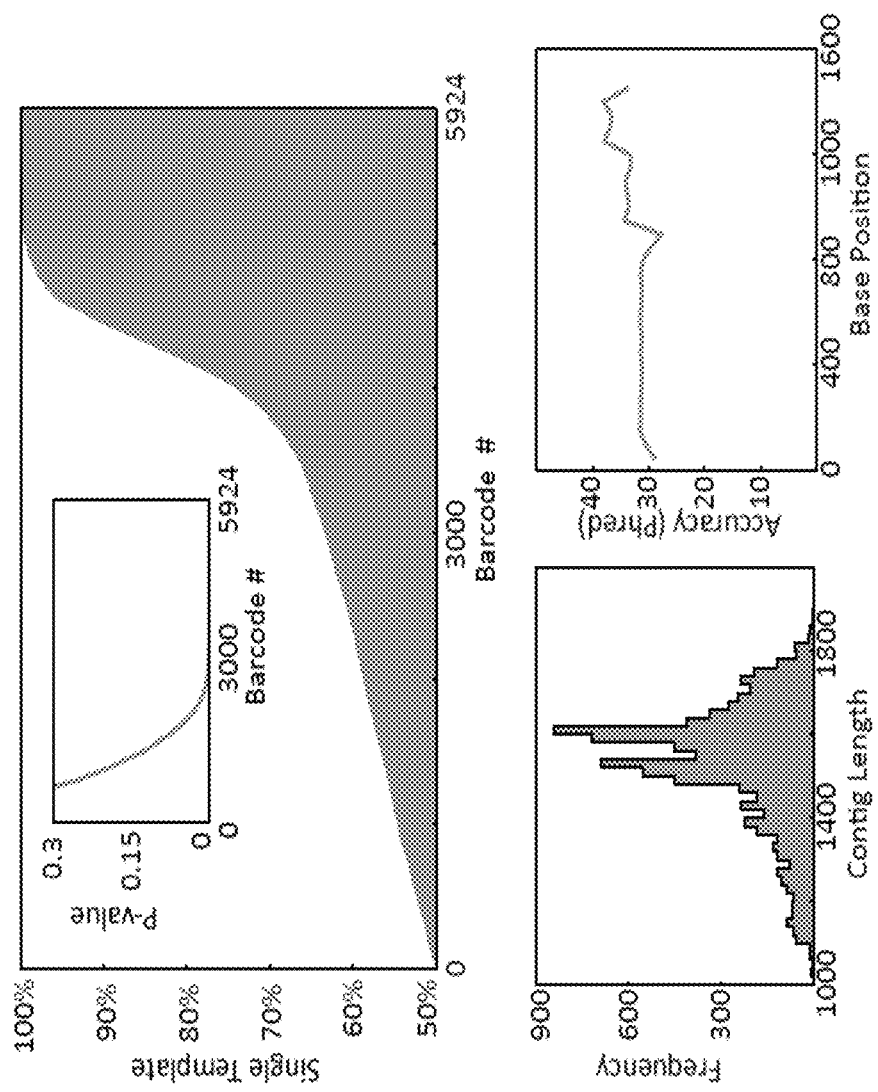
FIG. 24 provides a plot of the percentage of barcode groups that map to a single template as a function of the barcode group number, sorted in ascending order, upper plot. Inset shows the p-value that the barcode group composition could be generated by randomly populating fragmented reads from the two template molecules into the barcode clusters. The first 3000 barcodes have relatively high p-values, indicating that these clusters show a random mix of fragments from the two starting molecules, but higher barcode cluster numbers have compositions that cannot be explained by random compositions of reads, indicating that compartmentalization in the droplets is the most likely source of the cluster compositions. Lower left shows a histogram of the contig lengths assembled for each barcode cluster. In this experiment, two molecules were sequenced, the lengths of which correspond to the two peaks on the histogram. Lower right shows a plot of the accuracy of the assembled contigs, as calculated based on a Phred score, as a function of the base position. The high Phred scores result from sequencing each molecule deeply so that amplification and sequencing errors average out.

To assess the ability of the method to accurately reconstruct sequences from the barcode groups, a de novo assembler was used to assemble contigs for each barcode group. After assembly it was found that some molecules map to both of the templates, meaning that the droplets in which they were processed likely contained both templates, as shown in FIG. 24, upper. This could be due to double encapsulation or transfer of fragments during the microfluidic workflow or thermal steps, during which coalescence can occur. About a $3^{rd}$ of the data maps confidently to just one of the templates, indicating droplets that contained just single molecules. While multiple molecules may end up in a single droplet on occasion, the rate of this occurring can be reduced arbitrarily by diluting the targets during the encapsulation step, resulting in the generation of more empty droplets for every filled droplet. This wastes reagent but may be a desirable tradeoff when truly single molecule sequences are desired for every droplet. Nevertheless, even when multiple molecules are processed, the reads can still be grouped by barcode providing, for a given barcode group, a sample of short reads that need to reassembled into a small number of distinct contigs. While this may not always be desirable, it is similar to what is currently the norm in sequencing, wherein a collection of short reads comes from a single "cluster" including huge numbers of original fragments. However, assembling contigs in the context of currently available sequencing methods is much more challenging than when the currently described droplet barcoding is used. Hence, even in these instances, performing the reactions in compartmentalized volumes should greatly simplify reassembly.

After the de novo assembler was applied to each barcode group, a collection of the resulting contigs was obtained, a histogram of the lengths of which is plotted in FIG. 24, lower left. Two sharp peaks centered on the lengths of the known template molecules are clearly visible in the histogram, as are shoulders that represent contigs that were either smaller or larger than the targets. These contigs correspond to incorrect assemblies, either due to sequencing errors or incomplete data that prevented perfect assembly. This is a known challenge when performing de novo assembly—these algorithms often fail—and highlights the power of deeply sequencing single molecules using barcoding. With deeper sequencing of the library, this histogram will evolve, possibly generating sharper peaks.

Because the sequences of the starting molecules were known, it was possible to assess the accuracy of the assemblies by directly comparing them to the known references, which are plotted as a Phred score as a function of the base position in FIG. 24, lower right. A high average Phred score was obtained for all reassemblies, which is likely due to the multifold coverage obtained for reach molecule, allowing for the correction of amplification and sequencing errors.

Example 9: SMDS of Genomic Fragments

Figure 25:
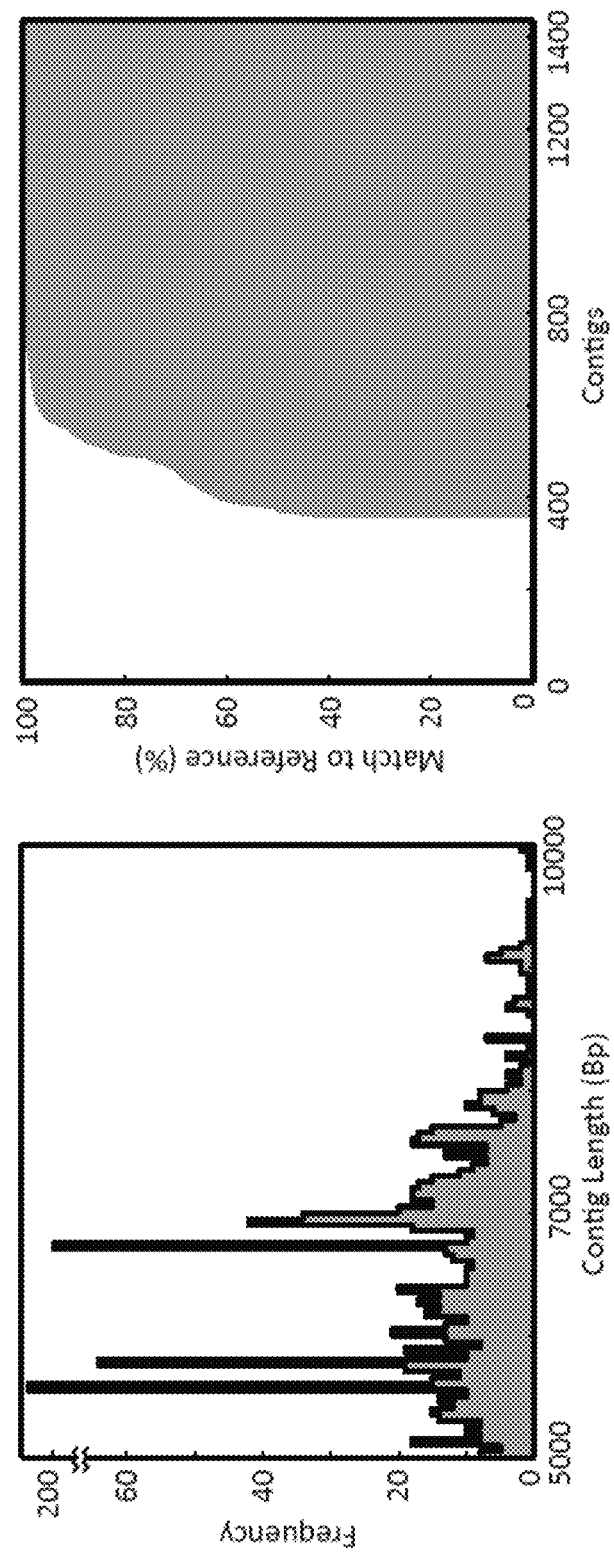
FIG. 25 provides a histogram (left plot) of assembled contig lengths using SMDS to sequence the *E. coli* genome. The genomes of *E. coli* cells were fragmented and single molecule fragments subjected to the SMDS workflow, using MDA to perform the initial target amplification rather than PCR. This permits deep sequencing of longer molecules than can be achieved using PCR to perform the first amplification. The right plot shows the percentage of contigs that map to the reference *E. coli* genome for each contig, sorted in ascending order.

To demonstrate the utility of SMDS for performing a realistic sequencing task, it was used to sequence diverse fragments of *E. coli* genomic DNA, FIG. 25.

Materials/Methods:

The DNA was fragmented into ~5-10 kb lengths and then processed with SMDS. In contrast to the test system described in Example 9, in this experiment multiple displacement amplification was used to amplify the target prior to the barcoding steps. MDA is a powerful tool for SMDS and has advantages relative to PCR because it can amplify molecules non-specifically and, also, does not require thermal cycling. In addition, whereas the efficiency of PCR drops off rapidly above molecules 10 kb in length, MDA can amplify molecules>10 kb bases in length. In SMDS, the major factor that limits the "read length" is generally the amplification step so that by switching from PCR to MDA, the read length of the approach can be effectively increased.

The SMDS process was performed on the *E. coli* DNA and similar bioinformatic analyses were performed as in the two-template experiment of Example 8, clustering barcode groups, removing groups that are sampled too sparsely, and performing de novo assembly on the groups with sufficient sampling.

Results:

A histogram of the resulting fragment length distributions is provided in FIG. 25, left. The histogram is relatively broad and constant from 5-8 kb, demonstrating that these lengths are well represented. However, there are some sharp peaks in the data which correspond to contigs that were observed many times. These contigs may be due to bias in the preparation of the library or merger of droplets during the process, resulting in a biased library in which these contigs are present more often than would be expected otherwise. Nevertheless, the histogram shows that a large number of long molecules were sequenced with the method. To determine whether the sequences were accurate, they were compared with the reference *E. coli* genome to perform sequence similarity calculation. It was found that about 400 molecules did not map to the genome, possibly representing contaminating DNA from other sources, and that 1000 molecules were a match to *E. coli*. This demonstrated that MDA with SMDS is an effective and powerful way to accurately sequence molecules that are longer than can be generated with PCR.

Example 10: Sequencing of Paired Antibody Heavy and Light Chains with Single Cell Droplet Barcoding An example in which correlating specific sequences within single cells is important is in the sequencing of antibody or T cell repertoires. Antibodies and T cell receptors are composed of two proteins bound together each of which is separately translated. In an antibody, the heavy and light chains assemble together such that the binding pocket of the antibody is in a fold joining the two chains. Characterizing the repertoires of people is important for studying autoimmune disease and identifying antibody-based therapies, but is challenging because there are huge numbers of B cells in the repertoires, each expressing a unique antibody, and because getting detailed information about each antibody requires sequencing both the heavy and light chains for each cell. This is challenging to do with existing methods because when cells are lysed, their transcripts can diffuse away and mix with those of other cells, again resulting in the loss of pairing information. This can be overcome by isolating single cells in wells or microfluidic chambers, but such methods are only scalable to tens or hundreds of cells.

Figure 26:
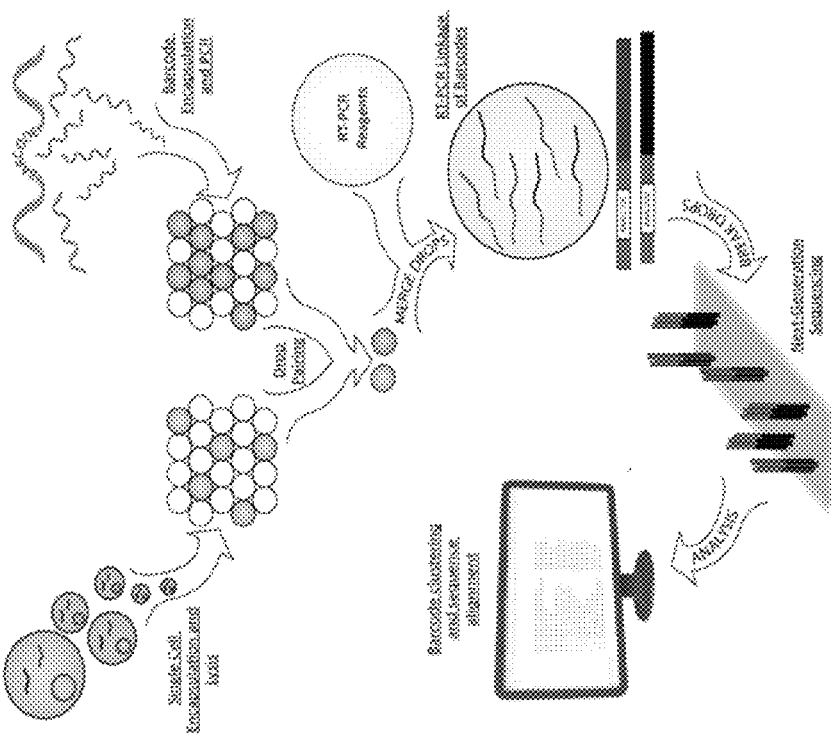
FIG. 26 provides a schematic of a workflow used for sequencing paired antibody or T-cell repertoires. Individual B or T cells are encapsulated in droplets, lysed, and combined with unique barcode droplets and RT-PCR reagent. Reverse transcriptase and overlap extension reactions are used to create cDNA products from the antibody transcripts and label them with unique barcodes so that they can be sequenced as a pool and the pairing of the heavy and light chains recovered by sorting according to barcodes.
Figure 26:
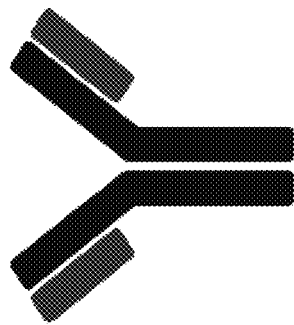
Figure 26:
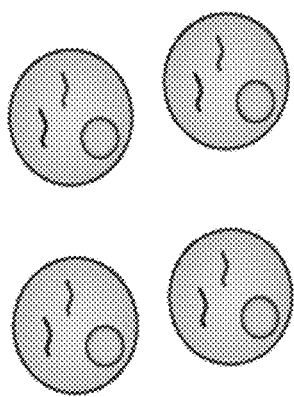

Droplet SOEing technology provides the ability to link together distinct sequences in single cells and the ability to perform this on millions of single cells using droplet barcoding, FIG. 26. In this approach, the B cells are loaded into droplet with lysis reagent, and lysed. They are then merged with the barcode droplet and droplets containing necessary reagents for SOE-PCR. As in SMDS, the barcode droplets contain many copies of a unique barcode. This allows a PCR reaction to be used to attach the barcodes to the heavy and light chains of the cells, so that the reads can be sequenced separately but then computationally clustered based on barcode.

To demonstrate the utility of this, droplet SOEing techniques were used to sequence the antibody repertoire of a Raji cell line that undergoes somatic hypermutation.

Figure 27:
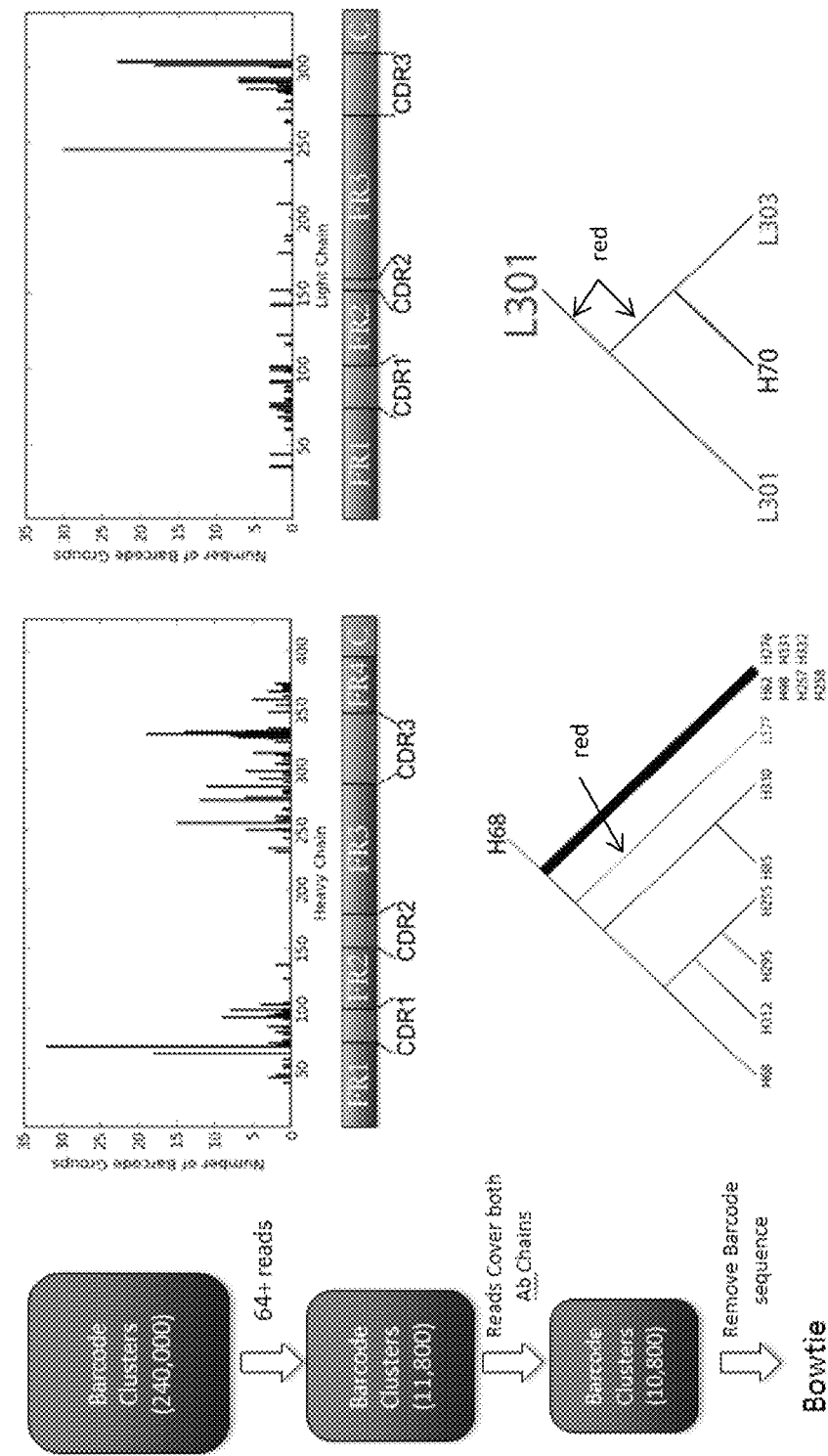
FIG. 27 provides data obtained using single cell barcoding to sequence the antibody repertoire of a Raji cell line that exhibits hypermutation in the antibody genes. Of the 240,000 barcode clusters recovered in the sequencing analysis, 11,800 had >64 reads and were kept and the others discarded. Of these, about 1000 only had reads from one of the chains, and were discarded. This provided 10,800 barcode groups, corresponding to single cells that could be used to measure hypermutation within the chains. The upper plots show the number of barcode groups that contain a mutation at the given location for the heavy chain (*center) and light chain (right). The structures of the genes of these two chains are provided below. From this data, distinct lineages of cells were observed and a tree was generated based on homology of the heavy chain (lower, center) and for the light chain. Due to the pairing, it was possible to trace mutants sharing the same heavy chain sequence (L177, read) and observe how these chains are paired with distinct light chain mutants (L301 and 303, red).

The cells were processed through the workflow shown in FIG. 26 and then similar bioinformatic methods as described in the SMDS process were utilized to discard low quality barcode groups. From this, it was possible to measure the mutational frequencies of the heavy and light chains of these genes, FIG. 27, and establish that the mutations cluster around hotspots known for hypermutation, as shown in the figure. Because the mutations accumulate as the cells replicate, the mutational distribution provides information which can be used to generate a tree of descendants, FIG. 27 lower. In addition, using both the heavy and light chains, it is possible to track how a specific mutant, L177, bifurcates into two lineages on the light chain, L301 and L303.

Example 11: Sequencing Single Cell Transcriptomes with Droplet Barcoding

Figure 28:
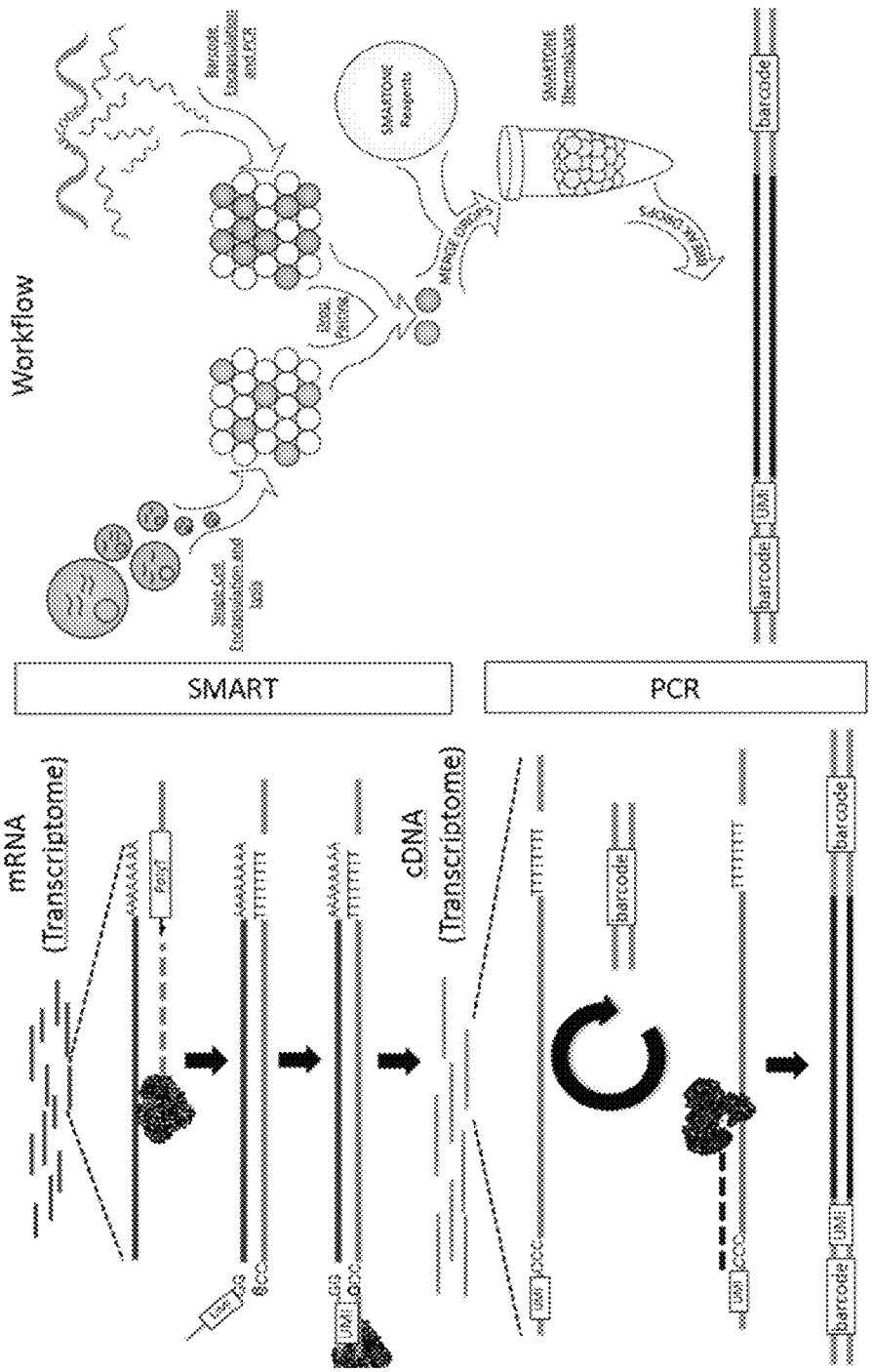
FIG. 28 provides a schematic of a droplet barcoding workflow for performing whole transcriptome single cell sequencing. The left panel shows molecular biology steps and right panel microfluidic processing steps. Single cells are encapsulated, lysed, and merged with droplets containing unique barcodes and RT-PCR reagents; the droplets are then thermocycled to perform the barcoding reaction prior to breaking the droplets, recovering the nucleic acids, and preparing them for sequencing. The process uses SMART/template switching with poly-T primers to create cDNA products from all mRNA in the cell. UMIs are attached during this step to enable correction of amplification bias. The barcodes are then attached to the cDNA products using SOE-PCR, producing barcoded molecules ready for sequencing preparation.

The barcoding strategy applied to sequencing the heavy and light chains of antibodies can be extended to sequencing whole transcriptomes. To accomplish this, rather than targeting the RT-PCR at only two antibody genes, a non-specific, whole transcriptome amplification method, like template switching SMART, can be utilized. Using oligo-dT primers, it's possible to hybridize to the poly-adenylated tails of all mRNA transcripts in a eukaryotic cell. Using the template switch mechanism, UMIs can be attached to the cDNA templates and the cDNA templates can be amplified, as shown in FIG. 28, upper left. At this point, known primers added during the cDNA synthesis can be used to attach barcodes using an SOE-PCR, as shown in FIG. 28, lower. This can be accomplished by encapsulating single cells in droplets, lysing them, and merging those droplets with ones containing barcode sequences and RT-PCR reagents, as shown in FIG. 28, right.

Figure 29:
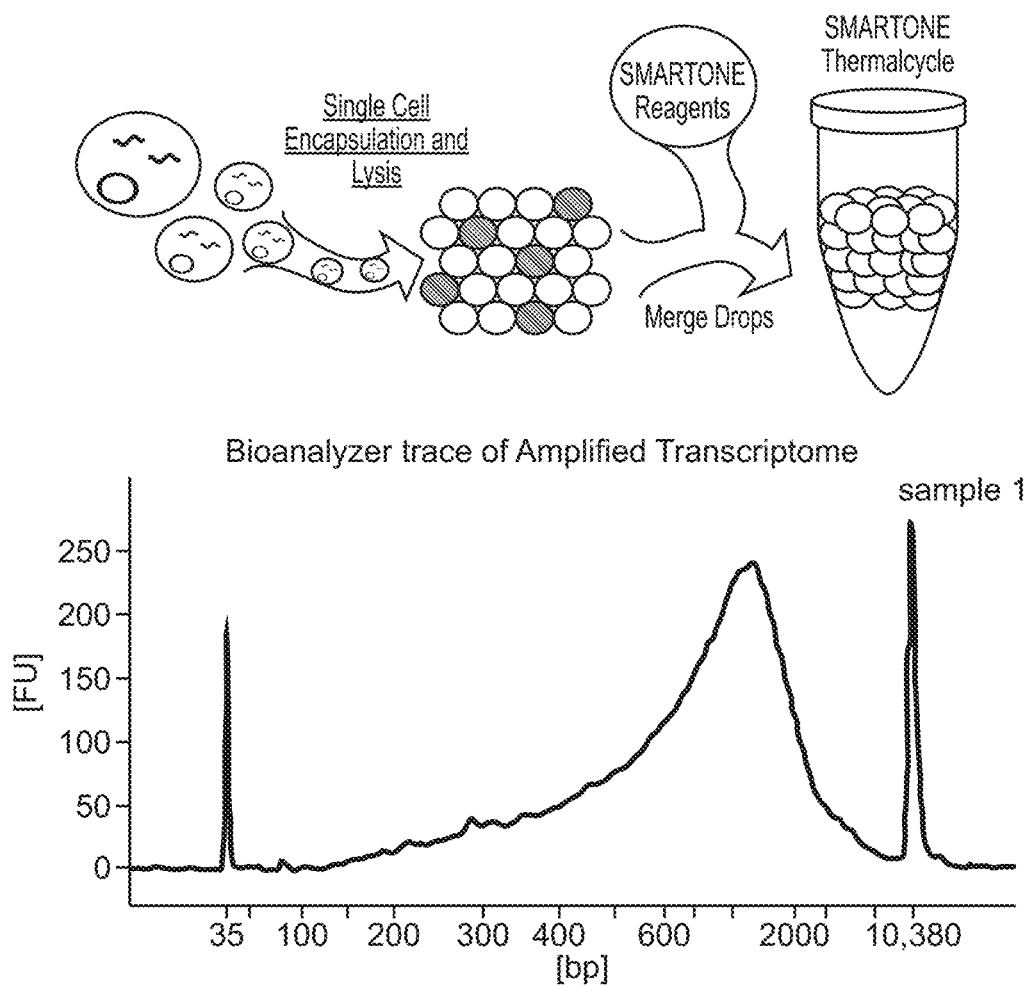
FIG. 29 provides bio analyzer data for amplified transcriptomes prepared with droplet barcoding. The data shows a broad distribution of cDNA products centered around 1500 bp, as expected for healthy transcriptome data. The lower plot shows a histogram of the cDNA molecule sizes again showing good correspondence with the expected distribution for mammalian cells.
Figure 29:
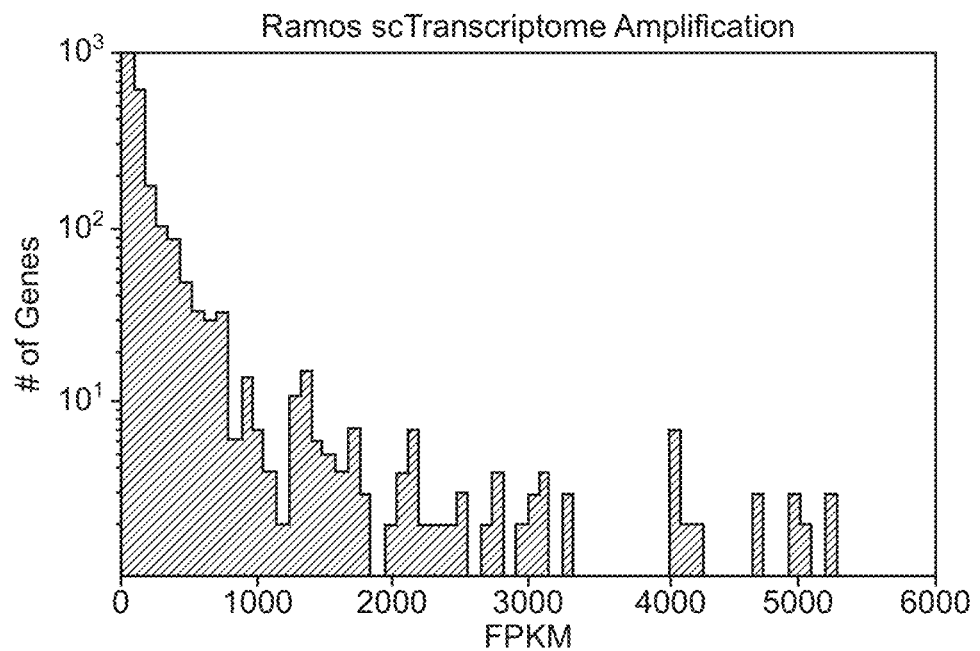

Because the lysate of the mammalian cell is digested with proteases and diluted to a suitable concentration, most enzymatic reactions are efficient in the droplets. When SMART barcoding was performed in the droplets, an efficient reaction was observed, as illustrated by a bioanalyzer trace of the cDNA products, which is broad and centered around 1500 base pairs, FIG. 29. In addition, when the number of genes was plotted as a function of fragments per kilobases of exon per million fragments mapped (FPKM), it followed the expected, healthy distribution for this mammalian cell type, showing that the mRNA is efficiently synthesized into cDNA of the correct length, as shown in FIG. 29, lower.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for detecting target molecules, the method comprising:
   providing a plurality of affinity reagents to a single cell under conditions sufficient for binding of one of the plurality of affinity reagents to a molecular target of the single cell to form an affinity reagent bound molecular target, the affinity reagent bound to the molecular target having an oligonucleotide including a first nucleic acid barcode, wherein the first nucleic acid barcode serves as an indicator of the affinity reagent binding to the molecular target;
   purifying the single cell by removing unbound affinity reagents of the plurality; encapsulating the single cell with the affinity reagent bound molecular target comprising
   the oligonucleotide including the first nucleic acid barcode in a discrete entity;
   lysing the single cell within the discrete entity such that the discrete entity comprises a released nucleic acid from within the single cell and the oligonucleotide including the first nucleic acid barcode;
   subsequent to lysing the single cell, encapsulating, with the oligonucleotide including the first nucleic acid barcode and the released nucleic acid from within the single cell or a product of the released nucleic acid, a plurality of primer sequences, a plurality of copies of a sequence comprising both a second nucleic acid barcode and a universal sequence, wherein the second nucleic acid barcode serves as an indicator of the discrete entity in which the oligonucleotide including the first nucleic acid barcode and the released nucleic acid are encapsulated;
   incorporating a first copy of the sequence comprising the second nucleic acid barcode and the universal sequence with the oligonucleotide including the first nucleic acid barcode by performing nucleic acid amplification using the universal sequence of the first copy and at least a first primer sequence;
   incorporating a second copy of the sequence comprising the second nucleic acid barcode and the universal sequence with the released nucleic acid or the product of the released nucleic acid by performing nucleic acid amplification using the universal sequence of the second copy and at least a second primer sequence; and
   sequencing the first nucleic acid barcode, the first copy of the sequence comprising the second nucleic acid barcode, and the second copy of the sequence comprising the second nucleic acid barcode.

2. The method of claim 1, wherein the affinity reagent comprises a peptide.

3. The method of claim 1, wherein the affinity reagent comprises an antibody or an antigen binding antibody fragment.

4. The method of claim 1, wherein the affinity reagent does not comprise an antibody.

5. The method of claim 1, wherein the affinity reagent comprises a drug.

6. The method of claim 1, wherein the molecular target is a component of a cell.

7. The method of claim 1, wherein the product of the released nucleic acid is generated by performing reverse transcription on the released nucleic acid.

8. The method of claim 7, wherein the reverse transcription occurs without nucleic acid amplification.

9. The method of claim 7, wherein the product of the released nucleic acid is further generated by performing nucleic acid amplification.

10. The method of claim 9, comprising sequencing the amplification product.

11. The method of claim 7, wherein the product of the released nucleic acid is generated by performing nucleic acid amplification after performing reverse transcription.

12. The method of claim 7, wherein the product of the released nucleic acid is generated by performing reverse transcription on the released nucleic acid to produce a reverse transcription product and amplifying the reverse transcription product, wherein performing reverse transcription and amplifying occur in a single step.

13. The method of claim 7, further comprising sequencing the reverse transcription product.

14. The method of claim 1, comprising amplifying the oligonucleotide before incorporating the second nucleic acid barcode.

15. The method of claim 1, wherein the incorporating comprises linking the first nucleic acid barcode and the first copy of the second nucleic acid barcode to produce a composite nucleic acid barcode molecule.

16. A method for detecting target molecules, the method comprising:
   providing a plurality of affinity reagents to a single cell under conditions sufficient for binding of one of the plurality of affinity reagents to a molecular target of the single cell to form an affinity reagent bound molecular target, the affinity reagent bound to the molecular target having an oligonucleotide including a first nucleic acid barcode, wherein the first nucleic acid barcode serves as an indicator of the affinity reagent binding to the molecular target;

purifying the single cell by removing unbound affinity reagents of the plurality; encapsulating the single cell with the affinity reagent bound molecular target comprising the oligonucleotide including the first nucleic acid barcode in a discrete entity;

lysing the single cell within the discrete entity such that the discrete entity comprises a RNA molecule from within the single cell, a DNA molecule from within the single cell, and the oligonucleotide including the first nucleic acid barcode, wherein the lysing comprises digesting cellular proteins of the single cell using a proteinase K;

subsequent to lysing the single cell, encapsulating, with the oligonucleotide including the first nucleic acid barcode, a cDNA molecule derived from the RNA molecule from within the single cell, and the DNA molecule from within the single cell, a plurality of primer sequences, a plurality of copies of a sequence comprising both a second nucleic acid barcode and a universal sequence, wherein the second nucleic acid barcode serves as an indicator of the discrete entity;

incorporating a first copy of the sequence comprising the second nucleic acid barcode and the universal sequence with the oligonucleotide including the first nucleic acid barcode by performing nucleic acid amplification using the universal sequence of the first copy and at least a first primer sequence;

incorporating a second copy of the sequence comprising the second nucleic acid barcode and the universal sequence with the cDNA molecule derived from the RNA molecule y, performing nucleic acid amplification using the universal sequence of the second copy and at least a second primer sequence;

incorporating a third copy of the sequence comprising the second nucleic acid barcode and the universal sequence with the DNA molecule by performing nucleic acid amplification using the universal sequence of the third copy and at least a third primer sequence; and sequencing the first nucleic acid barcode, the first copy of the sequence comprising the second nucleic acid barcode, the second copy of the sequence comprising the second nucleic acid barcode, and the third copy of the sequence comprising the second nucleic acid barcode.

17. A method for detecting target molecules, the method comprising:

providing a plurality of affinity reagents to a single cell under conditions sufficient for binding of one of the plurality of affinity reagents to a molecular target of the single cell to form an affinity reagent bound molecular target, the affinity reagent bound to the molecular target having an oligonucleotide including a first nucleic acid barcode, wherein the first nucleic acid barcode serves as an indicator of the affinity reagent binding to the molecular target;

purifying the single cell by removing unbound affinity reagents of the plurality; encapsulating the single cell with the affinity reagent bound molecular target comprising the oligonucleotide including the first nucleic acid barcode in a discrete entity;

lysing the single cell within the discrete entity such that the discrete entity comprises a released nucleic acid from within the single cell and the oligonucleotide including the first nucleic acid barcode, wherein the lysing comprises digesting cellular proteins of the single cell using a proteinase K;

subsequent to lysing the single cell, encapsulating, with the oligonucleotide including the first nucleic acid barcode and the released nucleic acid from within the single cell or a product of the released nucleic acid, a plurality of primer sequences, a plurality of copies of a sequence comprising both a second nucleic acid barcode and a universal sequence, wherein the second nucleic acid barcode serves as an indicator of the discrete entity;

incorporating a first copy of the sequence comprising the second nucleic acid barcode and the universal sequence with the oligonucleotide including the first nucleic acid barcode by performing nucleic acid amplification using the universal sequence of the first copy and at least a first primer sequence;

incorporating a second copy of the sequence comprising the second nucleic acid barcode and the universal sequence with the released nucleic acid or the product of the released nucleic acid by performing nucleic acid amplification using the universal sequence of the second copy and at least a second primer sequence; and sequencing the first nucleic acid barcode, the first copy of the sequence comprising the second nucleic acid barcode, and the second copy of the sequence comprising the second nucleic acid barcode.

18. The method of claim 1, wherein the oligonucleotide including the first nucleic acid barcode further comprises a unique molecular identifier that uniquely identifies the one of the plurality of affinity reagents.

19. The method of claim 18, further comprising: sequencing the unique molecular identifier; and correcting for amplification bias using the sequenced unique molecular identifier.

20. The method of claim 1, wherein the universal sequence is complementary to a portion of the first primer sequence and a portion of the second primer sequence, wherein performing nucleic acid amplification using the universal sequence of the first copy and at least the first primer sequence comprises hybridizing the universal sequence of the first copy to the portion of the first primer sequence, and wherein performing nucleic acid amplification using the universal sequence of the second copy and at least the second primer sequence comprises hybridizing the universal sequence of the second copy to the portion of the second primer sequence.

* * * * *

UNITED STATES PATENT AND TRADEMARK OFFICE
CERTIFICATE OF CORRECTION

PATENT NO. : 11,732,287 B2
APPLICATION NO. : 15/940850
DATED : August 22, 2023
INVENTOR(S) : Adam R. Abate et al.

It is certified that error appears in the above-identified patent and that said Letters Patent is hereby corrected as shown below:

In the Specification

In Column 7, Line 5, delete "(Fab)$_2$," and insert -- (Fab′)$_2$, --.

In Column 15, Line 40, delete "on/and or" and insert -- on and/or --.

In Column 19, Line 12, delete "(NNNNNNN region" and insert -- region (NNNNNNN --.

In Column 53, Line 23, delete "and or" and insert -- and/or --.

In Column 66, Lines 12-13, delete "polybutylenterephthalate (PBT)," and insert -- polybutyleneterephthalate (PBT), --.

In Column 66, Line 15, delete "polyphenylenether (PPE)," and insert -- polyphenyleneether (PPE), --.

In Column 68, Line 42, delete "mircochannel," and insert -- microchannel, --.

In Column 68, Line 48, delete "less 34" and insert -- less, 34 --.

In Column 70, Line 1, delete "Fan-Male" and insert -- Fan-blade --.

In Column 71, Line 8, delete "70′′′" and insert -- 70° --.

In Column 73, Lines 4-5, delete "600 and 1100° C." and insert -- 600° C. and 1100° C. --.

In Column 76, Line 37, delete "thereof" and insert -- thereof. --.

In Column 77, Line 32, delete "thereof" and insert -- thereof. --.

Signed and Sealed this
Twenty-third Day of January, 2024

Katherine Kelly Vidal
*Director of the United States Patent and Trademark Office*

CERTIFICATE OF CORRECTION (continued)
U.S. Pat. No. 11,732,287 B2

In Column 78, Line 41, delete "thereof" and insert -- thereof. --.

In Column 79, Line 39, delete "thereof" and insert -- thereof. --.

In Column 80, Line 15, delete "thereof" and insert -- thereof. --.

In Column 81, Line 12, delete "thereof" and insert -- thereof. --.

In Column 81, Line 56, delete "thereof" and insert -- thereof. --.

In Column 82, Line 20, delete "thereof" and insert -- thereof. --.

In Column 82, Line 47, delete "thereof" and insert -- thereof. --.

In Column 83, Line 14, delete "thereof" and insert -- thereof. --.

In Column 95, Line 23, delete "thereof" and insert -- thereof. --.

In Column 99, Line 60, delete "thereof" and insert -- thereof. --.

In Column 104, Line 43, delete "thereof" and insert -- thereof. --.

In Column 105, Line 22, delete "thereof" and insert -- thereof. --.

In Column 106, Line 5, delete "thereof" and insert -- thereof. --.

In Column 110, Line 34, delete "thereof" and insert -- thereof. --.

In Column 113, Line 8, delete "disaggretating" and insert -- disaggregating --.

In Column 113, Line 10, delete "and or" and insert -- and/or --.

In Column 113, Line 47, delete "oligonucelotides" and insert -- oligonucleotides --.

In Column 114, Line 65, delete "oligonucelotides" and insert -- oligonucleotides --.

In Column 116, Line 67, delete "(LCR)" and insert -- (LCR). --.

In Column 118, Line 18, delete "cleavage" and insert -- cleavage. --.

In Column 118, Line 52, delete "oligonucelotides" and insert -- oligonucleotides --.

In Column 119, Line 36, delete "Deoxyribunucleotides" and insert -- Deoxyribonucleotides --.

In Column 120, Line 12, delete "oligonucelotides" and insert -- oligonucleotides --.

CERTIFICATE OF CORRECTION (continued)
U.S. Pat. No. 11,732,287 B2

In Column 120, Line 20, delete "concatamer" and insert -- concatemer --.

In Column 120, Line 24, delete "concatmer" and insert -- concatemer --.

In Column 120, Line 54, delete "methods" and insert -- methods. --.

In Column 120, Line 66, delete "Deoxyribunucleotides" and insert -- Deoxyribonucleotides --.

In Column 123, Line 56, before "µL" delete "ul".

In Column 123, Line 59, delete "$H_{20}$" and insert -- $H_2O$ --.

In Column 124, Line 43, before "2010," insert -- Genome Biology. --.

In Column 125, Line 11, delete "H2O" and insert -- $H_2O$ --.

In Column 125, Line 39, delete "$H_{20}$" and insert -- $H_2O$ --.

In Column 125, Line 42, delete "150 Barcode" and insert --150 µL/hr, Barcode --.

In Column 125, Line 65, delete "H2O" and insert -- $H_2O$ --.

In the Claims

In Column 131, Line 30, in Claim 16, delete "y," and insert -- by, --.